US00RE44760E

(19) United States
(12) Reissued Patent
Crooke et al.

(10) Patent Number: US RE44,760 E
(45) Date of Reissued Patent: Feb. 11, 2014

(54) ANTISENSE MODULATION OF APOLIPOPROTEIN B-EXPRESSION

(71) Applicant: Genzyme Corporation, Cambridge, MA (US)

(72) Inventors: Rosanne M. Crooke, Carlsbad, CA (US); Mark J. Graham, San Clemente, CA (US); Susan M. Freier, San Diego, CA (US)

(73) Assignee: Genzyme Corporation, Cambridge, MA (US)

(21) Appl. No.: 13/629,214

(22) Filed: Sep. 27, 2012

Related U.S. Patent Documents

Reissue of:
(64) Patent No.: 7,803,930
Issued: Sep. 28, 2010
Appl. No.: 10/920,612
Filed: Aug. 17, 2004

U.S. Applications:
(63) Continuation of application No. 10/712,795, filed on Nov. 13, 2003, now Pat. No. 7,511,131, and a continuation-in-part of application No. PCT/US03/15493, filed on May 15, 2003.

(60) Provisional application No. 60/426,234, filed on Nov. 13, 2002.

(51) Int. Cl.
*A61K 31/70* (2006.01)
*A61K 48/00* (2006.01)
*C07H 21/02* (2006.01)
*C07H 21/04* (2006.01)

(52) U.S. Cl.
USPC ..... 435/455; 536/24.5; 536/23.2; 536/24.1; 536/24.3; 536/24.31; 536/24.33; 435/325; 435/375; 435/377; 514/44 A

(58) Field of Classification Search
None
See application file for complete search history.

(56) References Cited

U.S. PATENT DOCUMENTS

| | | | |
|---|---|---|---|
| 5,220,006 | A | 6/1993 | Ross et al. |
| 5,434,058 | A | 7/1995 | Davidson et al. |
| 5,618,674 | A | 4/1997 | Sanchez-Pescador et al. |
| 5,656,612 | A | 8/1997 | Monia |
| 5,712,257 | A | 1/1998 | Carter |
| 5,786,206 | A | 7/1998 | Smith et al. |
| 5,801,154 | A | 9/1998 | Baracchini et al. |
| 5,877,009 | A | 3/1999 | Zannis et al. |
| 5,945,290 | A | 8/1999 | Cowsert |
| 5,998,148 | A | 12/1999 | Bennett et al. |
| 6,010,849 | A | 1/2000 | Edwards et al. |
| 6,033,910 | A | 3/2000 | Monia et al. |
| 6,096,516 | A | 8/2000 | Kwak et al. |
| 6,156,315 | A | 12/2000 | Goldberg et al. |
| 6,172,216 | B1 | 1/2001 | Bennett et al. |
| 6,184,212 | B1 | 2/2001 | Miraglia et al. |
| 6,235,470 | B1 | 5/2001 | Sidransky |
| 6,359,124 | B1 | 3/2002 | Ecker et al. |
| 6,448,079 | B1 | 9/2002 | Monia et al. |
| 6,500,672 | B1 | 12/2002 | Sladek et al. |
| 6,512,161 | B1 | 1/2003 | Rouy et al. |
| 6,534,277 | B1 | 3/2003 | Hancock et al. |
| 6,582,908 | B2 | 6/2003 | Fodor et al. |
| 6,660,737 | B2 | 12/2003 | Almstead et al. |
| 6,670,461 | B1 | 12/2003 | Wengel et al. |
| 6,852,536 | B2 | 2/2005 | Dobie et al. |
| 6,878,729 | B2 | 4/2005 | Almstead et al. |
| 6,949,367 | B1 | 9/2005 | Dempcy et al. |
| 7,407,943 | B2 | 8/2008 | Crooke et al. |
| 7,511,131 | B2 | 3/2009 | Crooke et al. |
| 7,598,227 | B2 | 10/2009 | Crooke et al. |
| 7,750,141 | B2 | 7/2010 | Crooke et al. |
| 7,803,930 | B2 | 9/2010 | Crooke et al. |
| 7,888,324 | B2 | 2/2011 | Crooke et al. |
| 2001/0053519 | A1 | 12/2001 | Fodor et al. |
| 2002/0068708 | A1 | 6/2002 | Wengel et al. |
| 2002/0123617 | A1 | 9/2002 | Starling et al. |
| 2003/0008373 | A1 | 1/2003 | Bartel et al. |
| 2003/0064950 | A1 | 4/2003 | Ntambi et al. |
| 2003/0083280 | A1 | 5/2003 | Crooke et al. |
| 2003/0087853 | A1 | 5/2003 | Crooke et al. |
| 2003/0215943 | A1 | 11/2003 | Crooke et al. |
| 2003/0228597 | A1 | 12/2003 | Cowsert et al. |
| 2003/0228613 | A1 | 12/2003 | Bornarth et al. |
| 2004/0171566 | A1 | 9/2004 | Monia et al. |
| 2004/0208856 | A1 | 10/2004 | Crooke et al. |
| 2004/0209838 | A1 | 10/2004 | Monia et al. |
| 2004/0214325 | A1 | 10/2004 | Crooke et al. |
| 2004/0241651 | A1 | 12/2004 | Olek et al. |
| 2004/0266714 | A1 | 12/2004 | Freier et al. |
| 2005/0009088 | A1 | 1/2005 | Crooke et al. |
| 2005/0014713 | A1 | 1/2005 | Freier |
| 2005/0043524 | A1 | 2/2005 | Bhanot et al. |
| 2005/0130923 | A1 | 6/2005 | Bhat et al. |
| 2005/0164271 | A1 | 7/2005 | Bhanot et al. |
| 2005/0272680 | A1 | 12/2005 | Bhanot et al. |

(Continued)

FOREIGN PATENT DOCUMENTS

| | | |
|---|---|---|
| EP | 0 332 435 | 9/1989 |
| EP | 0 530 794 | 3/1993 |

(Continued)

OTHER PUBLICATIONS

U.S. Appl. No. 60/159,462, filed Oct. 12, 1999, Eggerman et al.

(Continued)

*Primary Examiner* — Janet Epps-Smith
(74) *Attorney, Agent, or Firm* — Jones Day

(57) ABSTRACT

Antisense compounds, compositions and methods are provided for modulating the expression of apolipoprotein B. The compositions comprise antisense compounds, particularly antisense oligonucleotides, targeted to nucleic acids encoding apolipoprotein B. Methods of using these compounds for modulation of apolipoprotein B expression and for treatment of diseases associated with expression of apolipoprotein B are provided.

58 Claims, No Drawings

(56) References Cited

U.S. PATENT DOCUMENTS

| | | | |
|---|---|---|---|
| 2005/0287558 | A1 | 12/2005 | Crooke et al. |
| 2006/0009410 | A1 | 1/2006 | Crooke et al. |
| 2006/0025373 | A1 | 2/2006 | Bhanot et al. |
| 2006/0035858 | A1 | 2/2006 | Geary et al. |
| 2007/0031844 | A1 | 2/2007 | Khvorova et al. |
| 2007/0087987 | A1 | 4/2007 | Monia et al. |
| 2007/0238688 | A1 | 10/2007 | Bhanot et al. |
| 2007/0238690 | A1 | 10/2007 | Bhanot et al. |
| 2008/0146788 | A1 | 6/2008 | Bhat et al. |
| 2008/0242629 | A1 | 10/2008 | Crooke et al. |
| 2009/0306180 | A1 | 12/2009 | Bhanot et al. |
| 2009/0326040 | A1 | 12/2009 | Geary et al. |

FOREIGN PATENT DOCUMENTS

| | | | |
|---|---|---|---|
| EP | 0 911 344 | | 4/1999 |
| EP | 1 239 051 | | 9/2002 |
| EP | 1239051 | A2 * | 9/2002 |
| JP | 2002355074 | | 12/2002 |
| WO | WO 92/10590 | | 6/1992 |
| WO | WO 94/13794 | | 6/1994 |
| WO | WO 94/13794 | A1 | 6/1994 |
| WO | WO 97/20924 | | 6/1997 |
| WO | WO 97/35538 | A2 | 10/1997 |
| WO | WO 98/20166 | | 5/1998 |
| WO | WO 98/32846 | | 7/1998 |
| WO | WO 98/36641 | | 8/1998 |
| WO | WO 99/14226 | | 3/1999 |
| WO | WO 99/18237 | | 4/1999 |
| WO | WO 99/18986 | | 4/1999 |
| WO | WO 99/18986 | A1 | 4/1999 |
| WO | WO 99/35241 | | 7/1999 |
| WO | WO 00/00504 | | 1/2000 |
| WO | WO 00/56916 | | 9/2000 |
| WO | WO 00/56920 | | 9/2000 |
| WO | WO 01/12789 | | 2/2001 |
| WO | WO 01/30354 | | 5/2001 |
| WO | WO 01/30354 | A1 | 5/2001 |
| WO | WO 01/30395 | A1 | 5/2001 |
| WO | WO 01/52902 | | 7/2001 |
| WO | WO 0152902 | A1 * | 7/2001 |
| WO | WO 01/72765 | A1 | 10/2001 |
| WO | WO 01/77384 | | 10/2001 |
| WO | WO 01/77384 | A2 * | 10/2001 |
| WO | WO 02/26768 | | 4/2002 |
| WO | WO 03/011887 | | 2/2003 |
| WO | WO 03/074723 | | 9/2003 |
| WO | WO2003/074723 | A2 * | 9/2003 |
| WO | WO 03/097097 | | 11/2003 |
| WO | WO 03/097662 | | 11/2003 |
| WO | WO 2004/044181 | | 5/2004 |
| WO | WO 2004/077384 | | 9/2004 |
| WO | WO 2004/093783 | | 11/2004 |
| WO | WO 2005/049621 | | 6/2005 |
| WO | WO 2006/020676 | A2 | 2/2006 |
| WO | WO 2007/031081 | A2 | 3/2007 |
| WO | WO 2007/090071 | A2 | 8/2007 |
| WO | WO 2007/131238 | A2 | 11/2007 |
| WO | WO 2007/134181 | | 11/2007 |
| WO | WO 2008/118883 | A1 | 10/2008 |

OTHER PUBLICATIONS

Agrawal et al., "Antisense therapeutics: is it as simple as complementary base recognition?" Molecular Medicine Today (2000) 6: 72-81.

Bayarsaihan et al., "Single-strand-DNA-binding factors specifically recognize the pyrimidine element in the chick a2(I) collagen gene promoter" Biochem J. (1996) 314:293-296.

Bennett et al., "Inhibition of endothelial cell adhesion molecule expression with antisense oligonucleotides." Journal of Immunology (1994) 152(7)3530-3540.

Bennett et al., "Antisense Oligonucleotides as a Tool for Gene Functionalization and Target Validation," Biochimica et Biophysica Acta (1999) 1489:18-30.

Bonow, "Primary Prevention of Cardiovascular Disease: A Call to Action" Circulation (2002) 106:3140-3141.

Boren et al., "A simple and efficient method for making site-directed mutants, deletions, and fusions of large DNA such as PI and BAC clones" Genome Research (1996) 11:1123-1130.

Braasch et al., "Novel Antisense and Peptide Nucleic Acid Strategies for Controlling Gene Expression," Biochemistry 41:4503-4510, (2002).

Branch et al., "A good antisense molecule is hard to find," TIBS (1998) 23:45-50.

Burnett, "Drug evaluation: ISIS-301012, an antisense oligonucleotide for the treatment of hypercholesterolemia" Current Opinion in Molecular Therapeutics (2006) 8(5):46l-467.

Campos et al., "Distinct patterns of lipoproteins with apoB defines by presence of apoE or apoC-III in hypercholesterolemia and hypertriglyceridemia" J. Lipid Res. (2001) 42:1239-13491.

Chan et al., "Apolipoprotein B-100 kinetics in visceral obesity: Associations with plasma apolipoprotein C-III concentration," Metabolism Clin. and Experimental (2002) 51(8):1041-1046.

Crooke, "Progress in Antisense Technology" Ann. Rev. Med. (2004) 55:61-95.

Crooke, "Antisense oligonucleotides as therapeutics for hyperlipidaemias" Expert Opinion on Biological Therapy (2005) 5(7):907-917.

Cuchel et al., "Inhibition of Microsomal Triglyceride Transfer Protein in Familial Hypercholesterolemia" New England Journal of Medicine (2007) 356:148-156.

Dammerman et al., "An apolipoprotein CIII haplotype protective against hypertriglyceridemia is specified by promoter and 3' untranslated region polymorphisms" Proc. Natl. Acad. Sci. U. S. A., (1993) 90:4562-4566.

Davidson et al., "Apolipoprotein B: mRNA editing, lipoprotein assembly, and presecretory degradation" Annu. Rev. Nutr. (2000) 20:169-193.

Davis et al., "Atherosclerosis Is a Liver Disease of the Heart" Arteriscler. Thromb. Vasc. Biol. (2001) 21:887-898.

De Silva et al., "Overexpression of human apolipoprotein C-III in transgenic mice results in an accumulation of apolipoprotein B48 remnants that is corrected by excess apolipoprotein E" J. Biol. Chem. (1994) 269:2324-2335.

DeCatarina et al., "Fatty Acid Modulation of Endothelial Activation" American Journal of Clinical Nutrition (2000) 71 (suppl.):213S-223S.

Deeb et al., "Chromosomal localization of the human apolipoprotein B gene and detection of homologous RNA in monkey intestine" Proc. Natl. Acad. Sci. USA (1986) 83:419-422.

Deere et al., "Antisense Phosphorodiamidate Morpholino Oligomer Length and Target Position Effects on Gene-Specific Inhibition in *Escherichia coli*" Antimicrobial Agents and Chemotherapy (2005) 49:249-255.

Duivenvoorden et al., "Apolipoprotein C3 Deficiency Results in Diet-Inudced Obesity and Aggravated Insulin Resistance in Mice" Diabetes (2005) 54:664-671.

Elias et al., "Decreased Production Rates of VLDL Triglycerides and ApoB-100 in Subjects Heterozygous for Familial Hypobetalipoproteinemia," Metabolism of Triglycerides and ApoB-100 n FHBL, Arterioscler Therob Vasc Biol., (1999)9:2714-2721.

EMBL Accession No. A13426, Oct. 5, 1994.

EMBL Accession No. A23827, Apr. 2, 1995.

EMBL Accession No. A97152, Jan. 26, 2000.

EMBL Accession No. AR 152836, Aug. 9, 2001.

EMBL Accession No. L24258, Sep. 18, 1993.

EMBL Accession No. L27195, Jan. 6, 1994.

Farese et al., "Knockout of the mouse apolipoprotein B gene results in embryonic lethality in homozygotes and protection against diet-induced hypercholesterolemia in heterozygotes" Proc. Natl. Acad. Sci. USA (1995) 92:1774-1778.

Fluiter K., et al., "In vivo tumor growth inhibition and biodistribution studies of locked nucleic acid (LNA) antisense oligonucleotides," Nucleic Acids Research, 2003, vol. 31, No. 3, pp. 953-962.

(56) References Cited

OTHER PUBLICATIONS

Frieden M., et al, "Expanding the design horizon of antisense oligonucleotides with alpha-L-LNA," Nucleic Acids Research, Oxford University Press, Surrey, GB, vol. 31, No. 21, Nov. 1, 2003, pp. 6365-6372.
Funatsu et al., "Reduction in hepatic non-esterified fatty acid concentration after long-term treatment with atorvastatin lowers hepatic triglyceride synthesis and its secretion in sucrose-fed rats" Biochimica et Biophysica Acta (2002) 1580:161-170.
Ganji et al., "Niacin and cholesterol: role in cardiovascular disease (Review)" The Journal of Nutritional Biochemistry (2003) 14:293-305.
Gautschi et al., "Activity of a Novel bcl-2/bcl-xL-Bispecifc Antisense Oligonucleotide Against Tumors of Diverse Histologic Origins" J. Natl Cancer Inst (2001) 93:463-471.
Geary et al., "Pharmacokinetics of a Tumor Necrosis Factor-α Phosphorothioate 2'-O(2-Methoxyethyl) Modified Antisense Oligonucleotide: Comparison Across Species," Drug Metab Dispos 2003:31:1419-1428.
Genbank Accession No. NM_000384, Oct. 31, 2000, Huang et al.
Geneseq Accession No. AAA07969, Jan. 29. 2001.
Geneseq Accession No. AAA28208, Jan. 29, 2001.
Geneseq Accession No. AAV39607, Sep. 28, 1998.
Geneseq Accession No. AAX89306, Sep. 21, 1999. (from WO 99/35241).
Gewirtz et al., "Facilitating oligonucleotide delivery: Helping antisense deliver on its promise" PNAS USA (1996) 93:3161-3163.
Graham et al., "Inhibition of ApoB-100 as a Therapeutic Strategy for the Treatment of Hyperlipidemias" AHA Abstracts (2002) Abstract ID:20009.
Graham et al., "Pharmacological Inhibition of PCSK9 in Hyperlipiemic Mice Significantly Reduces Serum LDL-C While Increasing Hepatic Low-Density Lipoprotein Receptor Protein Abundance," Arterioscler. Thromb. Vasc. Biol. (Jun. 2007) vol. 27, No. 6, p. E36.
Hajjar et al., "The role of lipoprotein(a) in atherogenesis and thrombosis" Annu. Rev. Med. (1996) 47:423-442.
Hammond et al., "Post-transcriptional gene silencing by double-stranded RNA" Nature Reviews Genetics (2001) 2:110-119.
Hertz et al., "Mode of action of peroxisome proliferators as hypolipidemic drugs. Suppression of apolipoprotein C-III" J. Biol. Chem. (1995) 270:13470-13475.
Heymsfield, "Effects of Weight Loss With Orlistat on Glucose Tolerance and Progression to Type 2 Diabetes in Obese Adults" Archives of Internal Medicine 160:1321-1326, (2002).
Huang et al., "Hypobetalipoproteinemia due to an apolipoprotein B gene exon 21 deletion derived by Alu-Alu recombination" Journal of Biological Chemistry (1989) 264:11394-11400. (Genbank NM_000384).
Iijima et al., "Red Wine Polyphenols Inhibit Vascular Smooth Muscle Cell Migration Through Two Distinct Signaling Pathways" Circulation (2002) 105(20):2404-2410.
Innerarity et al., "Familial defective apolipoprotein B-100: low density lipoproteins with abnormal receptor binding" Proc. Natl. Acad. Sci. USA (1987) 84:6919-6923.
ISA, International Search Report for Application PCT /US00/29223 dated Dec. 26, 2000.
ISA, International Search Report dated Oct. 22, 2003 for Application PCT/US03/15493.
ISA, International Search Report dated Aug. 31, 2004 for Application CT/US03/36411.
ISA, International Search Report dated Apr. 10, 2006 for Application PCT/US05/028342.
ISA, Communication Relating to the Results of the Partial International Search dated Jan. 30, 2008 for Application PCT/US07/68401.
ISA, International Search Report dated Apr. 21, 2008 for Application PCT/US07/68401.
ISA, International Search Report dated Mar. 13, 2008 for Application PCT/US07/68403.
ISA, International Search Report dated Mar. 13, 2008 for Application PCT/US07/68404.
ISA, International Search Report dated Apr. 24, 2008 for Application PCT/US07/68410.
ISA, International Search Report dated Apr. 24, 2008 for Application PCT/US07/68412.
ISA, International Search Report dated Apr. 25, 2008 for Application PCT/US07/68415.
ISA, International Search Report dated Jul. 28, 2008 for Application PCT/US08/058072.
ISA, International Search Report dated May 25, 2010 for Application PCT/US10/27541.
"Isis 301012" retrieved from the intenet: URL: http://integrity.thomson-pharma.com/integrity/xmlxsl/pk_ref_list.xml_show_ficha_ref?p_refid=1132978 [retrieved Nov. 29, 2012].
Ito et al., "Hypertriglyceridemia as a result of human apo CIII gene expression in transgenic mice" Science (1990) 249:790-793.
James, W., "Towards gene-inhibition therapy; a review of progress and prospects in the field of antiviral antisense nucleic acids and ribozymes," Antiviral Chemistry and Chemotherapy, Apr. 191, vol. 2, No. 4, pp. 191-214, (1991).
Jen et al., "Suppression of Gene Expression by Targeted Disruption of Messenger RNA: Available Options and Current Strategies" Stem Cells (2000) 18:307-319.
Jong et al., "Role of ApoCs in Lipoprotein Metabolism—Functional Differences Between ApoC1, ApoC2, and ApoC3" Arterioscler. Thromb. Vasc. Biol. (1999) 19:472-484.
Jover et al., "Cytochrome P450 regulation by hepatocyte nuclear factor 4 in human hepatocytes: a study using adenovirus-mediated antisense targeting" Hepatology (2001) 33(3):668-675.
Karathanasis, "Apolipoprotein multigene family: tandem organization of human apolipoprotein A1, C111, and A1V genes" Proc. Natl. Acad. Sci. U. S. A. (1985) 82:6374-6378.
Kardassis et al., "Direct physical interactions between HNF-4 and Sp1 mediate synergistic transactivation of the apolipoprotein CIII promoter" Biochemistry (2002) 41:1217-1228.
Kardassis et al., "SMAD proteins transactivate the human ApoCIII promoter by interacting physically and functionally with hepatocyte nuclear factor 4" J. Biol. Chem. (2000) 275:41405-41414.
Kastelein et al., "Potent reduction of apolipoprotein B and low-density lipoprotein cholesterol by short-term administration of an antisense inhibitor of apolipoprotein B" Circulation (2006) 114(16):1729-1735.
Kawakami et al., Apolipoprotein CIII in Apolipoprotein B Lipoproteins Enhances the Adhesion of Human Monocytic Cells to Endothelial Cells, Circulation (2006) 113:691-700.
Klein et al., "P284: Apoprotein C-III (ApoCIII) Protein Concentrations and Gene Polymorphisms in Type I Diabetes" Aretioscler. Thromb. Vasc. Biol. (2002) 22(5):A-50.
Knopp, "Drug Treatment of Lipid Disorders" New Engl J. Med (1999) 341:498-511.
Koba et al., "Small dense LDL phenotype is associated with postprandial increases of large VLDL and remnant-like particles in patients with acute myocardial infarction" Atherosclerosis (2003) 170:131-140.
Lai et al., "Association between obesity and hyperlipidemia among children." Yale Journal of Biology and Medicine (2001) 74:205-210.
Latorra et al., "Enhanced allele-specific PCR discrimination in SNP genotyping using 3' locked nucleic acid (LNA) primers," Human Mutation (2003) 22:79-85.
Law et al., "Human apolipoprotein B-100: cloning, analysis of liver mRNA, and assignment of the gene to chromosome 2," Proc, Natl. Acad. Sci. USA (1985) 82:8340-8344.
Lee et al., "LDL Containing Apolipoprotein CIII Is an Independent Risk Factor for Coronary Events in Diabetic patients" Arteriosclerosis, Thrombosis, and Vascular Biology (2003) 23:853-858.
Levy-Wilson et al., "Isolation and DNA sequence of full-length cDNA for human preapolipoprotein CIII" DNA (1984) 3:359-364.
Li et al., "Common genetic variation in the promoter of the human apo CIII gene abolishes regulation by insulin and may contribute to hypertriglyceridemia" J. Clin. Invest. (1995) 96:2601-2605.
Ma et al. "Synthetic oligonucleotides as therapeutics: the coming age," Biotechnology Annual Review (2000) 5:155-196.

(56) References Cited

OTHER PUBLICATIONS

Maeda et al., "Molecular cloning of a human apo-C-III variant: Thr 74—Ala74 mutation prevents O-glycosylation" J. Lipid Res. (1987) 28:1405-1409.
Maeda et al., "Targeted disruption of the apolipoprotein C-III gene in mice results in hypotriglyceridemia and protection from postrandial hypertriglycridemia" J. Biol. Chem. (1994) 269:23610-23616.
Maxwell et al., "Proprotein Convertase Subtilisin Kexin 9: The Third Locus Implicated in Autosomal Dominant Hypercholesterolemia," Current Opinion in Lipidology, 2005, vol. 16, pp. 167-172.
McCormick et al., "Transgenic mice expressing human ApoB95 and ApoB97. Evidence that sequences within the carboxyl-terminal portion of human apoB100 are important for the assembly of lipoprotein," J. Biol. Chem. (1997) 272:23616-23622.
Merki et al., "A second generation antisense oligonucleotide directed to human apolipoprotein B-100 reduces lipoprotein(a) levels and oxidized phospholipids on apolipoprotein B-100 particles in lipoprotein(a)-transgenic mice," J. Amer. Coll. Cardiol. (2008) 51(1) Suppl. 1, A294.
Merki et al., "Antisense oligonucleotide directed to human apolipoprotein B-100 reduces lipoprotein(a) levels and oxidized phospholipids on apolipoprotein B-100 particles in lipoprotein(a)-transenic mice," Circulation (2008) 118:743-753.
Milner et al., "Selecting effective antisense reagents on combinatorial oligonucleotide arrays," Nature Biotechnology, Jun. 1997, Bol. 15, pp. 537-541.
NCBI Search Results, (ISPH-0592) dated Oct. 30, 2007, Mamm. Genome 6 (3), 192-195 (1995).
New England Biolabs, 1998/1999 Catalog, pp. 121 and 284.
Nielsen, "Systemic Delivery: The Last Hurdle?" Gene Therapy (2005) 12:956-957.
Nowak-Gottl et al., "Lipoprotein (a): its role in childhood thromboembolism," Pediatrics (1997) 99:1-3.
Ogami et al., "Purification and characterization of a heat stable nuclear factor (CIIIB1 involved in the regulation of the human ApoC-III gene" J. Biol. Chem. (1991) 266:9640-9646.
Olivieri et al., "ApoC-III polymorphisms and risk of coronary artery disease" J. Lipid Res. (2002) 43: 1450-1457.
Olivieri et al., "Apolipoprotein C-III, n-3 Polyunsaturated Fatty Acids, and "Insulin_Resistant" T-455C APOC3 Gene Polymorphisms in Heart Disease Patients: Exapmle of Gene-Diet Interaction" Clin. Chem. (2005) 51(2):360-367.
Opalinska et al., "Nucleic-Acid Therapeutics: Basic Principles and Recent Applications" Nature Rev. Drug Discov. (2002) 1:503-514.
Ostrander et al., "Dog (Clone: CXX.371) Primer for STS 371, 5' End, Sequence Tagged Site," EMBL XP002392182, Sep. 18, 1993.
Ostrander et al., "Dog Primer for STS 610, 3' End, Sequence Tagged Site," EMBL XP002392183, Jan. 6, 1994.
Parrish et al., "Functional anatomy of a dsRNA trigger: differential requirement for the two trigger strands in RNA interference," Molecular Cell (2000) 6:1077-1087.
Petersen et al., "Locked nucleic acid (LNA) recognition of RNA: NMR solution structures of LNA:RNA hybrids," Journal of the American Chemical Society (2002) 124:5974-5982.
Pittner et al "Effects of PYY[3-36] in rodent models of diabetes and obesity" Int. J. Obes. Relat. Metab. Disord. (2004) 28:963-971.
PR Newswire, "Isis Pharmaceuticals initiates phase I study of second-generation antisense drug for cardiovascular disease" New York, Dec. 29, 2003; Source: Isis Pharmaceuticals.
PR Newswire, "Second generation antisense drug for cardiovascular disease demonstrates significant durable reductions in cholesterol" New York, Aug. 11, 2004; Source: Isis Pharmaceuticals.
Protter et al., "Isolation and sequence analysis of the human apolipoprotein CIII gene and the intergenic region between the apo AI and apo ACIII genes" DNA (1984) 3:449-456.
Qidong, Tang et al., "The Inhibition of Antisense Oligodeoxynucleotides on the Expression of Apolipoprotein B in Rat Liver Cells," Zhongguo Dongmai Yinghua ZaZhi Bianjibu (Chinese Journal of Arteriosclerosis) (1999) 7:315-318.
Raspe et al., "Identification of Rev-erbalpha as a physiological repressor of apoC-III gene transcription" J. Lipid Res. (2002) 43:2172-2179.
Reynolds et al., "Rational siRNA design for RNA interference" Nature Biotechnology (2004) 22(3):326-330.
Roglans et al., "Atorvastatin Treatment Induced Peroxisome Proliferator-Activated Receptor Alpha Expression and Decreased Plasma Nonesterified Fatty Acids and Liver Triglyceride in Fructose-Fed Rats" Journal of Pharmacology and Experimental Therapeutics (2002) 302:232-239.
Rosenson, "Clinical Role of LDL and HDL Subclasses and Apoliprotein Measurements," ACC Current Journal Review, 33-37 (2004).
Rossi et al., "Introductory Remarks on the General Application of Antisense RNAs and Ribozymes," Methods: A Companion to Methods in Enzymology (1993) 5:1-5.
Rubies-Prat et al., "Low-density lipoprotein particle size, triglyceride-rich lipoproteins, and glucose tolerance in non-diabetic men with essential hypertension" Clinical and Experimental Hypertension (2001) 23:489-500.
Sanghvi et al., "Heterocyclic Base Modifications in Nucleic Acids and Their Applications in Antisense Oligonucleotides" Antisense Research and Applications (1993) pp. 273-288.
Schoonjans et al., "3-Hydroxy-3-methylglutaryl CoA reductase inhibitors reduce serum triglyceride levels through modulation of apolipoprotein C-III and lipoprotein lipase" FEBS Lett. (1999) 452:160-164.
Senior, "Antisense inhibitor provides new treatment approach for hypercholesterolaemia" Drug Discovery Today (2002) 7:840-841.
Sewell et al.., "Phase 1 Trial of Isis 104838, a 2'-Methoxyethyl Modified Antisense Oligonucleotide Targeting Tumor Necrosis Factor-α," The Journal of Pharmacology and Experimental Therapeutics (2002)303:1334-1343.
Shachter, "Apolipoproteins C-I and C-III as important modulators of lipoprotein metabolism" Curr. Opin. Lipidol. (2001) 12:297-304.
Sharpe et al., "Human apolipoproteins AI, AII, CII and CIII cDNA sequences and mRNA abundance" Nucleic Acids Res. (1984) 12:3917-3932.
Simeonov et al., "Single nucleotide polymorphism genotyping using short, fluorescently labeled locked nucleic acid (LNA) probes and fluorescence polarization detection," Nucleic Acids Research (2002) 30:E91.
Skrapari et al., "Glibenclamide improves postprandial hypertriglyceridaemia in type 2 diabetic patients by reducing chylomicrons but not the very low-density lipoprotein subfraction levels," Diabet Med (2001) 18:781-785.
Sniderman et al "Substrate Delivery as a Determinant of Hepatic ApoB Secretion," Arterioscler Thromb Vasc Biol., (1993)13:629-636.
Tamm et al., "Antisense therapy in oncology: new hope for an old idea?" The Lancet (2001)358:489-497.
Tanaka et al., "Regulation of apolipoprotein B production and secretion in response to the change of intracellular cholesteryl ester contents in rabbit hepatocytes," Journal of Biological Chemistry (1993) 268:12713-12718.
Ugawa et al., "YM-53601, a novel squalene synthase inhibitor, suppresses lipgenic biosynthesis and lipid secretion in rodents" British Journal of Pharmacology (2003) 139:140-146.
Vessby et al., "Diverging effects of cholestyramine on apolipoprotein B and lipoprotein Lp(a). A dose-response study of the effects of cholestyramine in hypercholesterolaemia," Atherosclerosis (1982) 44:61-71.
Vu-Dac et al., "Retinoids increase human apo C-III expression at the transcriptional level via the retinoid X receptor. Contribution to the hypertriglyceridemic action of retinoids." J. Clin. Invest. (1998) 102:625-632.
Wimberly, "Rosuvastatin (Crestor) a new statin for the treatment of dyslipidemia" PharmaNote (2003) 19:1-6.
Woolf et al., "Specificity of antisense oligonucleotides in vivo" PNAS (1992) 89:7305-7309.
Yamamoto et al., "Overexpression of PACAP in Transgenic Mouse Pancreatic B-Cells Enhances Insulin Secretion and Ameliorates Streptozotocin-induced Diabetes" Diabetes (2003) 52:1155-1162.

(56) References Cited

OTHER PUBLICATIONS

Yu et al., "Antisense oligonucleotide inhibition of DGAT2 expression reduced hepatic steatosis diet-induded obese mice," Obesity Research ( 2003) 11 (Suppl): A48.
Yu et al., "Antisense oligonucleotide reduction of DGAT2 expression improves hepatic steatosis and hyperlipidemia in obese mice," Hepatology (2005) 42(2):362-371.
Yu et al., "Pharmacokinetics and Pharmacodynamics of an Antisense Phosphorothioate Oligonucleotide Targeting Fas mRNA in Mice," J. Pharmacol. Exp. Ther. (2001)296:388-395.
Parrish et al. Molecular Cell 2000, vol. 6, pp. 1077-1087.*
Hammond et al. Post-transcriptional gene silencing by double-stranded RNA. Nature Genetics 2001, vol. 2: 110-119.*
Enhanced allele-specific PCR discrimination in SNP genotyping using 3 locked nucleic acid (LNA) primers Human Mutation vol. 22, Issue 1, Date: Jul. 2003, pp. 79-85 David Latorra, Krista Campbell, Andreas Wolter, J. Michael Hurley.*
U.S. Appl. No. 60/159,462, Eggerman et al.
Katan et al., "Characteristics of Human Hypo- and Hyper-responders to Dietary Chlesterol," *American Journal of Epidemiology* 125(3):387-399 (1987).
Kim et al., Genetically modified mice for the study of apolipoprotein B,: *Journal of Lipid Research* 39: 703-723 (1998).
McCormick et al., "Transgenic Mice Expressing Human ApoB95 and ApoB97," *The Journal of Biological Chemistry* 272(38):23616-23622 (1997).
Nishina et al., "Synthetic low and high fat diets for the study of atheriosclerosis in the mouse," *Journal of Lipid Research* 31:859-869 (1990).
Sandkamp et al., "Lipoprotein(a) Is an Independent Risk Factor for Myocardial Infarction at a Young Age," *Clin. Chem.* 36/1:20-23 (1990).
Seed et al., "Relation of Serum Lipoprotein(a) Concentration and Apolipoprotein(a) Phenotype to Coronary heart Disease in Patients with Familial Hypercholesterolemia," *The New England Journal of Medicine* 1494-1498 (1990).
Tang Quidong et al., "The Inhibition of Antisense Oligodeoxynucleotides on the Expression of Apolipoprotein B in Rat Liver Cells," *Chinese Journal of Arteriorsclerosis* 7(4):315-318 (1999).
Veniant et al., "Susceptibility to Atherosclerosis in Mice expressing Exclusively Apolipoprotein B48 or Apolipoprotein B100," *J. Clin. Invest* 100(1):180-188 (1997).
Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.
Eggerman et al. "Use of Oligonucleotides to Target Nucleic Acid Sequences Encoding Apolipoprotein B to Devrease Serum Apolipoprotein B and Cholesterol Levels" Federal Register vol. 65, No. 110 (2000).
Patil et al., DNA-based therapeutics and DNA delivery systems: A comprehensive review, 2005. The AAPS Journal, vol. 7, pp. E61-E77.
De Mesmaeker, et al. 1995. *Backbone Modifications in Oligonucleotides and Peptide Nucleic Acid Systems.* Current Opinion in Structural Chemistry, 5: 343-355.
Supplementary Partial European Search Report from PCT/US0224247 dated Jul. 27, 2006.
EMBL Accession No. A13429, Oct. 5, 1994.
EMBL Accession No. I13154, Aug. 2, 1995.
Tang, et al. 1999. The Inhibition of Antisense Oligodeoxynucleotides on the Expression of Apolipoprotein B in Rat Liver Cells. *Chinese Journal of Arteriosclerosis,* vol. 7, No. 4.
Crooke et al., "Chapter 1: Basic Principles of Antisense Therapeutics" *Antisense Research and Applications* (1998) 131:1-50.
Advisory Action for U.S. Appl. No. 09/920,022 (ISPH-0592) dated Feb. 28, 2006.
Lemonidis, et al., "Abstracts of the 11$^{th}$ International Congress on Cardiovascular Pharmacotherapy. Montreal, Canada, May 18-21, 2002," Cardiovascular Drugs and Therapy/Sponsored by the International Society of Cardiovascular Pharmacotherapy 2002, vol. 16, Suppl. 1, P471, SP002565482.
Rojanasakul, Y, "Antisense Oligonucleotide Therapeutics: Drug Delivery and Targeting," Advanced Drug Delivery Reviews, (1996), vol. 18, pp. 115-131. XP002913878.
Smith et al., "Rational Selection of Antisense Oligonucleotide Sequences," European Journal of Pharmaceutical Sciences, (2000), vol. 11, No. 3, pp. 191-198, XP002372482.
EPO, European Search Report Dated Feb. 8, 2010 for Application No. 09015376.8.

* cited by examiner

ANTISENSE MODULATION OF APOLIPOPROTEIN B-EXPRESSION

Matter enclosed in heavy brackets [ ] appears in the original patent but forms no part of this reissue specification; matter printed in italics indicates the additions made by reissue.

This application is a continuation of U.S. application Ser. No. 10/712,795, filed Nov. 13, 2003 now U.S. Pat. No. 7,511,131, U.S. application Ser. No. 10/712,795 claims priority to U.S. provisional Application Ser. No. 60/426,234, filed Nov. 13, 2002, and claims priority under 35 U.S.C. §365(a) to PCT application US03/15493, filed on May 15, 2003, both of which are incorporated herein by reference in their entirety.

FIELD OF THE INVENTION

The present invention provides compositions and methods for modulating the expression of apolipoprotein B. In particular, this invention relates to compounds, particularly oligonucleotides, specifically hybridizable with nucleic acids encoding apolipoprotein B. Such compounds have been shown to modulate the expression of apolipoprotein B.

BACKGROUND OF THE INVENTION

Lipoproteins are globular, micelle-like particles that consist of a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, which transport dietary lipids from intestine to tissues; very low density lipoproteins (VLDL); intermediate density lipoproteins (IDL); low density lipoproteins (LDL); all of which transport triacylglycerols and cholesterol from the liver to tissues; and high density lipoproteins (HDL), which transport endogenous cholesterol from tissues to the liver.

Lipoprotein particles undergo continuous metabolic processing and have variable properties and compositions. Lipoprotein densities increase without decreasing particle diameter because the density of their outer coatings is less than that of the inner core. The protein components of lipoproteins are known as apoliproteins. At least nine apolipoproteins are distributed in significant amounts among the various human lipoproteins.

Apolipoprotein B (also known as ApoB, apolipoprotein B-100; ApoB-100, apolipoprotein B-48; ApoB-48 and Ag(x) antigen), is a large glycoprotein that serves an indispensable role in the assembly and secretion of lipids and in the transport and receptor-mediated uptake and delivery of distinct classes of lipoproteins. The importance of apolipoprotein B spans a variety of functions, from the absorption and processing of dietary lipids to the regulation of circulating lipoprotein levels (Davidson and Shelness, Annu. Rev. Nutr., 2000, 20, 169-193). This latter property underlies its relevance in terms of atherosclerosis susceptibility, which is highly correlated with the ambient concentration of apolipoprotein B-containing lipoproteins (Davidson and Shelness, Annu. Rev. Nutr., 2000, 20, 169-193).

Two forms of apolipoprotein B exist in mammals. ApoB-100 represents the full-length protein containing 4536 amino acid residues synthesized exclusively in the human liver (Davidson and Shelness, Annu. Rev. Nutr., 2000, 20, 169-193). A truncated form known as ApoB-48 is colinear with the amino terminal 2152 residues and is synthesized in the small intestine of all mammals (Davidson and Shelness, Annu. Rev. Nutr,, 2000, 20, 169-193).

ApoB-100 is the major protein component of LDL and contains the domain required for interaction of this lipoprotein species with the LDL receptor. In addition, ApoB-100 contains an unpaired cysteine residue which mediates an interaction with apolipoprotein(a) and generates another distinct atherogenic lipoprotein called Lp(a) (Davidson and Shelness, Annu. Rev. Nutr,, 2000, 20, 169-193).

In humans, ApoB-48 circulates in association with chylomicrons and chylomicron remnants and these particles are cleared by a distinct receptor known as the LDL-receptor-related protein (Davidson and Shelness, Annu. Rev. Nutr., 2000, 20, 169-193). ApoB-48 can be viewed as a crucial adaptation by which dietary lipid is delivered from the small intestine to the liver, while ApoB-100 participates in the transport and delivery of endogenous plasma cholesterol (Davidson and Shelness, Annu. Rev. Nutr., 2000, 20, 169-193).

The basis by which the common structural gene for apolipoprotein B produces two distinct protein isoforms is a process known as RNA editing. A site specific cytosine-to-uracil editing reaction produces a UAA stop codon and translational termination of apolipoprotein B to produce ApoB-48 (Davidson and Shelness, Annu. Rev. Nutr., 2000, 20, 169-193).

Apolipoprotein B was cloned in 1985 (Law et al., Proc. Natl. Acad. Sci. U.S.A., 1985, 82, 8340-8344) and mapped to chromosome 2p23-2p24 in 1986 (Deeb et al., Proc. Natl. Acad. Sci. U.S.A., 1986, 83, 419-422).

Disclosed and claimed in U.S. Pat. No. 5,786,206 are methods and compositions for determining the level of low density lipoproteins (LDL) in plasma which include isolated DNA sequences encoding epitope regions of apolipoprotein B-100 (Smith et al., 1998).

Transgenic mice expressing human apolipoprotein B and fed a high-fat diet were found to develop high plasma cholesterol levels and displayed an 11-fold increase in atherosclerotic lesions over non-transgenic littermates (Kim and Young, J. Lipid Res., 1998, 39, 703-723; Nishina et al., J. Lipid Res., 1990, 31, 859-869).

In addition, transgenic mice expressing truncated forms of human apolipoprotein B have been employed to identify the carboxyl-terminal structural features of ApoB-100 that are required for interactions with apolipoprotein(a) to generate the Lp(a) lipoprotein particle and to investigate structural features of the LDL receptor-binding region of ApoB-100 (Kim and Young, J. Lipid Res., 1998, 39, 703-723; McCormick et al., J. Biol. Chem., 1997, 272, 23616-23622).

Apolipoprotein B knockout mice (bearing disruptions of both ApoB-100 and ApoB-48) have been generated which are protected from developing hypercholesterolemia when fed a high-fat diet (Farese et al., Proc. Natl. Acad. Sci. U.S. A., 1995, 92, 1774-1778; Kim and Young, J. Lipid Res., 1998, 39, 703-723). The incidence of atherosclerosis has been investigated in mice expressing exclusively ApoB-100 or ApoB-48 and susceptibility to atherosclerosis was found to be dependent on total cholesterol levels. Whether the mice synthesized ApoB-100 or ApoB-48 did not affect the extent of the atherosclerosis, indicating that there is probably no major difference in the intrinsic atherogenicity of ApoB-100 versus ApoB-48 (Kim and Young, J. Lipid Res., 1998, 39, 703-723; Veniant et al., J. Clin. Invest., 1997, 100, 180-188).

Elevated plasma levels of the ApoB-100-containing lipoprotein Lp(a) are associated with increased risk for atherosclerosis and its manifestations, which may include hypercholesterolemia (Seed et al., N. Engl. J. Med., 1990, 322, 1494-1499), myocardial infarction (Sandkamp et al., Clin. Chem., 1990, 36, 20-23), and thrombosis (Nowak-Gottl et al., Pediatrics, 1997, 99, E11).

The plasma concentration of Lp(a) is strongly influenced by heritable factors and is refractory to most drug and dietary manipulation (Katan and Beynen, Am. J. Epidemiol., 1987, 125, 387-399; Vessby et al., Atherosclerosis, 1982, 44, 61-71). Pharmacologic therapy of elevated Lp(a) levels has been only modestly successful and apheresis remains the most effective therapeutic modality (Hajjar and Nachman, Annu. Rev. Med., 1996, 47, 423-442).

Disclosed and claimed in U.S. Pat. No. 6,156,315 and the corresponding PCT publication WO 99/18986 is a method for inhibiting the binding of LDL to blood vessel matrix in a subject, comprising administering to the subject an effective amount of an antibody or a fragment thereof, which is capable of binding to the amino-terminal region of apolipoprotein B, thereby inhibiting the binding of low density lipoprotein to blood vessel matrix (Goldberg and Pillarisetti, 2000; Goldberg and Pillarisetti, 1999).

Disclosed and claimed in U.S. Pat. No. 6,096,516 are vectors containing cDNA encoding murine recombinant antibodies which bind to human ApoB-100 for the purpose of for diagnosis and treatment of cardiovascular diseases (Kwak et al., 2000).

Disclosed and claimed in European patent application EP 911344 published Apr. 28, 1999 (and corresponding to U.S. Pat. No. 6,309,844) is a monoclonal antibody which specifically binds to ApoB-48 and does not specifically bind to ApoB-100, which is useful for diagnosis and therapy of hyperlipidemia and arterial sclerosis (Uchida and Kurano, 1998).

Disclosed and claimed in PCT publication WO 01/30354 are methods of treating a patient with a cardiovascular disorder, comprising administering a therapeutically effective amount of a compound to said patient, wherein said compound acts for a period of time to lower plasma concentrations of apolipoprotein B or apolipoprotein B-containing lipoproteins by stimulating a pathway for apolipoprotein B degradation (Fisher and Williams, 2001).

Disclosed and claimed in U.S. Pat. No. 5,220,006 is a cloned cis-acting DNA sequence that mediates the suppression of atherogenic apolipoprotein B (Ross et al., 1993).

Disclosed and claimed in PCT publication WO 01/12789 is a ribozyme which cleaves ApoB-100 mRNA specifically at position 6679 (Chan et al., 2001).

To date, strategies aimed at inhibiting apolipoprotein B function have been limited to Lp(a) apheresis, antibodies, antibody fragments and ribozymes. However, with the exception of Lp(a) apheresis, these investigative strategies are untested as therapeutic protocols. Consequently, there remains a long felt need for additional agents capable of effectively inhibiting apolipoprotein B function.

Antisense technology is emerging as an effective means of reducing the expression of specific gene products and may therefore prove to be uniquely useful in a number of therapeutic, diagnostic and research applications involving modulation of apolipoprotein B expression.

The present invention provides compositions and methods for modulating apolipoprotein B expression, including inhibition of the alternative isoform of apolipoprotein B, ApoB-48.

SUMMARY OF THE INVENTION

The present invention is directed to compounds, particularly antisense oligonucleotides, which are targeted to a nucleic acid encoding apolipoprotein B, and which modulate the expression of apolipoprotein B. Pharmaceutical and other compositions comprising the compounds of the invention are also provided. Further provided are methods of modulating the expression of apolipoprotein B in cells or tissues comprising contacting said cells or tissues with one or more of the antisense compounds or compositions of the invention. Further provided are methods of treating an animal, particularly a human, suspected of having or being prone to a disease or condition associated with expression of apolipoprotein B by administering a therapeutically or prophylactically effective amount of one or more of the antisense compounds or compositions of the invention.

In particular, the invention provides a compound 8 to 50 nucleobases in length targeted to a nucleic acid molecule encoding apolipoprotein B, wherein said compound specifically hybridizes with and inhibits the expression of a nucleic acid molecule encoding apolipoprotein B, said compound comprising at least 8 contiguous nucleobases of any one of SEQ ID NOs: 127-134, 136, 138-174, 176-317, 319-321, 323-333, 335-339, 341-374, 376-416, 418-500, 502-510, 512-804, 815, 816, 819-821, 824, 825, 827, 828, 830, 831, 833-835, 837-839, 842, 843, and 845-854.

The invention further provides compound 8 to 50 nucleobases in length which specifically hybridizes with at least an 8-nucleobase portion of an active site on a nucleic acid molecule encoding apolipoprotein B, said compound comprising at least 8 contiguous nucleobases of any one of SEQ ID NOs: 127-134, 136, 138-174, 176-317, 319-321, 323-333, 335-339, 341-374, 376-416, 418-500, 502-510, 512-804, 815, 816, 819-821, 824, 825, 827, 828, 830, 831, 833-835, 837-839, 842, 843, and 845-854, said active site being a region in said nucleic acid wherein binding of said compound to said site significantly inhibits apolipoprotein B expression as compared to a control.

The invention also provides a compound 8 to 50 nucleobases in length targeted to a nucleic acid molecule encoding apolipoprotein B, wherein said compound specifically hybridizes with said nucleic acid and inhibits expression of apolipoprotein B, wherein the apolipoprotein B is encoded by a polynucleotide selected from the group consisting of: (a) SEQ ID NO: 3 and (b) a naturally occurring variant apolipoprotein B-encoding polynucleotide that hybridizes to the complement of the polynucleotide of (a) under stringent conditions, said compound comprising at least 8 contiguous nucleobases of any one of SEQ ID NOs: 127-134, 136, 138-174, 176-317, 319-321, 323-333, 335-339, 341-374, 376-416, 418-500, 502-510, 512-804, 815, 816, 819-821, 824, 825, 827, 828, 830, 831, 833-835, 837-839, 842, 843, and 845-854.

In another aspect the invention provides a compound 8 to 50 nucleobases in length targeted to a nucleic acid molecule encoding apolipoprotein B, wherein said compound specifically hybridizes with said nucleic acid and inhibits expression of apolipoprotein B, wherein the apolipoprotein B is encoded by a polynucleotide selected from the group consisting of SEQ ID NO: 3 and SEQ ID NO: 17, said compound comprising at least 8 contiguous nucleobases of any one of SEQ ID NOs: 127-134, 136, 138-174, 176-317, 319-321, 323-333, 335-339, 341-374, 376-416, 418-500, 502-510, 512-804, 815, 816, 819-821, 824, 825, 827, 828, 830, 831, 833-835, 837-839, 842, 843, and 845-854.

The invention also provides a compound 8 to 50 nucleobases in length targeted to a nucleic acid molecule encoding apolipoprotein B, wherein said compound specifically hybridizes with an active site in said nucleic acid and inhibits expression of apolipoprotein B, said compound comprising at least 8 contiguous nucleobases of any one of SEQ ID NOs: 127-134, 136, 138-174, 176-317, 319-321, 323-333, 335-339, 341-374, 376-416, 418-500, 502-510, 512-804, 815, 816, 819-821, 824, 825, 827, 828, 830, 831, 833-835, 837-839, 842, 843, and 845-854, said active site being a region in said nucleic acid wherein binding of said compound to said site significantly inhibits apolipoprotein B expression as compared to a control.

In another aspect the invention provides an oligonucleotide mimetic compound 8 to 50 nucleobases in length targeted to a nucleic acid molecule encoding apolipoprotein B, wherein said compound specifically hybridizes with said nucleic acid and inhibits expression of apolipoprotein B, said compound comprising at least 8 contiguous nucleobases of any one of SEQ ID NOs: 127-134, 136, 138-174, 176-317, 319-321, 323-333, 335-339, 341-374, 376-416, 418-500, 502-510, 512-804, 815, 816, 819-821, 824, 825, 827, 828, 830, 831, 833-835, 837-839, 842, 843, and 845-854.

In another aspect, the invention provides an antisense compound 8 to 50 nucleobases in length, wherein said compound specifically hybridizes with nucleotides 2920-3420 as set forth in SEQ ID NO:3 and inhibits expression of mRNA encoding human apolipoprotein B after 16 to 24 hours by at least 30% in 80% confluent HepG2 cells in culture at a concentration of 150 nM. In preferred embodiments, the antisense compound 8 to 50 nucleobases in length specifically hybridizes with nucleotides 3230-3288 as set forth in SEQ ID NO:3 and inhibits expression of mRNA encoding human apolipoprotein B after 16 to 24 hours by at least 30% in 80% confluent HepG2 cells in culture at a concentration of 150 nM. In another aspect, the compounds inhibits expression of mRNA encoding apolipoprotein B by at least 50%, after 16 to 24 hours in 80% confluent HepG2 cells in culture at a concentration of 150 nM.

In one aspect, the compounds of the invention are targeted to a nucleic acid molecule encoding apolipoprotein B, wherein said compound specifically hybridizes with and inhibits expression of the long form of apolipoprotein B, ApoB-100. In another aspect, the compounds specifically hybridizes with said nucleic acid and inhibits expression of mRNA encoding apolipoprotein B by at least 5% in 80% confluent HepG2 cells in culture at an optimum concentration. In yet another aspect, the compounds inhibits expression of mRNA encoding apolipoprotein B by at least 10%, at least 15%, at least 20%, at least 25%, at least 30%, at least 35%, at least 40%, or at least 50%.

In one aspect, the compounds are antisense oligonucleotides, and in one embodiment the compound has a sequence comprising SEQ ID NO: 224, the antisense oligonucleotide hybridizes with a region complementary to SEQ ID NO: 224, the compound comprises SEQ ID NO: 224, the compound consists essentially of SEQ ID NO: 224 or the compound consists of SEQ ID NO: 224.

In another aspect, the compound has a sequence comprising SEQ ID NO: 247, the antisense oligonucleotide hybridizes with a region complementary to SEQ ID NO: 247, the compound comprises SEQ ID NO: 247, the compound consists essentially of SEQ ID NO: 247 or the compound consists of SEQ ID NO: 247.

In another aspect, the compound has a sequence comprising SEQ ID NO: 319, the antisense oligonucleotide hybridizes with a region complementary to SEQ ID NO: 319, the compound comprises SEQ ID NO: 319, the compound consists essentially of SEQ ID NO: 319 or the compound consists of SEQ ID NO: 319.

In one embodiment, the compounds comprise at least one modified internucleoside linkage, and in another embodiment, the modified internucleoside linkage is a phosphorothioate linkage.

In another aspect, the compounds comprise at least one modified sugar moiety, and in one aspect, the modified sugar moiety is a 2-O-methoxyethyl sugar moiety.

In another embodiment, the compounds comprise at least one modified nucleobase, and in one aspect, the modified nucleobase is a 5-methylcytosine.

In yet another aspect, the compounds are chimeric oligonucleotides. Preferred chimeric compounds include those having one or more phosphorothioate linkages and further comprising 2'-methoxyethoxyl nucleotide wings and a ten nucleobase 2'-deoxynucleotide gap.

In another aspect, the compounds specifically hybridizes with and inhibits the expression of a nucleic acid molecule encoding an alternatively spliced form of apolipoprotein B.

The invention also provide compositions comprising a compound of the invention and a pharmaceutically acceptable carrier or diluent. In one aspect, the composition further comprises a colloidal dispersion system, and in another aspect, the compound in the composition is an antisense oligonucleotide. In certain embodiments, the composition comprises an antisense compound of the invention hybridized to a complementary strand. Hybridization of the antisense strand can form one or more blunt ends or one or more overhanging ends. In some embodiments, the overhanging end comprises a modified base.

The invention further provides methods of inhibiting the expression of apolipoprotein B in cells or tissues comprising contacting said cells or tissues with a compound of the invention so that expression of apolipoprotein B is inhibited. Methods are also provided for treating an animal having a disease or condition associated with apolipoprotein B comprising administering to said animal a therapeutically or prophylactically effective amount of a compound of the invention so that expression of apolipoprotein B is inhibited. In various aspects, the condition is associated with abnormal lipid metabolism, the condition is associated with abnormal cholesterol metabolism, the condition is atherosclerosis, the condition is an abnormal metabolic condition, the abnormal metabolic condition is hyperlipidemia, the disease is diabetes, the diabetes is Type 2 diabetes, the condition is obesity, and/or the disease is cardiovascular disease.

The invention also provide methods of modulating glucose levels in an animal comprising administering to said animal a compound of the invention, and in one aspect, the animal is a human. In various embodiments, the glucose levels are plasma glucose levels, the glucose levels are serum glucose levels, and/or the animal is a diabetic animal.

The invention also provides methods of preventing or delaying the onset of a disease or condition associated with apolipoprotein B in an animal comprising administering to said animal a therapeutically or prophylactically effective amount of a compound of the invention. In one aspect, the animal is a human. In other aspects, the condition is an abnormal metabolic condition, the abnormal metabolic condition is hyperlipidemia, the disease is diabetes, the diabetes is Type 2 diabetes, the condition is obesity, the condition is atherosclerosis, the condition involves abnormal lipid metabolism, and/or the condition involves abnormal cholesterol metabolism.

The invention also provides methods of preventing or delaying the onset of an increase in glucose levels in an animal comprising administering to said animal a therapeutically or prophylactically effective amount of a compound of the invention. In one aspect, the animal is a human. In other aspects, the glucose levels are serum glucose levels, and/or the glucose levels are plasma glucose levels.

The invention also provides methods of modulating serum cholesterol levels in an animal comprising administering to said animal a therapeutically or prophylactically effective amount of a compound of the invention. In one aspect, the animal is a human.

The invention also provides methods of modulating lipoprotein levels in an animal comprising administering to said animal a therapeutically or prophylactically effective amount of a compound of the invention. In one aspect, the animal is a human. In other aspects, the lipoprotein is VLDL, the lipoprotein is HDL, and/or the lipoprotein is LDL.

The invention also provides methods of modulating serum triglyceride levels in an animal comprising administering to said animal a therapeutically or prophylactically effective amount of a compound of the invention. In one aspect, the animal is a human.

The invention also proves use of a compound of the invention for the manufacture of a medicament for the treatment of a disease or condition associated with apolipoprotein B expression, a medicament for the treatment of a condition associated with abnormal lipid metabolism, a medicament for the treatment of a condition associated with abnormal cholesterol metabolism, a medicament for the treatment of atherosclerosis, a medicament for the treatment of hyperlipidemia, a medicament for the treatment of diabetes, a medicament for the treatment of Type 2 diabetes, a medicament for the treatment of obesity, a medicament for the treatment of cardiovascular disease, a medicament for preventing or delaying the onset of increased glucose levels, a medicament for preventing or delaying the onset of increased serum glucose levels, a medicament for preventing or delaying the onset of increased plasma glucose levels, a medicament for the modulation of serum cholesterol levels, a medicament for the modulation of serum lipoprotein levels, a medicament for the modulation of serum VLDL levels, a medicament for the modulation of serum HDL levels, and/or a medicament for the modulation of serum LDL levels, a medicament for the modulation of serum triglyceride levels.

In another aspect, the invention provides methods of decreasing circulating lipoprotein levels comprising the step of administering to an individual an amount of a compound of the invention sufficient to reduce apolipoprotein B expression. In another aspect, the invention provides methods of reducing lipoprotein transport comprising the step of administering to an individual an amount of a compound of the invention sufficient to reduce apolipoprotein B expression. The invention also provides methods of reducing lipoprotein absorption/adsorption comprising the step of administering to an individual an amount of a compound of the invention sufficient to reduce apolipoprotein B expression.

In another aspect, the invention contemplates methods of decreasing circulating triglyceride levels comprising the step of administering to an individual an amount of a compound of the invention sufficient to reduce apolipoprotein B expression. Also provided are methods of reducing triglyceride transport comprising the step of administering to an individual an amount of a compound of the invention sufficient to reduce apolipoprotein B expression. The invention further provides methods of reducing triglyceride absorption/adsorption comprising the step of administering to an individual an amount of a compound of the invention sufficient to reduce apolipoprotein B expression.

In another aspect, the invention provides methods of decreasing circulating cholesterol levels, including cholesteryl esters and/or unesterified cholesterol, comprising the step of administering to an individual an amount of a compound of the invention sufficient to reduce apolipoprotein B expression. Also contemplated are methods of reducing cholesterol transport, including cholesteryl esters and/or unesterified cholesterol, comprising the step of administering to an individual an amount of a compound of the invention sufficient to reduce apolipoprotein B expression. The invention also provides methods of reducing cholesterol absorption/adsorption, including cholesteryl esters and/or unesterified cholesterol, comprising the step of administering to an individual an amount of a compound of the invention sufficient to reduce apolipoprotein B expression.

In another aspect, the invention provides methods of decreasing circulating lipid levels comprising the step of administering to an individual an amount of a compound of the invention sufficient to reduce apolipoprotein B expression. The invention also provides methods of reducing lipid transport in plasma comprising the step of administering to an individual an amount of a compound of the invention sufficient to reduce apolipoprotein B expression. In addition, the invention provides methods of reducing lipid absorption/adsorption comprising the step of administering to an individual an amount of a compound of the invention sufficient to reduce apolipoprotein B expression.

The invention further contemplates methods of decreasing circulating dietary lipid levels comprising the step of administering to an individual an amount of a compound of the invention sufficient to reduce apolipoprotein B expression. Also provided are methods of reducing dietary lipid transport comprising the step of administering to an individual an amount of a compound of the invention sufficient to reduce apolipoprotein B expression, as well as methods of reducing dietary lipid absorption/adsorption comprising the step of administering to an individual an amount of a compound of the invention sufficient to reduce apolipoprotein B expression.

In another aspect, the invention provides methods of decreasing circulating fatty acid levels comprising the step of administering to an individual an amount of a compound of the invention sufficient to reduce apolipoprotein B expression. The invention also provides methods of reducing fatty acid transport comprising the step of administering to an individual an amount of a compound of the invention sufficient to reduce apolipoprotein B expression. Also contemplated are methods of reducing fatty acid absorption comprising the step of administering to an individual an amount of a compound of the invention sufficient to reduce apolipoprotein B expression.

The invention also provides methods of decreasing circulating acute phase reactants comprising the step of administering to an individual an amount of a compound of the invention sufficient to reduce apolipoprotein B expression. In another aspect, the invention provides methods of reducing acute phase reactants transport comprising the step of administering to an individual an amount of a compound of the invention sufficient to reduce apolipoprotein B expression, as well as methods of reducing acute phase reactants absorption comprising the step of administering to an individual an amount of a compound of the invention sufficient to reduce apolipoprotein B expression.

In another aspect, the invention provides methods of decreasing circulating chylomicrons comprising the step of administering to an individual an amount of a compound of the invention sufficient to reduce apolipoprotein B expression, methods of reducing chylomicron transport comprising the step of administering to an individual an amount of a compound of the invention sufficient to reduce apolipoprotein B expression, and methods of reducing chylomicron absorption comprising the step of administering to an individual an amount of a compound of the invention sufficient to reduce apolipoprotein B expression.

The invention further provides methods of decreasing circulating chylomicron remnant particles comprising the step of administering to an individual an amount of a compound of the invention sufficient to reduce apolipoprotein B expression, methods of reducing chylomicron remnant transport comprising the step of administering to an individual an amount of a compound of the invention sufficient to reduce apolipoprotein B expression, and methods of reducing chylomicron remnant absorption comprising the step of administering to an individual an amount of a compound of the invention sufficient to reduce apolipoprotein B expression.

The invention further contemplates methods of decreasing circulating VLDL, IDL, LDL, and/or HDL comprising the step of administering to an individual an amount of a compound of the invention sufficient to reduce apolipoprotein B expression. Likewise, the invention provides methods of reducing VLDL, IDL, LDL, and/or HDL transport comprising the step of administering to an individual an amount of a compound of the invention sufficient to reduce apolipoprotein B expression, in addition to methods of reducing VLDL, IDL, LDL, and/or HDL absorption comprising the step of administering to an individual an amount of a compound of the invention sufficient to reduce apolipoprotein B expression.

In still another aspect, the invention provides methods of treating a condition associated with apolipoprotein B expression comprising the step of administering to an individual an amount of a compound of the invention sufficient to inhibit apolipoprotein B expression, said condition selected from hyperlipoproteinemia, familial type 3 hyperlipoprotienemia (familial dysbetalipoproteinemia), and familial hyperalphalipoprotienemia; hyperlipidemia, mixed hyperlipidemias, multiple lipoprotein-type hyperlipidemia, and familial combined hyperlipidemia; hypertriglyceridemia, familial hypertriglyceridemia, and familial lipoprotein lipase; hypercholesterolemia, familial hypercholesterolemia, polygenic hypercholesterolemia, and familial defective apolipoprotein B; cardiovascular disorders including atherosclerosis and coronary artery disease; peripheral vascular disease; von Gierke's disease (glycogen storage disease, type I); lipodystrophies (congenital and acquired forms); Cushing's syndrome; sexual ateloitic dwarfism (isolated growth hormone deficiency); diabetes mellitus; hyperthyroidism; hypertension; anorexia nervosa; Werner's syndrome; acute intermittent porphyria; primary biliary cirrhosis; extrahepatic biliary obstruction; acute hepatitis; hepatoma; systemic lupus erythematosis; monoclonal gammopathies (including myeloma, multiple myeloma, macroglobulinemia, and lymphoma); endocrinopathies; obesity; nephrotic syndrome; metabolic syndrome; inflammation; hypothyroidism; uremia (hyperurecemia); impotence; obstructive liver disease; idiopathic hypercalcemia; dysglobulinemia; elevated insulin levels; Syndrome X; Dupuytren's contracture; and Alzheimer's disease and dementia.

The invention also provides methods of reducing the risk of a condition comprising the step of administering to an individual an amount of a compound of the invention sufficient to inhibit apolipoprotein B expression, said condition selected from pregnancy; intermittent claudication; gout; and mercury toxicity and amalgam illness.

The invention further provides methods of inhibiting cholesterol particle binding to vascular endothelium comprising the step of administering to an individual an amount of a compound of the invention sufficient to inhibit apolipoprotein B expression, and as a result, the invention also provides methods of reducing the risk of: (i) cholesterol particle oxidization; (ii) monocyte binding to vascular endothelium; (iii) monocyte differentiation into macrophage; (iv) macrophage ingestion of oxidized lipid particles and release of cytokines (including, but limited to IL-1,TNF-alpha, TGF-beta); (v) platelet formation of fibrous fibrofatty lesions and inflammation; (vi) endothelium lesions leading to clots; and (vii) clots leading to myocardial infarction or stroke, also comprising the step of administering to an individual an amount of a compound of the invention sufficient to inhibit apolipoprotein B expression.

The invention also provides methods of reducing hyperlipidemia associated with alcoholism, smoking, use of oral contraceptives, use of glucocorticoids, use of beta-adrenergic blocking agents, or use of isotretinion (13-cis-retinoic acid) comprising the step of administering to an individual an amount of a compound of the invention sufficient to inhibit apolipoprotein B expression.

In certin aspects, the invention provides an antisense oligonucleotide compound 8 to 50 nucleobases in length comprising at least 8 contiguous nucleotides of SEQ ID NO:247 and having a length from at least 12 or at least 14 to 30 nucleobases.

In a further aspect, the invention provides an antisense oligonucleotide compound 20 nucleobases in length having a sequence of nucleobases as set forth in SEQ ID NO:247 and comprising 5-methylcytidine at nucleobases 2, 3, 5, 9, 12, 15, 17, 19, and 20, wherein every internucleoside linkage is a phosphothioate linkage, nucleobases 1-5 and 16-20 comprise a 2'-methoxyethoxyl modification, and nucleobases 6-15 are deoxynucleotides.

In another aspect, the invention provides a compound comprising a first nucleobase strand, 8 to 50 nucleobases in length and comprising a sequence of at least 8 contiguous nucleobases of the sequence set forth in SEQ ID NO:3, hybridized to a second nucleobase strand, 8 to 50 nucleobases in length and comprising a sequence sufficiently complementary to the first strand so as to permit stable hybridization, said compound inhibiting expression of mRNA encoding human apolipoprotein B after 16 to 24 hours by at least 30% or by at least 50% in 80% confluent HepG2 cells in culture at a concentration of 100 nM.

Further provided is a vesicle, such as a liposome, comprising a compound or composition of the invention Preferred methods of administration of the compounds or compositions of the invention to an animal are intravenously, subcutaneously, or orally. Administrations can be repeated.

In another aspect, the invention provides a method of reducing lipoprotein(a) secretion by hepatocytes comprising (a) contacting hepatocytes with an amount of a composition comprising a non-catalytic compound 8 to 50 nucleobases in length that specifically hybridizes with mRNA encoding human apolipoprotein B and inhibits expression of the mRNA after 16 to 24 hours by at least 30% or at least 50% in 80% confluent HepG2 cells in culture at a concentration of 150 nM, wherein said amount is effective to inhibit expression of apolipoprotein B in the hepatocytes; and (b) measuring lipoprotein(a) secretion by the hepatocytes.

The invention further provides a method of a treating a condition associated with apolipoprotein B expression in a primate, such as a human, comprising administering to the primate a therapeutically or prophylactically effective amount of a non-catalytic compound 8 to 50 nucleobases in length that specifically hybridizes with mRNA encoding human apolipoprotein B and inhibits expression of the mRNA after 16 to 24 hours by at least 30% or by at least 50% in 80% confluent HepG2 cells in culture at a concentration of 150 nM.

The invention provides a method of reducing apolipoprotein B expression in the liver of an animal, comprising administering to the animal between 2 mg/kg and 20 mg/kg of a non-catalytic compound 8 to 50 nucleobases in length that specifically hybridizes with mRNA encoding human apolipoprotein B by at least 30% or by at least 50% in 80% confluent HepG2 cells in culture at a concentration of 150 nM.

Also provided is a method of making a compound of the invention comprising specifically hybridizing in vitro a first nucleobase strand comprising a sequence of at least 8 contiguous nucleobases of the sequence set forth in SEQ ID NO:3 to a second nucleobase strand comprising a sequence sufficiently complementary to said first strand so as to permit stable hybridization.

The invention further provides use of a compound of the invention in the manufacture of a medicament for the treatment of any and all conditions disclosed herein.

DETAILED DESCRIPTION OF THE INVENTION

The present invention employs oligomeric compounds, particularly antisense oligonucleotides, for use in modulating the function of nucleic acid molecules encoding apolipoprotein B, ultimately modulating the amount of apolipoprotein B produced. This is accomplished by providing antisense compounds which specifically hybridize with one or more nucleic acids encoding apolipoprotein B. As used herein, the terms "target nucleic acid" and "nucleic acid encoding apolipoprotein B" encompass DNA encoding apolipoprotein B, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of apolipoprotein B. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding apolipoprotein B. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding apolipoprotein B, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (reviewed in (To, Comb. Chem. High Throughput Screen, 2000, 3, 235-41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. Thus, this term includes oligonucleotides composed of naturally-occurring nucleobases, sugars and covalent internucleoside (backbone) linkages (RNA and DNA) as well as oligonucleotides having non-naturally-occurring portions which function similarly (oligonucleotide mimetics). Oligonucleotide mimetics are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12, about 14, about 20 to about 30 nucleobases. Antisense compounds include ribozymes, external guide sequence (EGS)

oligonucleotides (oligozymes), and other short catalytic RNAs or catalytic oligonucleotides which hybridize to the target nucleic acid and modulate its expression. In preferred embodiments, the antisense compound is non-catalytic oligonucleotide, i.e., is not dependent on a catalytic property of the oligonucleotide for its modulating activity. Antisense compounds of the invention can include double-stranded molecules wherein a first strand is stably hybridized to a second strand.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoallylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne $(—CH_2—)_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-$OCH_2CH_2CH_2NH_2$), 2'-allyl (2'-$CH_2$—CH═$CH_2$), 2'-O-allyl (2'-O—$CH_2$—CH═$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyl-adenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently hound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmaco-dynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., dihexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6 -phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of apolipoprotein B is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding apolipoprotein B, enabling sandwich and other assays to easily be constructed to exploit this fact. Hybridization of the antisense oligonucleotides of the invention with a nucleic acid encoding apolipoprotein B can be detected by means known in the art. Such means may include conjugation of an enzyme to the oligonucleotide, radiolabelling of the oligonucleotide or any other suitable detection means. Kits using such detection means for detecting the level of apolipoprotein B in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline)

negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter (Idson, in Pharmaceutical Dosage Forms, Lieberman, Rieger and Banker (Eds.). 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1. p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose). and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.). 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs:

Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500). decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C 12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P.Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.)

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{12}15G$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S.

Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p.92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p.92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydrofusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 5.79-583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylazacycloalkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., Antisense Res. Dev., 1995, 5, 115-121; Takakura et al., Antisense & Nucl. Acid Drug Dev., 1996, 6, 177-183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Pulsatile Delivery

The compounds of the present invention may also be administered by pulsatile delivery. "Pulsatile delivery" refers to a pharmaceutical formulations that delivers a first pulse of drug combined with a penetration enhancer and a second pulse of penetration enhancer to promote absorption of drug which is not absorbed upon release with the first pulse of penetration enhancer.

One embodiment of the present invention is a delayed release oral formulation for enhanced intestinal drug absorption, comprising:

(a) a first population of carrier particles comprising said drug and a penetration enhancer, wherein said drug and said penetration enhancer are released at a first location in the intestine; and (b) a second population of carrier particles comprising a penetration enhancer and a delayed release coating or matrix, wherein the penetration enhancer is released at a second location in the intestine downstream from the first location, whereby absorption of the drug is enhanced when the drug reaches the second location.

Alternatively, the penetration enhancer in (a) and (b) is different.

This enhancement is obtained by encapsulating at least two populations of carrier particles. The first population of carrier particles comprises a biologically active substance and a penetration enhancer, and the second (and optionally additional) population of carrier particles comprises a penetration enhancer and a delayed release coating or matrix.

A "first pass effect" that applies to orally administered drugs is degradation due to the action of gastric acid and various digestive enzymes. One means of ameliorating first pass clearance effects is to increase the dose of administered drug, thereby compensating for proportion of drug lost to first pass clearance. Although this may be readily achieved with i.v. administration by, for example, simply providing more of the drug to an animal, other factors influence the bioavailability of drugs administered via non-parenteral means. For example, a drug may be enzymatically or chemically degraded in the alimentary canal or blood stream and/or may be impermeable or semipermeable to various mucosal membranes.

It is also contemplated that these pharmacutical compositons are capable of enhancing absorption of biologically active substances when administered via the rectal, vaginal, nasal or pulmonary routes. It is also contemplated that release of the biologically active substance can be achieved in any part of the gastrointestinal tract.

Liquid pharmaceutical compositions of oligonucleotide can be prepared by combining the oligonucleotide with a suitable vehicle, for example sterile pyrogen free water, or saline solution. Other therapeutic compounds may optionally be included.

The present invention also contemplates the use of solid particulate compositions. Such compositions preferably comprise particles of oligonucleotide that are of respirable size. Such particles can be prepared by, for example, grinding dry oligonucleotide by conventional means, fore example with a mortar and pestle, and then passing the resulting powder composition through a 400 mesh screen to segregate large particles and agglomerates. A solid particulate composition comprised of an active oligonucleotide can optionally contain a dispersant which serves to facilitate the formation of an aerosol, for example lactose.

In accordance with the present invention, oligonucleotide compositions can be aerosolized. Aerosolization of liquid particles can be produced by any suitable means, such as with a nebulizer. See, for example, U.S. Pat. No. 4,501,729. Nebulizers are commercially available devices which transform solutions or suspensions into a therapeutic aerosol mist either by means of acceleration of a compressed gas, typically air or oxygen, through a narrow venturi orifice or by means of ultrasonic agitation. Suitable nebulizers include those sold by Blairex® under the name PARI LC PLUS, PARI DURANEB 2000, PARI-BABY Size, PARI PRONEB Compressor with LC PLUS, PARI WALKHALER Compressor/Nebulizer System, PARI LC PLUS Reusable Nebulizer, and PARI LC Jet+ ®Nebulizer.

Exemplary formulations for use in nebulizers consist of an oligonucleotide in a liquid, such as sterile, pyragen free water, or saline solution, wherein the oligonucleotide comprises up to about 40% w/w of the formulation. Preferably, the oligonucleotide comprises less than 20% w/w. If desired, further additives such as preservatives (for example, methyl hydroxybenzoate) antioxidants, and flavoring agents can be added to the composition.

Solid particles comprising an oligonucleotide can also be aerosolized using any solid particulate medicament aerosol generator known in the art. Such aerosol generators produce respirable particles, as described above, and further produce reproducible metered dose per unit volume of aerosol. Suitable solid particulate aerosol generators include insufflators and metered dose inhalers. Metered dose inhalers are used in the art and are useful in the present invention.

Preferably, liquid or solid aerosols are produced at a rate of from about 10 to 150 liters per minute, more preferably from about 30 to 150 liters per minute, and most preferably about 60 liters per minute.

Enhanced bioavailability of biologically active substances is also achieved via the oral administration of the compositions and methods of the present invention. The term "bioavailability" refers to a measurement of what portion of an administered drug reaches the circulatory system when a non-parenteral mode of administration is used to introduce the drug into an animal.

Penetration enhancers include, but are not limited to, members of molecular classes such as surfactants, fatty acids, bile salts, chelating agents, and non-chelating non-surfactant molecules. (Lee et al., Critical Reviews in Therapeutic Drug Carrier Systems, 1991, p. 92). Carriers are inert molecules that may be included in the compositions of the present invention to interfere with processes that lead to reduction in the levels of bioavailable drug.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

Combination Therapy

The invention also provides methods of combination therapy, wherein one or more compounds of the invention and one or more other therapeutic/prophylactic compounds are administered treat a condition and/or disease state as described herein. In various aspects, the compound(s) of the invention and the therapeutic/prophylactic compound(s) are co-administered as a mixture or administered individually. In one aspect, the route of administration is the same for the compound(s) of the invention and the therapeutic/prophylactic compound(s), while in other aspects, the compound(s) of the invention and the therapeutic/prophylactic compound(s) are administered by a different routes. In one embodiment, the dosages of the compound(s) of the invention and the therapeutic/prophylactic compound(s) are amounts that are therapeutically or prophylactically effective for each compound when administered individually. Alternatively, the combined administration permits use of lower dosages than would be required to achieve a therapeutic or prophylactic effect if administered individually, and such methods are useful in decreasing one or more side effects of the reduced-dose compound.

In one aspect, a compound of the present invention and one or more other therapeutic/prophylactic compound(s) effective at treating a condition are administered wherein both compounds act through the same or different mechanisms. Therapeutic/prophylactic compound(s) include, but are not limited to, bile salt sequestering resins (e.g., cholestyramine, colestipol, and colesevelam hydrochloride), HMGCoA-redectase inhibitors (e.g., lovastatin, cerivastatin, prevastatin, atorvastatin, simvastatin, and fluvastatin), nicotinic acid, fibric acid derivatives (e.g., clofibrate, gemfibrozil, fenofibrate, bezafibrate, and ciprofibrate), probucol, neomycin, dextrothyroxine, plant-stanol esters, cholesterol absorption inhibitors (e.g., ezetimibe), implitapide, inhibitors of bile acid transporters (apical sodium-dependent bile acid transporters), regulators of hepatic CYP7a, estrogen replacement therapeutics (e.g., tamoxigen), and anti-inflammatories (e.g., glucocorticoids).

Accordingly, the invention further provides use of a compound of the invention and one or more other therapeutic/prophylactic compound(s) as described herein in the manufacture of a medicament for the treatment and/or prevention of a disease or condition as described herein.

Targeted Delivery

In another aspect, methods are provided to target a compound of the invention to a specific tissue, organ or location in the body. Exemplary targets include liver, lung, kidney, heart, and atherosclerotic plaques within a blood vessel. Methods of targeting compounds are well known in the art.

In one embodiment, the compound is targeted by direct or local administration. For example, when targeting a blood vessel, the compound is administered directly to the relevant portion of the vessel from inside the lumen of the vessel, e.g., single balloon or double balloon catheter, or through the adventitia with material aiding slow release of the compound, e.g., a pluronic gel system as described by Simons et al., Nature 359: 67-70 (1992). Other slow release techniques for local delivery of the compound to a vessel include coating a stent with the compound. Methods of delivery of antisense compounds to a blood vessel are disclosed in U.S. Pat. No. 6,159,946, which is incorporated by reference in its entirety.

When targeting a particular tissue or organ, the compound may be administered in or around that tissue or organ. For example, U.S. Pat. No. 6,547,787, incorporated herein by reference in its entirety, discloses methods and devices for targeting therapeutic agents to the heart. In one aspect, administration occurs by direct injection or by injection into a blood vessel associated with the tissue or organ. For example, when targeting the liver, the compound may be administered by injection or infusion through the portal vein.

In another aspect, methods of targeting a compound are provided which include associating the compound with an agent that directs uptake of the compound by one or more cell types. Exemplary agents include lipids and lipid-based structures such as liposomes generally in combination with an organ- or tissue-specific targeting moiety such as, for example, an antibody, a cell surface receptor, a ligand for a cell surface receptor, a polysaccharide, a drug, a hormone, a hapten, a special lipid and a nucleic acid as described in U.S. Pat. No. 6,495,532, the disclosure of which is incorporated herein by reference in its entirety. U.S. Pat. No. 5,399,331, the disclosure of which is incorporated herein by reference in its entirety, describes the coupling of proteins to liposomes through use of a crosslinking agent having at least one maleimido group and an amine reactive function; U.S. Pat. Nos. 4,885,172, 5,059,421 and 5,171,578, the disclosures of which are incorporated herein by reference in their entirety, describe linking proteins to liposomes through use of the glycoprotein streptavidin and coating targeting liposomes with polysaccharides. Other lipid based targeting agents include, for example, micelle and crystalline products as described in U.S. Pat. No. 6,217,886, the disclosure of which is incorporated herein by reference in its entirety.

In another aspect, targeting agents include porous polymeric microspheres which are derived from copolymeric and homopolymeric polyesters containing hydrolyzable ester linkages which are biodegradable, as described in U.S. Pat. No. 4,818,542, the disclosure of which is incorporated herein by reference in its entirety. Typical polyesters include polyglycolic (PGA) and polylactic (PLA) acids, and copolymers of glycolide and L(-lactide) (PGL), which are particularly suited for the methods and compositions of the present invention in that they exhibit low human toxicity and are biodegradable. The particular polyester or other polymer, oligomer, or copolymer utilized as the microspheric polymer matrix is not critical and a variety of polymers may be utilized depending on desired porosity, consistency, shape and size distribution. Other biodegradable or bioerodable polymers or copolymers include, for example, gelatin, agar, starch, arabinogalactan, albumin, collagen, natural and synthetic materials or polymers, such as, poly(ϵ-caprolactone), poly(ϵ-caprolactone-CO-lactic acid), poly(ϵ-caprolactone-CO-glycolic acid), poly(β-hydroxy butyric acid), polyethylene oxide, polyethylene, poly(alkyl-2-cyanoacrylate), (e.g., methyl, ethyl, butyl), hydrogels such as poly(hydroxyethyl methacrylate), polyamides (e.g., polyacrylamide), poly(amino acids) (i.e., L-leucine, L-aspartic acid, β-methyl-L-aspartate, β-benzyl-L-aspartate, glutamic acid), poly(2-hydroxyethyl DL-aspartamide), poly(ester urea), poly(L-phenylalanine/ethylene glycol/1,6-diisocyanatohexane) and poly(methyl methacrylate). The exemplary natural and synthetic polymers suitable for targeted delivery are either readily available commercially or are obtainable by condensation polymerization reactions from the suitable monomers or, comonomers or oligomers.

In still another embodiment, U.S. Pat. No. 6,562,864, the disclosure of which is incorporated herein by reference in its entirety, describes catechins, including epi and other carbocationic isomers and derivatives thereof, which as monomers, dimers and higher multimers can form complexes with nucleophilic and cationic bioactive agents for use as delivery agents. Catechin multimers have a strong affinity for polar proteins, such as those residing in the vascular endothelium, and on cell/organelle membranes and are particularly useful for targeted delivery of bioactive agents to select sites in vivo. In treatment of vascular diseases and disorders, such as atherosclerosis and coronary artery disease, delivery agents include substituted catechin multimers, including amidated catechin multimers which are formed from reaction between catechin and nitrogen containing moities such as ammonia.

Other targeting strategies of the invention include ADEPT (antibody-directed enzyme prodrug therapy), GDEPT (gene-directed EPT) and VDEPT (virus-directed EPT) as described in U.S. Pat. No. 6,433,012, the disclosure of which is incorporated herein by reference in its entirety.

The present invention further provides medical devices and kits for targeted delivery, wherein the device is, for example, a syringe, stent, or catheter. Kits include a device for administering a compound and a container comprising a compound of the invention. In one aspect, the compound is preloaded into the device. In other embodiments, the kit provides instructions for methods of administering the compound and dosages. U.S. patents describing medical devices and kits for delivering antisense compounds include U.S. Pat. Nos. 6,368,356; 6,344,035; 6,344,028; 6,287,285; 6,200,304; 5,824,049; 5,749,915; 5,674,242; 5,670,161; 5,609,629; 5,593,974; and 5,470,307 (all incorporated herein by reference in their entirety).

While the present invention has been described with specificity in accordance with certain embodiments, the following examples serve only to illustrate the invention and are not intended to limit the same.

EXAMPLES

Example 1

Nucleoside Phosphoramidites for Oligonucleotide Synthesis Deoxy and 2'-alkoxy amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., Nucleic Acids Research, 1993, 21, 3197-3203] using commercially available phosphoramidites (Glen Research, Sterling Va. or ChemGenes, Needham Mass.).

2'-Fluoro amidites

2'-Fluorodeoxyadenosine amidites

2'-fluoro oligonucleotides were synthesized as described previously [Kawasaki, et. al., J. Med. Chem., 1993, 36, 831-841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups.

Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites are prepared as follows, or alternatively, as per the methods of Martin, P., Helvetica Chimica Acta, 1995, 78, 486-504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10-25%) to give a white solid, mp 222-4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3' -O-Acetyl -2'-O-methoxyethyl -5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using Teac/hexane(4:1). Pure product fractions were evaporated to yield 96 g (84%). An additional 1.5 g was recovered from later fractions.

3'-O-Acetyl-21-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0-10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in Teac (1 L) and the insoluble solids were removed by filtration. The filtrate was washed with 1×300 mL of $NaHCO_3$ and 2×300 mL of saturated NaCl, dried over sodium sulfate and evaporated. The residue was triturated with Teac to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in Teac (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O- Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using Teac/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L) Tetrazole diisopropylamine (7.1 g) and 2-cyanoethoxy-tetra (isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using Teac/hexane (3:1) as the eluting solvent. The pure fractions were combined to give 90.6 g (87%) of the title compound.

2'-O-(Aminooxyethyl) nucleoside amidites and 2'-O-(dimethylaminooxyethyl) nucleoside amidites 2'-(Dimethylaminooxyethoxy) nucleoside amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anyhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40-100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-α-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-Dimethoxytrityl-2'-O-[2(2-N,N-dimethylaminoethoxy)ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-ditriethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P═O) oligonucleotides are synthesized on an automated DNA synthesizer (Applied Biosystems model 380B) using standard phosphoramidite chemistry with oxidation by iodine.

Phosphorothioates (P═S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P═O or P═S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(Methoxyethyl)] Chimeric Phosphorothioate Oligonucleotides

[2'-O-(2-methoxyethyl)]—[2'-deoxy]—[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl) Phosphodiester] Chimeric Oligonucleotides

[2'-O-(2-methoxyethyl phosphodiester]—[2'-deoxy phosphorothioate]—[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., J. Biol. Chem. 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multichannel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 7 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

HepG2 Cells:

The human hepatoblastoma cell line HepG2 was obtained from the American Type Culture Collection (Manassas, Va.). HepG2 cells were routinely cultured in Eagle's MEM supplemented with 10% fetal calf serum, non-essential amino acids, and 1 mM sodium pyruvate (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analyses, cells may be seeded onto 100 mm or other standard tissue culture plates and treated similarly, using appropriate volumes of medium and oligonucleotide.

AML12 Cells:

The AML12 (alpha mouse liver 12) cell line was established from hepatocytes from a mouse (CD1 strain, line MT42) transgenic for human TGF alpha. Cells are cultured in a 1:1 mixture of Dulbecco's modified Eagle's medium and Ham's F12 medium with 0.005 mg/ml insulin, 0.005 mg/ml transferrin, 5 ng/ml selenium, and 40 ng/ml dexamethasone, and 90%; 10% fetal bovine serum. For subculturing, spent medium is removed and fresh media of 0.25% trypsin, 0.03% EDTA solution is added. Fresh trypsin solution (1 to 2 ml) is added and the culture is left to sit at room temperature until the cells detach.

Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analyses, cells may be seeded onto 100 mm or other standard tissue culture plates and treated similarly, using appropriate volumes of medium and oligonucleotide.

Primary Mouse Hepatocytes:

Primary mouse hepatocytes were prepared from CD-1 mice purchased from Charles River Labs (Wilmington, Mass.) and were routinely cultured in Hepatoyte Attachment Media (Gibco) supplemented with 10% Fetal Bovine Serum (Gibco/Life Technologies, Gaithersburg, Md.), 250 nM dexamethasone (Sigma), and 10 nM bovine insulin (Sigma). Cells were seeded into 96-well plates (Falcon-Primaria #3872) at a density of 10000 cells/well for use in RT-PCR analysis.

For Northern blotting or other analyses, cells are plated onto 100 mm or other standard tissue culture plates coated with rat tail collagen (200 ug/mL) (Becton Dickinson) and treated similarly using appropriate volumes of medium and oligonucleotide.

Hep3B Cells:

The human hepatocellular carcinoma cell line Hep3B was obtained from the American Type Culture Collection (Manassas, Va.). Hep3B cells were routinely cultured in Dulbeccos's MEM high glucose supplemented with 10% fetal calf serum, L-glutamine and pyridoxine hydrochloride (Gibco/Life Technologies, Gaithersburg, Md.). Cells were routinely passaged by trypsinization and dilution when they reached 90% confluence. Cells were seeded into 24-well plates (Falcon-Primaria #3846) at a density of 50,000 cells/well for use in RT-PCR analysis.

For Northern blotting or other analyses, cells may be seeded onto 100 mm or other standard tissue culture plates and treated similarly, using appropriate volumes of medium and oligonucleotide.

Rabbit Primary Hepatocytes:

Primary rabbit hepatocytes were purchased from Invitro Technologies (Gaithersburg, Md.) and maintained in Dulbecco's modified Eagle's medium (Gibco). When purchased, the cells had been seeded into 96-well plates for use in RT-PCR analysis and were confluent.

For Northern blotting or other analyses, cells may be seeded onto 100 mm or other standard tissue culture plates and treated similarly using appropriate volumes of medium and oligonucleotide.

HeLa Cells:

The human epitheloid carcinoma cell line HeLa was obtained from the American Tissue Type Culture Collection (Manassas, Va.). HeLa cells were routinely cultured in DMEM, high glucose (Invitrogen Corporation, Carlsbad, Calif.) supplemented with 10% fetal bovine serum (Invitrogen Corporation, Carlsbad, Calif.). Cells were seeded into 24-well plates (Falcon-Primaria #3846) at a density of 50,000 cells/well for use in RT-PCR analysis. Cells were routinely passaged by trypsinization and dilution when they reached 90% confluence. Cells 96-well plates (Falcon-Primaria #3872) at a density of 5,000 cells/well for use in RT-PCR analysis. For Northern blotting or other analyses, cells may be seeded onto 100 mm or other standard tissue culture plates and treated similarly, using appropriate volumes of medium and oligonucleotide.

Human Mammary Epithelial Cells:

Normal human mammary epithelial cells (HMECs) were obtained from the American Type Culture Collection (Manassas Va.). HMECs were routinely cultured in DMEM low glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #353872, BD Biosciences, Bedford, Mass.) at a density of 7000 cells/well for use in RT-PCR analysis. For Northern blotting or other analyses, cells may be seeded onto 100 mm or other standard tissue culture plates and treated similarly, using appropriate volumes of medium and oligonucleotide.

Treatment with Antisense Compounds:

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPOFECTIN™ (Gibco BRL) and the desired concentration of oligonucleotide. After 4-7 hours of treatment, the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 5 nM to 300 nM.

Example 10

Analysis of Oligonucleotide Inhibition of Apolipoprotein B Expression

Antisense modulation of apolipoprotein B expression can be assayed in a variety of ways known in the art. For example, apolipoprotein B mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., Current Protocols in Molecular Biology, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of apolipoprotein B can be quantitated in a variety of ways well known in the art, such as immunoprecipitation, Western blot analysis (immunoblotting), ELISA or fluorescence-activated cell sorting (FACS). Antibodies directed to apolipoprotein B can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Example 11

Poly(A)+ mRNA Isolation

Poly(A)+ mRNA was isolated according to Miura et al., Clin. Chem., 1996, 42, 1758-1764. Other methods for poly (A)+ mRNA isolation are taught in, for example, Ausubel, F. M. et al., Current Protocols in Molecular Biology, Volume 1, pp. 4.5.1-4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Apolipoprotein B mRNA Levels

Quantitation of apolipoprotein B mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 μL PCR cocktail (1× TAQMAN™ buffer A, 5.5 mM $MgCl_2$, 300 μM each of DATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL total RNA solution. The RT reaction was carried out by incubation for 30 minutes at 48°

C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, Analytical Biochemistry, 1998, 265, 368-374.

In this assay, 175 μL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human apolipoprotein B were designed to hybridize to a human apolipoprotein B sequence, using published sequence information (GenBank accession number NM_000384.1, incorporated herein as SEQ ID NO: 3). For human apolipoprotein B the PCR primers were: forward primer: TGCTAAAGGCACATATGGCCT (SEQ ID NO: 4) reverse primer: CTCAGGTTGGACTCTCCATTGAG (SEQ ID NO: 5) and the PCR probe was: FAM-CTTGTCAGAGGGATCCTAACACTGGCCG-TAMRA (SEQ ID NO: 6) where FAM (PE-Applied Biosystems, Foster City, Calif.) is the fluorescent reporter dye) and TAMRA (PE-Applied Biosystems. Foster City, Calif.) is the quencher dye. For human GAPDH the PCR primers were: forward primer: GAAGGTGAAGGTCGGAGTC (SEQ ID NO: 7) reverse primer: GAAGATGGTGATGGGATTTC (SEQ ID NO: 8) and the PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to mouse apolipoprotein B were designed to hybridize to a mouse apolipoprotein B sequence, using published sequence information (GenBank accession number M35186, incorporated herein as SEQ ID NO: 10). For mouse apolipoprotein B the PCR primers were: forward primer: CGTGGGCTCCAGCATTCTA (SEQ ID NO: 11) reverse primer: AGTCATTTCTGCCTTTGCGTC (SEQ ID NO: 12) and the PCR probe was: FAM-CCAATGGTCGGGCACTGCTCAA-TAMRA SEQ ID NO: 13) where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were: forward primer: GGCAAATTCAACGGCACAGT (SEQ ID NO: 14) reverse primer: GGGTCTCGCTCCTGGAAGAT (SEQ ID NO:15) and the PCR probe was: 5' JOE-AAGGCCGAGAATGGGAAGCTTGTCATC-TAMRA 3' (SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Apolipoprotein B mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway. N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human apolipoprotein B, a human apolipoprotein B specific probe was prepared by PCR using the forward primer TGCTAAAGGCACATATGGCCT (SEQ ID NO: 4) and the reverse primer CTCAGGTTGGACTCTCATTGAG (SEQ ID NO: 5). To normalize for variations in loading and transfer efficiency membranes were stripped and probed for human glyceraldehyde-3-phosphate dehydrogenase (GAPDH) RNA (Clontech, Palo Alto. Calif.).

To detect mouse apolipoprotein B, a human apolipoprotein B specific probe was prepared by PCR using the forward primer CGTGGGCTCCAGCATTCTA (SEQ ID NO: 11) and the reverse primer AGTCATTTCTGCCTTTGCGTC (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Apolipoprotein B Expression by Chimeric Phosphorothioate Oligonucleotides Having 2'-MOE Wings and a Deoxy Gap In accordance with the present invention, a series of oligonucleotides was designed to target different regions of the human apolipoprotein B RNA, using published sequence (GenBank accession number NM_000384.1, incorporated herein as SEQ ID NO: 3). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide. All cytidine residues are 5-methylcytidines. The compounds were analyzed for their effect on human apolipoprotein B mRNA levels in HepG2 cells by quantitative real-time PCR as described in other examples herein. Data are averages from two experiments in which HepG2 cells were treated with 150 nM of the compounds in Table 1. If present, "N.D." indicates "no data".

TABLE 1

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 147780 | 5'UTR | 3 | 1 | CCGCAGGTCCCGGTGGGAAT | 40 | 17 |
| 147781 | 5'UTR | 3 | 21 | ACCGAGAAGGGCACTCAGCC | 35 | 18 |
| 147782 | 5'UTR | 3 | 71 | GCCTCGGCCTCGCGGCCCTG | 67 | 19 |
| 147783 | Start Codon | 3 | 114 | TCCATCGCCAGCTGCGGTGG | N.D. | 20 |
| 147784 | Coding | 3 | 151 | CAGCGCCAGCAGCGCCAGCA | 70 | 21 |
| 147785 | Coding | 3 | 181 | GCCCGCCAGCAGCAGCAGCA | 29 | 22 |
| 147786 | Coding | 3 | 321 | CTTGAATCAGCAGTCCCAGG | 34 | 23 |
| 147787 | Coding | 3 | 451 | CTTCAGCAAGGCTTTGCCCT | N.D. | 24 |
| 147788 | Coding | 3 | 716 | TTTCTGTTGCCACATTGCCC | 95 | 25 |
| 147789 | Coding | 3 | 911 | GGAAGAGGTGTTGCTCCTTG | 24 | 26 |
| 147790 | Coding | 3 | 951 | TGTGCTACCATCCCATACTT | 33 | 27 |
| 147791 | Coding | 3 | 1041 | TCAAATGCGAGGCCCATCTT | N.D. | 28 |
| 147792 | Coding | 3 | 1231 | GGACACCTCAATCAGCTGTG | 26 | 29 |
| 147793 | Coding | 3 | 1361 | TCAGGGCCACCAGGTAGGTG | N.D. | 30 |
| 147794 | Coding | 3 | 1561 | GTAATCTTCATCCCCAGTGC | 47 | 31 |
| 147795 | Coding | 3 | 1611 | TGCTCCATGGTTTGGCCCAT | N.D. | 32 |
| 147796 | Coding | 3 | 1791 | GCAGCCAGTCGCTTATCTCC | 8 | 33 |
| 147797 | Coding | 3 | 2331 | GTATAGCCAAAGTGGTCCAC | N.D. | 34 |
| 147798 | Coding | 3 | 2496 | CCCAGGAGCTGGAGGTCATG | N.D. | 35 |
| 147799 | Coding | 3 | 2573 | TTGAGCCCTTCCTGATGACC | N.D. | 36 |
| 147800 | Coding | 3 | 2811 | ATCTGGACCCCACTCCTAGC | N.D. | 37 |
| 147801 | Coding | 3 | 2842 | CAGACCCGACTCGTGGAAGA | 38 | 38 |
| 147802 | Coding | 3 | 3367 | GCCCTCAGTAGATTCATCAT | N.D. | 39 |
| 147803 | Coding | 3 | 3611 | GCCATGCCACCCTCTTGGAA | N.D. | 40 |
| 147804 | Coding | 3 | 3791 | AACCCACGTGCCGGAAAGTC | N.D. | 41 |
| 147805 | Coding | 3 | 3841 | ACTCCCAGATGCCTTCTGAA | N.D. | 42 |
| 147806 | Coding | 3 | 4281 | ATGTGGTAACGAGCCCGAAG | 100 | 43 |
| 147807 | Coding | 3 | 4391 | GGCGTAGAGACCCATCACAT | 25 | 44 |
| 147808 | Coding | 3 | 4641 | GTGTTAGGATCCCTCTGACA | N.D. | 45 |
| 147809 | Coding | 3 | 5241 | CCCAGTGATAGCTCTGTGAG | 60 | 46 |
| 147810 | Coding | 3 | 5355 | ATTTCAGCATATGAGCCCAT | 0 | 47 |
| 147811 | Coding | 3 | 5691 | CCCTGAACCTTAGCAACAGT | N.D. | 48 |
| 147812 | Coding | 3 | 5742 | GCTGAAGCCAGCCCAGCGAT | N.D. | 49 |
| 147813 | Coding | 3 | 5891 | ACAGCTGCCCAGTATGTTCT | N.D. | 50 |
| 147814 | Coding | 3 | 7087 | CCCAATAAGATTTATAACAA | 34 | 51 |
| 147815 | Coding | 3 | 7731 | TGGCCTACCAGAGACAGGTA | 45 | 52 |
| 147816 | Coding | 3 | 7841 | TCATACGTTTAGCCCAATCT | 100 | 53 |

TABLE 1-continued

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 147817 | Coding | 3 | 7901 | GCATGGTCCCAAGGATGGTC | 0 | 54 |
| 147818 | Coding | 3 | 8491 | AGTGATGGAAGCTGCGATAC | 30 | 55 |
| 147819 | Coding | 3 | 9181 | ATGAGCATCATGCCTCCCAG | N.D. | 56 |
| 147820 | Coding | 3 | 9931 | GAACACATAGCCGAATGCCG | 100 | 57 |
| 147821 | Coding | 3 | 10263 | GTGGTGCCCTCTAATTTGTA | N.D. | 58 |
| 147822 | Coding | 3 | 10631 | CCCGAGAAAGAACCGAACCC | N.D. | 59 |
| 147823 | Coding | 3 | 10712 | TGCCCTGCAGCTTCACTGAA | 19 | 60 |
| 147824 | Coding | 3 | 11170 | GAAATCCCATAAGCTCTTGT | N.D. | 61 |
| 147825 | Coding | 3 | 12301 | AGAAGCTGCCTCTTCTTCCC | 72 | 62 |
| 147826 | Coding | 3 | 12401 | TCAGGGTGAGCCCTGTGTGT | 80 | 63 |
| 147827 | Coding | 3 | 12471 | CTAATGGCCCCTTGATAAAC | 13 | 64 |
| 147828 | Coding | 3 | 12621 | ACGTTATCCTTGAGTCCCTG | 12 | 65 |
| 147829 | Coding | 3 | 12741 | TATATCCCAGGTTTCCCCGG | 64 | 66 |
| 147830 | Coding | 3 | 12801 | ACCTGGGACAGTACCGTCCC | N.D. | 67 |
| 147831 | 3'UTR | 3 | 13921 | CTGCCTACTGCAAGGCTGGC | 0 | 68 |
| 147832 | 3'UTR | 3 | 13991 | AGAGACCTTCCGAGCCCTGG | N.D. | 69 |
| 147833 | 3'UTR | 3 | 14101 | ATGATACACAATAAAGACTC | 25 | 70 |

As shown in Table 1, SEQ ID NOs 17, 18, 19, 21, 23, 25, 27, 31, 38, 43, 46, 51, 52, 53, 55, 57, 62, 63 and 66 demonstrated at least 30% inhibition of human apolipoprotein B expression in this assay and are therefore preferred. The target sites to which these preferred sequences are complementary are herein referred to as "active sites" and are therefore preferred sites for targeting by compounds of the present invention. As apolipoprotein B exists in two forms in mammals (ApoB-48 and ApoB-100) which are colinear at the amino terminus, antisense oligonucleotides targeting nucleotides 1-6530 hybridize to both forms, while those targeting nucleotides 6531-14121 are specific to the long form of apolipoprotein B.

Example 16

Antisense Inhibition of Human Apolipoprotein B Expression by Chimeric Phosphorothioate Oligonucleotides Having 2'-MOE Wings and a Deoxy Gap-Dose Response Study In accordance with the present invention, a subset of the antisense oligonuclotides in Example 15 were further investigated in dose-response studies. Treatment doses were 50, 150 and 250 nM. The compounds were analyzed for their effect on human apolipoprotein B mRNA levels in HepG2 cells by quantitative real-time PCR as described in other examples herein. Data are averages from two experiments and are shown in Table 2.

TABLE 2

Inhibition of human apolipoprotein B mRNA levels by chimeric phosphorothioate oligonucleotides having 2'-MOE wings and a deoxy gap

| | Percent Inhibition | | |
|---|---|---|---|
| ISIS # | 50 nM | 150 nM | 250 nM |
| 147788 | 54 | 63 | 72 |
| 147806 | 23 | 45 | 28 |
| 147816 | 25 | 81 | 65 |
| 147820 | 10 | 0 | 73 |

Example 17

Antisense Inhibition of Mouse Apolipoprotein B Expression by Chimeric Phosphorothioate Oligonucleotides Having 2'-MOE Wings and a Deoxy Gap In accordance with the present invention, a series of oligonucleotides was designed to target different regions of the mouse apolipoprotein B RNA, using published sequence (GenBank accession number M35186, incorporated herein as SEQ ID NO: 10). The oligonucleotides are shown in Table 3. "Target site" indicates the first (5'-most) nucleotide number on the particular target sequence to which the oligonucleotide binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P═S) throughout the oligonucleotide. All cytidine residues are 5-methylcytidines. The compounds were analyzed for their effect on mouse apolipoprotein B mRNA levels in primary mouse hepatocytes by quantitative real-R time PCR as described in other examples herein. Primary mouse hepatocytes were treated with 150 nM of the compounds in Table 3. Data are averages from two experiments. If present, "N.D." indicates "no data".

TABLE 3

Inhibition of mouse apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 147475 | Coding | 10 | 13 | ATTGTATGTGAGAGGTGAGG | 79 | 71 |
| 147476 | Coding | 10 | 66 | GAGGAGATTGGATCTTAAGG | 13 | 72 |
| 147477 | Coding | 10 | 171 | CTTCAAATTGGGACTCTCCT | N.D | 73 |
| 147478 | Coding | 10 | 211 | TCCAGGAATTGAGCTTGTGC | 78 | 74 |
| 147479 | Coding | 10 | 238 | TTCAGGACTGGAGGATGAGG | N.D | 75 |
| 147480 | Coding | 10 | 291 | TCTCACCCTCATGCTCCATT | 54 | 76 |
| 147481 | Coding | 10 | 421 | TGACTGTCAAGGGTGAGCTG | 24 | 77 |
| 147482 | Coding | 10 | 461 | GTCCAGCCTAGGAACACTCA | 59 | 78 |
| 147483 | Coding | 10 | 531 | ATGTCAATGCCACATGTCCA | N.D | 79 |
| 147484 | Coding | 10 | 581 | TTCATCCGAGAAGTTGGGAC | 49 | 80 |
| 147485 | Coding | 10 | 601 | ATTTGGGACGAATGTATGCC | 64 | 81 |
| 147486 | Coding | 10 | 711 | AGTTGAGGAAGCCAGATTCA | N.D | 82 |
| 147487 | Coding | 10 | 964 | TTCCCAGTCAGCTTTAGTGG | 73 | 83 |
| 147488 | Coding | 10 | 1023 | AGCTTGCTTGTTGGGCACGG | 72 | 84 |
| 147489 | Coding | 10 | 1111 | CCTATACTGGCTTCTATGTT | 5 | 85 |
| 147490 | Coding | 10 | 1191 | TGAACTCCGTGTAAGGCAAG | N.D | 86 |
| 147491 | Coding | 10 | 1216 | GAGAAATCCTTCAGTAAGGG | 71 | 87 |
| 147492 | Coding | 10 | 1323 | CAATGGAATGCTTGTCACTG | 68 | 88 |
| 147493 | Coding | 10 | 1441 | GCTTCATTATAGGAGGTGGT | 41 | 89 |
| 147494 | Coding | 10 | 1531 | ACAACTGGGATAGTGTAGCC | 84 | 90 |
| 147495 | Coding | 10 | 1631 | GTTAGGACCAGGGATTGTGA | 0 | 91 |
| 147496 | Coding | 10 | 1691 | ACCATGGAAAACTGGCAACT | 19 | 92 |
| 147497 | Coding | 10 | 1721 | TGGGAGGAAAAACTTGAATA | N.D | 93 |
| 147498 | Coding | 10 | 1861 | TGGGCAACGATATCTGATTG | 0 | 94 |
| 147499 | Coding | 10 | 1901 | CTGCAGGGCGTCAGTGACAA | 29 | 95 |
| 147500 | Coding | 10 | 1932 | GCATCAGACGTGATGTTCCC | N.D | 96 |
| 147501 | Coding | 10 | 2021 | CTTGGTTAAACTAATGGTGC | 18 | 97 |
| 147502 | Coding | 10 | 2071 | ATGGGAGCATGGAGGTTGGC | 16 | 98 |
| 147503 | Coding | 10 | 2141 | AATGGATGATGAAACAGTGG | 26 | 99 |
| 147504 | Coding | 10 | 2201 | ATCAATGCCTCCTGTTGCAG | N.D | 100 |
| 147505 | Coding | 10 | 2231 | GGAAGTGAGACTTTCTAAGC | 76 | 101 |
| 147506 | Coding | 10 | 2281 | AGGAAGGAACTCTTGATATT | 58 | 102 |
| 147507 | Coding | 10 | 2321 | ATTGGCTTCATTGGCAACAC | 81 | 103 |

TABLE 3-continued

Inhibition of mouse apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 147759 | Coding | 10 | 1 | AGGTGAGGAAGTTGGAATTC | 19 | 104 |
| 147760 | Coding | 10 | 121 | TTGTTCCCTGAAGTTGTTAC | N.D | 105 |
| 147761 | Coding | 10 | 251 | GTTCATGGATTCCTTCAGGA | 45 | 106 |
| 147762 | Coding | 10 | 281 | ATGCTCCATTCTCACATGCT | 46 | 107 |
| 147763 | Coding | 10 | 338 | TGCGACTGTGTCTGATTTCC | 34 | 108 |
| 147764 | Coding | 10 | 541 | GTCCCTGAAGATGTCAATGC | 97 | 109 |
| 147765 | Coding | 10 | 561 | AGGCCCAGTTCCATGACCCT | 59 | 110 |
| 147766 | Coding | 10 | 761 | GGAGCCCACGTGCTGAGATT | 59 | 111 |
| 147767 | Coding | 10 | 801 | CGTCCTTGAGCAGTGCCCGA | 5 | 112 |
| 147768 | Coding | 10 | 1224 | CCCATATGGAGAAATCCTTC | 24 | 113 |
| 147769 | Coding | 10 | 1581 | CATGCCTGGAAGCCAGTGTC | 89 | 114 |
| 147770 | Coding | 10 | 1741 | GTGTTGAATCCCTTGAAATC | 67 | 115 |
| 147771 | Coding | 10 | 1781 | GGTAAAGTTGCCCATGGCTG | 68 | 116 |
| 147772 | Coding | 10 | 1041 | GTTATAAAGTCCAGCATTGG | 78 | 117 |
| 147773 | Coding | 10 | 1931 | CATCAGACGTGATGTTCCCT | 85 | 118 |
| 147774 | Coding | 10 | 1956 | TGGCTAGTTTCAATCCCCTT | 84 | 119 |
| 147775 | Coding | 10 | 2002 | CTGTCATGACTGCCCTTTAC | 52 | 120 |
| 147776 | Coding | 10 | 2091 | GCTTGAAGTTCATTGAGAAT | 92 | 121 |
| 147777 | Coding | 10 | 2291 | TTCCTGAGAAAGGAAGGAAC | N.D | 122 |
| 147778 | Coding | 10 | 2331 | TCAGATATACATTGGCTTCA | 14 | 123 |

As shown in Table 3, SEQ ID Nos 71, 74, 76, 78, 81, 83, 84, 87, 88, 90, 101, 102, 103, 109, 111, 111, 114, 115, 116, 117, 118, 119, 120 and 121 demonstrated at least 50% inhibition of mouse apolipoprotein B expression in this assay and are therefore preferred. The target sites to which these preferred sequences are complementary are herein referred to as "active sites" and are therefore preferred sites for targeting by compounds of the present invention.

Example 18

Antisense Inhibition Mouse Apolipoprotein B Expression by Chimeric Phosphorothioate Oligonucleotides Having 2'-MOE Wings and a Deoxy Gap—Dose Response Study In accordance with the present invention, a subset of the antisense oligonuclotides in Example 17 were further investigated in dose-response studies. Treatment doses were 50, 150 and 300 nM. The compounds were analyzed for their effect on mouse apolipoprotein B mRNA levels in primary hepatocytes cells by quantitative real-time PCR as described in other examples herein. Data are averages from two experiments and are shown in Table 4.

TABLE 4

Inhibition of mouse apolipoprotein B mRNA levels by chimeric phosphorothioate oligonucleotides having 2'-MOE wings and a deoxy gap

| | Percent Inhibition | | |
|---|---|---|---|
| ISIS # | 50 nM | 150 nM | 300 nM |
| 147483 | 56 | 88 | 89 |
| 147764 | 48 | 84 | 90 |
| 147769 | 3 | 14 | 28 |
| 147776 | 0 | 17 | 44 |

Example 19

Western Blot Analysis of Apolipoprotein B Protein Levels

Western blot analysis (immunoblot analysis) was carried out using standard methods. Cells were harvested 16-20 h after oligonucleotide treatment, washed once with PBS, suspended in Laemmli buffer (100 ul/well), boiled for 5 minutes and loaded on a 16% SDS-PAGE gel. Gels were run for 1.5 hours at 150 V, and transferred to membrane for western blotting. Appropriate primary antibody directed to apolipoprotein B was used, with a radiolabelled or fluorescently labeled secondary antibody directed against the primary antibody species. Bands were visualized using a PHOSPHO- RIMAGER™ (Molecular Dynamics, Sunnyvale Calif.) or the ECL+ chemiluminescent detection system (Amersham Biosciences, Piscataway, N.J.).

Example 20

Effects of Antisense Inhibition of Apolipoprotein B (ISIS 147764) in C57BL/6 mice: Lean Animals vs. High Fat Fed Animals.

C57BL/6 mice, a strain reported to be susceptible to hyperlipidemia-induced atherosclerotic plaque formation were used in the following studies to evaluate antisense oligonucleotides as potential lipid lowering compounds in lean versus high fat fed mice.

Male C57BL/6 mice were divided into two matched groups; (1) wild-type control animals (lean animals) and (2) animals receiving a high fat diet (60% kcal fat). Control animals received saline treatment and were maintained on a normal rodent diet. After overnight fasting, mice from each group were dosed intraperitoneally every three days with saline or 50 mg/kg ISIS 147764 (SEQ ID No: 109) for six weeks. At study termination and forty eight hours after the final injections, animals were sacrificed and evaluated for target mRNA levels in liver, cholesterol and triglyceride levels, liver enzyme levels and serum glucose levels.

The results of the comparative studies are shown in Table 5.

TABLE 5

Effects of ISIS 147764 treatment on apolipoprotein B mRNA, cholesterol, lipid, triglyceride, liver enzyme and glucose levels in lean and high fat mice.

| Treatment | Percent Change | | | | | | | | |
|---|---|---|---|---|---|---|---|---|---|
| | | | Lipoproteins | | | | Liver Enzymes | | |
| Group | mRNA | CHOL | VLDL | LDL | HDL | TRIG | AST | ALT | GLUC |
| Lean-control | −73 | −63 | No change | −64 | −44 | −34 | Slight decrease | No change | No change |
| High Fat Group | −87 | −67 | No change | −87 | −65 | No change | Slight decrease | Slight increase | −28 |

It is evident from these data that treatment with ISIS 147764 lowered cholesterol as well as LDL and HDL lipoproteins and serum glucose in both lean and high fat mice and that the effects demonstrated are, in fact, due to the inhibition of apolipoprotein B expression as supported by the decrease in mRNA levels. No significant changes in liver enzyme levels were observed, indicating that the antisense oligonucleotide was not toxic to either treatment group.

Example 21

Effects of Antisense Inhibition of Apolipoprotein B (ISIS 147764) on High Fat Fed Mice; 6 Week Timecourse Study In accordance with the present invention, a 6-week timecourse study was performed to further investigate the effects of ISIS 147764 on lipid and glucose metabolism in high fat fed mice.

Male C57BL/6 mice (n=8) receiving a high fat diet (60% kcal fat) were evaluated over the course of 6 weeks for the effects of treatment with the antisense oligonucleotide, ISIS 147764. Control animals received saline treatment (50 mg/kg). A subset of animals received a daily oral dose (20 mg/kg) atorvastatin calcium (Lipitor®, Pfizer Inc.). All mice, except atorvastatin-treated animals, were dosed intraperitoneally every three days (twice a week), after fasting overnight, with 5, 25, 50 mg/kg ISIS 147764 (SEQ ID No: 109) or saline (50 mg/kg) for six weeks. Serum cholesterol and lipoproteins were analyzed at 0, 2 and 6 week interim timepoints. At study termination, animals were sacrificed 48 hours after the final injections and evaluated for levels of target mRNA levels in liver, cholesterol, lipoprotein, triglyceride, liver enzyme (AST and ALT) and serum glucose levels as well as body, liver, spleen and fat pad weights.

Example 22

Effects of Antisense Inhibition of Apolipoprotein B (ISIS 147764) in High Fat Fed Mice—mRNA Expression in Liver Male C57BL/6 mice (n=8) receiving a high fat diet (60% kcal fat) were evaluated over the course of 6 weeks for the effects of ISIS 147764 on mRNA expression. Control animals received saline treatment (50 mg/kg). Mice were dosed intraperitoneally every three days (twice a week), after fasting overnight, with 5, 25, 50 mg/kg ISIS 147764 (SEQ ID No: 109) or saline (50 mg/kg) for six weeks. At study termination, animals were sacrificed 48 hours after the final injections and evaluated for levels of target mRNA levels in liver. ISIS 147764 showed a dose-response effect, reducing mRNA levels by 15, 75 and 88% at doses of 5, 25 and 50 mg/kg, respectively.

Liver protein samples collected at the end of the treatment period were subjected to immunoblot analysis using an antibody directed to mouse apolipoprotein B protein (Gladstone Institute, San Francisco, Calif.). These data demonstrate that treatment with ISIS 147764 decreases apolipoprotein B protein expression in liver in a dose-dependent manner, in addition to reducing mRNA levels.

Example 23

Effects of Antisense Inhibition of Apolipoprotein B (ISIS 147764) on Serum Cholesterol and Triglyceride Levels Male C57BL/6 mice (n=8) receiving a high fat diet (60% kcal fat) were evaluated over the course of 6 weeks for the effects of ISIS 147764 on serum cholesterol and triglyceride levels. Control animals received saline treatment (50 mg/kg). Mice were dosed intraperitoneally every three days (twice a week), after fasting overnight, with 5, 25, 50 mg/kg ISIS 147764 (SEQ ID No: 109) or saline (50 mg/kg) for six weeks.

Serum cholesterol levels were measured at 0, 2 and 6 weeks and this data is shown in Table 6. Values in the table are expressed as percent inhibition and are normalized to the saline control.

In addition to serum cholesterol, at study termination, animals were sacrificed 48 hours after the final injections and evaluated for triglyceride levels.

Mice treated with ISIS 147764 showed a reduction in both serum cholesterol (240 mg/dL for control animals and 225, 125 and 110 mg/dL for doses of 5, 25, and 50 mg/kg, respectively) and triglycerides (115 mg/dL for control animals and 125, 150 and 85 mg/dL for doses of 5, 25, and 50 mg/kg, respectively) to normal levels by study end. These data were also compared to the effects of atorvastatin calcium at an oral dose of 20 mg/kg which showed only a minimal decrease in serum cholesterol of 20 percent at study termination.

TABLE 6

Percent Inhibition of mouse apolipoprotein B cholesterol levels by ISIS 147764

| | Percent Inhibition | | | |
|---|---|---|---|---|
| time | Saline | 5 mg/kg | 25 mg/kg | 50 mg/kg |
| 0 weeks | 0 | 0 | 0 | 0 |
| 2 weeks | 0 | 5 | 12 | 20 |
| 6 weeks | 0 | 10 | 45 | 55 |

Example 24

Effects of Antisense Inhibition of Apolipoprotein B (ISIS 147764) on Lipoprotein Levels Male C57BL/6 mice (n=8) receiving a high fat diet (60% kcal fat) were evaluated over the course of 6 weeks for the effects of ISIS 147764 on lipoprotein (VLDL, LDL and HDL) levels. Control animals received saline treatment (50 mg/kg). Mice were dosed intraperitoneally every three days (twice a week), after fasting overnight, with 5, 25, 50 mg/kg ISIS 147764 (SEQ ID No: 109) or saline (50 mg/kg) for six weeks.

Lipoprotein levels were measured at 0, 2 and 6 weeks and this data is shown in Table 7. Values in the table are expressed as percent inhibition and are normalized to the saline control. Negative values indicate an observed increase in lipoprotein levels.

These data were also compared to the effects of atorvastatin calcium at a daily oral dose of 20 mg/kg at 0, 2 and 6 weeks.

These data demonstrate that at a dose of 50 mg/kg, ISIS 147764 is capable of lowering all categories of serum lipoproteins investigated to a greater extent than atorvastatin.

TABLE 7

Percent Inhibition of mouse apolipoprotein B lipoprotein levels by ISIS 147764 as compared to atorvastatin

| | | Percent Inhibition | | | | |
|---|---|---|---|---|---|---|
| | | Dose | | | | |
| Lipoprotein | Time (weeks) | Saline | 5 mg/kg | 25 mg/kg | 50 mg/kg | atorvastatin (20 mg/kg) |
| VLDL | 0 | 0 | 0 | 0 | 0 | 0 |
| | 2 | 0 | 25 | 30 | 40 | 15 |
| | 6 | 0 | 10 | −30 | 15 | −5 |
| LDL | 0 | 0 | 0 | 0 | 0 | 0 |
| | 2 | 0 | −30 | 10 | 40 | 10 |
| | 6 | 0 | −10 | 55 | 90 | −10 |
| HDL | 0 | 0 | 0 | 0 | 0 | 0 |
| | 2 | 0 | 5 | 10 | 10 | 15 |
| | 6 | 0 | 10 | 45 | 50 | 20 |

Example 25

Effects of Antisense Inhibition of Apolipoprotein B (ISIS 147764) on Serum AST and ALT Levels Male C57BL/6 mice (n=8) receiving a high fat diet (60% kcal fat) were evaluated over the course of 6 weeks for the effects of ISIS 147764 on liver enzyme (AST and ALT) levels. Increased levels of the liver enzymes ALT and AST indicate toxicity and liver damage. Control animals received saline treatment (50 mg/kg). Mice were dosed intraperitoneally every three days (twice a week), after fasting overnight, with 5, 25, 50 mg/kg ISIS 147764 (SEQ ID No: 109) or saline (50 mg/kg) for six weeks. AST and ALT levels were measured at 6 weeks.

Mice treated with ISIS 147764 showed no significant change in AST levels over the duration of the study compared to saline controls (105, 70 and 80 IU/L for doses of 5, 25 and 50 mg/kg, respectively compared to 65 IU/L for saline control). Mice treated with atorvastatin at a daily oral dose of 20 mg/kg had AST levels of 85 IU/L.

ALT levels were increased by all treatments with ISIS 147764 over the duration of the study compared to saline controls (50, 70 and 100 IU/L for doses of 5, 25 and 50 mg/kg, respectively compared to 25 IU/L for saline control). Mice treated with atorvastatin at a daily oral dose of 20 mg/kg had AST levels of 40 IU/L.

Example 26

Effects of Antisense Inhibition of Apolipoprotein B (ISIS 147764) on Serum Glucose Levels Male C57BL/6 mice (n=8) receiving a high fat diet (60% kcal fat) were evaluated over the course of 6 weeks for the effects of ISIS 147764 on serum glucose levels. Control animals received saline treatment (50 mg/kg). Mice were dosed intraperitoneally every three days (twice a week), after fasting overnight, with 5, 25, 50 mg/kg ISIS 147764 (SEQ ID No: 109) or saline (50 mg/kg) for six weeks.

At study termination, animals were sacrificed 48 hours after the final injections and evaluated for serum glucose levels. ISIS 147764 showed a dose-response effect, reducing serum glucose levels to 225, 190 and 180 mg/dL at doses of 5, 25 and 50 mg/kg, respectively compared to the saline control of 300 mg/dL. Mice treated with atorvastatin at a daily oral dose of 20 mg/kg had serum glucose levels of 215 mg/dL. These data demonstrate that ISIS 147764 is capable of reducing serum glucose levels in high fat fed mice.

Example 27

Effects of Antisense Inhibition of Apolipoprotein B (ISIS 147764) on Body, Spleen, Liver and Fat Pad Weight Male C57BL/6 mice (n=8) receiving a high fat diet (60% kcal fat) were evaluated over the course of 6 weeks for the effects of ISIS 147764 on body, spleen, liver and fat pad weight. Control animals received saline treatment (50 mg/kg). Mice were dosed intraperitoneally every three days (twice a week), after fasting overnight, with 5, 25, 50 mg/kg ISIS 147764 (SEQ ID No: 109) or saline (50 mg/kg) for six weeks.

At study termination, animals were sacrificed 48 hours after the final injections and body, spleen, liver and fat pad fights were measured. These data are shown in Table 8. Values are expressed as percent change in body weight or ogan weight compared to the saline-treated control animals. Data from mice treated with atorvastatin at a daily dose of 20 mg/kg are also shown in the table. Negative values indicated a decrease in weight.

TABLE 8

Effects of antisense inhibition of mouse apolipoprotein B on body and organ weight

| | Percent Change | | | |
|---|---|---|---|---|
| | Dose | | | Atorvastatin |
| Tissue | 5 mg/kg | 25 mg/kg | 50 mg/kg | 20 mg/kg |
| Total Body Wt. | 5 | 5 | −4 | 1 |
| Spleen | 10 | 10 | 46 | 10 |
| Liver | 18 | 70 | 80 | 15 |
| Fat | 10 | 6 | −47 | 7 |

These data show a decrease in fat over the dosage range of ISIS 147764 counterbalanced by an increase in both spleen and liver weight with increased dose to give an overall decrease in total body weight.

Example 28

Effects of Antisense Inhibition of Apolipoprotein B (ISIS 147764) in B6.129P-Apoe$^{tmlUnc}$ Knockout Mice: Lean Animals vs. High Fat Fed Animals.

B6.129P-ApoE$^{tml/Unc}$ knockout mice (herein referred to as ApoE knockout mice) obtained from The Jackson Laboratory (Bar Harbor, Me.), are homozygous for the Apoe$^{tml/Unc}$ mutation and show a marked increase in total plasma cholesterol levels that are unaffected by age or sex. These animals present with fatty streaks in the proximal aorta at 3 months of age. These lesions increase with age and progress to lesions with less lipid but more elongated cells, typical of a more advanced stage of pre-atherosclerotic lesion.

The mutation in these mice resides in the apolipoprotein E (ApoE) gene. The primary role of the ApoE protein is to transport cholesterol and triglycerides throughout the body. It stabilizes lipoprotein structure, binds to the low density lipoprotein receptor (LDLR) and related proteins, and is present in a subclass of HDLs, providing them the ability to bind to LDLR. ApoE is expressed most abundantly in the liver and brain. Female B6.129P-ApoetmlUnc knockout mice (ApoE knockout mice) were used in the following studies to evaluate antisense oligonucleotides as potential lipid lowering compounds.

Female ApoE knockout mice ranged in age from 5 to 7 weeks and were placed on a normal diet for 2 weeks before study initiation. ApoE knockout mice were then fed ad libitum a 60% fat diet, with 0.15% added cholesterol to induce dyslipidemia and obesity. Control animals were maintained on a high-fat diet with no added cholesterol. After overnight fasting, mice from each group were dosed intraperitoneally every three days with saline, 50 mg/kg of a control antisense oligonucleotide (ISIS 29837; TCGATCTCCTTTTATGCCCG; SEQ ID NO. 124) or 5, 25 or 50 mg/kg ISIS 147764 (SEQ ID No: 109) for six weeks.

The control oligonucleotide is a chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide. All cytidine residues are 5-methylcytidines.

At study termination and forty eight hours after the final injections, animals were sacrificed and evaluated for target mRNA levels in liver by RT-PCR methods verified by Northern Blot analysis, glucose levels, cholesterol and lipid levels by HPLC separation methods and triglyceride and liver enzyme levels (performed by LabCorp Preclinical Services; San Diego, Calif.). Data from ApoE knockout mice treated with atorvastatin at a daily dose of 20 mg/kg are also shown in the table for comparison.

The results of the comparative studies are shown in Table 9. Data are normalized to saline controls.

TABLE 9

Effects of ISIS 147764 treatment on apolipoprotein B mRNA, cholesterol, glucose, lipid, triglyceride and liver enzyme levels in ApoE knockout mice.

| | | Percent Inhibition | | | | |
|---|---|---|---|---|---|---|
| | | Dose | | | | |
| | | Control | 5 mg/kg | 25 mg/kg | 50 mg/kg | atorvastatin (20 mg/kg) |
| mRNA | | 0 | 2 | 42 | 70 | 10 |
| | | Glucose Levels (mg/dL) | | | | |
| Glucose | | 225 | 195 | 209 | 191 | 162 |
| | | Cholesterol Levels (mg/dL) | | | | |
| Cholesterol | | 1750 | 1630 | 1750 | 1490 | 938 |
| | | Lipoprotein Levels (mg/dL) | | | | |
| Lipoprotein | HDL | 51 | 49 | 62 | 61 | 42 |
| | LDL | 525 | 475 | 500 | 325 | 250 |
| | VLDL | 1190 | 1111 | 1194 | 1113 | 653 |
| | | Liver Enzyme Levels (IU/L) | | | | |
| Liver Enzymes | AST | 55 | 50 | 60 | 85 | 75 |
| | ALT | 56 | 48 | 59 | 87 | 76 |

It is evident from these data that treatment with ISIS 147764 lowered glucose and cholesterol as well as all lipoproteins investigated (HDL, LDL and VLDL) in ApoE knockout mice. Further, these decreases correlated with a decrease in both protein and RNA levels of apolipoprotein B, demonstrating an antisense mechanism of action. No significant changes in liver enzyme levels were observed, indicating that the antisense oligonucleotide was not toxic to either treatment group.

Example 29

Antisense Inhibition of Human Apolipoprotein B Expression by Chimeric Phosphorothioate Oligonucleotides Having 2'-MOE Wings and a Deoxy Gap: Additional Oligonucleotides In accordance with the present invention, another series of oligonucleotides was designed to target different regions of the human apolipoprotein B RNA, using published sequence (GenBank accession number NM_000384.1, incorporated herein as SEQ ID NO: 3). The oligonucleotides are shown in Table 10. "Target site" indicates the first (5'-most) nucleotide number on the particular target sequence to which the oligonucleotide binds. All compounds in Table 10 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide. All cytidine residues are 5-methylcytidines. The compounds were analyzed for their effect on human apolipoprotein B mRNA levels in HepG2 cells by quantitative real-time PCR as described in other examples herein. Data are averages from two experiments in which HepG2 cells were treated with 150 nM of the compounds in Table 10. If present, "N.D." indicates "no data".

TABLE 10

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 270965 | 5'UTR | 3 | 199 | TTCCTCTTCGGCCCTGGCGC | 75 | 124 |
| 270986 | coding | 3 | 299 | CTCCACTGGAACTCTCAGCC | 0 | 125 |
| 270997 | exon:exon junction | 3 | 359 | CCTCCAGCTCAACCTTGCAG | 0 | 126 |
| 270988 | coding | 3 | 429 | GGGTTGAAGCCATACACCTC | 6 | 127 |
| 270989 | exon:exon junction | 3 | 509 | CCAGCTTGAGCTCATACCTG | 64 | 128 |
| 270990 | coding | 3 | 584 | CCCTCTTGATGTTCAGGATG | 42 | 129 |
| 270991 | coding | 3 | 669 | GAGCAGTTTCCATACACGGT | 21 | 130 |
| 270992 | coding | 3 | 699 | CCCTTCCTCGTCTTGACGGT | 8 | 131 |
| 270993 | coding | 3 | 756 | TTGAAGCGATCACACTGCCC | 69 | 132 |
| 270994 | coding | 3 | 799 | GCCTTTGATGAGAGCAAGTG | 51 | 133 |
| 270995 | coding | 3 | 869 | TCCTCTTAGCGTCCAGTGTG | 40 | 134 |
| 270996 | coding | 3 | 1179 | CCTCTCAGCTCAGTAACCAG | 0 | 135 |
| 270997 | coding | 3 | 1279 | GCACTGAGGCTGTCCACACT | 24 | 136 |
| 270998 | coding | 3 | 1419 | CGCTGATCCCTCGCCATGTT | 1 | 137 |
| 270999 | coding | 3 | 1459 | GTTGACCGCGTGGCTCAGCG | 76 | 138 |
| 271000 | coding | 3 | 1499 | GCAGCTCCTGGGTCCCTGTA | 22 | 139 |
| 271001 | coding | 3 | 1859 | CCCATGGTAGAATTTGGACA | 53 | 140 |
| 271002 | exon:exon junction | 3 | 2179 | AATCTCGATGAGGTCAGCTG | 48 | 141 |
| 271003 | coding | 3 | 2299 | GACACCATCAGGAACTTGAC | 46 | 142 |
| 271004 | coding | 3 | 2459 | GCTCCTCTCCCAAGATGCGG | 10 | 143 |
| 271005 | coding | 3 | 2518 | GGCACCCATCAGAAGCAGCT | 32 | 144 |
| 271006 | coding | 3 | 2789 | AGTCCGGAATGATGATGCCC | 42 | 145 |
| 271007 | coding | 3 | 2919 | CTGAGCAGCTTGACTGGTCT | 26 | 146 |
| 271008 | coding | 3 | 3100 | CCCGGTCAGCGGATAGTAGG | 37 | 147 |
| 271010 | exon:exon junction | 3 | 3449 | TGTCACAACTTAGGTGGCCC | 57 | 148 |
| 271011 | coding | 3 | 3919 | GTCTGGCAATCCCATGTTCT | 51 | 149 |
| 271012 | coding | 3 | 4089 | CCCACAGACTTGAAGTGGAG | 55 | 150 |
| 271013 | coding | 3 | 4579 | GAACTGCCCATCAATCTTGA | 19 | 151 |
| 271014 | coding | 3 | 5146 | CCCAGAGAGGCCAAGCTCTG | 54 | 152 |
| 271015 | coding | 3 | 5189 | TGTGTTCCCTGAAGCGGCCA | 43 | 153 |
| 271016 | coding | 3 | 5269 | ACCCAGAATCATGGCCTGAT | 19 | 154 |
| 271017 | coding | 3 | 6049 | GGTGCCTGTCTGCTCAGCTG | 30 | 155 |

TABLE 10-continued

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 271018 | coding | 3 | 6520 | ATGTGAAACTTGTCTCTCCC | 44 | 156 |
| 271019 | coding | 3 | 6639 | TATGTCTGCAGTTGAGATAG | 15 | 157 |
| 271020 | coding | 3 | 6859 | TTGAATCCAGGATGCAGTAC | 35 | 158 |
| 271021 | coding | 3 | 7459 | GAGTCTCTGAGTCACCTCAC | 38 | 159 |
| 271022 | coding | 3 | 7819 | GATAGAATATTGCTCTGCAA | 100 | 160 |
| 271023 | coding | 3 | 7861 | CCCTTGCTCTACCAATGCTT | 44 | 161 |
| 271025 | coding | 3 | 8449 | TCCATTCCCTATGTCAGCAT | 16 | 162 |
| 271026 | coding | 3 | 8589 | GACTCCTTCAGAGCCAGCGG | 39 | 163 |
| 271027 | coding | 3 | 8629 | CCCATGCTCCGTTCTCAGGT | 26 | 164 |
| 271028 | coding | 3 | 8829 | CGCAGGTCAGCCTGACTAGA | 98 | 165 |
| 271030 | coding | 3 | 9119 | CAGTTAGAACACTGTGGCCC | 52 | 166 |
| 271031 | coding | 3 | 10159 | CAGTGTGATGACACTTGATT | 49 | 167 |
| 271032 | coding | 3 | 10301 | CTGTGGCTAACTTCAATCCC | 22 | 168 |
| 271033 | coding | 3 | 10349 | CAGTACTGTTATGACTACCC | 34 | 169 |
| 271034 | coding | 3 | 10699 | CACTGAAGACCGTGTGCTCT | 35 | 170 |
| 271035 | coding | 3 | 10811 | TCGTACTGTGCTCCCAGAGG | 23 | 171 |
| 271036 | coding | 3 | 10839 | AAGAGGCCCTCTAGCTGTAA | 95 | 172 |
| 271037 | coding | 3 | 11039 | AAGACCCAGAATGAATCCGG | 23 | 173 |
| 271038 | coding | 3 | 11779 | GTCTACCTCAAAGCGTGCAG | 29 | 174 |
| 271039 | coding | 3 | 11939 | TAGAGGCTAACGTACCATCT | 4 | 175 |
| 271041 | coding | 3 | 12149 | CCATATCCATGCCCACGGTG | 37 | 176 |
| 271042 | coding | 3 | 12265 | AGTTTCCTCATCAGATTCCC | 57 | 177 |
| 271043 | coding | 3 | 12380 | CCCAGTGGTACTTGTTGACA | 68 | 178 |
| 271044 | coding | 3 | 12526 | CCCAGTGGTGCCACTGGCTG | 22 | 179 |
| 271045 | coding | 3 | 12579 | GTCAACAGTTCCTGGTACAG | 19 | 180 |
| 271046 | coding | 3 | 12749 | CCCTAGTGTATATCCCAGGT | 61 | 181 |
| 271048 | coding | 3 | 13009 | CTGAAGATTACGTAGCACCT | 7 | 182 |
| 271049 | coding | 3 | 13299 | GTCCAGCCAACTATACTTGG | 54 | 183 |
| 271050 | coding | 3 | 13779 | CCTGGAGCAAGCTTCATGTA | 42 | 184 |
| 281586 | exon:exon junction | 3 | 229 | TGGACAGACCAGGCTGACAT | 80 | 185 |
| 281587 | coding | 3 | 269 | ATGTGTACTTCCGGAGGTGC | 77 | 186 |
| 281588 | coding | 3 | 389 | TCTTCAGGATGAAGCTGCAG | 80 | 187 |
| 281589 | coding | 3 | 449 | TCAGCAAGGCTTTGCCCTCA | 90 | 188 |
| 281590 | coding | 3 | 529 | CTGCTTCCCTTCTGGAATGG | 84 | 189 |
| 281591 | coding | 3 | 709 | TGCCACATTGCCCTTCCTCG | 90 | 190 |
| 281592 | coding | 3 | 829 | GCTGATCAGAGTTGACAAGG | 56 | 191 |
| 281593 | coding | 3 | 849 | TACTGACAGGACTGGCTGCT | 93 | 192 |

TABLE 10-continued

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 281594 | coding | 3 | 889 | GATGGCTTCTGCCACATGCT | 74 | 193 |
| 281595 | coding | 3 | 1059 | GATGTGGATTTGGTGCTCTC | 76 | 194 |
| 281596 | coding | 3 | 1199 | TGACTGCTTCATCACTGAGG | 77 | 195 |
| 281597 | coding | 3 | 1349 | GGTAGGTGACCACATCTATC | 36 | 196 |
| 281598 | coding | 3 | 1390 | TCGCAGCTGCTGTGCTGAGG | 70 | 197 |
| 281599 | exon:exon junction | 3 | 1589 | TTCCAATGACCCGCAGAATC | 74 | 198 |
| 281600 | coding | 3 | 1678 | GATCATCAGTGATGGCTTTG | 52 | 199 |
| 281601 | coding | 3 | 1699 | AGCCTGGATGGCAGCTTTCT | 83 | 200 |
| 281602 | coding | 3 | 1749 | GTCTGAAGAAGAACCTCCTG | 84 | 201 |
| 281603 | coding | 3 | 1829 | TATCTGCCTGTGAAGGACTC | 82 | 202 |
| 281604 | coding | 3 | 1919 | CTGAGTTCAAGATATTGGCA | 78 | 203 |
| 281605 | exon:exon junction | 3 | 2189 | CTTCCAAGCCAATCTCGATG | 82 | 204 |
| 281606 | coding | 3 | 2649 | TGCAACTGTAATCCAGCTCC | 86 | 205 |
| 281607 | exon:exon junction | 3 | 2729 | CCAGTTCAGCCTGCATGTTG | 84 | 206 |
| 281608 | coding | 3 | 2949 | GTAGAGACCAAATGTAATGT | 62 | 207 |
| 281609 | coding | 3 | 3059 | CGTTGGAGTAAGCGCCTGAG | 70 | 208 |
| 281610 | exon:exon junction | 3 | 3118 | CAGCTCTAATCTGGTGTCCC | 69 | 209 |
| 281611 | coding | 3 | 3189 | CTGTCCTCTCTCTGGAGCTC | 93 | 210 |
| 281612 | coding | 3 | 3289 | CAAGGTCATACTCTGCCGAT | 83 | 211 |
| 281613 | coding | 3 | 3488 | GTATGGAAATAACACCCTTG | 70 | 212 |
| 281614 | coding | 3 | 3579 | TAAGCTGTAGCAGATGAGTC | 63 | 213 |
| 281615 | coding | 3 | 4039 | TAGATCTCTGGAGGATTTGC | 81 | 214 |
| 281616 | coding | 3 | 4180 | GTCTAGAACACCCAGGAGAG | 66 | 215 |
| 281617 | coding | 3 | 4299 | ACCACAGAGTCAGCCTTCAT | 89 | 216 |
| 281618 | coding | 3 | 4511 | AAGCAGACATCTGTGGTCCC | 90 | 217 |
| 281619 | coding | 3 | 4660 | CTCTCCATTGAGCCGGCCAG | 96 | 218 |
| 281620 | coding | 3 | 4919 | CCTGATATTCAGAACGCAGC | 89 | 219 |
| 281621 | coding | 3 | 5009 | CAGTGCCTAAGATGTCAGCA | 53 | 220 |
| 281622 | coding | 3 | 5109 | AGCACCAGGAGACTACACTT | 88 | 221 |
| 281623 | coding | 3 | 5212 | CCCATCCAGACTGAATTTTG | 59 | 222 |
| 281624 | coding | 3 | 5562 | GGTTCTAGCCGTAGTTTCCC | 75 | 223 |
| 281625 | coding | 3 | 5589 | AGGTTACCAGCCACATGCAG | 94 | 224 |
| 281626 | coding | 3 | 5839 | ATGTGCATCGATGGTCATGG | 88 | 225 |
| 281627 | coding | 3 | 5869 | CCAGAGAGCGAGTTTCCCAT | 82 | 226 |
| 281628 | coding | 3 | 5979 | CTAGACACGAGATGATGACT | 81 | 227 |

TABLE 10-continued

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 281629 | coding | 3 | 6099 | TCCAAGTCCTGGCTGTATTC | 83 | 228 |
| 281630 | coding | 3 | 6144 | CGTCCAGTAAGCTCCACGCC | 82 | 229 |
| 281631 | coding | 3 | 6249 | TCAACGGCATCTCTCATCTC | 88 | 230 |
| 281632 | coding | 3 | 6759 | TGATAGTGCTCATCAAGACT | 75 | 231 |
| 281633 | coding | 3 | 6889 | GATTCTGATTTGGTACTTAG | 73 | 232 |
| 281634 | coding | 3 | 7149 | CTCTCGATTAACTCATGGAC | 81 | 233 |
| 281635 | coding | 3 | 7549 | ATACACTGCAACTGTGGCCT | 89 | 234 |
| 281636 | coding | 3 | 7779 | GCAAGAGTCCACCAATCAGA | 68 | 235 |
| 281637 | coding | 3 | 7929 | AGAGCCTGAAGACTGACTTC | 74 | 236 |
| 281638 | coding | 3 | 8929 | TCCCTCATCTGAGAATCTGG | 66 | 237 |
| 281640 | coding | 3 | 10240 | CAGTGCATCAATGACAGATG | 87 | 238 |
| 281641 | coding | 3 | 10619 | CCGAACCCTTGACATCTCCT | 72 | 239 |
| 281642 | coding | 3 | 10659 | GCCTCACTAGCAATAGTTCC | 59 | 240 |
| 281643 | coding | 3 | 10899 | GACATTTGCCATGGAGAGAG | 61 | 241 |
| 281644 | coding | 3 | 11209 | CTGTCTCCTACCAATGCTGG | 26 | 242 |
| 281645 | exon:exon junction | 3 | 11979 | TCTGCACTGAAGTCACGGTG | 78 | 243 |
| 281646 | coding | 3 | 12249 | TCCCGGACCCTCAACTCAGT | 76 | 244 |
| 281648 | 3'UTR | 3 | 13958 | GCAGGTCCAGTTCATATGTG | 81 | 245 |
| 281649 | 3'UTR | 3 | 14008 | GCCATCCTTCTGAGTTCAGA | 76 | 246 |
| 301012 | exon:exon junction | 3 | 3249 | GCCTCAGTCTGCTTCGCACC | 87 | 247 |
| 301013 | 5'UTR | 3 | 3 | CCCCGCAGGTCCCGGTGGGA | 82 | 248 |
| 301014 | 5'UTR | 3 | 6 | CAGCCCCGCAGGTCCCGGTG | 88 | 249 |
| 301015 | 5'UTR | 3 | 23 | CAACCGAGAAGGGCACTCAG | 53 | 250 |
| 301016 | 5'UTR | 3 | 35 | CCTCAGCGGCAGCAACCGAG | 62 | 251 |
| 301017 | 5'UTR | 3 | 36 | TCCTCAGCGGCAGCAACCGA | 47 | 252 |
| 301018 | 5'UTR | 3 | 37 | CTCCTCAGCGGCAGCAACCG | 45 | 253 |
| 301019 | 5'UTR | 3 | 39 | GGCTCCTCAGCGGCAGCAAC | 70 | 254 |
| 301020 | 5'UTR | 3 | 43 | GGCGGGCTCCTCAGCGGCAG | 85 | 255 |
| 301021 | 5'UTR | 3 | 116 | GGTCCATCGCCAGCTGCGGT | 89 | 256 |
| 301022 | Start Codon | 3 | 120 | GGCGGGTCCATCGCCAGCTG | 69 | 257 |
| 301023 | Stop Codon | 3 | 13800 | TAGAGGATGATAGTAAGTTC | 69 | 258 |
| 301024 | 3'UTR | 3 | 13824 | AAATGAAGATTTCTTTTAAA | 5 | 259 |
| 301025 | 3'UTR | 3 | 13854 | TATGTGAAAGTTCAATTGGA | 76 | 260 |
| 301026 | 3'UTR | 3 | 13882 | ATATAGGCAGTTTGAATTTT | 57 | 261 |
| 301027 | 3'UTR | 3 | 13903 | GCTCACTGTATGGTTTTATC | 89 | 262 |

TABLE 10-continued

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 301028 | 3'UTR | 3 | 13904 | GGCTCACTGTATGGTTTTAT | 93 | 263 |
| 301029 | 3'UTR | 3 | 13908 | GGCTGGCTCACTGTATGGTT | 90 | 264 |
| 301030 | 3'UTR | 3 | 13909 | AGGCTGGCTCACTGTATGGT | 90 | 265 |
| 301031 | 3'UTR | 3 | 13910 | AAGGCTGGCTCACTGTATGG | 90 | 266 |
| 301032 | 3'UTR | 3 | 13917 | CTACTGCAAGGCTGGCTCAC | 63 | 267 |
| 301033 | 3'UTR | 3 | 13922 | ACTGCCTACTGCAAGGCTGG | 77 | 268 |
| 301034 | 3'UTR | 3 | 13934 | TGCTTATAGTCTACTGCCTA | 88 | 269 |
| 301035 | 3'UTR | 3 | 13937 | TTCTGCTTATAGTCTACTGC | 82 | 270 |
| 301036 | 3'UTR | 3 | 13964 | TTTGGTGCAGGTCCAGTTCA | 88 | 271 |
| 301037 | 3'UTR | 3 | 13968 | CAGCTTTGGTGCAGGTCCAG | 90 | 272 |
| 301038 | 3'UTR | 3 | 13970 | GCCAGCTTTGGTGCAGGTCC | 86 | 273 |
| 301039 | 3'UTR | 3 | 13974 | TGGTGCCAGCTTTGGTGCAG | 73 | 274 |
| 301040 | 3'UTR | 3 | 13978 | GCCCTGGTGCCAGCTTTGGT | 74 | 275 |
| 301041 | 3'UTR | 3 | 13997 | GAGTTCAGAGACCTTCCGAG | 85 | 276 |
| 301042 | 3'UTR | 3 | 14012 | AAATGCCATCCTTCTGAGTT | 81 | 277 |
| 301043 | 3'UTR | 3 | 14014 | AAAAATGCCATCCTTCTGAG | 81 | 278 |
| 301044 | 3'UTR | 3 | 14049 | AAAATAACTCAGATCCTGAT | 76 | 279 |
| 301045 | 3'UTR | 3 | 14052 | AGCAAAATAACTCAGATCCT | 90 | 280 |
| 301046 | 3'UTR | 3 | 14057 | AGTTTAGCAAAATAACTCAG | 80 | 281 |
| 301047 | 3'UTR | 3 | 14064 | TCCCCCAAGTTTAGCAAAAT | 56 | 282 |
| 301048 | 3'UTR | 3 | 14071 | TTCCTCCTCCCCCAAGTTTA | 67 | 283 |
| 301217 | 3'UTR | 3 | 14087 | AGACTCCATTTATTTGTTCC | 81 | 284 |

Example 30

Antisense Inhibition of Apolipoprotein B—Gene Walk

In accordance with the present invention, a "gene walk" was conducted in which another series of oligonucleotides was designed to target the regions of the human apolipoprotein B RNA (GenBank accession number NM_000384.1, incorporated herein as SEQ ID NO: 3) which are near the target site of SEQ ID Nos 224 or 247. The oligonucleotides are shown in Table 11. "Target site" indicates the first (5'-most) nucleotide number on the particular target sequence to which the oligonucleotide binds. All compounds in Table 11 are chimeric oligonucleotides ("gapmers") 20 nucleotides in length, composed of a central "gap" region consisting often 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide. All cytidine residues are 5-methylcytidines. The compounds were analyzed for their effect on human apolipoprotein B mRNA levels in HepG2 cells by quantitative real-time PCR as described in other examples herein. Treatment doses were 50 nM and 150 nM and are indicated in Table 11. Data are averages from two experiments. If present, "N.D." indicates "no data".

TABLE 11

Inhibition of human apolipoprotein B mRNA levels by chimeric phosphorothioate oligonucleotides having 2'-MOE wings and a deoxy gap - Gene walk

| ISIS # | REGION | TARGET SEQ ID NO | TARGET SITE | SEQUENCE | % INHIB 150 nm | % INHIB 50 nm | SEQ ID NO |
|---|---|---|---|---|---|---|---|
| 308589 | exon:exon junction | 3 | 3230 | CTTCTGCTTGAGTTACAAAC | 94 | 20 | 285 |

TABLE 11-continued

Inhibition of human apolipoprotein B mRNA levels by chimeric phosphorothioate oligonucleotides having 2'-MOE wings and a deoxy gap - Gene walk

| ISIS # | REGION | TARGET SEQ ID NO | TARGET SITE | SEQUENCE | % INHIB 150 nm | % INHIB 50 nm | SEQ ID NO |
|---|---|---|---|---|---|---|---|
| 308590 | exon:exon junction | 3 | 3232 | ACCTTCTGCTTGAGTTACAA | 98 | 26 | 286 |
| 308591 | exon:exon junction | 3 | 3234 | GCACCTTCTGCTTGAGTTAC | 92 | 76 | 287 |
| 308592 | exon:exon junction | 3 | 3236 | TCGCACCTTCTGCTTGAGTT | 96 | 49 | 288 |
| 308593 | exon:exon junction | 3 | 3238 | CTTCGCACCTTCTGCTTGAG | 80 | 41 | 289 |
| 308594 | exon:exon junction | 3 | 3240 | TGCTTCGCACCTTCTGCTTG | 88 | 57 | 290 |
| 308595 | exon:exon junction | 3 | 3242 | TCTGCTTCGCACCTTCTGCT | 82 | 60 | 291 |
| 308596 | exon:exon junction | 3 | 3244 | AGTCTGCTTCGCACCTTCTG | 94 | 81 | 292 |
| 308597 | exon:exon junction | 3 | 3246 | TCAGTCTGCTTCGCACCTTC | 91 | 66 | 293 |
| 308598 | exon:exon junction | 3 | 3248 | CCTCAGTCTGCTTCGCACCT | 85 | 59 | 294 |
| 308599 | exon:exon junction | 3 | 3250 | AGCCTCAGTCTGCTTCGCAC | 94 | 79 | 295 |
| 308600 | coding | 3 | 3252 | GTAGCCTCAGTCTGCTTCGC | 89 | 72 | 296 |
| 308601 | coding | 3 | 3254 | TGGTAGCCTCAGTCTGCTTC | 91 | 63 | 297 |
| 308602 | coding | 3 | 3256 | CATGGTAGCCTCAGTCTGCT | 92 | 83 | 298 |
| 308603 | coding | 3 | 3258 | GTCATGGTAGCCTCAGTCTG | 97 | 56 | 299 |
| 308604 | coding | 3 | 3260 | ATGTCATGGTAGCCTCAGTC | 90 | 73 | 300 |
| 308605 | coding | 3 | 3262 | GAATGTCATGGTAGCCTCAG | 81 | 50 | 301 |
| 308606 | coding | 3 | 3264 | TTGAATGTCATGGTAGCCTC | 97 | 54 | 302 |
| 308607 | coding | 3 | 3266 | ATTTGAATGTCATGGTAGCC | 77 | 9 | 303 |
| 308608 | coding | 3 | 3268 | ATATTTGAATGTCATGGTAG | 85 | 70 | 304 |
| 308609 | coding | 3 | 5582 | CAGCCACATGCAGCTTCAGG | 96 | 78 | 305 |
| 308610 | coding | 3 | 5584 | ACCAGCCACATGCAGCTTCA | 90 | 40 | 306 |
| 308611 | coding | 3 | 5586 | TTACCAGCCACATGCAGCTT | 95 | 59 | 307 |
| 308612 | coding | 3 | 5588 | GGTTACCAGCCACATGCAGC | 90 | 75 | 308 |
| 308613 | coding | 3 | 5590 | TAGGTTACCAGCCACATGCA | 87 | 43 | 309 |
| 308614 | coding | 3 | 5592 | TTTAGGTTACCAGCCACATG | 92 | 74 | 310 |
| 308615 | coding | 3 | 5594 | CTTTTAGGTTACCAGCCACA | 85 | 45 | 311 |
| 308616 | coding | 3 | 5596 | TCCTTTTAGGTTACCAGCCA | 81 | 39 | 312 |
| 308617 | coding | 3 | 5598 | GCTCCTTTTAGGTTACCAGC | 87 | 77 | 313 |
| 308618 | coding | 3 | 5600 | AGGCTCCTTTTAGGTTACCA | 77 | 61 | 314 |
| 308619 | coding | 3 | 5602 | GTAGGCTCCTTTTAGGTTAC | 74 | 69 | 315 |
| 308620 | coding | 3 | 5604 | TGGTAGGCTCCTTTTAGGTT | 88 | 69 | 316 |
| 308621 | coding | 3 | 5606 | TTTGGTAGGCTCCTTTTAGG | 91 | 56 | 317 |

As shown in Tables 10 and 11, SEQ ID Nos 124, 128, 129, 132, 133, 134, 138, 140, 141, 142, 144, 145, 147, 148, 149, 150, 152, 153, 155, 156, 158, 159, 160, 161, 163, 165, 166, 167, 169, 170, 172, 176, 177, 178, 181, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 243, 244, 245, 246, 247, 248, 249, 250, 251, 252, 253, 254, 255, 256, 257, 258, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303. 304, 305, 306, 307, 308, 309, 310, 311, 312, 313, 314, 315, 316, and 317 demonstrated at least 30% inhibition of human apolipoprotein B expression in this assay and are therefore preferred. More preferred are SEQ ID Nos 224, 247, and 262. The target regions to which these preferred sequences are complementary are herein referred to as "preferred target segments" and are therefore preferred for targeting by compounds of the present invention. These preferred target segments are shown in Table 18. The sequences represent the reverse complement of the preferred antisense compounds shown in Tables 10 and 11. "Target site" indicates the first (5'-most) nucleotide number on the particular target nucleic acid to which the oligonucleotide binds. Also shown in Table 18 is the species in which each of the preferred target segments was found.

Example 31

Antisense Inhibition of Human Apolipoprotein B Expression by Chimeric Phosphorothioate Oligonucleotides Having 2'-MOE Wings and a Deoxy Gap: Targeting GenBank Accession Number M14162.1

In accordance with the present invention, another series of oligonucleotides was designed to target different regions of the human apolipoprotein B RNA, using published sequence (GenBank accession number M14162.1, incorporated herein as SEQ ID NO: 318). The oligonucleotides are shown in Table 12. "Target site" indicates the first (5'-most) nucleotide number on the particular target sequence to which the oligonucleotide binds. All compounds in Table 12 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide. All cytidine residues are 5-methylcytidines. The compounds were analyzed for their effect on human apolipoprotein B mRNA levels in HepG2 cells by quantitative real-time PCR as described in other examples herein. Data are averages from two experiments in which HepG2 cells were treated with 150 nM of the compounds in Table 12. If present, "N.D." indicates "no data".

TABLE 12

Inhibition of human apolipoprotein B mRNA levels by chimeric phosphorothioate oligonucleotides having 2'-MOE wings and a deoxy gap

| ISIS # REGION | TARGET SEQ ID NO | TARGET SITE | SEQUENCE | % INHIB | SEQ ID NO |
|---|---|---|---|---|---|
| 271009 coding | 318 | 3121 | GCCTCAGTCTGCTTCGCGCC | 75 | 319 |
| 271024 coding | 318 | 8031 | GCTCACTGTTCAGCATCTGG | 27 | 320 |
| 271029 coding | 318 | 8792 | TGAGAATCTGGGCGAGGCCC | N.D. | 321 |
| 271040 coding | 318 | 11880 | GTCCTTCATATTTGCCATCT | 0 | 322 |
| 271047 coding | 318 | 12651 | CCTCCCTCATGAACATAGTG | 32 | 323 |
| 281639 coding | 318 | 9851 | GACGTCAGAACCTATGATGG | 38 | 324 |
| 281647 coding | 318 | 12561 | TGAGTGAGTCAATCAGCTTC | 73 | 325 |

Example 32

Antisense Inhibition of Human Apolipoprotein B—Gene Walk Targeting GenBank Accession Number M14162.1

In accordance with the present invention, a "gene walk" was conducted in which another series of oligonucleotides was designed to target the regions of the human apolipoprotein B RNA (GenBank accession number M14162.1, incorporated herein as SEQ ID NO: 318) which are near the target site of SEQ ID NO: 319. The oligonucleotides are shown in Table 13. "Target site" indicates the first (5'-most) nucleotide number on the particular target sequence to which the oligonucleotide binds. All compounds in Table 13 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide. All cytidine residues are 5-methylcytidines. The compounds were analyzed for their effect on human apolipoprotein B mRNA levels in HepG2 cells by quantitative real-time PCR as described in other examples herein. Treatment doses were 50 nM and 150 nM and are indicated in Table 13. Data are averages from two experiments. If present, "N.D." indicates "no data".

TABLE 13

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB 150 nm | % INHIB 50 nm | SEQ ID NO |
|---|---|---|---|---|---|---|---|
| 308622 | coding | 318 | 3104 | GCCTTCTGCTTGAGTTACAA | 87 | 25 | 326 |
| 308623 | coding | 318 | 3106 | GCGCCTTCTGCTTGAGTTAC | 71 | 62 | 327 |
| 308624 | coding | 318 | 3108 | TCGCGCCTTCTGCTTGAGTT | 89 | 69 | 328 |
| 308625 | coding | 318 | 3110 | CTTCGCGCCTTCTGCTTGAG | 83 | 64 | 329 |
| 308626 | coding | 318 | 3116 | AGTCTGCTTCGCGCCTTCTG | 94 | 38 | 330 |
| 308627 | coding | 318 | 3118 | TCAGTCTGCTTCGCGCCTTC | 89 | 67 | 331 |
| 308628 | coding | 318 | 3120 | CCTCAGTCTGCTTCGCGCCT | 92 | 61 | 332 |
| 308629 | coding | 318 | 3122 | AGCCTCAGTCTGCTTCGCGC | 95 | 77 | 333 |

As shown in Tables 12 and 13, SEQ ID Nos 319, 323, 324, 325, 326, 327, 328, 329, 330, 331, 332, and 333 demonstrated at least 30% inhibition of human apolipoprotein B expression in this assay and are therefore preferred. More preferred is SEQ ID NO: 319. The target regions to which these preferred sequences are complementary are herein referred to as "preferred target segments" and are therefore preferred for targeting by compounds of the present invention. These preferred target segments are shown in Table 18. The sequences represent the reverse complement of the preferred antisense compounds shown in Tables 12 and 13. "Target site" indicates the first (5'-most) nucleotide number on the particular target nucleic acid to which the oligonucleotide binds. Also shown in Table 18 is the species in which each of the preferred target segments was found.

Example 33

Antisense Inhibition of Human Apolipoprotein B Expression by Chimeric Phosphorothioate Oligonucleotides Having 2'-MOE Wings and a Deoxy Gap—Targeting the Genomic Sequence In accordance with the present invention, another series of oligonucleotides was designed to target different regions of the human apolipoprotein B RNA, using published sequence (the complement of nucleotides 39835 to 83279 of the sequence with GenBank accession number NT_022227.9, representing a genomic sequence, incorporated herein as SEQ ID NO: 334). The oligonucleotides are shown in Table 14. "Target site" indicates the first (5'-most) nucleotide number on the particular target sequence to which the oligonucleotide binds. All compounds in Table 14 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of2'-methoxyethyl (2'-MOE)nucleotides. The internucleoside (backbone) linkages are phosphorothioate (P═S) throughout the oligonucleotide. All cytidine residues are 5-methylcytidines. The compounds were analyzed for their effect on human apolipoprotein B mRNA levels in HepG2 cells by quantitative real-time PCR as described in other examples herein. Data are averages from two experiments in which HepG2 cells were treated with 150 nM of the oligonucleotides in Table 14. If present, "N.D." indicates "no data".

TABLE 14

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 301049 | intron:exon junction | 334 | 904 | TCTGTAAGACAGGAGAAAGA | 41 | 335 |
| 301050 | intron:exon junction | 334 | 913 | ATTTCCTCTTCTGTAAGACA | 22 | 336 |
| 301051 | exon:intron junction | 334 | 952 | GATGCCTTACTTGGACAGAC | 27 | 337 |
| 301052 | intron | 334 | 1945 | AGAAATAGCTCTCCCAAGGA | 13 | 338 |
| 301053 | intron:exon junction | 334 | 1988 | GTCGCATCTTCTAACGTGGG | 45 | 339 |
| 301054 | exon:intron junction | 334 | 2104 | TCCTCCATACCTTGCAGTTG | 0 | 340 |
| 301055 | intron | 334 | 2722 | TGGCTCATGTCTACCATATT | 49 | 341 |
| 301056 | intron | 334 | 2791 | CAGTTGAAATGCAGCTAATG | 35 | 342 |
| 301057 | intron | 334 | 3045 | TGCAGACTAGGAGTGAAAGT | 30 | 343 |
| 301058 | intron | 334 | 3117 | AGGAGGATGTCCTTTTATTG | 27 | 344 |

TABLE 14-continued

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 301059 | intron | 334 | 3290 | ATCAGAGCACCAAAGGGAAT | 12 | 345 |
| 301060 | intron:exon junction | 334 | 3381 | CCAGCTCAACCTGAGAATTC | 17 | 346 |
| 301061 | exon:intron junction | 334 | 3527 | CATGACTTACCTGGACATGG | 52 | 347 |
| 301062 | intron | 334 | 3566 | CCTCAGCGGACACACACACA | 21 | 348 |
| 301063 | intron | 334 | 3603 | GTCACATCCGTGCCTGGTGC | 41 | 349 |
| 301064 | intron | 334 | 3864 | CAGTGCCTCTGGGACCCCAC | 60 | 350 |
| 301065 | intron | 334 | 3990 | AGCTGCAGTGGCCGATCAGC | 50 | 351 |
| 301066 | intron | 334 | 4251 | GACCTCCCCAGCCACGTGGA | 61 | 352 |
| 301067 | intron | 334 | 4853 | TCTGATCACCATACATTACA | 45 | 353 |
| 301068 | intron | 334 | 5023 | ATTTCCCACTGGGTACTCTC | 44 | 354 |
| 301069 | intron | 334 | 5055 | GGCTGAAGCCCATGCTGACT | 44 | 355 |
| 301070 | intron | 334 | 5091 | GTTGGACAGTCATTCTTTTG | 38 | 356 |
| 301071 | intron | 334 | 5096 | CACTTGTTGGACAGTCATTC | 48 | 357 |
| 301072 | intron | 334 | 5301 | ATTTTAAATTACAGTAGATA | 43 | 358 |
| 301073 | intron | 334 | 5780 | CTGTTCTCCACCCATATCAG | 37 | 359 |
| 301074 | intron:exon junction | 334 | 6353 | GAGCTCATACCTGTCCCAGA | 75 | 360 |
| 301075 | intron | 334 | 6534 | TTCAAGGGCCACTGCTATCA | 52 | 361 |
| 301076 | intron | 334 | 6641 | CCAGTATTTCACGCCAATCC | 36 | 362 |
| 301077 | intron | 334 | 6661 | GGCAGGAGGAACCTCGGGCA | 55 | 363 |
| 301078 | intron | 334 | 6721 | TTTTAAAATTAGACCCAACC | 22 | 364 |
| 301079 | intron | 334 | 6727 | TGACTGTTTTAAAATTAGAC | 20 | 365 |
| 301080 | intron | 334 | 6788 | CCCAGCAAACACAGGTGAAG | 25 | 366 |
| 301081 | intron | 334 | 7059 | GAGTGTGGTCTTGCTAGTGC | 46 | 367 |
| 301082 | intron | 334 | 7066 | CTATGCAGAGTGTGGTCTTG | 41 | 368 |
| 301083 | intron | 334 | 7189 | AGAAGATGCAACCACATGTA | 29 | 369 |
| 301084 | intron:exon junction | 334 | 7209 | ACACGGTATCCTATGGAGGA | 49 | 370 |
| 301085 | exon:intron junction | 334 | 7365 | TGGGACTTACCATGCCTTTG | 11 | 371 |
| 301086 | intron | 334 | 7702 | GGTTTTGCTGCCCTACATCC | 30 | 372 |
| 301087 | intron | 334 | 7736 | ACAAGGAGTCCTTGTGCAGA | 40 | 373 |
| 301088 | intron | 334 | 8006 | ATGTTCACTGAGACAGGCTG | 41 | 374 |
| 301089 | intron | 334 | 8215 | GAAGGTCCATGGTTCATCTG | 0 | 375 |
| 301090 | intron | 334 | 8239 | ATTAGACTGGAAGCATCCTG | 39 | 376 |
| 301091 | intron | 334 | 8738 | GAGATTGGAGACGAGCATTT | 35 | 377 |
| 301092 | exon:intron junction | 334 | 8881 | CATGACCTACTTGTAGGAGA | 22 | 378 |
| 301093 | intron | 334 | 9208 | TGGATTTGGATACACAAGTT | 42 | 379 |
| 301094 | intron | 334 | 9244 | ACTCAATATATATTCATTGA | 22 | 380 |
| 301095 | intron | 334 | 9545 | CAAGGAAGCACACCATGTCA | 38 | 381 |

TABLE 14-continued

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 301096 | intron:exon junction | 334 | 9563 | ATACTTATTCCTGGTAACCA | 24 | 382 |
| 301097 | intron | 334 | 9770 | GGTAGCCAGAACACCAGTGT | 50 | 383 |
| 301098 | intron | 334 | 9776 | ACTAGAGGTAGCCAGAACAC | 34 | 384 |
| 301099 | intron | 334 | 10149 | ACCACCTGACATCACAGGTT | 24 | 385 |
| 301100 | intron | 334 | 10341 | TACTGTGACCTATGCCAGGA | 55 | 386 |
| 301101 | intron | 334 | 10467 | GGAGGTGCTACTGTTGACAT | 42 | 387 |
| 301102 | intron | 334 | 10522 | TCCAGACTTGTCTGAGTCTA | 47 | 388 |
| 301103 | intron | 334 | 10547 | TCTAAGAGGTAGAGCTAAAG | 7 | 389 |
| 301104 | intron | 334 | 10587 | CCAGAGATGAGCAACTTAGG | 38 | 390 |
| 301105 | intron | 334 | 10675 | GGCCATGTAAATTGCTCATC | 7 | 391 |
| 301106 | intron | 334 | 10831 | AAAGAAACTATCCTGTATTC | 12 | 392 |
| 301107 | intron:exon junction | 334 | 10946 | TTCTTAGTACCTGGAAGATG | 23 | 393 |
| 301108 | exon:intron junction | 334 | 11166 | CATTAGATACCTGGACACCT | 29 | 394 |
| 301109 | intron | 334 | 11337 | GTTTCATGGAACTCAGCGCA | 44 | 395 |
| 301110 | intron | 334 | 11457 | CTGGACAGCACCTGCAATAG | 35 | 396 |
| 301111 | intron | 334 | 11521 | TGAAGGGTAGAGAAATCATA | 9 | 397 |
| 301112 | exon:intron junction | 334 | 12111 | GGAAACTCACTTGTTGACCG | 25 | 398 |
| 301113 | intron | 334 | 12155 | AGGTGCAAGATGTTCCTCTG | 46 | 399 |
| 301114 | intron | 334 | 12162 | TGCACAGAGGTGCAAGATGT | 16 | 400 |
| 301115 | intron | 334 | 12221 | CACAAGAGTAAGGAGCAGAG | 39 | 401 |
| 301116 | intron | 334 | 12997 | GATGGATGGTGAGAAATTAC | 33 | 402 |
| 301117 | intron | 334 | 13025 | TAGACAATTGAGACTCAGAA | 39 | 403 |
| 301118 | intron | 334 | 13057 | ATGTGCACACAAGGACATAG | 33 | 404 |
| 301119 | intron | 334 | 13634 | ACATACAAATGGCAATAGGC | 33 | 405 |
| 301120 | intron | 334 | 13673 | TAGGCAAAGGACATGAATAG | 30 | 406 |
| 301121 | coding | 334 | 14448 | TTATGATAGCTACAGAATAA | 29 | 407 |
| 301122 | exon:intron junction | 334 | 14567 | CTGAGATTACCCGCAGAATC | 32 | 408 |
| 301123 | intron | 334 | 14587 | GATGTATGTCATATAAAAGA | 26 | 409 |
| 301124 | intron:exon junction | 334 | 14680 | TTTCCAATGACCTGCATTGA | 48 | 410 |
| 301125 | intron | 334 | 15444 | AGGGATGGTCAATCTGGTAG | 57 | 411 |
| 301126 | intron | 334 | 15562 | GGCTAATAAATAGGGTAGTT | 22 | 412 |
| 301127 | intron | 334 | 15757 | TCCTAGAGCACTATCAAGTA | 41 | 413 |
| 301128 | intron:exon junction | 334 | 15926 | CCTCCTGGTCCTGCAGTCAA | 56 | 414 |
| 301129 | intron | 334 | 16245 | CATTTGCACAAGTGTTTGTT | 35 | 415 |
| 301130 | intron | 334 | 16363 | CTGACACACCATGTTATTAT | 10 | 416 |
| 301131 | intron:exon junction | 334 | 16399 | CTTTTTCAGACTAGATAAGA | 0 | 417 |

TABLE 14-continued

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 301132 | exon:intron junction | 334 | 16637 | TCACACTTACCTCGATGAGG | 29 | 418 |
| 301133 | intron | 334 | 17471 | AAGAAAATGGCATCAGGTTT | 13 | 419 |
| 301134 | intron:exon junction | 334 | 17500 | CCAAGCCAATCTGAGAAAGA | 25 | 420 |
| 301135 | exon:intron junction | 334 | 17677 | AAATACACACCTGCTCATGT | 20 | 421 |
| 301136 | exon:intron junction | 334 | 17683 | CTTCACAAATACACACCTGC | 20 | 422 |
| 301137 | intron | 334 | 18519 | AGTGGAAGTTTGGTCTCATT | 41 | 423 |
| 301138 | intron | 334 | 18532 | TTGCTAGCTTCAAAGTGGAA | 44 | 424 |
| 301139 | intron | 334 | 18586 | TCAAGAATAAGCTCCAGATC | 41 | 425 |
| 301140 | intron | 334 | 18697 | GCATACAAGTCACATGAGGT | 34 | 426 |
| 301141 | intron | 334 | 18969 | TACAAGGTGTTTCTTAAGAA | 38 | 427 |
| 301142 | intron | 334 | 19250 | ATGCAGCCAGGATGGGCCTA | 54 | 428 |
| 301143 | intron:exon junction | 334 | 19340 | TTACCATATCCTGAGAGTTT | 55 | 429 |
| 301144 | intron | 334 | 19802 | GCAAAGGTAGAGGAAGGTAT | 32 | 430 |
| 301145 | intron | 334 | 19813 | AAGGACCTTCAGCAAAGGTA | 36 | 431 |
| 301146 | intron | 334 | 20253 | CATAGGAGTACATTTATATA | 23 | 432 |
| 301147 | intron | 334 | 20398 | ATTATGATAAAATCAATTTT | 19 | 433 |
| 301148 | intron | 334 | 20567 | AGAAATTTCACTAGATAGAT | 31 | 434 |
| 301149 | intron | 334 | 20647 | AGCATATTTTGATGAGCTGA | 44 | 435 |
| 301150 | intron | 334 | 20660 | GAAAGGAAGGACTAGCATAT | 39 | 436 |
| 301151 | intron:exon junction | 334 | 20772 | CCTCTCCAATCTGTAGACCC | 28 | 437 |
| 301152 | intron | 334 | 21316 | CTGGATAACTCAGACCTTTG | 40 | 438 |
| 301153 | intron | 334 | 21407 | AGTCAGAAAACAACCTATTC | 11 | 439 |
| 301154 | intron:exon junction | 334 | 21422 | CAGCCTGCATCTATAAGTCA | 31 | 440 |
| 301155 | exon:intron junction | 334 | 21634 | AAAGAATTACCCTCCACTGA | 33 | 441 |
| 301156 | intron | 334 | 21664 | TCTTTCAAACTGGCTAGGCA | 39 | 442 |
| 301157 | intron | 334 | 21700 | GCCTGGCAAAATTCTGCAGG | 37 | 443 |
| 301158 | intron | 334 | 22032 | CTACCTCAAATCAATATGTT | 28 | 444 |
| 301159 | intron | 334 | 22048 | TGCTTTACCTACCTAGCTAC | 36 | 445 |
| 301160 | intron | 334 | 22551 | ACCTTGTGTGTCTCACTCAA | 49 | 446 |
| 301161 | intron | 334 | 22694 | ATGCATTCCCTGACTAGCAC | 34 | 447 |
| 301162 | intron | 334 | 22866 | CATCTCTGAGCCCCTTACCA | 24 | 448 |
| 301163 | intron | 334 | 22903 | GCTGGGCATGCTCTCTCCCC | 51 | 449 |
| 301164 | intron | 334 | 22912 | GCTTTCGCAGCTGGGCATGC | 55 | 450 |
| 301165 | intron | 334 | 23137 | ACTCCTTTCTATACCTGGCT | 47 | 451 |
| 301166 | intron | 334 | 23170 | ATTCTGCCTCTTAGAAAGTT | 38 | 452 |
| 301167 | intron | 334 | 23402 | CCAAGCCTCTTTACTGGGCT | 29 | 453 |
| 301168 | intron | 334 | 23882 | CACTCATGACCAGACTAAGA | 35 | 454 |

TABLE 14-continued

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 301169 | intron | 334 | 23911 | ACCTCCCAGAAGCCTTCCAT | 22 | 455 |
| 301170 | intron | 334 | 24184 | TTCATATGAAATCTCCTACT | 40 | 456 |
| 301171 | intron | 334 | 24425 | TATTTAATTTACTGAGAAAC | 7 | 457 |
| 301172 | intron:exon junction | 334 | 24559 | TAATGTGTTGCTGGTGAAGA | 35 | 458 |
| 301173 | exon:intron junction | 334 | 24742 | CATCTCTAACCTGGTGTCCC | 21 | 459 |
| 301174 | intron | 334 | 24800 | GTGCCATGCTAGGTGGCCAT | 37 | 460 |
| 301175 | intron | 334 | 24957 | AGCAAATTGGGATCTGTGCT | 29 | 461 |
| 301176 | intron | 334 | 24991 | TCTGGAGGCTCAGAAACATG | 57 | 462 |
| 301177 | intron | 334 | 25067 | TGAAGACAGGGAGCCACCTA | 40 | 463 |
| 301178 | intron | 334 | 25152 | AGGATTCCCAAGACTTTGGA | 38 | 464 |
| 301179 | intron:exon junction | 334 | 25351 | CAGCTCTAATCTAAAGACAT | 22 | 465 |
| 301180 | exon:intron junction | 334 | 25473 | GAATACTCACCTTCTGCTTG | 6 | 466 |
| 301181 | intron | 334 | 26047 | ATCTCTCTGTCCTCATCTTC | 28 | 467 |
| 301182 | intron | 334 | 26749 | CCAACTCCCCCTTTCTTTGT | 37 | 468 |
| 301183 | intron | 334 | 26841 | TCTGGGCCAGGAAGACACGA | 68 | 469 |
| 301184 | intron | 334 | 27210 | TATTGTGTGCTGGGCACTGC | 52 | 470 |
| 301185 | intron:exon junction | 334 | 27815 | TGCTTCGCACCTGGACGAGT | 51 | 471 |
| 301186 | exon:intron junction | 334 | 28026 | CCTTCTTTACCTTAGGTGGC | 37 | 472 |
| 301187 | intron | 334 | 28145 | GCTCTCTCTGCCACTCTGAT | 47 | 473 |
| 301188 | intron | 334 | 28769 | AACTTCTAAAGCCAACATTC | 27 | 474 |
| 301189 | intron:exon junction | 334 | 28919 | TGTGTCACAACTATGGTAAA63 | 475 | |
| 301190 | exon:intron junction | 334 | 29095 | AGACACATACCATAATGCCA | 22 | 476 |
| 301191 | intron:exon junction | 334 | 29204 | TTCTCTTCATCTGAAAATAC | 21 | 477 |
| 301192 | intron | 334 | 29440 | TGAGGATGTAATTAGCACTT | 27 | 478 |
| 301193 | intron:exon junction | 334 | 29871 | AGCTCATTGCCTACAAAATG | 31 | 479 |
| 301194 | intron | 334 | 30181 | GTTCTCATGTTTACTAATGC | 40 | 480 |
| 301195 | intron | 334 | 30465 | GAATTGAGACAACTTGATTT | 26 | 481 |
| 301196 | intron:exon junction | 334 | 30931 | CCGGCCATCGCTGAAATGAA | 54 | 482 |
| 301197 | exon:intron junction | 334 | 31305 | CATAGCTCACCTTGCACATT | 28 | 483 |
| 301198 | intron | 334 | 31325 | CGGTGCACCCTTTACCTGAG | 28 | 484 |
| 301199 | intron:exon junction | 334 | 31813 | TCTCCAGATCCTAACATAAA | 19 | 485 |
| 301200 | intron | 334 | 39562 | TTGAATGACACTAGATTTTC | 37 | 486 |

TABLE 14-continued

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 301201 | intron | 334 | 39591 | AAAATCCATTTTCTTTAAAG | 12 | 487 |
| 301202 | intron | 334 | 39654 | CAGCTCACACTTATTTTAAA | 7 | 488 |
| 301203 | intron:exon junction | 334 | 39789 | GTTCCCAAAACTGTATAGGA | 36 | 489 |
| 301204 | exon:intron junction | 334 | 39904 | AGCTCCATACTGAAGTCCTT | 37 | 490 |
| 301205 | intron | 334 | 39916 | CAATTCAATAAAAGCTCCAT | 31 | 491 |
| 301206 | intron | 334 | 39938 | GTTTTCAAAAGGTATAAGGT | 28 | 492 |
| 301207 | intron:exon junction | 334 | 40012 | TTCCCATTCCCTGAAAGCAG | 13 | 493 |
| 301208 | exon:intron junction | 334 | 40196 | TGGTATTTACCTGAGGGCTG | 21 | 494 |
| 301209 | intron | 334 | 40412 | ATAAATAATAGTGCTGATGG | 39 | 495 |
| 301210 | intron | 334 | 40483 | CTATGGCTGAGCTTGCCTAT | 33 | 496 |
| 301211 | intron | 334 | 40505 | CTCTCTGAAAAATATACCCT | 17 | 497 |
| 301212 | intron | 334 | 40576 | TTGATGTATCTCATCTAGCA | 41 | 498 |
| 301213 | intron | 334 | 40658 | TAGAACCATGTTTGGTCTTC | 35 | 499 |
| 301214 | intron | 334 | 40935 | TTTCTCTTTATCACATGCCC | 29 | 500 |
| 301215 | intron | 334 | 41066 | TATAGTACACTAAAACTTCA | 1 | 501 |
| 301216 | intron:exon junction | 334 | 41130 | CTGGAGAGGACTAAACAGAG | 49 | 502 |

As shown in Table 14, SEQ ID Nos 335, 339, 341, 342, 343, 347, 349, 350, 351, 352, 353, 354, 355, 356, 357, 358, 359, 360, 361, 362, 363, 367, 368, 370, 372, 373, 374, 376, 377, 379, 381, 383, 384, 386, 387, 388, 390, 395, 396, 399, 401, 402, 403, 404, 405, 406, 408, 410, 411, 413, 414, 415, 423, 424, 425, 426, 427, 428, 429, 430, 431, 434, 435, 436, 438, 440, 441, 442, 443, 445, 446, 447, 449, 450, 451, 452, 454, 456, 458, 460, 462, 463, 464, 468, 469, 470, 471, 472, 473, 475, 479, 480, 482, 486, 489, 490, 491, 495, 496, 498, 499, and 502 demonstrated at least 30% inhibition of human apolipoprotein B expression in this assay and are therefore preferred. The target regions to which these preferred sequences are complementary are herein referred to as "preferred target segments" and are therefore preferred for targeting by compounds of the present invention. These preferred target segments are shown in Table 18. The sequences represent the reverse complement of the preferred antisense compounds shown in Table 14. "Target site" indicates the first (5'-most) nucleotide number on the particular target nucleic acid to which the oligonucleotide binds. Also shown in Table 18 is the species in which each of the preferred target segments was found.

Example 34

Antisense Inhibition of Human Apolipoprotein B Expression by Chimeric Phosphorothioate Oligonucleotides Having 2'-MOE Wings and a Deoxy Gap—Targeting GenBank Accession Number In accordance with the present invention, another series of oligonucleotides was designed to target different regions of the human apolipoprotein B RNA, using published sequence (the complement of the sequence with GenBank accession number AI249040.1, incorporated herein as SEQ ID NO: 503). The oligonucleotides are shown in Table 15. "Target site" indicates the first (5'-most) nucleotide number on the particular target sequence to which the oligonucleotide binds. All compounds in Table 15 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide. All cytidine residues are 5-methylcytidines. The compounds were analyzed for their effect on human apolipoprotein B mRNA levels in HepG2 cells by quantitative real-time PCR as described in other examples herein. Data are averages from two experiments in which HepG2 cells were treated with 150 nM of the oligonucleotides in Table 15. If present, "N.D." indicates "no data".

TABLE 15

Inhibition of human apolipoprotein B mRNA levels by chimeric phosphorothioate oligonucleotides having 2'-MOE wings and a deoxy gap

| ISIS # REGION | TARGET SEQ ID NO | TARGET SITE | SEQUENCE | % INHIB | SEQ ID NO |
|---|---|---|---|---|---|
| 301218 3'UTR | 503 | 484 | ACATTTTATCAATGCCCTCG | 23 | 504 |
| 301219 3'UTR | 503 | 490 | GCCAGAACATTTTATCAATG | 35 | 505 |
| 301220 3'UTR | 503 | 504 | AGAGGTTTTGCTGTGCCAGA | 51 | 506 |
| 301221 3'UTR | 503 | 506 | CTAGAGGTTTTGCTGTGCCA | 61 | 507 |
| 301222 3'UTR | 503 | 507 | TCTAGAGGTTTTGCTGTGCC | 14 | 508 |
| 301223 3'UTR | 503 | 522 | AATCACACTATGTGTTCTAG | 26 | 509 |
| 301224 3'UTR | 503 | 523 | AAATCACACTATGTGTTCTA | 33 | 510 |
| 301225 3'UTR | 503 | 524 | TAAATCACACTATGTGTTCT | 3 | 511 |
| 301226 3'UTR | 503 | 526 | CTTAAATCACACTATGTGTT | 39 | 512 |
| 301227 3'UTR | 503 | 536 | TATTCTGTTACTTAAATCAC | 23 | 513 |

As shown in Table 15, SEQ ID Nos 505, 506, 507, 510, and 512 demonstrated at least 30% inhibition of human apolipoprotein B expression in this assay and are therefore preferred. The target regions to which these preferred sequences are complementary are herein referred to as "preferred target segments" and are therefore preferred for targeting by compounds of the present invention. These preferred target segments are shown in Table 18. The sequences represent the reverse complement of the preferred antisense compounds shown in Table 15. "Target site" indicates the first (5'-most) nucleotide number on the particular target nucleic acid to which the oligonucleotide binds. Also shown in Table 18 is the species in which each of the preferred target segments was found.

Example 35 Antisense Inhibition of Human Apolipoprotein B Expression by Chimeric Phosphorothioate Oligonucleotides Having 2'-MOE Wings and a Deoxy Gap—Variation in Position of the Gap In accordance with the present invention, a series of antisense compounds was designed to target different regions of the human apolipoprotein B RNA, using published sequences (GenBank accession number NM_000384.1, incorporated herein as SEQ ID NO: 3). The compounds are shown in Table 16. "Target site" indicates the first (5'most) nucleotide number on the particular target sequence to which the compound binds. All compounds in Table 16 are chimeric oligonucleotides ("gapmers") 20 nucleotides in length. The "gap" region consists of 2'-deoxynucleotides, which is flanked on one or both sides (5' and 3' directions) by "wings" composed of 2'-methoxyethyl (2'-MOE)nucleotides. The number of 2'-MOE nucleotides on either side of the gap varies such that the total number of 2'-MOE nucleotides always equals 10 and the total length of the chimeric oligonucleotide is 20 nucleotides. The exact structure of each oligonucleotide is designated in Table 16 as the "gap structure" and the 2'-deoxynucleotides are in bold type. A designation of 8~10~2, for instance, indicates that the first (5'-most) 8 nucleotides and the last (3'-most) 2 nucleotides are 2'-MOE nucleotides and the 10 nucleotides in the gap are 2'-deoxynucleotides. The internucleoside (backbone) linkages are phosphorothioate (P═S) throughout the oligonucleotide. All cytidine residues are 5-methylcytidines. The compounds were analyzed for their effect on human apolipoprotein B mRNA levels by quantitative real-time PCR as described in other examples herein. Data, shown in Table 16, are averages from three experiments in which HepG2 cells were treated with the antisense oligonucleotides of the present invention at doses of 50 nM and 150 nM. If present, "N.D." indicates "no data".

TABLE 16

Inhibition of human apolipoprotein B mRNA levels by chimeric phosphorothioate oligonucleotides having 2'-MOE wings and a variable deoxy gap

| ISIS # | TARGET SEQ ID NO | TARGET SITE | SEQUENCE | % INHIB 150 nm | % INHIB 50 nm | gap structure | SEQ ID NO |
|---|---|---|---|---|---|---|---|
| 308631 | 3 | 5589 | AGGTTACCAGCCACATGCAG | 94 | 74 | 0~10~10 | 224 |
| 308632 | 3 | 3249 | GCCTCAGTCTGCTTCGCACC | 97 | 41 | 0~10~10 | 247 |
| 308634 | 3 | 5589 | AGGTTACCAGCCACATGCAG | 67 | 45 | 10~10~0 | 224 |
| 308635 | 3 | 3249 | GCCTCAGTCTGCTTCGCACC | 93 | 69 | 10~10~0 | 247 |

TABLE 16-continued

Inhibition of human apolipoprotein B mRNA levels by chimeric phosphorothioate oligonucleotides having 2'-MOE wings and a variable deoxy gap

| ISIS # | TARGET SEQ ID NO | TARGET SITE | SEQUENCE | % INHIB 150 nm | % INHIB 50 nm | gap structure | SEQ ID NO |
|---|---|---|---|---|---|---|---|
| 308637 | 3 | 5589 | AGGTTACCAGCCACATGCAG | 95 | 79 | 1~10~9 | 224 |
| 308638 | 3 | 3249 | GCCTCAGTCTGCTTCGCACC | 94 | 91 | 1~10~9 | 247 |
| 308640 | 3 | 5589 | AGGTTACCAGCCACATGCAG | 96 | 76 | 2~10~8 | 224 |
| 308641 | 3 | 3249 | GCCTCAGTCTGCTTCGCACC | 89 | 77 | 2~10~8 | 247 |
| 308643 | 3 | 5589 | AGGTTACCAGCCACATGCAG | 96 | 56 | 3~10~7 | 224 |
| 308644 | 3 | 3249 | GCCTCAGTCTGCTTCGCACC | 93 | 71 | 3~10~7 | 247 |
| 308646 | 3 | 5589 | AGGTTACCAGCCACATGCAG | 76 | 50 | 4~10~6 | 224 |
| 308647 | 3 | 3249 | GCCTCAGTCTGCTTCGCACC | 86 | 53 | 4~10~6 | 247 |
| 308649 | 3 | 5589 | AGGTTACCAGCCACATGCAG | 91 | 68 | 6~10~4 | 224 |
| 308650 | 3 | 3249 | GCCTCAGTCTGCTTCGCACC | 94 | 74 | 6~10~4 | 247 |
| 308652 | 3 | 5589 | AGGTTACCAGCCACATGCAG | 95 | 73 | 7~10~3 | 224 |
| 308653 | 3 | 3249 | GCCTCAGTCTGCTTCGCACC | 89 | 73 | 7~10~3 | 247 |
| 308655 | 3 | 5589 | AGGTTACCAGCCACATGCAG | 83 | 84 | 8~10~2 | 224 |
| 305656 | 3 | 3249 | GCCTCAGTCTGCTTCGCACC | 97 | 37 | 8~10~2 | 247 |
| 308658 | 3 | 5589 | AGGTTACCAGCCACATGCAG | 78 | 86 | 9~10~1 | 224 |
| 308659 | 3 | 3249 | GCCTCAGTCTGCTTCGCACC | 93 | 70 | 9~10~1 | 247 |
| 308660 | 3 | 3254 | TGGTAGCCTCAGTCTGCTTC | 92 | 72 | 2~10~8 | 514 |
| 308662 | 3 | 3254 | TGGTAGCCTCAGTCTGCTTC | 83 | 76 | 8~10~2 | 514 |

As shown in Table 16, SEQ ID Nos 224, 247, and 514 demonstrated at least 30% inhibition of human apolipoprotein B expression in this assay at both doses. These data suggest that the oligonucleotides are effective with a number of variations in the gap placement. The target regions to which these preferred sequences are complementary are herein referred to as "preferred target segments" and are therefore preferred for targeting by compounds of the present invention. These preferred target segments are shown in Table 18. The sequences represent the reverse complement of the preferred antisense compounds shown in Table 16. "Target site" indicates the first (5'-most) nucleotide number on the particular target nucleic acid to which the oligonucleotide binds. Also shown in Table 8 is the species in which each of the preferred target segments was found.

Example 36

Antisense Inhibition of Human Apolipoprotein B Expression by Chimeric Phosphorothioate Oligonucleotides Having 2'-MOE Wings and a Deoxy Gap—Variation in Position of the Gap of SEQ ID Nos: 319 and 515

In accordance with the present invention, a series of antisense compounds was designed based on SEQ ID Nos 319 and 515, with variations in the gap structure. The compounds are shown in Table 17. "Target site" indicates the first (5'-most) nucleotide number on the particular target sequence to which the compound binds. All compounds in Table 17 are chimeric oligonucleotides ("gapmers") 20 nucleotides in length. The "gap" region consists of 2'-deoxynucleotides, which is flanked on one or both sides (5' and 3' directions) by "wings" composed of 2'-methoxyethyl (2'-MOE)nucleotides. The number of 2'-MOE nucleotides on either side of the gap varies such that the total number of 2'-MOE nucleotides always equals 10 and the total length of the chimeric oligonucleotide is 20 nucleotides. The exact structure of each oligonucleotide is designated in Table 17 as the "gap structure" and the 2'-deoxynucleotides are in bold type. A designation of 8~10~2, for instance, indicates that the first (5'-most) 8 nucleotides and the last (3'-most) 2 nucleotides are 2'-MOE nucleotides and the 10 nucleotides in the gap are 2'-deoxynucleotides. The internucleoside (backbone) linkages are phosphorothioate (P═S) throughout the oligonucleotide. All cytidine residues are 5-methylcytidines. The compounds were analyzed for their effect on human apolipoprotein B mRNA levels by quantitative real-time PCR as described in other examples herein. Data, shown in Table 17, are averages from three experiments in which HepG2 cells were treated with the antisense oligonucleotides of the present invention at doses of 50 nM and 150 nM. If present, "N.D." indicates "no data".

TABLE 17

Inhibition of human apolipoprotein B mRNA levels by chimeric phosphorothioate oligonucleotides having 2'-MOE wings and a variable deoxy gap

| ISIS # | TARGET SEQ ID NO | TARGET SITE | SEQUENCE | % INHIB 150 nm | % INHIB 50 nm | gap structure | SEQ ID NO |
|---|---|---|---|---|---|---|---|
| 308630 | 318 | 3121 | GCCTCAGTCTGCTTCGCGCC | 89 | 69 | 0~10~10 | 319 |
| 308633 | 318 | 3121 | GCCTCAGTCTGCTTCGCGCC | 83 | 66 | 10~10~0 | 319 |
| 308636 | 318 | 3121 | GCCTCAGTCTGCTTCGCGCC | 91 | 81 | 1~10~9 | 319 |
| 308639 | 318 | 3121 | GCCTCAGTCTGCTTCGCGCC | 94 | 86 | 2~10~8 | 319 |
| 308642 | 318 | 3121 | GCCTCAGTCTGCTTCGCGCC | 95 | 85 | 3~10~7 | 319 |
| 308645 | 318 | 3121 | GCCTCAGTCTGCTTCGCGCC | 98 | 57 | 4~10~6 | 319 |
| 308648 | 318 | 3121 | GCCTCAGTCTGCTTCGCGCC | 89 | 78 | 6~10~4 | 319 |
| 308651 | 318 | 3121 | GCCTCAGTCTGCTTCGCGCC | 88 | 87 | 7~10~3 | 319 |
| 308654 | 318 | 3121 | GCCTCAGTCTGCTTCGCGCC | 90 | 81 | 8~10~2 | 319 |
| 308657 | 318 | 3121 | GCCTCAGTCTGCTTCGCGCC | 78 | 61 | 9~10~1 | 319 |
| 308661 | 318 | 3116 | AGTCTGCTTCGCGCCTTCTG | 91 | 70 | 2~10~8 | 515 |
| 308663 | 318 | 3116 | AGTCTGCTTCGCGCCTTCTG | 84 | 44 | 8~10~2 | 515 |

As shown in Table 17, SEQ ID Nos 319 and 515 demonstrated at least 44% inhibition of human apolipoprotein B expression in this assay for either dose. These data suggest that the compounds are effective with a number of variations in gap placement. The target regions to which these preferred sequences are complementary are herein preferred to as "preferred target segments" and are therefore preferred for targeting by compounds of the present invention. These preferred target segments are shown in Table 18. The sequences represent the reverse complement of the preferred antisense compounds shown in Table 17. "Target site" indicates the first (5'-most) nucleotide number on the particular target nucleic acid to which the oligonucleotide binds. Also shown in Table 18 is the species in which each of the preferred target segments was found.

TABLE 18

Sequence and position of preferred target segments identified in apolipoprotein B.

| SITE ID | TARGET SEQ ID NO | TARGET SITE | SEQUENCE | REV COMP OF SEQ ID NO | ACTIVE IN | SEQ ID NO |
|---|---|---|---|---|---|---|
| 187342 | 3 | 199 | GCGCCAGGGCCGAAGAGGAA | 124 | *H. sapiens* | 516 |
| 187346 | 3 | 509 | CAGGTATGAGCTCAAGCTGG | 128 | *H. sapiens* | 517 |
| 187347 | 3 | 584 | CATCCTGAACATCAAGAGGG | 129 | *H. sapiens* | 518 |
| 187350 | 3 | 756 | GGGCAGTGTGATCGCTTCAA | 132 | *H. sapiens* | 519 |
| 187351 | 3 | 799 | CACTTGCTCTCATCAAAGGC | 133 | *H. sapiens* | 520 |
| 187352 | 3 | 869 | CACACTGGACGCTAAGAGGA | 134 | *H. sapiens* | 521 |
| 187356 | 3 | 1459 | CGCTGAGCCACGCGGTCAAC | 138 | *H. sapiens* | 522 |
| 187358 | 3 | 1859 | TGTCCAAATTCTACCATGGG | 140 | *H. sapiens* | 523 |
| 187359 | 3 | 2179 | CAGCTGACCTCATCGAGATT | 141 | *H. sapiens* | 524 |
| 187360 | 3 | 2299 | GTCAAGTTCCTGATGGTGTC | 142 | *H. sapiens* | 525 |
| 107362 | 3 | 2518 | AGCTGCTTCTGATGGGTGCC | 144 | *H. sapiens* | 526 |
| 187363 | 3 | 2789 | GGGCATCATCATTCCGGACT | 145 | *H. sapiens* | 527 |
| 187365 | 3 | 3100 | CCTACTATCCGCTGACCGGG | 147 | *H. sapiens* | 528 |
| 187367 | 3 | 3449 | GGGCCACCTAAGTTGTGACA | 148 | *H. sapiens* | 529 |

TABLE 18-continued

Sequence and position of preferred target segments identified in apolipoprotein B.

| SITE ID | TARGET SEQ ID NO | TARGET SITE | SEQUENCE | REV COMP OF SEQ ID NO | ACTIVE IN | SEQ ID NO |
|---|---|---|---|---|---|---|
| 187368 | 3 | 3919 | AGAACATGGGATTGCCAGAC | 149 | *H. sapiens* | 530 |
| 187369 | 3 | 4089 | CTCCACTTCAAGTCTGTGGG | 150 | *H. sapiens* | 531 |
| 187371 | 3 | 5146 | CAGAGCTTGGCCTCTCTGGG | 152 | *H. sapiens* | 532 |
| 187372 | 3 | 5189 | TGGCCGCTTCAGGGAACACA | 153 | *H. sapiens* | 533 |
| 187374 | 3 | 6049 | CAGCTGAGCAGACAGGCACC | 155 | *H. sapiens* | 534 |
| 187375 | 3 | 6520 | GGGAGAGACAAGTTTCACAT | 156 | *H. sapiens* | 535 |
| 187377 | 3 | 6859 | GTACTGCATCCTGGATTCAA | 158 | *H. sapiens* | 536 |
| 187378 | 3 | 7459 | GTGAGGTGACTCAGAGACTC | 159 | *H. sapiens* | 537 |
| 187379 | 3 | 7819 | TTGCAGAGCAATATTCTATC | 160 | *H. sapiens* | 538 |
| 187380 | 3 | 7861 | AAGCATTGGTAGAGCAAGGG | 161 | *H. sapiens* | 539 |
| 187383 | 3 | 8589 | CCGCTGGCTCTGAAGGAGTC | 163 | *H. sapiens* | 540 |
| 187385 | 3 | 8829 | TCTAGTCAGGCTGACCTGCG | 165 | *H. sapiens* | 541 |
| 187387 | 3 | 9119 | GGGCCACAGTGTTCTAACTG | 166 | *H. sapiens* | 542 |
| 187388 | 3 | 10159 | AATCAAGTGTCATCACACTG | 167 | *H. sapiens* | 543 |
| 187390 | 3 | 10349 | GGGTAGTCATAACAGTACTG | 169 | *H. sapiens* | 544 |
| 187391 | 3 | 10699 | AGAGCACACGGTCTTCAGTG | 170 | *H. sapiens* | 545 |
| 187393 | 3 | 10839 | TTACAGCTAGAGGGCCTCTT | 172 | *H. sapiens* | 546 |
| 187398 | 3 | 12149 | CACCGTGGGCATGGATATGG | 176 | *H. sapiens* | 547 |
| 187399 | 3 | 12265 | GGGAATCTGATGAGGAAACT | 177 | *H. sapiens* | 548 |
| 187400 | 3 | 12380 | TGTCAACAAGTACCACTGGG | 178 | *H. sapiens* | 549 |
| 187403 | 3 | 12749 | ACCTGGGATATACACTAGGG | 181 | *H. sapiens* | 550 |
| 187406 | 3 | 13299 | CCAAGTATAGTTGGCTGGAC | 183 | *H. sapiens* | 551 |
| 187407 | 3 | 13779 | TACATGAAGCTTGCTCCAGG | 184 | *H. sapiens* | 552 |
| 197724 | 3 | 229 | ATGTCAGCCTGGTCTGTCCA | 185 | *H. sapiens* | 553 |
| 197725 | 3 | 269 | GCACCTCCGGAAGTACACAT | 186 | *H. sapiens* | 554 |
| 197726 | 3 | 389 | CTGCAGCTTCATCCTGAAGA | 187 | *H. sapiens* | 555 |
| 197727 | 3 | 449 | TGAGGGCAAAGCCTTGCTGA | 188 | *H. sapiens* | 556 |
| 197728 | 3 | 529 | CCATTCCAGAAGGGAAGCAG | 189 | *H. sapiens* | 557 |
| 197729 | 3 | 709 | CGAGGAAGGGCAATGTGGCA | 190 | *H. sapiens* | 558 |
| 197730 | 3 | 829 | CCTTGTCAACTCTGATCAGC | 191 | *H. sapiens* | 559 |
| 197731 | 3 | 849 | AGCAGCCAGTCCTGTCAGTA | 192 | *H. sapiens* | 560 |
| 197732 | 3 | 889 | AGCATGTGGCAGAAGCCATC | 193 | *H. sapiens* | 561 |
| 197733 | 3 | 1059 | GAGAGCACCAAATCCACATC | 194 | *H. sapiens* | 562 |
| 197734 | 3 | 1199 | CCTCAGTGATGAAGCAGTCA | 195 | *H. sapiens* | 563 |
| 197735 | 3 | 1349 | GATAGATGTGGTCACCTACC | 196 | *H. sapiens* | 564 |
| 197736 | 3 | 1390 | CCTCAGCACAGCAGCTGCGA | 197 | *H. sapiens* | 565 |
| 197737 | 3 | 1589 | GATTCTGCGGGTCATTGGAA | 198 | *H. sapiens* | 566 |

TABLE 18-continued

Sequence and position of preferred target segments identified in apolipoprotein B.

| SITE ID | TARGET SEQ ID NO | TARGET SITE | SEQUENCE | REV COMP OF SEQ ID NO | ACTIVE IN | SEQ ID NO |
|---|---|---|---|---|---|---|
| 197738 | 3 | 1678 | CAAAGCCATCACTGATGATC | 199 | *H. sapiens* | 567 |
| 197739 | 3 | 1699 | AGAAAGCTGCCATCCAGGCT | 200 | *H. sapiens* | 568 |
| 197740 | 3 | 1749 | CAGGAGGTTCTTCTTCAGAC | 201 | *H. sapiens* | 569 |
| 197741 | 3 | 1829 | GAGTCCTTCACAGGCAGATA | 202 | *H. sapiens* | 570 |
| 197742 | 3 | 1919 | TGCCAATATCTTGAACTCAG | 203 | *H. sapiens* | 571 |
| 197743 | 3 | 2189 | CATCGAGATTGGCTTGGAAG | 204 | *H. sapiens* | 572 |
| 197744 | 3 | 2649 | GGAGCTGGATTACAGTTGCA | 205 | *H. sapiens* | 573 |
| 197745 | 3 | 2729 | CAACATGCAGGCTGAACTGG | 206 | *H. sapiens* | 574 |
| 197746 | 3 | 2949 | ACATTACATTTGGTCTCTAC | 207 | *H. sapiens* | 575 |
| 197747 | 3 | 3059 | CTCAGGCGCTTACTCCAACG | 208 | *H. sapiens* | 576 |
| 197748 | 3 | 3118 | GGGACACCAGATTAGAGCTG | 209 | *H. sapiens* | 577 |
| 197749 | 3 | 3189 | GAGCTCCAGAGAGAGGACAG | 210 | *H. sapiens* | 578 |
| 197750 | 3 | 3289 | ATCGGCAGAGTATGACCTTG | 211 | *H. sapiens* | 579 |
| 197751 | 3 | 3488 | CAAGGGTGTTATTTCCATAC | 212 | *H. sapiens* | 580 |
| 197752 | 3 | 3579 | GACTCATCTGCTACAGCTTA | 213 | *H. sapiens* | 581 |
| 197753 | 3 | 4039 | GCAAATCCTCCAGAGATCTA | 214 | *H. sapiens* | 582 |
| 197754 | 3 | 4180 | CTCTCCTGGGTGTTCTAGAC | 215 | *H. sapiens* | 583 |
| 197755 | 3 | 4299 | ATGAAGGCTGACTCTGTGGT | 216 | *H. sapiens* | 584 |
| 197756 | 3 | 4511 | GGGACCACAGATGTCTGCTT | 217 | *H. sapiens* | 585 |
| 197757 | 3 | 4660 | CTGGCCGGCTCAATGGAGAG | 218 | *H. sapiens* | 586 |
| 197758 | 3 | 4919 | GCTGCGTTCTGAATATCAGG | 219 | *H. sapiens* | 587 |
| 197759 | 3 | 5009 | TGCTGACATCTTAGGCACTG | 220 | *H. sapiens* | 588 |
| 197760 | 3 | 5109 | AAGTGTAGTCTCCTGGTGCT | 221 | *H. sapiens* | 589 |
| 197761 | 3 | 5212 | CAAAATTCAGTCTGGATGGG | 222 | *H. sapiens* | 590 |
| 197762 | 3 | 5562 | GGGAAACTACGGCTAGAACC | 223 | *H. sapiens* | 591 |
| 197763 | 3 | 5589 | CTGCATGTGGCTGGTAACCT | 224 | *H. sapiens* | 592 |
| 197764 | 3 | 5839 | CCATGACCATCGATGCACAT | 225 | *H. sapiens* | 593 |
| 197765 | 3 | 5869 | ATGGGAAACTCGCTCTCTGG | 226 | *H. sapiens* | 594 |
| 197766 | 3 | 5979 | AGTCATCATCTCGTGTCTAG | 227 | *H. sapiens* | 595 |
| 197767 | 3 | 6099 | GAATACAGCCAGGACTTGGA | 228 | *H. sapiens* | 596 |
| 197768 | 3 | 6144 | GGCGTGGAGCTTACTGGACG | 229 | *H. sapiens* | 597 |
| 197769 | 3 | 6249 | GAGATGAGAGATGCCGTTGA | 230 | *H. sapiens* | 598 |
| 197770 | 3 | 6759 | AGTCTTGATGAGCACTATCA | 231 | *H. sapiens* | 599 |
| 197771 | 3 | 6889 | CTAAGTACCAAATCAGAATC | 232 | *H. sapiens* | 600 |
| 197772 | 3 | 7149 | GTCCATGAGTTAATCGAGAG | 233 | *H. sapiens* | 601 |
| 197773 | 3 | 7549 | AGGCCACAGTTGCAGTGTAT | 234 | *H. sapiens* | 602 |
| 197774 | 3 | 7779 | TCTGATTGGTGGACTCTTGC | 235 | *H. sapiens* | 603 |

TABLE 18-continued

Sequence and position of preferred target segments identified in apolipoprotein B.

| SITE ID | TARGET SEQ ID NO | TARGET SITE | SEQUENCE | REV COMP OF SEQ ID NO | ACTIVE IN | SEQ ID NO |
|---|---|---|---|---|---|---|
| 197775 | 3 | 7929 | GAAGTCAGTCTTCAGGCTCT | 236 | *H. sapiens* | 604 |
| 197776 | 3 | 8929 | CCAGATTCTCAGATGAGGGA | 237 | *H. sapiens* | 605 |
| 197770 | 3 | 10240 | CATCTGTCATTGATGCACTG | 238 | *H. sapiens* | 606 |
| 197779 | 3 | 10619 | AGGAGATGTCAAGGGTTCGG | 239 | *H. sapiens* | 607 |
| 197780 | 3 | 10659 | GGAACTATTGCTAGTGAGGC | 240 | *H. sapiens* | 608 |
| 197781 | 3 | 10899 | CTCTCTCCATGGCAAATGTC | 241 | *H. sapiens* | 609 |
| 197783 | 3 | 11979 | CACCGTGACTTCAGTGCAGA | 243 | *H. sapiens* | 610 |
| 197784 | 3 | 12249 | ACTGAGTTGAGGGTCCGGGA | 244 | *H. sapiens* | 611 |
| 197786 | 3 | 13958 | CACATATGAACTGGACCTGC | 245 | *H. sapiens* | 612 |
| 197787 | 3 | 14008 | TCTGAACTCAGAAGGATGGC | 246 | *H. sapiens* | 613 |
| 216825 | 3 | 3249 | GGTGCGAAGCAGACTGAGGC | 247 | *H. sapiens* | 614 |
| 216826 | 3 | 3 | TCCCACCGGGACCTGCGGGG | 248 | *H. sapiens* | 615 |
| 216827 | 3 | 6 | CACCGGGACCTGCGGGGCTG | 249 | *H. sapiens* | 616 |
| 216828 | 3 | 23 | CTGAGTGCCCTTCTCGGTTG | 250 | *H. sapiens* | 617 |
| 216829 | 3 | 35 | CTCGGTTGCTGCCGCTGAGG | 251 | *H. sapiens* | 618 |
| 216830 | 3 | 36 | TCGGTTGCTGCCGCTGAGGA | 252 | *H. sapiens* | 619 |
| 216831 | 3 | 37 | CGGTTGCTGCCGCTGAGGAG | 253 | *H. sapiens* | 620 |
| 216832 | 3 | 39 | GTTGCTGCCGCTGAGGAGCC | 254 | *H. sapiens* | 621 |
| 216833 | 3 | 43 | CTGCCGCTGAGGAGCCCGCC | 255 | *H. sapiens* | 622 |
| 216834 | 3 | 116 | ACCGCAGCTGGCGATGGACC | 256 | *H. sapiens* | 623 |
| 216835 | 3 | 120 | CAGCTGGCGATGGACCCGCC | 257 | *H. sapiens* | 624 |
| 216836 | 3 | 13800 | GAACTTACTATCATCCTCTA | 258 | *H. sapiens* | 625 |
| 216838 | 3 | 13854 | TCCAATTGAACTTTCACATA | 260 | *H. sapiens* | 626 |
| 216839 | 3 | 13882 | AAAATTCAAACTGCCTATAT | 261 | *H. sapiens* | 627 |
| 216840 | 3 | 13903 | GATAAAACCATACAGTGAGC | 262 | *H. sapiens* | 628 |
| 216841 | 3 | 13904 | ATAAAACCATACAGTGAGCC | 263 | *H. sapiens* | 629 |
| 216842 | 3 | 13908 | AACCATACAGTGAGCCAGCC | 264 | *H. sapiens* | 630 |
| 216843 | 3 | 13909 | ACCATACAGTGAGCCAGCCT | 265 | *H. sapiens* | 631 |
| 216844 | 3 | 13910 | CCATACAGTGAGCCAGCCTT | 266 | *H. sapiens* | 632 |
| 216845 | 3 | 13917 | GTGAGCCAGCCTTGCAGTAG | 267 | *H. sapiens* | 633 |
| 216846 | 3 | 13922 | CCAGCCTTGCAGTAGGCAGT | 268 | *H. sapiens* | 634 |
| 216847 | 3 | 13934 | TAGGCAGTAGACTATAAGCA | 269 | *H. sapiens* | 635 |
| 216848 | 3 | 13937 | GCAGTAGACTATAAGCAGAA | 270 | *H. sapiens* | 636 |
| 216849 | 3 | 13964 | TGAACTGGACCTGCACCAAA | 271 | *H. sapiens* | 637 |
| 216850 | 3 | 13968 | CTGGACCTGCACCAAAGCTG | 272 | *H. sapiens* | 638 |
| 216851 | 3 | 13970 | GGACCTGCACCAAAGCTGGC | 273 | *H. sapiens* | 639 |
| 216852 | 3 | 13974 | CTGCACCAAAGCTGGCACCA | 274 | *H. sapiens* | 640 |

TABLE 18-continued

Sequence and position of preferred target segments identified in apolipoprotein B.

| SITE ID | TARGET SEQ ID NO | TARGET SITE | SEQUENCE | REV COMP OF SEQ ID NO | ACTIVE IN | SEQ ID NO |
|---|---|---|---|---|---|---|
| 216853 | 3 | 13978 | ACCAAAGCTGGCACCAGGGC | 275 | *H. sapiens* | 641 |
| 216854 | 3 | 13997 | CTCGGAAGGTCTCTGAACTC | 276 | *H. sapiens* | 642 |
| 216855 | 3 | 14012 | AACTCAGAAGGATGGCATTT | 277 | *H. sapiens* | 643 |
| 216856 | 3 | 14014 | CTCAGAAGGATGGCATTTTT | 278 | *H. sapiens* | 644 |
| 216857 | 3 | 14049 | ATCAGGATCTGAGTTATTTT | 279 | *H. sapiens* | 645 |
| 216858 | 3 | 14052 | AGGATCTGAGTTATTTTGCT | 280 | *H. sapiens* | 646 |
| 216859 | 3 | 14057 | CTGAGTTATTTTGCTAAACT | 281 | *H. sapiens* | 647 |
| 216860 | 3 | 14064 | ATTTTGCTAAACTTGGGGGA | 282 | *H. sapiens* | 648 |
| 216861 | 3 | 14071 | TAAACTTGGGGGAGGAGGAA | 283 | *H. sapiens* | 649 |
| 217030 | 3 | 14087 | GGAACAAATAAATGGAGTCT | 284 | *H. sapiens* | 650 |
| 224316 | 3 | 3230 | GTTTGTAACTCAAGCAGAAG | 285 | *H. sapiens* | 651 |
| 224317 | 3 | 3232 | TTGTAACTCAAGCAGAAGGT | 286 | *H. sapiens* | 652 |
| 224318 | 3 | 3234 | GTAACTCAAGCAGAAGGTGC | 287 | *H. sapiens* | 653 |
| 224319 | 3 | 3236 | AACTCAAGCAGAAGGTGCGA | 288 | *H. sapiens* | 654 |
| 224320 | 3 | 3238 | CTCAAGCAGAAGGTGCGAAG | 289 | *H. sapiens* | 655 |
| 224321 | 3 | 3240 | CAAGCAGAAGGTGCGAAGCA | 290 | *H. sapiens* | 656 |
| 224322 | 3 | 3242 | AGCAGAAGGTGCGAAGCAGA | 291 | *H. sapiens* | 657 |
| 224323 | 3 | 3244 | CAGAAGGTGCGAAGCAGACT | 292 | *H. sapiens* | 658 |
| 224324 | 3 | 3246 | GAAGGTGCGAAGCAGACTGA | 293 | *H. sapiens* | 659 |
| 224325 | 3 | 3248 | AGGTGCGAAGCAGACTGAGG | 294 | *H. sapiens* | 660 |
| 224326 | 3 | 3250 | GTGCGAAGCAGACTGAGGCT | 295 | *H. sapiens* | 661 |
| 224327 | 3 | 3252 | GCGAAGCAGACTGAGGCTAC | 296 | *H. sapiens* | 662 |
| 224328 | 3 | 3254 | GAAGCAGACTGAGGCTACCA | 297 | *H. sapiens* | 663 |
| 224329 | 3 | 3256 | AGCAGACTGAGGCTACCATG | 298 | *H. sapiens* | 664 |
| 224330 | 3 | 3258 | CAGACTGAGGCTACCATGAC | 299 | *H. sapiens* | 665 |
| 224331 | 3 | 3260 | GACTGAGGCTACCATGACAT | 300 | *H. sapiens* | 666 |
| 224332 | 3 | 3262 | CTGAGGCTACCATGACATTC | 301 | *H. sapiens* | 667 |
| 224333 | 3 | 3264 | GAGGCTACCATGACATTCAA | 302 | *H. sapiens* | 668 |
| 224334 | 3 | 3266 | GGCTACCATGACATTCAAAT | 303 | *H. sapiens* | 669 |
| 224335 | 3 | 3268 | CTACCATGACATTCAAATAT | 304 | *H. sapiens* | 670 |
| 224336 | 3 | 5582 | CCTGAAGCTGCATGTGGCTG | 305 | *H. sapiens* | 671 |
| 224337 | 3 | 5584 | TGAAGCTGCATGTGGCTGGT | 306 | *H. sapiens* | 672 |
| 224338 | 3 | 5586 | AAGCTGCATGTGGCTGGTAA | 307 | *H. sapiens* | 673 |
| 224339 | 3 | 5588 | GCTGCATGTGGCTGGTAACC | 308 | *H. sapiens* | 674 |
| 224340 | 3 | 5590 | TGCATGTGGCTGGTAACCTA | 309 | *H. sapiens* | 675 |
| 224341 | 3 | 5592 | CATGTGGCTGGTAACCTAAA | 310 | *H. sapiens* | 676 |
| 224342 | 3 | 5594 | TGTGGCTGGTAACCTAAAAG | 311 | *H. sapiens* | 677 |

TABLE 18-continued

Sequence and position of preferred target segments identified in apolipoprotein B.

| SITE ID | TARGET SEQ ID NO | TARGET SITE | SEQUENCE | REV COMP OF SEQ ID NO | ACTIVE IN | SEQ ID NO |
|---|---|---|---|---|---|---|
| 224343 | 3 | 5596 | TGGCTGGTAACCTAAAAGGA | 312 | *H. sapiens* | 678 |
| 224344 | 3 | 5598 | GCTGGTAACCTAAAAGGAGC | 313 | *H. sapiens* | 679 |
| 224345 | 3 | 5600 | TGGTAACCTAAAAGGAGCCT | 314 | *H. sapiens* | 680 |
| 224346 | 3 | 5602 | GTAACCTAAAAGGAGCCTAC | 315 | *H. sapiens* | 681 |
| 224347 | 3 | 5604 | AACCTAAAAGGAGCCTACCA | 316 | *H. sapiens* | 682 |
| 224348 | 3 | 5606 | CCTAAAAGGAGCCTACCAAA | 317 | *H. sapiens* | 683 |
| 187366 | 318 | 3121 | GGCGCGAAGCAGACTGAGGC | 319 | *H. sapiens* | 684 |
| 187404 | 318 | 12651 | CACTATGTTCATGAGGGAGG | 323 | *H. sapiens* | 685 |
| 197777 | 318 | 9851 | CCATCATAGGTTCTGACGTC | 324 | *H. sapiens* | 686 |
| 197785 | 318 | 12561 | GAAGCTGATTGACTCACTCA | 325 | *H. sapiens* | 687 |
| 224349 | 318 | 3104 | TTGTAACTCAAGCAGAAGGC | 326 | *H. sapiens* | 688 |
| 224350 | 318 | 3106 | GTAACTCAAGCAGAAGGCGC | 327 | *H. sapiens* | 689 |
| 224351 | 318 | 3108 | AACTCAAGCAGAAGGCGCGA | 328 | *H. sapiens* | 690 |
| 224352 | 318 | 3110 | CTCAAGCAGAAGGCGCGAAG | 329 | *H. sapiens* | 691 |
| 224353 | 318 | 3116 | CAGAAGGCGCGAAGCAGACT | 330 | *H. sapiens* | 692 |
| 224354 | 318 | 3118 | GAAGGCGCGAAGCAGACTGA | 331 | *H. sapiens* | 693 |
| 224355 | 318 | 3120 | AGGCGCGAAGCAGACTGAGG | 332 | *H. sapiens* | 694 |
| 224356 | 318 | 3122 | GCGCGAAGCAGACTGAGGCT | 333 | *H. sapiens* | 695 |
| 224328 | 3 | 3254 | GAAGCAGACTGAGGCTACCA | 514 | *H. sapiens* | 696 |
| 224353 | 318 | 3116 | CAGAAGGCGCGAAGCAGACT | 515 | *H. sapiens* | 697 |
| 216862 | 334 | 904 | TCTTTCTCCTGTCTTACAGA | 335 | *H. sapiens* | 698 |
| 216866 | 334 | 1988 | CCCACGTTAGAAGATGCGAC | 339 | *H. sapiens* | 699 |
| 216868 | 334 | 2722 | AATATGGTAGACATGAGCCA | 341 | *H. sapiens* | 700 |
| 216869 | 334 | 2791 | CATTAGCTGCATTTCAACTG | 342 | *H. sapiens* | 701 |
| 216870 | 334 | 3045 | ACTTTCACTCCTAGTCTGCA | 343 | *H. sapiens* | 702 |
| 216874 | 334 | 3527 | CCATGTCCAGGTAAGTCATG | 347 | *H. sapiens* | 703 |
| 216876 | 334 | 3603 | GCACCAGGCACGGATGTGAC | 349 | *H. sapiens* | 704 |
| 216877 | 334 | 3864 | GTGGGGTCCCAGAGGCACTG | 350 | *H. sapiens* | 705 |
| 216878 | 334 | 3990 | GCTGATCGGCCACTGCAGCT | 351 | *H. sapiens* | 706 |
| 216879 | 334 | 4251 | TCCACGTGGCTGGGGAGGTC | 352 | *H. sapiens* | 707 |
| 216880 | 334 | 4853 | TGTAATGTATGGTGATCAGA | 353 | *H. sapiens* | 708 |
| 216881 | 334 | 5023 | GAGAGTACCCAGTGGGAAAT | 354 | *H. sapiens* | 709 |
| 216882 | 334 | 5055 | AGTCAGCATGGGCTTCAGCC | 355 | *H. sapiens* | 710 |
| 216883 | 334 | 5091 | CAAAAGAATGACTGTCCAAC | 356 | *H. sapiens* | 711 |
| 216884 | 334 | 5096 | GAATGACTGTCCAACAAGTO | 357 | *H. sapiens* | 712 |
| 216885 | 334 | 5301 | TATCTACTGTAATTTAAAAT | 358 | *H. sapiens* | 713 |
| 216886 | 334 | 5780 | CTGATATGGGTGGAGAACAG | 359 | *H. sapiens* | 714 |

TABLE 18-continued

Sequence and position of preferred target segments identified in apolipoprotein B.

| SITE ID | TARGET SEQ ID NO | TARGET SITE | SEQUENCE | REV COMP OF SEQ ID NO | ACTIVE IN | SEQ ID NO |
|---|---|---|---|---|---|---|
| 216887 | 334 | 6353 | TCTGGGACAGGTATGAGCTC | 360 | *H. sapiens* | 715 |
| 216888 | 334 | 6534 | TGATAGCAGTGGCCCTTGAA | 361 | *H. sapiens* | 716 |
| 216889 | 334 | 6641 | GGATTGGCGTGAAATACTGG | 362 | *H. sapiens* | 717 |
| 216890 | 334 | 6661 | TGCCCGAGGTTCCTCCTGCC | 363 | *H. sapiens* | 718 |
| 216894 | 334 | 7059 | GCACTAGCAAGACCACACTC | 367 | *H. sapiens* | 719 |
| 216895 | 334 | 7066 | CAAGACCACACTCTGCATAG | 368 | *H. sapiens* | 720 |
| 216897 | 334 | 7209 | TCCTCCATAGGATACCGTGT | 370 | *H. sapiens* | 721 |
| 216899 | 334 | 7702 | GGATGTAGGGCAGCAAAACC | 372 | *H. sapiens* | 722 |
| 216900 | 334 | 7736 | TCTGCACAAGGACTCCTTGT | 373 | *H. sapiens* | 723 |
| 216901 | 334 | 8006 | CAGCCTGTCTCAGTGAACAT | 374 | *H. sapiens* | 724 |
| 216903 | 334 | 8239 | CAGGATGCTTCCAGTCTAAT | 376 | *H. sapiens* | 725 |
| 216904 | 334 | 8738 | AAATGCTCGTCTCCAATCTC | 377 | *H. sapiens* | 726 |
| 216906 | 334 | 9208 | AACTTGTGTATCCAAATCCA | 379 | *H. sapiens* | 727 |
| 216908 | 334 | 9545 | TGACATGGTGTGCTTCCTTG | 381 | *H. sapiens* | 728 |
| 216910 | 334 | 9770 | ACACTGGTGTTCTGGCTACC | 383 | *H. sapiens* | 729 |
| 216911 | 334 | 9776 | GTGTTCTGGCTACCTCTAGT | 384 | *H. sapiens* | 730 |
| 216913 | 334 | 10341 | TCCTGGCATAGGTCACAGTA | 386 | *H. sapiens* | 731 |
| 216914 | 334 | 10467 | ATGTCAACAGTAGCACCTCC | 387 | *H. sapiens* | 732 |
| 216915 | 334 | 10522 | TACACTCAGACAAGTCTGGA | 388 | *H. sapiens* | 733 |
| 216917 | 334 | 10587 | CCTAAGTTGCTCATCTCTGG | 390 | *H. sapiens* | 734 |
| 216922 | 334 | 11337 | TGCGCTGAGTTCCATGAAAC | 395 | *H. sapiens* | 735 |
| 216923 | 334 | 11457 | CTATTGCAGGTGCTCTCCAG | 396 | *H. sapiens* | 736 |
| 216926 | 334 | 12155 | CAGAGGAACATCTTGCACCT | 399 | *H. sapiens* | 737 |
| 216928 | 334 | 12221 | CTCTGCTCCTTACTCTTGTG | 401 | *H. sapiens* | 738 |
| 216929 | 334 | 12987 | GTAATTTCTCACCATCCATC | 402 | *H. sapiens* | 739 |
| 216930 | 334 | 13025 | TTCTGAGTCTCAATTGTCTA | 403 | *H. sapiens* | 740 |
| 216931 | 334 | 13057 | CTATGTCCTTGTGTGCACAT | 404 | *H. sapiens* | 741 |
| 216932 | 334 | 13634 | GCCTATTGCCATTTGTATGT | 405 | *H. sapiens* | 742 |
| 216933 | 334 | 13673 | CTATTCATGTCCTTTGCCTA | 406 | *H. sapiens* | 743 |
| 216935 | 334 | 14567 | GATTCTGCGGGTAATCTCAG | 408 | *H. sapiens* | 744 |
| 216937 | 334 | 14680 | TCAATGCAGGTCATTGGAAA | 410 | *H. sapiens* | 745 |
| 216938 | 334 | 15444 | CTACCAGATTGACCATCCCT | 411 | *H. sapiens* | 746 |
| 216940 | 334 | 15757 | TACTTGATAGTGCTCTAGGA | 413 | *H. sapiens* | 747 |
| 216941 | 334 | 15926 | TTGACTGCAGGACCAGGAGG | 414 | *H. sapiens* | 748 |
| 216942 | 334 | 16245 | AACAAACACTTGTGCAAATG | 415 | *H. sapiens* | 749 |
| 216950 | 334 | 18519 | AATGAGACCAAACTTCCACT | 423 | *H. sapiens* | 750 |
| 216951 | 334 | 18532 | TTCCACTTTGAAGCTAGCAA | 424 | *H. sapiens* | 751 |

TABLE 18-continued

Sequence and position of preferred target segments identified in apolipoprotein B.

| SITE ID | TARGET SEQ ID NO | TARGET SITE | SEQUENCE | REV COMP OF SEQ ID NO | ACTIVE IN | SEQ ID NO |
|---|---|---|---|---|---|---|
| 216952 | 334 | 18586 | GATCTGGAGCTTATTCTTGA | 425 | *H. sapiens* | 752 |
| 216953 | 334 | 18697 | ACCTCATGTGACTTGTATGC | 426 | *H. sapiens* | 753 |
| 216954 | 334 | 18969 | TTCTTAAGAAACACCTTGTA | 427 | *H. sapiens* | 754 |
| 216955 | 334 | 19250 | TAGGCCCATCCTGGCTGCAT | 428 | *H. sapiens* | 755 |
| 216956 | 334 | 19340 | AAACTCTCAGGATATGGTAA | 429 | *H. sapiens* | 756 |
| 216957 | 334 | 19802 | ATACCTTCCTCTACCTTTGC | 430 | *H. sapiens* | 757 |
| 216958 | 334 | 19813 | TACCTTTGCTGAAGGTCCTT | 431 | *H. sapiens* | 758 |
| 216961 | 334 | 20567 | ATCTATCTAGTGAAATTTCT | 434 | *H. sapiens* | 759 |
| 216962 | 334 | 20647 | TCAGCTCATCAAAATATGCT | 435 | *H. sapiens* | 760 |
| 216963 | 334 | 20660 | ATATGCTAGTCCTTCCTTTC | 436 | *H. sapiens* | 761 |
| 216965 | 334 | 21316 | CAAAGGTCTGAGTTATCCAG | 438 | *H. sapiens* | 762 |
| 216967 | 334 | 21422 | TGACTTATAGATGCAGGCTG | 440 | *H. sapiens* | 763 |
| 216968 | 334 | 21634 | TCAGTGGAGGGTAATTCTTT | 441 | *H. sapiens* | 764 |
| 216969 | 334 | 21664 | TGCCTAGCCAGTTTGAAAGA | 442 | *H. sapiens* | 765 |
| 216970 | 334 | 21700 | CCTGCAGAATTTTGCCAGGC | 443 | *H. sapiens* | 766 |
| 216972 | 334 | 22048 | GTAGCTAGGTAGGTAAAGCA | 445 | *H. sapiens* | 767 |
| 216973 | 334 | 22551 | TTGAGTGAGACACACAAGGT | 446 | *H. sapiens* | 768 |
| 216974 | 334 | 22694 | GTGCTAGTCAGGGAATGCAT | 447 | *H. sapiens* | 769 |
| 216976 | 334 | 22903 | GGGGAGAGAGCATGCCCAGC | 449 | *H. sapiens* | 770 |
| 216977 | 334 | 22912 | GCATGCCCAGCTGCGAAAGC | 450 | *H. sapiens* | 771 |
| 216978 | 334 | 23137 | AGCCAGGTATAGAAAGGAGT | 451 | *H. sapiens* | 772 |
| 216979 | 334 | 23170 | AACTTTCTAAGAGGCAGAAT | 452 | *H. sapiens* | 773 |
| 216981 | 334 | 23882 | TCTTAGTCTGGTCATGAGTG | 454 | *H. sapiens* | 774 |
| 216983 | 334 | 24184 | AGTAGGAGATTTCATATGAA | 456 | *H. sapiens* | 775 |
| 216985 | 334 | 24559 | TCTTCACCAGCAACACATTA | 458 | *H. sapiens* | 776 |
| 216987 | 334 | 24800 | ATGGCCACCTAGCATGGCAC | 460 | *H. sapiens* | 777 |
| 216989 | 334 | 24991 | CATGTTTCTGAGCCTCCAGA | 462 | *H. sapiens* | 778 |
| 216990 | 334 | 25067 | TAGGTGGCTCCCTGTCTTCA | 463 | *H. sapiens* | 779 |
| 216991 | 334 | 25152 | TCCAAAGTCTTGGGAATCCT | 464 | *H. sapiens* | 780 |
| 216995 | 334 | 26749 | ACAAAGAAAGGGGGAGTTGG | 468 | *H. sapiens* | 781 |
| 216996 | 334 | 26841 | TCGTGTCTTCCTGGCCCAGA | 469 | *H. sapiens* | 782 |
| 216997 | 334 | 27210 | GCAGTGCCCAGCACACAATA | 470 | *H. sapiens* | 783 |
| 216998 | 334 | 27815 | ACTCGTCCAGGTGCGAAGCA | 471 | *H. sapiens* | 784 |
| 216999 | 334 | 28026 | GCCACCTAAGGTAAAGAAGG | 472 | *H. sapiens* | 785 |
| 217000 | 334 | 28145 | ATCAGAGTGGCAGAGAGAGC | 473 | *H. sapiens* | 786 |
| 217002 | 334 | 28919 | TTTACCATAGTTGTGACACA | 475 | *H. sapiens* | 787 |
| 217006 | 334 | 29871 | CATTTTGTAGGCAATGAGCT | 479 | *H. sapiens* | 788 |

TABLE 18-continued

Sequence and position of preferred target segments identified in apolipoprotein B.

| SITE ID | TARGET SEQ ID NO | TARGET SITE | SEQUENCE | REV COMP OF SEQ ID NO | ACTIVE IN | SEQ ID NO |
|---|---|---|---|---|---|---|
| 217007 | 334 | 30181 | GCATTAGTAAACATGAGAAC | 480 | *H. sapiens* | 789 |
| 217009 | 334 | 30931 | TTCATTTCAGCGATGGCCGG | 482 | *H. sapiens* | 790 |
| 217013 | 334 | 39562 | GAAAATCTAGTGTCATTCAA | 486 | *H. sapiens* | 791 |
| 217016 | 334 | 39789 | TCCTATACAGTTTTGGGAAC | 489 | *H. sapiens* | 792 |
| 217017 | 334 | 39904 | AAGGACTTCAGTATGGAGCT | 490 | *H. sapiens* | 793 |
| 217018 | 334 | 39916 | ATGGAGCTTTTATTGAATTG | 491 | *H. sapiens* | 794 |
| 217022 | 334 | 40412 | CCATCAGCACTATTATTTAT | 495 | *H. sapiens* | 795 |
| 217023 | 334 | 40483 | ATAGGCAAGCTCAGCCATAG | 496 | *H. sapiens* | 796 |
| 217025 | 334 | 40576 | TGCTAGATGAGATACATCAA | 498 | *H. sapiens* | 797 |
| 217026 | 334 | 40658 | GAAGACCAAACATGGTTCTA | 499 | *H. sapiens* | 798 |
| 217029 | 334 | 41130 | CTCTGTTTAGTCCTCTCCAG | 502 | *H. sapiens* | 799 |
| 217032 | 503 | 490 | CATTGATAAAATGTTCTGGC | 505 | *H. sapiens* | 800 |
| 217033 | 503 | 504 | TCTGGCACAGCAAAACCTCT | 506 | *H. sapiens* | 801 |
| 217034 | 503 | 506 | TGGCACAGCAAAACCTCTAG | 507 | *H. sapiens* | 802 |
| 217037 | 503 | 523 | TAGAACACATAGTGTGATTT | 510 | *H. sapiens* | 803 |
| 217039 | 503 | 526 | AACACATAGTGTGATTTAAG | 512 | *H. sapiens* | 804 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to there referred target segments and consequently inhibit the expression of apolipoprotein B.

According to the present invention, antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 37

Antisense Inhibition of Human Apolipoprotein B Expression—Dose Response of Oligonucleotides In accordance with the present invention, 12 oligonucleotides described in Examples 29 and 31 were further investigated in a dose response study. The control oligonucleotides used in this study were ISIS 18076 (SEQ ID NO: 805) and ISIS 13650 (SEQ ID NO: 806).

All compounds in this study, including the controls, were chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P═S) throughout the oligonucleotides. All cytidine residues are 5-methylcytidines.

In the dose-response experiment, with mRNA levels as the endpoint, HepG2 cells were treated with the antisense oligonucleotides or the control oligonucleotides at doses of 37, 75, 150, and 300 nM oligonucleotide. Data were obtained by real-time quantitative PCR as described in other examples herein and are averaged from two experiments with mRNA levels in the treatment groups being normalized to an untreated control group. The data are shown in Table 19.

TABLE 19

Inhibition of apolipoprotein B mRNA levels by chimeric phosphorothioate oligonucleotides having 2'-MOE wings and a deoxy gap - Dose Response

| | % inhibition Dose | | | | |
|---|---|---|---|---|---|
| ISIS # | 37 nM | 75 nM | 150 nM | 300 nM | SEQ ID NO |
| 271009 | 82 | 91 | 94 | 96 | 319 |
| 281625 | 62 | 76 | 84 | 94 | 224 |
| 301014 | 75 | 90 | 96 | 98 | 249 |
| 301027 | 80 | 90 | 95 | 96 | 262 |
| 301028 | 70 | 79 | 85 | 92 | 263 |
| 301029 | 54 | 67 | 79 | 85 | 264 |
| 301030 | 64 | 75 | 87 | 92 | 265 |
| 301031 | 61 | 82 | 92 | 96 | 266 |
| 301034 | 73 | 87 | 93 | 97 | 269 |
| 301036 | 67 | 83 | 92 | 95 | 271 |
| 301037 | 73 | 85 | 69 | 96 | 272 |
| 301045 | 77 | 86 | 94 | 98 | 280 |

Example 38

Antisense Inhibition of Human Apolipoprotein B Expression—Dose Response—Lower Dose Range In accordance with the present invention, seven oligonucleotides described in Examples 29, 31, 35, and 36 were further investigated in a dose response study. The control oligonucleotides used in this study were ISIS 18076 (SEQ ID NO: 805), ISIS 13650 (SEQ ID NO: 806), and ISIS 129695 (SEQ ID NO: 807).

All compounds in this study, including the controls, were chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P═S) throughout the oligonucleotides. All cytidine residues are 5-methylcytidines.

In the dose-response experiment, with mRNA levels as the endpoint, HepG2 cells were treated with the antisense oligonucleotides or the control oligonucleotides at doses of 12.5, 37, 75, 150, and 300 nM oligonucleotide. Data were obtained by real-time quantitative PCR as described in other examples herein and are averaged from two experiments with mRNA levels in the treatment groups being normalized to an untreated control group. The data are shown in Table 20.

TABLE 20

Inhibition of apolipoprotein B mRNA levels by chimeric phosphorothioate oligonucleotides having 2'-MOE wings and a deoxy gap - Dose Response

| | % inhibition Dose | | | | | |
|---|---|---|---|---|---|---|
| ISIS # | 12.5 nM | 37 nM | 75 nM | 150 nM | 300 nM | SEQ ID # |
| 271009 | 67 | 86 | 92 | 94 | 95 | 319 |
| 281625 | 44 | 66 | 83 | 85 | 94 | 224 |
| 301012 | 63 | 79 | 90 | 92 | 95 | 247 |
| 368638 | 42 | 73 | 91 | 96 | 97 | 247 |
| 308642 | 59 | 84 | 91 | 97 | 98 | 319 |
| 308651 | 57 | 76 | 84 | 90 | 88 | 319 |
| 308658 | 29 | 61 | 73 | 78 | 90 | 224 |

Example 39

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., J. Am. Chem. Soc., 1998, 120, 11820-11821; Matteucci, M. D. and Caruthers, M. H. J. Am. Chem. Soc., 1981, 103, 3185-3191; Beaucage, S. L. and Caruthers, M. H. Tetrahedron Lett., 1981, 22, 1859-1862; Dahl, B. J., et al., Acta Chem. Scand, 1990, 44, 639-641; Reddy, M. P., et al., Tetrahedron Lett., 1994, 25, 4311-4314; Wincott, F. et al., Nucleic Acids Res., 1995, 23, 2677-2684; Griffin, B. E., et al., Tetrahedron, 1967, 23, 2301-2313; Griffin, B. E., et al., Tetrahedron, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be stably annealed by methods known in the art to form double stranded (duplexed) antisense compounds. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 40

Design and Screening of Duplexed Antisense Compounds Targeting Apolipoprotein B

In accordance with the present invention, a series of nucleic acid duplexes comprising the antisense compounds of the present invention and their complements are designed to target apolipoprotein B. The nucleobase sequence of the antisense strand of the duplex comprises at least a portion of an oligonucleotide described herein. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. The antisense and sense strands of the duplex comprise from about 17 to 25 nucleotides, or from about 19 to 23 nucleotides. Alternatively, the antisense and sense strands comprise 20, 21 or 22 nucleotides.

For example, a duplex comprising an antisense strand having the sequence CGAGAGGCGGACGGGACCG (SEQ ID NO: 893) and having a two-nucleobase overhang of deoxythymidine(dT) would have the following structure:

```
  cgagaggcggacgggac-    Antisense Strand
cgTT
  ||||||||||||||||||    (SEQ ID NO: 894)

TTgctctccgcctgccctggc   Complement (SEQ. ID NO: 895)
```

In another embodiment, a duplex comprising an antisense strand having the same sequence CGAGAGGCGGACGGGACCG (SEQ ID NO: 893) may be prepared with blunt ends (no single stranded overhang) as shown:

```
cgagaggcggacgggaccg   Antisense Strand
||||||||||||||||||    (SEQ ID NO: 893)
gctctccgcctgccctggc   Complement (SEQ. ID NO: 896)
```

RNA strands of the duplex can be synthesized by methods disclosed herein or purchased from Dharmacon Research Inc., (Lafayette, Colo.). Once synthesized, the complementary strands are stably annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate apolipoprotein B expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 41

Design of Phenotypic Assays and In Vivo Studies for the use of Apolipoprotein B Inhibitors Phenotypic Assays Once apolipoprotein B inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of apolipoprotein B in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with apolipoprotein B inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the apolipoprotein B inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate annuals, which includes humans.

The clinical trial is subjected to rigorous controls to ensure that individuals are not unnecessarily put at risk and that they are fully informed about their role in the study.

To account for the psychological effects of receiving treatments, volunteers are randomly given placebo or apolipoprotein B inhibitor. Furthermore, to prevent the doctors from being biased in treatments, they are not informed as to whether the medication they are administering is a apolipoprotein B inhibitor or a placebo. Using this randomization approach, each volunteer has the same chance of being given either the new treatment or the placebo.

Volunteers receive either the apolipoprotein B inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding apolipoprotein B or apolipoprotein B protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and apolipoprotein B inhibitor treatment. In general, the volunteers treated with placebo have little or no response to treatment, whereas the volunteers treated with the apolipoprotein B inhibitor show positive trends in their disease state or condition index at the conclusion of the study.

Example 42

Antisense Inhibition of Rabbit Apolipoprotein B Expression by Chimeric Phosphorothioate Oligonucleotides having 2'-MOE Wings and a Deoxy Gap In accordance with the present invention, a series of oligonucleotides was designed to target different regions of rabbit apolipoprotein B, using published sequences (GenBank accession number X07480.1, incorporated herein as SEQ ID NO: 808, GenBank accession number M17780.1, incorporated herein as SEQ ID NO: 809, and a sequence was derived using previously described primers (Tanaka, Journ. Biol. Chem., 1993,268, 12713-12718) representing an mRNA of the rabbit apolipoprotein B, incorporated herein as SEQ ID NO: 810). The oligonucleotides are shown in Table 21. "Target site" indicates the first (5'-most) nucleotide number on the particular target sequence to which the oligonucleotide binds. All compounds in Table 21 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide. All cytidine residues are 5-methylcytidines. The compounds were analyzed for their effect on rabbit apolipoprotein B mRNA levels in primary rabbit hepatocytes by quantitative real-time PCR as described in other examples herein. Primary rabbit hepatocytes were treated with 150 nM of the compounds in Table 21. For rabbit apolipoprotein B the PCR primers were:

forward primer: AAGCACCCCCAATGTCACC (SEQ ID NO: 811)

reverse primer: GGGATGGCAGAGCCAATGTA (SEQ ID NO: 812) and the PCR probe was: FAM-TCCTGGATTCAAGCTTCTATGTGCCTTCA-TAMRA (SEQ ID NO: 813) where FAM (PE-Applied Biosystems, Foster City, Calif.) is the fluorescent reporter dye) and TAMRA (PE-Applied Biosystems, Foster City, Calif.) is the quencher dye. Data are averages from two experiments. If present, "N.D." indicates "no data".

TABLE 21

Inhibition of rabbit apolipoprotein B mRNA levels by chimeric phosphorothioate oligonucleotides having 2'-MOE wings and a deoxy gap

| ISIS # | TARGET SEQ ID NO | TARGET SITE | SEQUENCE | % INHIB | SEQ ID NO |
|---|---|---|---|---|---|
| 233149 | 808 | 1 | TGCTTGGAGAAGGTAAGATC | 0 | 814 |
| 233150 | 810 | 1 | GCGTTGTCTCCGATGTTCTG | 20 | 815 |
| 233151 | 809 | 13 | TAATCATTAACTTGCTGTGG | 20 | 816 |
| 233152 | 808 | 22 | TCAGCACGTAGCAATGCATT | 0 | 817 |
| 233153 | 808 | 31 | GCCTGATACTCAGCACGTAG | 0 | 818 |
| 233154 | 809 | 31 | CAATTGAATGTACTCAGATA | 18 | 819 |
| 233155 | 808 | 51 | ACCTCAGTGACTTGTAATCA | 47 | 820 |
| 233156 | 809 | 51 | CACTGGAAACTTGTCTCTCC | 23 | 821 |
| 233157 | 809 | 71 | AGTAGTTAGTTTCTCCTTGG | 0 | 822 |
| 233159 | 808 | 121 | TCAGTGCCCAAGATGTCAGC | 0 | 823 |
| 233160 | 810 | 121 | ATTGGAATAATGTATCCAGG | 81 | 824 |

TABLE 21-continued

Inhibition of rabbit apolipoprotein B mRNA levels by chimeric phosphorothioate oligonucleotides having 2'-MOE wings and a deoxy gap

| ISIS # | TARGET SEQ ID NO | TARGET SITE | SEQUENCE | % INHIB | SEQ ID NO |
|---|---|---|---|---|---|
| 233161 | 809 | 130 | TTGGCATTATCCAATGCAGT | 28 | 825 |
| 233162 | 808 | 151 | GTTGCCTTGTGAGCAGCAGT | 0 | 826 |
| 233163 | 810 | 151 | ATTGTGAGTGGAGATACTTC | 80 | 827 |
| 233164 | 809 | 171 | CATATGTCTGAAGTTGAGAC | 8 | 828 |
| 233165 | 808 | 181 | GTAGATACTCCATTTTGGCC | 0 | 829 |
| 233166 | 810 | 181 | GGATCACATGACTGAATGCT | 82 | 830 |
| 233167 | 808 | 201 | TCAAGCTGGTTGTTGCACTG | 28 | 831 |
| 233168 | 808 | 211 | GGACTGTACCTCAAGCTGGT | 0 | 832 |
| 233169 | 808 | 231 | GCTCATTCTCCAGCATCAGG | 14 | 833 |
| 233170 | 809 | 251 | TTGATCTATAATACTAGCTA | 23 | 834 |
| 233172 | 810 | 282 | ATGGAAGACTGGCAGCTCTA | 86 | 835 |
| 233173 | 808 | 301 | TTGTGTTCCTTGAAGCGGCC | 3 | 836 |
| 233174 | 809 | 301 | TGTGCACGGATATGATAACG | 21 | 837 |
| 233175 | 810 | 306 | GACCTTGAGTAGATTCCTGG | 90 | 838 |
| 233176 | 810 | 321 | GAAATCTGGAAGAGAGACCT | 62 | 839 |
| 233177 | 808 | 331 | GTAGCTTTCCCATCTAGGCT | 0 | 840 |
| 233178 | 808 | 346 | GATAACTCTGTGAGGGTAGC | 0 | 841 |
| 233179 | 810 | 371 | ATGTTGCCCATGGCTGGAAT | 65 | 842 |
| 233180 | 809 | 381 | AAGATGCAGTACTACTTCCA | 13 | 843 |
| 233181 | 808 | 382 | GCACCCAGAATCATGGCCTG | 0 | 844 |
| 233182 | 809 | 411 | CTTGATACTTGGTATCCACA | 59 | 845 |
| 233183 | 810 | 411 | CAGTGTAATGATCGTTGATT | 88 | 846 |
| 233184 | 810 | 431 | TAAAGTCCAGCATTGGTATT | 69 | 847 |
| 233185 | 810 | 451 | CAACAATGTCTGATTGGTTA | 73 | 848 |
| 233186 | 810 | 473 | GAAGAGGAAGAAAGGATATG | 60 | 849 |
| 233187 | 810 | 481 | TGACAGATGAAGAGGAAGAA | 66 | 850 |
| 233188 | 810 | 500 | TTGTACTGTAGTGCATCAAT | 74 | 851 |
| 233189 | 809 | 511 | GCCTCAATCTGTTGTTTCAG | 46 | 852 |
| 233190 | 810 | 520 | ACTTGAGCGTGCCCTCTAAT | 69 | 853 |
| 233191 | 809 | 561 | GAAATGGAATTGTAGTTCTC | 31 | 854 |

Example 43

Antisense Inhibition of Rabbit Apolipoprotein B Expression by Chimeric Phosphorothioate Oligonucleotides having 2'-MOE Wings and a Deoxy gap-Dose Response Study In accordance with the present invention, a subset of the antisense oligonuclotides in Example 42 was further investigated in dose-response studies. Treatment doses were 10, 50, 150 and 300 nM. ISIS 233160 (SEQ ID NO: 824), ISIS 233166 (SEQ ID NO: 830), ISIS 233172 (SEQ ID NO: 835), ISIS 233175 (SEQ ID NO: 838), and ISIS 233183 (SEQ ID NO: 846) were analyzed for their effect on rabbit apolipoprotein B mRNA levels in primary rabbit hepatocytes by quantitative real-time PCR as described in other examples herein. Data are averages from two experiments and are shown in Table 22.

TABLE 22

Inhibition of rabbit apolipoprotein B mRNA levels by chimeric phosphorothioate oligonucleotides having 2'-MOE wings and a deoxy gap

| | Percent Inhibition | | | |
|---|---|---|---|---|
| ISIS # | 300 nM | 150 nM | 50 nM | 10 nM |
| 233160 | 80 | 74 | 67 | 33 |
| 233166 | 73 | 79 | 81 | 66 |
| 233172 | 84 | 81 | 76 | 60 |
| 233175 | 93 | 90 | 85 | 67 |
| 233183 | 80 | 81 | 71 | 30 |

Example 44

Effects of Antisense Inhibition of Apolipoprotein B in LDLr−/− Mice—Dose Response LDL receptor-deficient mice (LDLr(−/−)mice), a strain that cannot edit the apolipoprotein B mRNA and therefore synthesize exclusively apolipoprotein B-100, have markedly elevated LDL cholesterol and apolipoprotein B-100 levels and develop extensive atherosclerosis.

LDLr(−/−) mice, purchased from Taconic (Germantown, N.Y.) were used to evaluate antisense oligonucleotides for their potential to lower apolipoprotein B mRNA or protein levels, as well as phenotypic endpoints associated with apolipoprotein B. LDLr(−/−) mice were separated into groups of males and females. LDLr(−/−) mice were dosed intraperitoneally twice a week for six weeks with either 10, 25, or 50 mg/kg of ISIS 147764 (SEQ ID NO: 109) or ISIS 270906 (SEQ ID NO: 856) which is a 4 base mismatch of ISIS 147764, or with saline, or 20 mg/kg of Atorvastatin. At study termination animals were sacrificed and evaluated for several phenotypic markers.

ISIS 147764 was able to lower cholesterol, triglycerides, and mRNA levels in a dose-dependent manner in both male and female mice while the 4-base mismatch ISIS 270906 was not able to do this. The results of the study are summarized in Table 23.

TABLE 23

Effects of ISIS 147764 treatment in male and female LDLr-/-mice on apolipoprotein B mRNA, liver enzyme, cholesterol, and triglyceride levels.

| | Dose | Liver Enzymes IU/L | | Lipoproteins mg/dL | | | | mRNA % |
|---|---|---|---|---|---|---|---|---|
| ISIS No. | mg/kg | AST | ALT | CHOL | HDL | LDL | TRIG | control |
| | | | | Males | | | | |
| Saline | | 68.4 | 26.6 | 279.2 | 125.4 | 134.7 | 170.6 | 100.0 |
| 147764 | 10 | 57.6 | 29.8 | 314.2 | 150.0 | 134.7 | 198.6 | 61.7 |
| | 25 | 112.6 | 78.8 | 185.0 | 110.6 | 66.2 | 104.2 | 30.7 |
| | 50 | 163.6 | 156.8 | 165.6 | 107.8 | 51.2 | 113.4 | 16.6 |
| 270906 | 50 | 167.4 | 348.0 | 941.0 | 244.2 | 541.9 | 844.8 | N.D. |
| Atorvastatin | 20 | N.D. | N.D. | N.D. | N.D. | N.D. | N.D. | 110.9 |
| | | | | Females | | | | |
| Saline | | 65.0 | 23.4 | 265.8 | 105.8 | 154.9 | 121.4 | 100.0 |
| 147764 | 10 | 82.0 | 27.2 | 269.6 | 121.0 | 127.8 | 140.8 | 64.2 |
| | 25 | 61.4 | 32.2 | 175.8 | 99.5 | 68.9 | 100.4 | 41.3 |
| | 50 | 134.6 | 120.4 | 138.2 | 92.2 | 45.9 | 98.0 | 18.5 |
| 270906 | 50 | 96.0 | 88.6 | 564.6 | 200.0 | 310.0 | 240.4 | N.D. |
| Atorvastatin | 20 | N.D. | N.D. | N.D. | N.D. | N.D. | N.D. | 109.0 |

Example 45

Effects of Antisense Inhibition of Apolipoprotein B in Cynomolgus Monkeys

Cynomolgus monkeys fed an atherogenic diet develop atherosclerosis with many similarities to atherosclerosis of human beings. Female Cynomolgus macaques share several similarities in lipoproteins and the cardiovascular system with humans. In addition to these characteristics, there are similarities in reproductive biology. The Cynomolgus female has a 28-day menstrual cycle like that of women. Plasma hormone concentrations have been measured throughout the Cynomolgus menstrual cycle, and the duration of the follicular and luteal phases, as well as plasma estradiol and progesterone concentrations across the cycle, are also remarkably similar to those in women.

Cynomolgus monkeys (male or female) can be used to evaluate antisense oligonucleotides for their potential to lower apolipoprotein B mRNA or protein levels, as well as phenotypic endpoints associated with apolipoprotein B including, but not limited to cardiovascular indicators, atherosclerosis, lipid diseases, obesity, and plaque formation. One study could include normal and induced hypercholesterolemic monkeys fed diets that are normal or high in lipid and cholesterol. Cynomolgus monkeys can be dosed in a variety of regimens, one being subcutaneously with 10-20 mg/kg of the oligomeric compound for 1-2 months. Parameters that may observed during the test period could include: total plasma cholesterol, LDL-cholesterol, HDL-cholesterol, triglyceride, arterial wall cholesterol content, and coronary intimal thickening.

Example 46

Sequencing of Cynomolgus Monkey (Macaca fascicularis) Apolipoprotein B Preferred Target Segment In accordance with the present invention, a portion of the cynomolgus monkey apolipoprotein B mRNA not available in the art, was amplified. Positions 2920 to 3420 of the human apolipoprotein B mRNA sequence (GenBank accession number NM_000384.1, incorporated herein as SEQ ID NO: 3) contain the preferred target segment to which ISIS 301012 hybridizes and the corresponding segment of cynomolgus monkey apolipoprotein B mRNA was amplified and sequenced. The site to which ISIS 301012 hybridizes in the human apolipoprotein B was amplified by placing primers at 5' position 2920 and 3' position 3420. The cynomolgus monkey hepatocytes were purchased from In Vitro Technologies (Gaithersburg, Md.). The 500 bp fragments were produced using human and cynomolgus monkey 1° hepatocyte cDNA and were produced by reverse transcription of purified total RNA followed by 40 rounds of PCR amplification. Following gel purification of the human and cynomolgus amplicons, the forward and reverse sequencing reactions of each product were performed by Retrogen (Invitrogen kit was used to create the single-stranded cDNA and provided reagents for Amplitaq PCR reaction). This cynomolgus monkey sequence is incorporated herein as SEQ ID NO: 855 and is 96% identical to positions 2920 to 3420 of the human apolipoprotein B mRNA.

Example 47

Effects of Antisense Inhibition of Human Apolipoprotein B Gene (ISIS 281625 and 301012) in C57BL/6NTac-TgN (APOB100) Transgenic Mice C57BL/6NTac-TgN(APOB100) transgenic mice have the human apolipoprotein B gene "knocked-in". These mice express high levels of human apolipoprotein B100 resulting in mice with elevated serum levels of LDL cholesterol. These mice are useful in identifying and evaluating compounds to reduce elevated levels of LDL cholesterol and the risk of atherosclerosis. When fed a high fat cholesterol diet, these mice develop significant foam cell accumulation underlying the endothelium and within the media, and have significantly more complex atherosclerotic lesions than control animals.

C57BL/6NTac-TgN(APOB100) mice were divided into two groups—one group receiving oligonucleotide treatment and control animals receiving saline treatment. After overnight fasting, mice were dosed intraperitoneally twice a week with saline or 25 mg/kg ISIS 281625 (SEQ ID No: 224) or ISIS 301012 (SEQ ID No: 247) for eight weeks. At study termination and forty eight hours after the final injections, animals were sacrificed and evaluated for target mRNA levels in liver, cholesterol and triglyceride levels, and liver enzyme levels. In addition, the endogenous mouse apolipoprotein B levels in liver were measured to evaluate any effects of these antisense oligonucletides targeted to the human apolipoprotein B.

Upon treatment with either ISIS 281625 or ISIS 301012, the AST and ALT levels were increased, yet did not exceed normal levels (~300 IU/L). Cholesterol levels were slightly increased relative to saline treatment, while triglyceride levels were slightly decreased. Treatment with either of these oligonucleotides targeted to the human apolipoprotein B which is expressed in these mice markedly decreased the mRNA levels of the human apolipoprotein, while the levels of the endogenous mouse apolipoprotein B were unaffected, indicating that these oligonucleotides exhibit specificity for the human apolipoprotein B. The results of the comparative studies are shown in Table 24.

TABLE 24

Effects of ISIS 281625 and 301012 treatment in mice on apolipoprotein B mRNA, liver enzyme, cholesterol, and triglyceride levels.

| | | ISIS No. | |
|---|---|---|---|
| | SALINE | 281625 | 301012 |
| Liver Enzymes IU/L | | | |
| AST | 70.3 | 265.8 | 208.4 |
| ALT | 32.8 | 363.8 | 137.4 |
| Lipoproteins mg/dL | | | |
| CHOL | 109.5 | 152.0 | 145.1 |
| HDL | 67.3 | 84.6 | 98.6 |
| LDL | 30.2 | 49.8 | 36.6 |
| TRIG | 194.5 | 171.1 | 157.8 |
| mRNA % control | | | |
| human mRNA | 100.0 | 45.2 | 23.7 |
| mouse mRNA | 100.0 | 111.0 | 94.6 |

Following 2 and 4 weeks of ISIS 301012 treatment, LDL-cholesterol levels were significantly reduced to 22 mg/dL and 17 mg/dL, respectively.

Apolipoprotein B protein levels in liver were also evaluated at the end of the 8 week treatment period. Liver protein was isolated and subjected to immunoblot analysis using antibodies specific for human or mouse apolipoprotein B protein (US Biologicals, Swampscott, Mass. and Santa Cruz Biotechnology, Inc., Santa Cruz, Calif., respectively). Immunoblot analysis of liver protein samples reveals a reduction in the expression of both forms of human apolipoprotein B, apolipoprotein B-100 and apolipoprotein B-48. Mouse apolipoprotein B levels in liver were not significantly changed, as judged by immunoblot analysis.

Serum samples were also collected at 2, 4, 6 and 8 weeks and were evaluated for human apolipoprotein B expression by using a human apolipoprotein B specific ELISA kit (ALerCHEK Inc., Portland, Me.). Quantitation of serum human apolipoprotein B protein by ELISA revealed that treatment with ISIS 281625 reduced serum human apolipoprotein B protein by 31, 26, 11 and 26% at 2, 4, 6 and 8 weeks, respectively, relative to saline-treated animals. Treatment with ISIS 301012 reduced serum human apolipoprotein B protein by 70, 87, 81 and 41% at 2, 4, 6 and 8 weeks, respectively, relative to saline-treated control animals. Serum from transgenic mice was also subjected to immunoblot analysis using both human and mouse specific apolipoprotein B antibodies (US Biologicals, Swampscott, Mass. and Santa Cruz Biotechnology, Inc., Santa Cruz, Calif., respectively). Immunoblot analysis of serum samples taken from animals shows a similar pattern of human apolipoprotein B expression, with a significant reduction in serum apolipoprotein B protein after 2, 4 and 6 weeks of treatment and a slight reduction at 8 weeks. Mouse apolipoprotein B in serum was not significantly changed, as judged by immunoblot analysis.

Example 48

Effects of Antisense Inhibition of Apolipoprotein B (ISIS 233172, 233175, 281625, 301012, and 301027) in C57BL/6 Mice C57BL/6 mice, a strain reported to be susceptible to hyperlipidemia-induced atherosclerotic plaque formation were used in the following studies to evaluate the toxicity in mice of several antisense oligonucleotides targeted to human or rabbit apolipoprotein B.

C57BL/6 mice were divided into two groups—one group receiving oligonucleotide treatment and control animals receiving saline treatment. After overnight fasting, mice were dosed intraperitoneally twice a week with saline or 25 mg/kg of one of several oligonucleotides for two weeks. The antisense oligonucleotides used in the present study were ISIS 233172 (SEQ ID NO: 835) and ISIS 233175 (SEQ ID NO: 838), both targeted to rabbit apolipoprotein B, and ISIS 281625 (SEQ ID NO: 224), ISIS 301012 (SEQ ID NO: 247), and ISIS 301027 (SEQ ID NO: 262), targeted to human apolipoprotein B. At study termination and forty eight hours after the final injections, animals were sacrificed and evaluated for liver enzyme levels, body weight, liver weight, and spleen weight.

The levels of liver enzymes in mice were decreased relative to saline treatment for three of the antisense oligonucleotide. However, the rabbit oligonucleotide ISIS 233175 and the human oligonucleotide ISIS 301027 both elicited drastically increased levels of these liver enzymes, indicating toxicity. For all of the oligonucleotides tested, the change in weight of body, liver, and spleen were minor. The results of the comparative studies are shown in Table 25.

TABLE 25

Effects of antisense oligonucleotides targeted to human or rabbit apolipoprotein Bou mouse apolipoprotein B mRNA, liver enzyme, cholesterol, and triglyceride levels.

| | | ISIS No. | | | | |
|---|---|---|---|---|---|---|
| | SALINE | 233172 | 233175 | 281625 | 301012 | 301027 |
| Liver Enzymes | | | | | | |
| AST IU/L | 104.5 | 94.3 | 346.7 | 89.5 | 50.6 | 455.3 |
| ALT IU/L | 39.5 | 43.3 | 230.2 | 36.2 | 21.2 | 221.3 |
| Weight | | | | | | |
| BODY | 21.2 | 21.3 | 21.5 | 20.9 | 21.3 | 21.2 |
| LIVER | 1.1 | 1.3 | 1.4 | 1.2 | 1.1 | 1.3 |
| SPLEEN | 0.1 | 0.1 | 0.1 | 0.1 | 0.1 | 0.1 |

Example 49

Time Course Evaluation of Oligonucleotide at two Different Doses

C57BL/6 mice, a strain reported to be susceptible to hyperlipidemia-induced atherosclerotic plaque formation were used in the following studies to evaluate the toxicity in mice of several antisense oligonucleotides targeted to human apolipoprotein B.

Female C57BL/6 mice were divided into two groups—one group receiving oligonucleotide treatment and control animals receiving saline treatment. After overnight fasting, mice were dosed intraperitoneally twice a week with saline or 25 mg/kg or 50 mg/kg of ISIS 281625 (SEQ ID NO: 224), ISIS 301012 (SEQ ID NO: 247), or ISIS 301027 (SEQ ID NO: 262). After 2 weeks, a blood sample was taken from the tail of the mice and evaluated for liver enzyme. After 4 weeks, and study termination, animals were sacrificed and evaluated for liver enzyme levels.

For ISIS 281625 and ISIS 301012, AST and ALT levels remained close to those of saline at either dose after 2 weeks. After 4 weeks, AST and ALT levels showed a moderate increase over saline treated animals for the lower dose, but a large increase at the higher dose. ISIS 301027, administered at either dose, showed a small increase in AST and ALT levels after 2 weeks and a huge increase in AST and ALT levels after 4 weeks. The results of the studies are summarized in Table 26.

TABLE 26

AST and ALT levels in mice treated with ISIS 281625, 301012, or 301027 after 2 and 4 weeks

| | | AST (IU/L) | | ALT (IU/L) | |
|---|---|---|---|---|---|
| | Dose | 2 weeks | 4 weeks | 2 weeks | 4 weeks |
| | | SALINE | | | |
| ISIS No. | (mg/kg) | 49.6 | 63.2 | 22.4 | 25.2 |
| 261625 | 25 | 40.8 | 75 | 21.2 | 31.8 |
| | 50 | 44.4 | 152.4 | 30.8 | 210.4 |
| 301012 | 25 | 37.2 | 89.8 | 22.4 | 24.8 |
| | 50 | 38.4 | 107.4 | 23.2 | 29.2 |
| 301027 | 25 | 55.4 | 537.6 | 27.2 | 311.2 |
| | 50 | 64 | 1884 | 34.8 | 1194 |

Example 50

Effects of Antisense Inhibition of Apolipoprotein B (ISIS 147483 and 147764) in ob/ob Mice Leptin is a hormone produced by fat that regulates appetite. Deficiencies in this hormone in both humans and non-human animals leads to obesity. ob/ob mice have a mutation in the leptin gene which results in obesity and hyperglycemia. As such, these mice are a useful model for in investigation of obesity and diabetes and treatments designed to treat these conditions.

Ob/ob mice receiving a high fat, high cholesterol diet (60% kcal fat supplemented with 0.15% cholesterol) were treated with one of several oligonucleotides to evaluate their effect on apolipoprotein B-related phenotypic endpoints in ob/ob mice. After overnight fasting, mice from each group were dosed intraperitoneally twice a week with 50 mg/kg of ISIS 147483 (SEQ ID NO: 79), or 147764 (SEQ ID NO: 109), or the controls ISIS 116847 (SEQ ID NO: 857), or 141923 (SEQ ID NO: 858), or saline for six weeks. At study termination and forty eight hours after the final injections, animals were sacrificed and evaluated for target mRNA levels in liver, cholesterol and triglyceride levels, liver enzyme levels, serum glucose levels, and PTEN levels.

ISIS 147483 and 147764 were both able to lower apolipoprotein B mRNA levels, as well as glucose, cholesterol, and triglyceride levels. The results of the comparative studies are shown in Table 27.

TABLE 27

Effects of ISIS 147483 and 147764 treatment in ob/ob mice on apolipoprotein B mRNA, cholesterol, lipid, triglyceride, liver crmime, glucose, and PTEN levels.

| | | | ISIS No. | | | |
|---|---|---|---|---|---|---|
| | | SALINE | 116847 | 141923 | 147483 | 147764 |
| Glucose mg/dL | | 269.6 | 135.5 | 328.5 | 213.2 | 209.2 |
| Liver Enzymes | | | | | | |
| IU/L | AST | 422.3 | 343.2 | 329.3 | 790.2 | 406.5 |
| | ALT | 884.3 | 607.5 | 701.7 | 941.7 | 835.0 |
| Lipoproteins | | | | | | |
| mg/dL | CHOL | 431.9 | 287.5 | 644.3 | 250.0 | 286.3 |
| | TRIG | 128.6 | 196.5 | 196.5 | 99.8 | 101.2 |

TABLE 27-continued

Effects of ISIS 147483 and 147764 treatment in ob/ob mice on apolipoprotein B mRNA, cholesterol, lipid, triglyceride, liver crmime, glucose, and PTEN levels.

| | | | ISIS No. | | | |
|---|---|---|---|---|---|---|
| | | SALINE | 116847 | 141923 | 147483 | 147764 |
| mRNA | % control | | | | | |
| | ApoB | 100.0 | 77.0 | 100.0 | 25.2 | 43.1 |
| | PTEN | 100.0 | 20.0 | 113.6 | 143.2 | 115.3 |

Example 51

Antisense Inhibition of Apolipoprotein B in High Fat Fed Mice: Time-Dependent Effects In a further embodiment of the invention, the inhibition of apolipoprotein B mRNA in mice was compared to liver oligonucleotide concentration, total cholesterol, LDL-cholesterol and HDL-cholesterol. Male C57Bl/6 mice receiving a high fat diet (60% fat) were evaluated over the course of 6 weeks for the effects of treatment with twice weekly intraperitoneal injections of 50 mg/kg ISIS 147764 (SEQ ID NO: 109) or 50 mg/kg of the control oligonucleotide ISIS 141923 (SEQ ID NO: 858). Control animals received saline treatment. Animals were sacrificed after 2 days, 1, 2, 4 and 6 weeks of treatment. Each treatment group at each time point consisted of 8 mice.

Target expression in liver was measured by real-time PCR as described by other examples herein and is expressed as percent inhibition relative to saline treated mice. Total, LDL- and HDL-cholesterol levels were measured by routine clinical analysis using an Olympus Clinical Analyzer (Olympus America Inc., Melville, N.Y.) and are presented in mg/dL. Results from saline-treated animals are shown for comparison. Intact oligonucleotide in liver tissue was measured by capillary gel electrophoresis and is presented as micrograms of oligonucleotide per gram of tissue. All results are the average of 8 animals and are shown in Table 28.

TABLE 28

Correlation between liver drug concentration, apolipoprotein B mRNA expression and serum lipids during ISIS 147764 treatment

| | | Treatment period | | | | |
|---|---|---|---|---|---|---|
| | ISIS # | 2 days | 1 week | 2 weeks | 4 weeks | 6 weeks |
| % Inhibition | 141923 | 9 | 4 | 7 | 0 | 0 |
| apolipoprotein B mRNA | 147764 | 50 | 57 | 73 | 82 | 88 |
| Intact | 141923 | 58 | 61 | 152 | 261 | 631 |
| oligonucleotide ug/g | 147764 | 85 | 121 | 194 | 340 | 586 |
| Total | saline | 105 | 152 | 144 | 180 | 191 |
| cholesterol | 141923 | 99 | 146 | 152 | 169 | 225 |
| mg/dL | 147764 | 101 | 128 | 121 | 75 | 73 |
| LDL- | saline | 8 | 32 | 28 | 50 | 46 |
| cholesterol | 141923 | 8 | 27 | 27 | 38 | 56 |
| mg/dL | 147764 | 7 | 19 | 14 | 7 | 7 |
| HDL- | saline | 74 | 117 | 114 | 127 | 141 |
| cholesterol | 141923 | 70 | 116 | 122 | 128 | L66 |
| mg/dL | 147764 | 76 | 107 | 105 | 66 | 64 |

These results illustrate that inhibition of apolipoprotein B mRNA by ISIS 147764 occurred within 2 days of treatment, increased with successive treatments and persisted for 6 weeks of treatment. Quantitation of liver oligonucleotide levels reveals a strong correlation between the extent of target inhibition and liver drug concentration. Furthermore, at 1, 2, 3 and 4 weeks of treatment, a inverse correlation between inhibition of target mRNA and cholesterol levels (total, HDL and LDL) is observed, with cholesterol levels lowering as percent inhibition of apolipoprotein B mRNA becomes greater. Serum samples were subjected to immunoblot analysis using an antibody to detect mouse apolipoprotein B protein (Gladstone Institute, San Francisco, Calif.). The expression of protein follows the same pattern as that of the mRNA, with apolipoprotein B protein in serum markedly reduced within 48 hours and lowered throughout the 6 week treatment period.

The oligonucleotide treatments described in this example were duplicated to investigate the extent to which effects of ISIS 147764 persist following cessation of treatment. Mice were treated as described, and sacrificed 1, 2, 4, 6 and 8 weeks following the cessation of oligonucleotide treatment. The same parameters were analyzed and the results are shown in Table 29.

TABLE 29

Correlation between liver drug concentration, apolipoprotein B mRNA expression, and serum lipids after cessation of dosing

| | | Treatment period | | | | |
|---|---|---|---|---|---|---|
| | ISIS # | 1 week | 2 weeks | 4 weeks | 6 weeks | 8 weeks |
| % Inhi- | 141923 | 15 | 2 | 7 | 11 | 7 |
| bition | 147764 | 82 | 78 | 49 | 37 | 19 |
| apolipoprotein B mRNA | | | | | | |
| Intact | 141923 | 297 | 250 | 207 | 212 | 128 |
| oligonucleotide | 147764 | 215 | 168 | 124 | 70 | 43 |
| ug/g | | | | | | |
| Total | saline | 114 | 144 | 195 | 221 | 160 |
| cholesterol | 141923 | 158 | 139 | 185 | 186 | 151 |
| mg/dL | 147764 | 69 | 67 | 111 | 138 | 135 |
| LDL- | saline | 21 | 24 | 34 | 37 | 22 |
| cholesterol | 141923 | 24 | 24 | 32 | 32 | 24 |
| mg/dL | 147764 | 14 | 14 | 18 | 24 | 21 |
| HDL- | saline | 86 | 109 | 134 | 158 | 117 |
| cholesterol | 141923 | 121 | 105 | 135 | 136 | 108 |
| mg/dL | 147764 | 51 | 49 | 79 | 100 | 94 |

These data demonstrate that after termination of oligonucleotide treatment, the effects of ISIS 147764, including apolipoprotein B mRNA inhibition, and cholesterol lowering, persist for up to 8 weeks. Immunoblot analysis demonstrates that apolipoprotein B protein levels follow a pattern similar that observed for mRNA expression levels.

Example 52

Effects of Antisense Inhibition of Human Apolipoprotein B Gene by 301012 in C57BL/6NTac-TgN(APOB100) Transgenic Mice: Dosing Study C57BL/6Tac-TgN(APOB100) transgenic mice have the human apolipoprotein B gene "knocked-in". These mice express high levels of human apolipoprotein B resulting in mice with elevated serum levels of LDL cholesterol. These mice are useful in identifying and evaluating compounds to reduce elevated levels of LDL cholesterol and the risk of atherosclerosis. When fed a high fat cholesterol diet, these mice develop significant foam cell accumulation underlying the endothelium and within the media, and have significantly more complex atherosclerotic plaque lesions than control animals.

A long-term study of inhibition of human apolipoprotein B by ISIS 301012 in C57BL/6NTac-TgN(APOB100) mice (Taconic, Germantown, N.Y.) was conducted for a 3 month period. Mice were dosed intraperitoneally twice a week with 10 or 25 mg/kg ISIS 301012 (SEQ ID No: 247) for 12 weeks. Saline-injected animals served as controls. Each treatment group comprised 4 animals.

After 2, 4, 6, 8 and 12 weeks of treatment, serum samples were collected for the purpose of measuring human apolipoprotein B protein. Serum protein was quantitated using an ELISA kit specific for human apolipoprotein B (ALerCHEK Inc., Portland, Me.). The data are shown in Table 30 and each result represents the average of 4 animals. Data are normalized to saline-treated control animals.

TABLE 30

Reduction of human apolipoprotein B protein in transgenic mouse serum following ISIS 331012 treatment

| Dose of oligonucleotide mg/kg | % Reduction in human apolipoprotein B protein in serum | | | | |
|---|---|---|---|---|---|
| | 2 weeks | 4 weeks | 6 weeks | 8 weeks | 12 weeks |
| 10 | 76 | 78 | 73 | 42 | 85 |
| 25 | 80 | 87 | 86 | 47 | 79 |

These data illustrate that following 2, 4, 6 or 12 weeks of treatment with ISIS 301012, the level of human apolipoprotein B protein in serum from transgenic mice is lowered by approximately 80%, demonstrating that in addition to inhibiting mRNA expression, ISIS 301012 effectively inhibits human apolipoprotein B protein expression in mice carrying the human apolipoprotein B transgene. Apolipoprotein B protein in serum was also assessed by immunoblot analysis using an antibody directed to human apolipoprotein B protein (US Biologicals, Swampscott, Mass.). This analysis shows that the levels human apolipoprotein B protein, both the apolipoprotein B-100 and apolipoprotein B-48 forms, are lowered at 2, 4, 6 and 12 weeks of treatment. Immunoblot analysis using a mouse apolipoprotein B specific antibody (Santa Cruz Biotechnology, Inc., Santa Cruz, Calif.) reveals no significant change in the expression of the mouse protein in serum.

At the beginning of the treatment (start) and after 2, 4, 6 and 8 weeks of treatment, serum samples were collected and total, LDL- and HDL-cholesterol levels were measured by routine clinical analysis using an Olympus Clinical Analyzer (Olympus America Inc., Melville, N.Y.), and these data are presented in Table 31. Results are presented as mg/dL in serum and represent the average of 4 animals. Results from the saline control animals are also shown.

TABLE 31

Effects of ISIS 301012 on serum lipids in human apolipoprotein B transgenic mice

| | Treatment | Treatment period | | | | |
|---|---|---|---|---|---|---|
| | | Start | 2 weeks | 4 weeks | 6 weeks | 8 weeks |
| Total cholesterol mg/dL | Saline | 120 | 110 | 129 | 121 | 126 |
| | 10 | 115 | 97 | 111 | 120 | 122 |
| | 25 | 107 | 101 | 107 | 124 | 147 |
| HDL-cholesterol mg/dL | Saline | 67 | 61 | 69 | 62 | 64 |
| | 10 | 70 | 69 | 78 | 72 | 79 |
| | 25 | 64 | 73 | 76 | 80 | 91 |
| LDL- | Saline | 39 | 41 | 50 | 45 | 47 |

TABLE 31-continued

Effects of ISIS 301012 on serum lipids in human apolipoprotein B transgenic mice

| | Treatment | Treatment period | | | | |
|---|---|---|---|---|---|---|
| | | Start | 2 weeks | 4 weeks | 6 weeks | 8 weeks |
| cholesterol mg/dL | 10 | 35 | 20 | 23 | 37 | 33 |
| | 25 | 33 | 19 | 19 | 37 | 44 |

These data demonstrate that LDL-cholesterol is lowered by treatment with 10 or 25 mg/kg of ISIS 147764 during the first 4 weeks of treatment.

The study was terminated forty eight hours after the final injections in the eighth week of treatment, when animals were sacrificed and evaluated for target mRNA levels in liver, apolipoprotein B protein levels in liver and serum cholesterol and liver enzyme levels. In addition, the expression of endogenous mouse apolipoprotein B levels in liver was measured to evaluate any effects of ISIS 301012 on mouse apolipoprotein B mRNA expression.

Human and mouse apolipoprotein B mRNA levels in livers of animals treated for 12 weeks were measured by real-time PCR as described herein. Each result represents the average of data from 4 animals. The data were normalized to saline controls and are shown in Table 32.

TABLE 32

Effects of ISIS 301012 on human and mouse apolipoprotein B mRNA levels in transgenic mice

| mRNA species measured | % Inhibition Dose of ISIS 301012 | |
|---|---|---|
| | 10 mg/kg | 25 mg/kg |
| human apolipoprotein B | 65 | 75 |
| mouse apolipoprotein B | 6 | 6 |

These data demonstrate that following 12 weeks of treatment with ISIS 301012, human apolipoprotein B mRNA is reduced by as much as 75% in the livers of transgenic mice, whereas mouse liver apolipoprotein B mRNA was unaffected. Furthermore, ELISA analysis of apolipoprotein B protein in livers of transgenic mice reveals an 80% and 82% reduction in the human protein following 10 and 20 mg/kg ISIS 301012, respectively. Immunoblot analysis using an antibody directed to human apolipoprotein B also demonstrates a reduction in the expression of human apolipoprotein B, both the apolipoprotein B-100 and apolipoprotein B-48 forms, in the livers of transgenic mice. Immunoblot analysis using an antibody directed to mouse apolipoprotein B protein (Santa Cruz Biotechnology, Inc., Santa Cruz, Calif.) reveals that expression of the mouse protein in liver does not change significantly.

ALT and AST levels in serum were also measured using the Olympus Clinical Analyzer (Olympus America Inc., Melville, N.Y.) and showed that following treatment with ISIS 301012, the AST and ALT levels were increased, yet did not exceed normal levels (~300 IU/L), indicating a lack of toxicity due to ISIS 301012 treatment.

Example 53

Assessment of In vitro Immunostimulatory Effects of ISIS 301012

Immunostimulatory activity is defined by the production of cytokines upon exposure to a proinflammatory agent. In a further embodiment of the invention, ISIS 301012 was tested for immunostimulatory, or proinflammatory, activity. These studies were performed by MDS Pharma Services (Saint Germain sur l'Arbresle, France). Whole blood was collected from naive B6C3F1 mice, which had not been knowingly exposed to viral, chemical or radiation treatment. Cultured blood cells were exposed to 0.5, 5 or 50 μM of ISIS 301012 for a period of 14 to 16 hours. Antisense oligonucleotides known to possess proinflammatory activity served as positive controls. Each treatment was performed in triplicate. At the end of the treatment period, supernatants were collected and cytokine analysis was performed using a flow cytometry method with the mouse Inflammation CBA kit (Becton Dickinson, Franklin Lakes, N.J.). The results revealed that ISIS 301012 does not stimulate the release of any of the tested cytokines, which were interleukin-12p70 (IL-12p70), tumor necrosis factor-alpha (TNF-alpha), interferon-gamma (IFN-gamma), interleukin-6 (IL-6), macrophage chemoattractant protein-1 (MCP-1) and interleukin-10 (IL-10). Thus, ISIS 301012 does not possess immunostimulatory activity, as determined by the in vitro immunostimulatory assay.

Example 54

Comparative Genomic Analysis of Apolipoprotein B

In accordance with the present invention, a comparative genomic analysis of apolipoprotein B sequences from human, mouse and monkey was performed and illustrated that apolipoprotein B sequences are conserved across species. The organization of human and mouse apolipoprotein B genes is also highly conserved. The human and mouse genes are comprised of 29 and 26 exons, respectively. The mouse mRNA is approximately 81% homologous to the human sequence. The complete sequence and gene structure of the apolipoprotein B gene in non-human primates have not been identified. However, as illustrated in Example 46, a 500 base pair fragment which contains the ISIS 301012 target sequence exhibits approximately 96% identity to the human sequence.

The binding site for ISIS 301012 lies within the coding region, within exon 22 of the human apolipoprotein B mRNA. When the ISIS 301012 binding sites from human, mouse and monkey were compared, significant sequence diversity was observed. Although the overall sequence conservation between human and monkey over a 500 nucleotide region was approximately 96%, the ISIS 301012 binding site of the monkey sequence contains 2 mismatches relative to the human sequence. Likewise, though the mouse apolipoprotein B mRNA sequence is approximately 81% homologous to human, within the ISIS 301012 binding site, 5 nucleotides are divergent. The sequence comparisons for the ISIS 301012 binding site for human, mouse and monkey apolipoprotein B sequences are shown in Table 33. Mismatched nucleotides relative to the ISIS 301012 target sequence are underlined.

TABLE 33

Comparison of ISIS 301012 binding site among human, monkey and mouse apolipoprotein B sequences

| Species | # Mismatches | ISIS 301012 target sequence |
|---|---|---|
| Human | 0 | aggtgcgaagcagactgagg |
| Monkey | 2 | aggtgtaaagcagactgagg |
| Mouse | 5 | aggagtgcagcagtctgaag |

The target sequence to which the mouse antisense oligonucleotide ISIS 147764 hybridizes lies within exon 24 of the mouse apolipoprotein B gene. The sequence comparisons for the ISIS 147764 binding site in mouse and human apolipoprotein B sequences are shown in Table 34. Mismatched nucleotides relative to the ISIS 147764 target sequence are underlined.

TABLE 34

Comparison of ISIS 147764 binding site between mouse and human apolipoprotein B sequences

| Species | # Mismatches | ISIS 147764 binding site |
|---|---|---|
| Human | 5 | gcattgacatcttcagggac |
| Mouse | 0 | gcatggacttcttctggaaa |

Example 55

BLAST Analysis of ISIS 301012

In accordance with the present invention, the number of regions in the human genome to which ISIS 301012 will hybridize with perfect complementarity was determined. Percent complementarity of an antisense compound with a region of a target nucleic acid was determined using BLAST programs (basic local alignment search tools) and PowerBLAST programs known in the art (Altschul et al., J. Mol. Biol., 1990, 215, 403-410; Zhang and Madden, Genome Res., 1997, 7, 649-656). This analysis assessed sequence complementarity in genomic or pre-mRNA regions and in coding sequences.

In genomic regions, ISIS 301012 shows perfect sequence complementarity to the apolipoprotein B gene only. No target sequences with one mismatch relative to ISIS 301012 were found. Two mismatches are found between the ISIS 301012 target sequence and the heparanase gene, and 3 mismatches are found between the ISIS 301012 target sequence and 28 unique genomic sites.

In RNA sequences, perfect sequence complementarity is found between ISIS 301012 and the apolipoprotein B mRNA and three expressed sequence tags that bear moderate similarity to a human apolipoprotein B precursor. A single mismatch is found between ISIS 301012 and an expressed sequence tag similar to the smooth muscle form of myosin light chain.

Example 56

Antisense Inhibition of Apolipoprotein B in Primary Human Hepatocytes: Dose Response Studies In accordance with the present invention, antisense oligonucleotides targeted to human apolipoprotein B were tested in dose response studies in primary human hepatocytes. Preplated primary human hepatocytes were purchased from Invitro Technologies (Baltimore, Md.). Cells were cultured in high-glucose DMEM (Invitrogen Corporation, Carlsbad, Calif.) supplemented with 10% fetal bovine serum (Invitrogen Corporation, Carlsbad, Calif.), 100 units/mL and 100 μg/mL streptomycin (Invitrogen Corporation, Carlsbad, Calif.).

Human primary hepatocytes were treated with ISIS 301012 (SEQ ID NO: 247) at 10, 50, 150 or 300 nM. Untreated cells and cells treated with the scrambled control oligonucleotide ISIS 113529 (CTCTTACTGTGCTGTGGACA, SEQ ID NO: 859) served as two groups of control cells. ISIS 113529 is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide. All cytidines are 5-methylcytidines.

Oligonucleotides were introduced into cells through LIPOFECTIN-mediated transfection as described by other examples herein. Cells were harvested both 24 and 48 hours after treatment with oligonucleotide, and both RNA and protein were isolated. Additionally, the culture media from treated cells was collected for ELISA analysis of apolipoprotein B protein secretion.

Apolipoprotein B mRNA expression was determined by real-time PCR of RNA samples as described by other examples herein. Each result represents 6 experiments. The data are normalized to untreated control cells and are shown in Table 35.

TABLE 35

Inhibition of apolipoprotein B mRNA by antisense oligonucleotides in human primary hepatocytes

| Dose of oligonucleotide | Treatment (hours) | % Inhibition of apolipoprotein B mRNA ISIS # 301012 | 113529 |
|---|---|---|---|
| 10 nM | 24 | 65 | N.D. |
| | 48 | 33 | N.D. |
| 50 nM | 24 | 75 | N.D. |
| | 48 | 48 | N.D. |
| 150 nM | 24 | 90 | 16 |
| | 48 | 78 | 5 |
| 300 nM | 24 | 89 | 10 |
| | 48 | 72 | 18 |

These data demonstrate that ISIS 301012 inhibits apolipoprotein B expression in a dose-dependent manner in human primary hepatocytes.

Apolipoprotein secreted from into the cultured cell media was measured in the samples treated with 50 and 150 nM of oligonucleotide, using a target protein specific ELISA kit (ALerCHEK Inc., Portland, Me.). Each result represents 3 experiments. The data are normalized to untreated control cells and are shown in Table 36.

TABLE 36

Inhibition of apolipoprotein B protein secretion from human primary hepatocytes by ISIS 301012

| Dose | Treatment (hours) | % Change in apolipoprotein B protein secretion ISIS # 301012 | 113529 |
|---|---|---|---|
| 150 nM | 24 | −57 | +6 |
| | 48 | −75 | +4 |

TABLE 36-continued

Inhibition of apolipoprotein B protein secretion from human primary hepatocytes by ISIS 301012

| Dose | Treatment (hours) | % Change in apolipoprotein B protein secretion ISIS # 301012 | 113529 |
|---|---|---|---|
| 300 nM | 24 | −41 | −2 |
| | 48 | −48 | −5 |

Protein samples from 50, 150 and 300 nM doses after 24 hours and 150 and 300 nM doses after 48 hours were subjected to immunoblot analysis as described by other examples herein, using a human apolipoprotein B protein specific antibody purchased from US Biological (Swampscott, Mass.). Immunoblot analysis further demonstrates that apolipoprotein B protein in human hepatocytes is reduced in a dose-dependent manner following antisense oligonucleotide treatment with ISIS 301012.

An additional experiment was performed to test the effects of ISIS 271009 (SEQ ID NO: 319), ISIS 281625 (SEQ ID NO: 224) and ISIS 301027 (SEQ ID NO: 262) on human apolipoprotein B mRNA in human primary hepatocytes. Cells were cultured as described herein and treated with 5, 10, 50 or 150 nM of ISIS 271009, ISIS 281625 or ISIS 301027 for a period of 24 hours. The control oligonucleotides ISIS 13650 (SEQ ID NO: 806) and ISIS 113529 (SEQ ID NO: 859) were used at 50 or 150 nM. Human apolipoprotein B mRNA expression was evaluated by real-time PCR as described by other examples herein. Apolipoprotein B protein secreted into the cultured cell media was measured in the samples treated with 50 and 150 nM of oligonucleotide, using a target protein specific ELISA kit (ALerCHEK Inc., Portland, Me.).

The data, shown in Table 37, represent the average 2 experiments and are normalized to untreated control cells. Where present, a "+" indicates that gene expression was increased.

TABLE 37

Antisense inhibition of human apolipoprotein B mRNA by ISIS 271009, ISIS 281625 and ISIS 301027

| | Oligonucleotide dose | ISIS 271009 | ISIS 281625 | ISIS 301027 | ISIS 13650 | ISIS 113529 |
|---|---|---|---|---|---|---|
| % Inhibition of apolipoprotein B mRNA expression | 5 nM | +4 | 8 | 11 | N.D. | N.D. |
| | 10 nM | 5 | 22 | 37 | N.D. | N.D. |
| | 50 nM | 52 | 49 | 50 | 38 | 0 |
| | 150 nM | 81 | 52 | 70 | 26 | 14 |
| % Inhibition of apolipoprotein B protein secretion | 50 nM | 17 | 18 | 21 | N.D. | N.D. |
| | 150 nM | 32 | 18 | 32 | +18 | +1 |

These data demonstrate that ISIS 271009, ISIS 281625 and ISIS 301027 inhibit apolipoprotein B mRNA expression in a dose-dependent manner in human primary hepatocytes. ISIS 271009 and ISIS 301027 inhibit the secretion of apolipoprotein B protein from cells in a dose-dependent manner.

Example 57

Effects of apolipoprotein B-100 Antisense Oligonucleotides on Apolipoprotein(a) Expression Lipoprotein(a) [Lp(a)] contains two disulfide-linked distinct proteins, apolipoprotein(a) and apolipoprotein B (Rainwater and Kammerer, J. Exp. Zool., 1998, 282, 54-61). In accordance with the present invention, antisense oligonucleotides targeted to apolipoprotein B were tested for effects on the expression of the apolipoprotein(a) component of the lipoprotein(a) particle in primary human hepatocytes.

Primary human hepatocytes (InVitro Technologies, Baltimore, Md.), cultured and transfected as described herein, were treated with 5, 10, 50 or 150 nM of ISIS 271009 (SEQ ID NO: 319), 281625 (SEQ ID NO: 224), 301012 (SEQ ID NO: 247) or 301027 (SEQ ID NO: 262). Cells were also treated with 50 or 150 nM of the control oligonucleotides ISIS 113529 (SEQ ID NO: 859) or ISIS 13650 (SEQ ID NO: 806). Untreated cells served as a control. Following 24 hours of oligonucleotide treatment, apolipoprotein(a) mRNA expression was measured by quantitative real-time PCR as described in other examples herein.

Probes and primers to human apolipoprotein(a) were designed to hybridize to a human apolipoprotein(a) sequence, using published sequence information (GenBank accession number NM_005577.1, incorporated herein as SEQ ID NO: 860). For human apolipoprotein(a) the PCR primers were:
forward primer: CAGCTCCTTATTGTTATACGAGGGA (SEQ ID NO: 861)
reverse primer: TGCGTCTGAGCATTGCGT (SEQ ID NO: 862) and the PCR probe was: FAM-CCCGGTGTCAG-GTGGGAGTACTGC-TAMRA (SEQ ID NO: 863) where FAM is the fluorescent dye and TAMRA is the quencher dye.

Data are the average of three experiments and are expressed as percent inhibition relative to untreated controls. The results are shown in Table 38. A "+" or "−" preceding the number indicates that apolipoprotein(a) expression was increased or decreased, respectively, following treatment with antisense oligonucleotides.

TABLE 38

Effects of apolipoprotein B antisense oligonucleotides on apolipoprotein(a) expression

| Oligo-nucleotide | % Change in apolipoprotein(a) mRNA expression following antisense inhibition of apolipoprotein B ISIS # | | | | | |
|---|---|---|---|---|---|---|
| Dose | 271009 | 281625 | 301012 | 301027 | 13650 | 113529 |
| 5 nM | +70 | −9 | +34 | −16 | N.D. | N.D. |
| 10 nM | +31 | −23 | +86 | −45 | N.D. | N.D. |
| 50 nM | +25 | −34 | +30 | −39 | −68 | +14 |
| 150 nM | −47 | +32 | +38 | −43 | −37 | −9 |

These results illustrate that ISIS 301012 did not inhibit the expression of apolipoprotein(a) in human primary hepatocytes. ISIS 271009 inhibited apolipoprotein(a) expression at the highest dose. ISIS 281625 and ISIS 301027 decreased the levels of apolipoprotein(a) mRNA.

Example 58

Inhibition of Lipoprotein(a) Particle Secretion with Antisense Oligonucleotides Targeted to Apolipoprotein B-100

In accordance with the present invention, the secretion of lipoprotein(a) particles, which are comprised of one apolipoprotein(a) molecule covalently linked to one apolipoprotein B molecule, was evaluated in primary human hepatocytes treated with antisense oligonucleotides targeted to the apolipoprotein B component of lipoprotein(a).

Primary human hepatocytes (InVitro Technologies, Baltimore, Md.), cultured and transfected as described herein, were treated for 24 hours with 50 or 150 nM of ISIS 271009 (SEQ ID NO: 319), 281625 (SEQ ID NO: 224), 301012 (SEQ ID NO: 247) or 301027 (SEQ ID NO: 262). Cells were also treated with 150 nM of the control oligonucleotides ISIS 113529 (SEQ ID NO: 859) or ISIS 13650 (SEQ ID NO: 806). Untreated cells served as a control. Following 24 hours of oligonucleotide treatment, the amount of lipoprotein(a) in the culture medium collected from the treated cells was measured using a commercially available ELISA kit (ALerCHEK Inc., Portland, Me.). The results are the average of three experiments and are expressed as percent change in lipoprotein(a) secretion relative to untreated controls. The data are shown in Table 39. A "+" or "−" preceding the number indicates that lipoprotein(a) particle secretion was increased or decreased, respectively, following treatment with antisense oligonucleotides targeted to apolipoprotein B.

TABLE 39

Inhibition of lipoprotein(a) particle secretion with antisense oligonucleotides targeted to apolipoprotein B

| Oligo-nucleotide | % Change in lipoprotein(a) secretion ISIS # | | | | | |
|---|---|---|---|---|---|---|
| Dose | 271009 | 281625 | 301012 | 301027 | 13650 | 113529 |
| 50 nM | −25 | −26 | −27 | −33 | N.D. | N.D. |
| 150 nM | −42 | −24 | −37 | −44 | +14 | +14 |

These data demonstrate that antisense inhibition of apolipoprotein B, a component of the lipoprotein(a) particle, can reduce the secretion of lipoprotein(a) from human primary hepatocytes. In addition, this reduction in lipoprotein(a) secretion is not necessarily concomitant with a decrease in apolipoprotein(a) mRNA expression, as shown in Example 57.

Example 59

Mismatched and Truncated Derivatives of ISIS 301012

As demonstrated herein, ISIS 301012 (SEQ ID NO: 247) reduces apolipoprotein B mRNA levels in cultured human cell lines as well as in human primary hepatocytes. In a further embodiment of the invention, a study was performed using nucleotide sequence derivatives of ISIS 301012. A series of oligonucleotides containing from 1 to 7 base mismatches, starting in the center of the ISIS 301012 sequence, was designed. This series was designed to introduce the consecutive loss of Watson-Crick base pairing between ISIS 301012 and its target mRNA sequence. These compounds are shown in Table 40. The antisense compounds with mismatched nucleotides relative to ISIS 301012 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide.

An additional derivative of ISIS 301012 was designed, comprising the ISIS 301012 sequence with 2'MOE nucleotides throughout the oligonucleotide (uniform 2'-MOE). This compound is 20 nucleotides in length, with phosphorothioate linkages throughout the oligonucleotide. This compound is also shown in Table 40.

HepG2 cells were treated with 50 or 150 nM of the compounds in Table 40 for a 24 hour period, after which RNA was isolated and target expression was measured by real-time PCR as described herein. Untreated cells served as controls. The results are shown in Tables 40 and are normalized to untreated control samples.

TABLE 40

Effects of ISIS 301012 mismatched oligonucleotides and a uniform 2'MOE oligonucleotide on apolipoprotein B expression in HepG2 cells

| ISIS # | SEQUENCE | # Mismatches | % Change in apolipoprotein B mRNA expression Dose of oligonucleotide 50 | 150 | SEQ ID NO |
|---|---|---|---|---|---|
| 301012 | GCCTCAGTCTGCTTCGCACC | 0 | -44 | -75 | 247 |
| | Mismatch Series, chimeric oligonucleotides | | | | |
| 332770 | GCCTCAGTCTTCTTCGCACC | 1 | +7 | -22 | 864 |
| 332771 | GCCTCAGTCTTATTCGCACC | 2 | +37 | +37 | 865 |
| 332772 | GCCTCAGTATTATTCGCACC | 3 | +99 | +84 | 866 |
| 332773 | GCCTCATTATTATTCGCACC | 4 | +75 | +80 | 867 |
| 332774 | GCCTCATTATTATTAGCACC | 5 | +62 | +66 | 868 |
| 332775 | GCCTCATTATTATTATCACC | 6 | -1 | +10 | 869 |
| 332776 | GCCTAATTATTATTATCACC | 7 | +10 | +20 | 870 |
| | Uniform 2'-MOE oligonucleotide | | | | |
| 332769 | GCCTCAGTCTGCTTCGCACC | 0 | -11 | -14 | 247 |

The results of treatment of HepG2 cells with the compounds in Table 40 reveals that none of the compounds displays the dose-dependent inhibition observed following treatment with the parent ISIS 301012 sequence. ISIS 332770, which has only a single thymidine to cytosine substitution in the center of the oligonucleotide, was 3-fold less potent than ISIS 301012. Further nucleotide substitutions abrogated antisense inhibition of apolipoprotein B expression.

Phosphorothioate chimeric oligonucleotides are metabolized in vivo predominantly by endonucleolytic cleavage. In accordance with the present invention, a series of oligonucleotides was designed by truncating the ISIS 301012 sequence in 1 or 2 base increments from the 5' and/or 3' end. The truncated oligonucleotides represent the possible products that result from endonucleotlytic cleavage. These compounds are shown in Table 41. The compounds in Table 41 are chimeric oligonucleotides ("gapmers") of varying lengths, composed of a central "gap" region consisting of 2'-deoxynucleotides, which is flanked on both ends by 2'-methoxyethyl (2'-MOE)nucleotides. The exact structure of each chimeric oligonucleotide is designated in Table 41 as the "chimera structure". For example, a designation of 4~10~4 indicates that the first 4 (5' most) and last 4 (3' most) nucleotides are 2'-MOE nucleotides, and the 10 nucleotides in the gap are 2'-deoxynucleotides. 2'-MOE nucleotides are indicated by bold type. The internucleoside (backbone) linkages are phosphodiester (P═O) between underscored nucleotides; all other internucleoside linkages are phosphorothioate (P═S).

These compounds were tested for their ability to reduce the expression of apolipoprotein B mRNA. HepG2 cells were treated with 10, 50 or 150 nM of each antisense compound in Table 41 for a 24 hour period, after which RNA was isolated and target expression was measured by real-time PCR as described herein. Untreated cells served as controls. The results are shown in Tables 41 and are normalized to untreated control samples.

TABLE 41

Effect of ISIS 301012 truncation mutants on apolipoprotein B expression in HepG2 cells

| ISIS # | Target SEQ ID NO | Target Site | SEQUENCE | Chimeric structure | % Change in apolipoprotein B mRNA expression Dose of oligonucleotide 10 | 50 | 150 | SEQ ID NO |
|---|---|---|---|---|---|---|---|---|
| 301012 | 3 | 3249 | GCCTCAGTCTGCTTCGCACC | 5~10~5 | -51 | -72 | -92 | 247 |
| 331022 | 3 | 3249 | GCCTCAGTCTGCTTCGCAC | 5~10~4 | -33 | -49 | -87 | 871 |
| 332777 | 3 | 3249 | GCCTCAGTCTGCTTCGCA | 5~10~3 | -27 | -53 | -80 | 872 |
| 332778 | 3 | 3249 | GCCTCAGTCTGCTTC | 5~10~0 | -11 | -20 | -58 | 873 |
| 332780 | 3 | 3248 | CCTCAGTCTGCTTCGCAC | 4~10~4 | -3 | -43 | -74 | 874 |

TABLE 41-continued

Effect of ISIS 301012 truncation mutants on apolipoprotein B expression in HepG2 cells

| ISIS # | Target SEQ ID NO | Target Site | SEQUENCE | Chimeric structure | % Change in apolipoprotein B mRNA expression Dose of oligonucleotide 10 | 50 | 150 | SEQ ID NO |
|---|---|---|---|---|---|---|---|---|
| 332781 | 3 | 3247 | CTCAGTCTGCTTCGCA | 3~10~3 | -9 | -35 | -60 | 875 |
| 332782 | 3 | 3246 | TCAGTCTGCTTCGC | 2~10~2 | -16 | -16 | -69 | 876 |
| 332784 | 3 | 3249 | GCCTCAGTCT | 5~5~0 | +12 | -1 | +7 | 877 |
| 332785 | 3 | 3238 | GCTTCG CACC | 0~5~5 | +5 | -2 | -4 | 878 |

The results in Table 41 illustrate that inhibition of apolipoprotein B is dependent upon sequence length, as well as upon sequence complementarity and dose, as demonstrated in Table 41, but truncated versions of ISIS 301012 are to a certain degree capable of inhibiting apolipoprotein B mRNA expression.

Example 60

Design and Screening of dsRNAs Targeting Human Apolipoprotein B

In accordance with the present invention, a series of nucleic acid duplexes comprising the antisense compounds of the present invention and their complements were designed to target apolipoprotein B and are shown in Table 42. All compounds in Table 42 are oligoribonucleotides 20 nucleotides in length with phosphodiester internucleoside linkages (backbones) throughout the compound. The compounds were prepared with blunt ends. Table 41 shows the antisense strand of the dsRNA, and the sense strand is synthesized as the complement of the antisense strand. These sequences are shown to contain uracil (U) but one of skill in the art will appreciate that uracil (U) is generally replaced by thymine (T) in DNA sequences. "Targer site" indicates the first (5'-most) nucleotide number on the particular target sequence to which the compound binds. A subset of the compounds in Table 42 are the RNA equivalents of DNA antisense oligonucleotides described herein, and, where applicable, this is noted by the ISIS # of the DNA oligonucleotide in the column "RNA equivalent of ISIS #".

TABLE 42 dsRNAs targeted to human apolipoprotein B

| ISIS # | Region | Target SEQ ID NO | Target Site | Sequence | SEQ ID NO | RNA equivalent of ISIS # |
|---|---|---|---|---|---|---|
| 342855 | coding | 3 | 3249 | GCCUCAGUCUGCUUCGCACC | 247 | 301012 |
| 342856 | 3' UTR | 3 | 13903 | GCUCACUGUAUGGUUUUAUC | 262 | 301027 |
| 342857 | coding | 3 | 5589 | AGGUUACCAGCCACAUGCAG | 224 | 308361 |
| 342858 | coding | 3 | 669 | GAGCAGUUUCCAUACACGGU | 130 | 270991 |
| 342859 | coding | 3 | 1179 | CCUCUCAGCUCAGUAACCAG | 135 | 270996 |
| 342860 | coding | 3 | 2331 | GUAUAGCCAAAGUGGUCCAC | 34 | 147797 |
| 342861 | coding | 3 | 3579 | UAAGCUGUAGCAGAUGAGUC | 213 | 281614 |
| 342862 | 5' UTR | 3 | 6 | CAGCCCCGCAGGUCCCGGUG | 249 | 301014 |
| 342863 | 5' UTR | 3 | 116 | GGUCCAUCGCCAGCUGCGGU | 256 | 301021 |
| 342864 | 3' UTR | 3 | 13910 | AAGGCUGGCUCACUGUAUGG | 266 | 301031 |
| 342865 | 3' UTR | 3 | 13970 | GCCAGCUUUGGUGCAGGUCC | 273 | 301038 |
| 342866 | coding | 3 | 426 | UUGAAGCCAUACACCUCUUU | 879 | none |
| 342867 | coding | 3 | 3001 | UGACCAGGACUGCCUGUUCU | 880 | none |
| 342868 | coding | 3 | 5484 | GAAUAGGGCUGUAGCUGUAA | 881 | none |

TABLE 42-continued dsRNAs targeted to human apolipoprotein B

| ISIS # | Region | Target SEQ ID NO | Target Site | Sequence | SEQ ID NO | RNA equivalent of ISIS # |
|---|---|---|---|---|---|---|
| 342869 | coding | 3 | 6662 | UAUACUGAUCAAAUUGUAUC | 882 | none |
| 342870 | coding | 3 | 8334 | UGGAAUUCUGGUAUGUGAAG | 883 | none |
| 342871 | coding | 3 | 9621 | AAAUCAAAUGAUUGCUUUGU | 883 | none |
| 342872 | coding | 3 | 10155 | GUGAUGACACUUGAUUUAAA | 885 | none |
| 342873 | coding | 3 | 12300 | GAAGCUGCCUCUUCUUCCCA | 886 | none |
| 342874 | coding | 3 | 13629 | GAGAGUUGGUCUGAAAAAUC | 887 | none |

The dsRNA compounds in Table 42 were tested for their effects on human apolipoprotein mRNA in HepG2 cells. HepG2 cells were treated with 100 nM of dsRNA compounds mixed with 5 μg/mL LIPOFECTIN (Invitrogen Corporation, Carlsbad, Calif.) for a period of 16 hours. In the same experiment, HepG2 cells were also treated with 150 nM of subset of the antisense oligonucleotides described herein mixed with 3.75 μg/mL LIPOFECTIN; these compounds are listed in Table 43. Control oligonucleotides included ISIS 18078 (GTGCGCGCGAGCCCGAAATC, SEQ ID NO: 888), ISIS 18078 is a chimeric oligonucleotide ("gapmer") 20 nucleotides in length, composed of a central "gap" region consisting of 9 2'-deoxynucleotides, which is flanked on the 5' and 3' ends by a five-nucleotide "wing" and a six-nucleotide "wing", respectively. The wings are composed of 2'-methoxyethyl (2'-MOE)nucleotides. The internucleoside (backbone) linkages are phosphorothioate (P═S) throughout the oligonucleotide. All cytidines are 5-methylcytidines. The duplex of ISIS 263188 (CUUCUGGCAUCCGGUUUAGTT, SEQ ID NO: 889) and its complement was also used as a control. ISIS 263188 is an oligoribonucleotide 21 nucleotides in length with the 2 nucleotides on the 3' end being oligodeoxyribonucleotides (TT) and with phosphodiester internucleoside linkages (backbones) throughout the compound.

Cells were treated for 4 hours, after which human apolipoprotein B mRNA expression was measured as described by examples herein. Results were normalized to untreated control cells, which were not treated with LIPOFECTIN or oligonucleotide. Data are the average of 4 experiments and are presented in Table 43.

TABLE 43

Inhibition of apolipoprotein B mRNA by dsRNAs in HepG2 cells

| ISIS # | Dose | % Inhibition | SEQ ID # |
|---|---|---|---|
| 342855 | 100 nM | 53 | 247 |
| 342856 | 100 nM | 34 | 262 |
| 342857 | 100 nM | 55 | 224 |
| 342858 | 100 nM | 44 | 130 |
| 342859 | 100 nM | 23 | 135 |
| 342860 | 100 nM | 34 | 34 |
| 342861 | 100 nM | 42 | 213 |
| 342862 | 100 nM | 16 | 249 |
| 342863 | 100 nM | 34 | 256 |
| 342864 | 100 nM | 53 | 266 |
| 342865 | 100 nM | 50 | 273 |
| 342866 | 100 nM | 12 | 879 |
| 342867 | 100 nM | 26 | 880 |
| 342868 | 100 nM | 36 | 881 |

TABLE 43-continued

Inhibition of apolipoprotein B mRNA by dsRNAs in HepG2 cells

| ISIS # | Dose | % Inhibition | SEQ ID # |
|---|---|---|---|
| 342869 | 100 nM | 78 | 882 |
| 342870 | 100 nM | 71 | 883 |
| 342871 | 100 nM | 9 | 883 |
| 342872 | 100 nM | 2 | 885 |
| 342873 | 100 nM | 53 | 886 |
| 342874 | 100 nM | 73 | 887 |
| 281625 | 150 nM | 79 | 224 |
| 301012 | 150 nM | 77 | 247 |
| 301014 | 150 nM | 88 | 249 |
| 301021 | 150 nM | 67 | 256 |
| 301027 | 150 nM | 79 | 262 |
| 301028 | 150 nM | 85 | 263 |
| 301029 | 150 nM | 77 | 264 |
| 301030 | 150 nM | 70 | 265 |
| 301031 | 150 nM | 73 | 266 |
| 301037 | 150 nM | 80 | 272 |
| 301038 | 150 nM | 84 | 273 |
| 301045 | 150 nM | 77 | 280 |
| 263188 | 150 nM | 26 | 888 |
| 18078 | 150 nM | 13 | 889 |

Example 61

Antisense Inhibition of Apolipoprotein B in Cynomolgous Monkey Primary Hepatocytes As demonstrated in Example 46, the region containing the target site to which ISIS 301012 hybridizes shares 96% identity with the corresponding region of Cynomolgus monkey apolipoprotein B mRNA sequence. ISIS 301012 contains two mismatched nucleotides relative to the Cynomolgous monkey apolipoprotein B mRNA sequence to which it hybridizes. In a further embodiment of the invention, oligonucleotides were designed to target regions of the monkey apolipoprotein B mRNA, using the partial Cynomologous monkey apolipoprotein B sequence described herein (SEQ ID NO: 855) and an additional portion of Cynomolgous monkey apolipoprotein B RNA sequence, incorporated herein as SEQ ID NO: 890. The target site indicates the first (5'-most) nucleotide number on the particular target sequence to which the oligonucleotide binds. For ISIS 326358 (GCCTCAGTCTGCTTTACACC, SEQ ID NO: 891) the target site is nucleotide 168 of SEQ ID NO: 855 and for ISIS 315089 (AGATTACCAGCCATATGCAG, SEQ ID NO: 892) the target site is nucleotide 19 of SEQ ID NO: 890. ISIS 326358 and ISIS 315089 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide. All cytidine residues are 5-methylcytidines. ISIS 326358 and ISIS 315089 are the Cynomolgous monkey equivalents of the human apolipoprotein B antisense oligonucleotides ISIS 301012 (SEQ ID NO: 247) and ISIS 281625 (SEQ ID NO: 224), respectively.

Antisense inhibition by ISIS 301012 was compared to that of ISIS 326358, which is a perfect match to the Cynomolgous monkey apolipoprotein B sequence to which ISIS 301012 hybridizes. The compounds were analyzed for their effect on Cynomolgous monkey apolipoprotein B mRNA levels in primary Cynomolgous monkey hepatocytes purchased from In Vitro Technologies (Gaithersburg, Md.). Pre-plated primary Cynonomolgous monkey hepatocytes were purchased from InVitro Technologies (Baltimore, Md.). Cells were cultured in high-glucose DMEM (Invitrogen Corporation, Carlsbad, Calif.) supplemented with 10% fetal bovine serum (Invitrogen Corporation, Carlsbad, Calif.), 100 units/mL and 100 μg/mL streptomycin (Invitrogen Corporation, Carlsbad, Calif.).

Primary Cynomolgous monkey hepatocytes were treated with 10, 50, 150 or 300 nM of antisense oligonucleotides for 48 hours. ISIS 113529 (SEQ ID NO: 859) was used as a control oligonucleotide. Untreated cells also served as a control. Cynomolgous monkey apolipoprotein B mRNA levels were quantitated by real-time PCR using the human apolipoprotein B and GAPDH primers and probes described by other examples herein. The results, shown in Table 44, are the average of 6 experiments and are expressed as percent inhibition of apolipoprotein B mRNA normalized to untreated control cells.

TABLE 44

Inhibition of Cynomolgous monkey apolipoprotein B mRNA by ISIS 301012 and ISIS 326358

| Dose of | Time of treatment | % Inhibition of apolipoprotein B mRNA ISIS # | | |
|---|---|---|---|---|
| oligonucleotide | (hours) | 326358 | 301012 | 113529 |
| 10 nM | 24 | 35 | 24 | N.D. |
| | 48 | 85 | 76 | N.D. |
| 50 nM | 24 | 66 | 60 | N.D. |
| | 48 | 88 | 77 | N.D. |
| 150 nM | 24 | 61 | 56 | 5 |
| | 48 | 82 | 88 | 42 |
| 300 nM | 24 | 64 | 61 | 19 |
| | 48 | 87 | 86 | 13 |

These data demonstrate that both ISIS 326359 and ISIS 301012 (despite two mismatches with the Cynomolgous monkey apolipoprotein B sequence) can inhibit the expression of apolipoprotein B mRNA in cynomolgous monkey primary hepatocytes, in a dose- and time-dependent manner.

Apolipoprotein B protein secreted from primary Cynomolgous hepatocytes treated with 150 and 300 nM of oligonucleotide was measured by ELISA using an apolipoprotein B protein specific kit (ALerCHEK Inc., Portland, Me.). Each result represents the average of 3 experiments. The data are normalized to untreated control cells and are shown in Table 45.

TABLE 45

Reduction in apolipoprotein B protein secreted from Cynomolgous monkey hepatocytes following antisense oligonucleotide treatment

| Dose of | Time of treatment | % Reduction in secreted apolipoprotein B protein ISIS # | | |
|---|---|---|---|---|
| oligonucleotide | (hours) | 326358 | 301012 | 113529 |
| 150 nM | 24 | 21 | 31 | 11 |
| | 48 | 29 | 25 | 18 |
| 300 nM | 24 | 17 | 10 | 12 |
| | 48 | 35 | 17 | 8 |

These results demonstrate that antisense inhibition by ISIS 301012 and ISIS 326358 leads to a decrease in the secretion of apolipoprotein B protein from cultured primary Cynomolgous hepatocytes.

Additionally, protein was isolated from oligonucleotide-treated primary Cynomolgous monkey hepatocytes and subjected to immunoblot analysis to further assess apolipoprotein B protein expression. Immunoblotting was performed as described herein, using an antibody to human apolipoprotein B protein (US Biologicals, Swampscott, Mass.). Immunoblot analysis of apolipoprotein B expression following antisense oligonucleotide treatment with ISIS 326358 and ISIS 301012 reveals a substantial reduction in apolipoprotein B expression.

In a further embodiment of the invention, antisense inhibition by ISIS 281625 was compared to that by ISIS 315089, which is a perfect match to the Cynomolgous monkey apolipoprotein B sequence to which ISIS 281625 hybridizes. Primary Cynomolgous monkey hepatocytes, cultured as described herein, were treated with 10, 50, 150 or 300 nM of ISIS 315089 or ISIS 281625 for 24 hours. Cells were treated with the control oligonucleotide ISIS 13650 (SEQ ID NO: 806) at 150 and 300 nM or ISIS 113529 (SEQ ID NO: 859) at 300 nM. Untreated cells also served as a control. Cynomolgous monkey apolipoprotein B mRNA levels in primary Cynomolgous monkey hepatocytes was quantitated using real-time PCR with human primers and probe as described by other examples herein. The results, shown in Table 46, are the average of 3 experiments and are expressed as percent inhibition of apolipoprotein B mRNA normalized to untreated control cells. Where present, a "+" preceding the value indicates that mRNA expression was increased.

TABLE 46

Antisense inhibition of apolipoprotein B mRNA expression in Cynomolgous monkey hepatocytes

| Dose of | % Inhibition of apolipoprotein B mRNA ISIS # | | | |
|---|---|---|---|---|
| oligonucleotide | 315089 | 281625 | 13650 | 113529 |
| 10 nM | 70 | +5 | N.D. | N.D. |
| 50 nM | 83 | 41 | N.D. | N.D. |
| 150 nM | 81 | 35 | +50 | N.D. |
| 300 nM | 82 | 69 | 33 | 28 |

These data demonstrate that both ISIS 315089 and ISIS 281625 can inhibit the expression of apolipoprotein B mRNA in Cynomolgous monkey primary hepatocytes, in a dose-dependent manner.

Apolipoprotein B protein secreted primary Cynomolgous hepatocytes treated with 50 and 150 nM of ISIS 315089 and ISIS 281625 was measured by ELISA using an apolipoprotein B protein specific kit (ALerCHEK Inc., Portland, Me.). Each result represents the average of 3 experiments. The data are normalized to untreated control cells and are shown in Table 47.

TABLE 47

Reduction in apolipoprotein B protein secreted from Cynomolgous monkey hepatocytes following antisense oligonucleotide treatment

| Dose of | % Reduction of monkey apolipoprotein B protein secretion ISIS # | | | |
|---|---|---|---|---|
| oligonucleotide | 315089 | 281625 | 13650 | 113529 |
| 50 nM | 11 | 6 | 16 | N.D. |
| 150 nM | 25 | 13 | 13 | 12 |

These results demonstrate that antisense inhibition by 150 nM of ISIS 315089 leads to a decrease in the secretion of apolipoprotein B protein from cultured primary Cynomolgous hepatocytes.

ISIS 271009 (SEQ ID NO: 319) and ISIS 301027 (SEQ ID NO: 262) were also tested for their effects on apolipoprotein B mRNA and protein expression in Cynomolgous primary hepatoctyes. Cells, cultured as described herein, were treated with 10, 50 and 150 nM of ISIS 271009 or ISIS 301027 for 24 hours. Cells were treated with the control oligonucleotide ISIS 113529 (SEQ ID NO: 859) at 150 nM. Untreated cells also served as a control. Cynomolgous monkey apolipoprotein B mRNA levels in primary Cynomolgous monkey hepatocytes was quantitated using real-time PCR with human primers and probe as described by other examples herein. The results, shown in Table 48, are the average of 2 experiments and are expressed as percent inhibition of apolipoprotein B mRNA normalized to untreated control cells.

TABLE 48

Antisense inhibition of apolipoprotein B mRNA expression in Cynomolgous monkey hepatocytes

| Dose of | % Inhibition of apolipoprotein B mRNA ISIS # | | |
|---|---|---|---|
| oligonucleotide | 271009 | 301027 | 113529 |
| 10 nM | 42 | 40 | N.D. |
| 50 nM | 66 | 54 | N.D. |
| 150 nM | 69 | 67 | 11 |

These data demonstrate that both ISIS 271009 and ISIS 301027 can inhibit the expression of apolipoprotein B mRNA in Cynomolgous monkey primary hepatocytes, in a dose-dependent manner.

Apolipoprotein B protein secreted from primary Cynomolgous hepatocytes treated with 50 and 150 nM of ISIS 271009 and ISIS 301027 was measured by ELISA using an apolipoprotein B protein specific kit (ALerCHEK Inc., Portland, Me.). Each result represents the average of 3 experiments. The data are shown as percent reduction in secreted protein, normalized to untreated control cells, and are shown in Table 49. Where present, a "+" indicates that protein secretion was increased.

TABLE 49

Reduction in apolipoprotein B protein secreted from Cynomolgous monkey hepatocytes following antisense oligonucleotide treatment

| Dose of | % Reduction of monkey apolipoprotein B protein secretion ISIS # | | | |
|---|---|---|---|---|
| oligonucleotide | 271009 | 301027 | 13650 | 113529 |
| 50 nM | +30 | 25 | N.D. | N.D. |
| 150 nM | 26 | 31 | +1 | 15 |

These results demonstrate that antisense inhibition by ISIS 315089 and ISIS 281625 leads to a decrease in the secretion of apolipoprotein B protein from cultured primary Cynomolgous hepatocytes.

Example 62

Methods for Evaluating Hepatic Steatosis

Hepatic steatosis refers to the accumulation of lipids in the liver, or "fatty liver", which is frequently caused by alcohol consumption, diabetes and hyperlipidemia. Livers of animals treated with antisense oligonucleotides targeted to apolipoprotein B were evaluated for the presence of steatosis. Steatosis is assessed by histological analysis of liver tissue and measurement of liver triglyceride levels.

Tissue resected from liver is immediately immersed in Tissue Tek OCT embedding compound (Ted Pella, Inc., Redding, Calif.) and frozen in a 2-methyl-butane dry ice slurry. Tissue sections are cut at a thickness of 4-5 μm and then fixed in 5% neutral-buffered formalin. Tissue sections are stained with hematoxylin and eosin following standard histological procedures to visualize nuclei and cytoplasm, respectively, and oil red 0 according to the manufacturer's instructions (Newcomers Supply, Middleton, Wis.) to visualize lipids.

Alternatively, tissues are fixed in 10% neutral-buffered formalin, embedded in paraffin, sectioned at a thickness of 4-5 μm, deparaffinized and stained with hematoxylin and eosin, all according to standard histological procedures.

Quantitation of liver triglyceride content is also used to assess steatosis. Tissue triglyceride levels are measured using a Triglyceride GPO Assay (Sigma-Aldrich, St. Louis, Mo.).

Example 63

Effects of Antisense Inhibition by ISIS 301012 in Lean Mice: Long-Term Study

In accordance with the present invention, the toxicity of ISIS 301012 (SEQ ID NO: 247) is investigated in a long-term, 3 month study in mice. Two-month old male and female CD-1 mice (Charles River Laboratories, Wilmington, Mass.) are dosed with 2, 5, 12.5, 25 or 50 mg/kg of ISIS 301012 twice per week for first week, and every 4 days thereafter. The mice are maintained on a standard rodent diet. Saline and control oligonucleotide animals serve as controls and are injected on the same schedule. Each treatment group contains 6 to 10 mice of each sex, and each treatment group is duplicated, one group for a 1 month study termination, the other for a 3 month study termination. After the 1 or 3 month treatment periods, the mice are sacrificed and evaluated for target expression in liver, lipid levels in serum and indicators of toxicity. Liver samples are procured, RNA is isolated and apolipoprotein B mRNA expression is measured by real-time PCR as described in other examples herein. Serum lipids, including total cholesterol, LDL-cholesterol, HDL-cholesterol and triglycerides, are evaluated by routine clinical analysis using an Olympus Clinical Analyzer (Olympus America Inc., Melville, N.Y.). Ratios of LDL-cholesterol to HDL-cholesterol and total cholesterol to HDL-cholesterol are also calculated. Analyses of serum ALT and AST, inflammatory infiltrates in tissue and basophilic granules in tissue provide an assessment of toxicities related to the treatment. Hepatic steatosis, or accumulation of lipids in the liver, is assessed by routine histological analysis with oil red 0 stain and measurement of liver tissue triglycerides using a Triglyceride GPO Assay (Sigma-Aldrich, St. Louis, Mo.).

The toxicity study also includes groups of animals allowed to recover following cessation of oligonucleotide treatment. Both male and female CD-1 mice (Charles River Laboratories, Wilmington, Mass.) are treated with 5, 10, 50 mg/kg of ISIS 301012 twice per week for the first week and every 4 days thereafter. Saline and, control oligonucleotide injected animals serve as controls. Each treatment group includes 6 animals per sex. After 3 months of treatment, animals remain untreated for an additional 3 months, after which they are sacrificed. The same parameters are evaluated as in the mice sacrificed immediately after 3 months of treatment.

After one month of treatment, real-time PCR quantitation reveals that mouse apolipoprotein B mRNA levels in liver are reduced by 53%. Additionally, the expected dose-response toxicities were observed. ALT and AST levels, measured by routine clinical procedures on an Olympus Clinical Analyzer (Olympus America Inc., Melville, N.Y.), are increased in mice treated with 25 or 50 mg/kg of ISIS 301012. Tissues were prepared for analysis by routine histological procedures. Basophilic granules in liver and kidney tissue were observed at doses of ISIS 301012 above 12.5 mg/kg. Mild lymphohistiocytic infiltrates were observed in various tissues at doses greater than 12.5 mg/kg of ISIS 301012. Staining of tissue sections with oil red 0 reveals no steatosis present following the oligonucleotide treatments.

Example 64

Effects of Antisense Inhibition by ISIS 301012 in Lean CYNOMOLGOUS Monkeys: Long-term Study As discussed in Example 45, Cynomolgus monkeys (male or female) are used to evaluate antisense oligonucleotides for their potential to lower apolipoprotein B mRNA or protein levels, as well as phenotypic endpoints associated with apolipoprotein B including, but not limited to cardiovascular indicators, atherosclerosis, lipid diseases, obesity, and plaque formation. Accordingly, in a further embodiment of the invention, ISIS 301012 (SEQ ID NO: 247) is investigated in a long-term study for its effects on apolipoprotein B expression and serum lipids in Cynomolgous monkeys. Such a long-term study is also used to evaluate the toxicity of antisense compounds.

Male and female Cynomologous monkeys are treated with 2, 4 or 12 mg/kg of ISIS 301012 intravenously or 2 or 20 mg/kg subcutaneously at a frequency of every two days for the first week, and every 4 days thereafter, for 1 and 3 month treatment periods. Saline-treated animals serve as controls. Each treatment group includes 2 to 3 animals of each sex.

At a one month interval and at the 3 month study termination, the animals are sacrificed and evaluated for target expression in liver, lipid levels in serum and indicators of toxicity. Liver samples are procured, RNA is isolated and apolipoprotein B mRNA expression is measured by real-time PCR as described in other examples herein. Serum lipids, including total cholesterol, LDL-cholesterol, HDL-cholesterol and triglycerides, are evaluated by routine clinical analysis using an Olympus Clinical Analyzer (Olympus America Inc., Melville, N.Y.). Ratios of LDL-cholesterol to HDL-cholesterol and total cholesterol to HDL-cholesterol are also calculated. Analyses of serum ALT and AST, inflammatory infiltrates in tissue and basophilic granules in tissue provide an assessment of toxicities related to the treatment. Hepatic steatosis, or accumulation of lipids in the liver, is assessed by routine histological analysis with oil red 0 stain and measurement of liver tissue triglycerides using a Triglyceride GPO Assay (Sigma-Aldrich, St. Louis, Mo.).

Additional treatment groups consisting of 2 animals per sex are treated with saline (0 mg/kg), 12 or 20 mg/kg ISIS 301012 at a frequency of every two days for the first week, and every 4 days thereafter, for a 3 month period. Following the treatment period, the animals receive no treatment for an additional three months. These treatment groups are for the purpose of studying the effects of apolipoprotein B inhibition 3 months after cessation of treatment. At the end of the 3 month recovery period, animals are sacrificed and evaluated for the same parameters as the animals sacrificed immediately after 1 and 3 months of treatment.

The results from the one month interval of the long term treatment are shown in Table 50 and are normalized to saline-treated animals for mRNA and to untreated baseline values for lipid levels. Total cholesterol, LDL-cholesterol, HDL-cholesterol, LDL particle concentration and triglyceride levels in serum were measured by nuclear magnetic resonance spectroscopy by Liposcience (Raleigh, N.C.). Additionally, the concentration of intact oligonucleotide in liver was measured by capillary gel electrophoresis and is presented as micrograms of oligonucleotide per gram of liver tissue. Each result represents the average of data from 4 animals (2 males and 2 females).

TABLE 50

Effects of antisense inhibition by ISIS 301012 in lean Cynomolgous monkeys

| | | Intravenous delivery | | | Subcutaneous injection | |
|---|---|---|---|---|---|---|
| | Saline | 2 mg/kg | 4 mg/kg | 12 mg/kg | 3.5 mg/kg | 20 mg/kg |
| apolipoprotein B expression % change normalized to saline | | −45 | −76 | −96 | N.D. | −94 |
| antisense oligonucleotide concentration μg/g | | 92 | 179 | 550 | N.D. | 855 |
| Lipid parameters, % change normalized to untreated baseline value | | | | | | |
| Total cholesterol | +1 | −6 | −2 | −2 | +5 | −5 |
| LDL-cholesterol | +17 | +15 | +9 | +3 | −4 | −16 |
| HDL-cholesterol | −11 | −23 | −15 | −8 | +13 | +5 |

TABLE 50-continued

Effects of antisense inhibition by ISIS 301012 in lean Cynomolgous monkeys

| | | Intravenous delivery | | | Subcutaneous injection | |
|---|---|---|---|---|---|---|
| | Saline | 2 mg/kg | 4 mg/kg | 12 mg/kg | 3.5 mg/kg | 20 mg/kg |
| LDL/HDL | +62 | +94 | +38 | +44 | −15 | −19 |
| Total cholesterol/HDL | +30 | +44 | +22 | +21 | −7 | −10 |
| Triglyceride | +37 | +26 | +32 | +15 | +1 | −3 |
| LDL Particle concentration | +15 | +8 | +8 | −11 | −14 | −21 |

These data show that ISIS 301012 inhibits apolipoprotein B expression in a dose-dependent manner in a primate species and concomitantly lowers lipid levels at higher doses of ISIS 301012. Furthermore, these results demonstrate that antisense oligonucleotide accumulates in the liver in a dose-dependent manner.

Hepatic steatosis, or accumulation of lipids in the liver, was not observed following 4 weeks of treatment with the doses indicated. Expected dose-related toxicities were observed at the higher doses of 12 and 20 mg/kg, including a transient 1.2-1.3 fold increase in activated partial thromboplastin time (APTT) during the first 4 hours and basophilic granules in the liver and kidney (as assessed by routine histological examination of tissue samples). No functional changes in kidney were observed.

In a similar experiment, male and female Cynomolgous monkeys received an intravenous dose of ISIS 301012 at 4 mg/kg, every two days for the first week and every 4 days thereafter. Groups of animals were sacrificed after the first dose and the fourth dose, as well as 11, 15 and 23 days following the fourth and final dose. Liver RNA was isolated and apolipoprotein B mRNA levels were evaluated by real-time PCR as described herein. The results of this experiment demonstrate a 40% reduction in apolipoprotein B mRNA expression after a single intravenous dose of 4 mg/kg ISIS 301012. Furthermore, after 4 doses of ISIS 301012 at 4 mg/kg, target mRNA was reduced by approximately 85% and a 50% reduction in target mRNA was sustained for up to 16 days following the cessation of antisense oligonucleotide treatment.

Example 65

Microarray Analysis: Gene Expression Patterns in Lean Versus High-fat Fed Mice

Male C57Bl/6 mice were divided into the following groups, consisting of 5 animals each: (1) mice on a lean diet, injected with saline (lean control); (2) mice on a high fat diet; (3) mice on a high fat diet injected with 50 mg/kg of the control oligonucleotide 141923 (SEQ ID NO: 858); (4) mice on a high fat diet given 20 mg/kg atorvastatin calcium (Lipitor®, Pfizer Inc.); (5) mice on a high fat diet injected with 10, 25 or 50 mg/kg ISIS 147764 (SEQ ID NO: 109). Saline and oligonucleotide treatments were administered intraperitoneally twice weekly for 6 weeks. Atorvastatin was administered daily for 6 weeks. At study termination, liver samples were isolated from each animal and RNA was isolated for Northern blot qualitative assessment, DNA microarray and quantitative real-time PCR. Northern blot assessment and quantitative real-time PCR were performed as described by other examples herein.

For DNA microarray analysis, hybridization samples were prepared from 10 μg of total RNA isolated from each mouse liver according to the Affymetrix Expression Analysis Technical Manual (Affymetrix, Inc., Santa Clara, Calif.). Samples were hybridized to a mouse gene chip containing approximately 22,000 genes, which was subsequently washed and double-stained using the Fluidics Station 400 (Affymetrix, Inc., Santa Clara, Calif.) as defined by the manufacturer's protocol. Stained gene chips were scanned for probe cell intensity with the GeneArray scanner (Affymetrix, Inc., Santa Clara. Calif.). Signal values for each probe set were calculated using the Affymetrix Microarray Suite v5.0 software (Affymetrix, Inc., Santa Clara, Calif.). Each condition was profiled from 5 biological samples per group, one chip per sample. Fold change in expression was computed using the geometric mean of signal values as generated by Microarray Suite v5.0. Statistical analysis utilized one-way ANOVA followed by 9 pair-wise comparisons. All groups were compared to the high fat group to determine gene expression changes resulting from ISIS 147764 treatment. Microarray data was interpreted using hierarchical clustering to visualize global gene expression patterns.

The results of the microarray analysis reveal that treatment with ISIS 147764 drives the gene expression profile in high fat fed mice to the profile observed in lean mice. Real-time PCR analysis confirmed the reduction in mRNA expression for the following genes involved in the lipid metabolism: hepatic lipase, fatty acid synthase ATP-binding cassette, subfamily D (ALD) member 2, intestinal fatty acid binding protein 2, stearol CoA desaturase-1 and HMG CoA reductase.

Mouse apolipoprotein B mRNA and serum cholesterol levels, measured as described herein, were evaluated to confirm antisense inhibition by ISIS 147764 and ISIS 147483. Both mRNA and cholesterol levels were lowered in a dose-dependent manner following treatment with ISIS 147764 or ISIS 147483, as demonstrated in other examples herein. The 50 mg/kg dose of ISIS 147483 increased ALT and AST levels. The 10, 25 and 50 mg/kg doses of ISIS 147764 and the 10 and 25 mg/kg doses of ISIS 147483 did not significantly elevate ALT or AST levels.

Example 66

Evaluation of Hepatic Steatosis in Animals Treated with Apolipoprotein B Antisense Oligonucleotides Livers of animals treated with antisense oligonucleotides targeted to apolipoprotein B were evaluated for the presence of steatosis. Steatosis is assessed by histological analysis of liver tissue and measurement of liver triglyceride levels.

Evaluation of Steatosis in High Fat Fed Animals Treated with ISIS 147764 for 6 Weeks Liver tissue from ISIS 147764 (SEQ ID NO: 109) and control-treated animals described in Example 21 was evaluated for steatosis at study termination following 6 weeks of treatment. Tissue sections were stained with oil red 0 and hematoxylin to visualize lipids and nuclei, respectively. Tissue sections were also stained with hematoxylin and eosin to visualize nuclei and cytoplasm, respectively. Histological analysis of tissue sections stained by either method reveal no difference in steatosis between saline treated and ISIS 147764 treated animals, demonstrating that a 6 week treatment with ISIS 147764 does not lead to accumulation of lipids in the liver.

Evaluation of Steatosis Following Long-term Treatment with Apolipoprotein B Inhibitor in High-fat Fed Animals Male C57Bl/6 mice were treated with twice weekly intraperitoneal injections of 25 mg/kg ISIS 147764 (SEQ ID NO: 109) or 25 mg/kg ISIS 141923 (SEQ ID NO: 858) for 6, 12 and 20 weeks. Saline treated animals served as controls. Each treatment group contained 4 animals. Animals were sacrificed at 6, 12 and 20 weeks and liver tissue was procured for histological analysis and measurement of tissue triglyeride content. The results reveal no significant differences in liver tissue triglyceride content when ISIS 147764 treated animals are compared to saline treated animals. Furthermore, histological analysis of liver tissue section demonstrates that steatosis is reduced at 12 and 20 weeks following treatment of high fat fed mice with ISIS 147764, in comparison to saline control animals that received a high fat diet.

Evaluation of Steatosis in Lean Mice

The accumulation of lipids in liver tissue was also evaluated in lean mice. Male C67Bl/6 mice (Charles River Laboratories (Wilmington. Mass.) at 6 to 7 weeks of age were maintained on a standard rodent diet and were treated twice weekly with intraperitoneal injections of 25 or 50 mg/kg 147764 (SEQ ID NO: 109) or 147483 (SEQ ID NO: 79) for 6 weeks. Saline treated animals served as controls. Each treatment group was comprised of 4 animals. Animals were sacrificed after the 6 week treatment period, at which point liver tissue and serum were collected.

Apolipoprotein B mRNA levels were measured by real-time PCR as described by other examples herein. The data, shown in Table 51, represent the average of 4 animals and are presented as inhibition relative to saline treated controls. The results demonstrate that both ISIS 147483 and ISIS 147764 inhibit apolipoprotein B mRNA expression in lean mice in a dose-dependent manner.

TABLE 51

Antisense inhibition of apolipoprotein B mRNA in lean mice

| | Treatment and dose | | | |
|---|---|---|---|---|
| | ISIS 147483 | | ISIS 147764 | |
| | 25 mg/kg | 50 mg/kg | 25 mg/kg | 50 mg/kg |
| % inhibition apolipoprotein B mRNA | 79 | 91 | 48 | 77 |

Total cholesterol, LDL-cholesterol, HDL-cholesterol and triglycerides in serum were measured by routine clinical analysis using an Olympus Clinical Analyzer (Olympus America Inc., Melville, N.Y.). The liver enzymes ALT and ALT in serum were also measured using the Olympus Clinical Analyzer. These results demonstrate that ISIS 147764 lowers serum lipids relative to saline-treated control animals ALT and AST levels do not exceed the normal range for mice (300 IU/L), indicating a lack of treatment-associated toxicity. The results are the average of data from 4 animals and are shown in Table 52.

TABLE 52

Serum lipids and liver enzyme levels in lean mice treated with ISIS 147764 and ISIS 147483

| | Treatment and dose | | | | |
|---|---|---|---|---|---|
| | | ISIS 147483 | | ISIS 147764 | |
| | Saline | 25 mg/kg | 50 mg/kg | 25 mg/kg | 50 mg/kg |
| Serum lipids | | | | | |
| Total cholesterol mg/dL | 164 | 153 | 183 | 114 | 57 |
| LDL-cholesterol mg/dL | 25 | 26 | 39 | 29 | 18 |
| HDL-cholesterol mg/dL | 127 | 117 | 131 | 79 | 38 |
| Triglycerides mg/dL | 121 | 138 | 127 | 80 | 30 |
| Liver enzymes | | | | | |
| ALT IU/L | 105 | 73 | 57 | 47 | 48 |
| AST IU/L | 109 | 78 | 72 | 81 | 101 |

Liver tissue was prepared by routine histological methods to evaluate steatosis, as described herein. Examination of tissue samples stained with oil red 0 or hematoxylin and eosin reveals that treatment of lean mice with apolipoprotein B antisense oligonucleotides does not result in steatosis.

Six Month Study to Further Evaluate Steatosis in Mice Treated with Apolipoprotein B Antisense Oligonucleotides A long-term treatment of mice with antisense oligonucleotides targeted to apolipoprotein B is used to evaluate the toxicological and pharmacological effects of extended treatment with antisense compounds. Both male and female C57Bl/6 mice at 2 months of age are treated with 2, 5, 25 or 50 mg/kg of apolipoprotein B antisense oligonucleotide. Treatments are administered intraperitoneally every 2 days for the first week and every 4 days thereafter. Mice treated with saline alone or control oligonucleotide serve as control groups. Each treatment group contains 25 to 30 mice. After 6 months of treatment, a subset of the mice in each treatment group is sacrificed. The remaining mice are allowed a 3 month recovery period without treatment, after which they are sacrificed. Apolipoprotein B mRNA expression in liver is measured by real-time PCR as described by other methods herein. Liver tissue is also prepared for measurement of triglyceride content using a Triglyceride GPO Assay (Sigma-Aldrich, St. Louis, Mo.). Serum is collected and evaluated for lipid content, including total cholesterol, LDL-cholesterol, HDL-cholesterol and triglyceride, using an Olympus Clinical Analyzer (Olympus America Inc., Melville, N.Y.). The liver enzymes ALT and AST are also measured in serum, also using the clinical analyzer. Serum samples are subjected to immunoblot analysis using an antibody directed to apolipoprotein B (Santa Cruz Biotechnology, Inc., Santa Cruz, Calif.). Liver, kidney and other tissues are prepared by routine procedures for histological analyses. Tissues are evaluated for the presence of basophilic granules and inflammatory infiltrates. Steatosis is evaluated by oil red 0 stain of liver tissue sections.

Example 67

A Mouse Model for Atherosclerotic Plaque Formation: Human Apolipoprotein R Transgenic Mice Lacking the LDL Receptor Gene The LDL receptor is responsible for clearing apolipoprotein B-containing LDL particles. Without the LDL receptor, animals cannot effectively clear apolipoprotein B-containing LDL particles from the plasma. Thus the serum levels of apolipoprotein B and LDL cholesterol are markedly elevated. Mice expressing the human apolipoprotein B transgene (TgN-hApoB +/+) and mice deficient for the LDL receptor (LDLr −/−) are both used as animal models of atherosclerotic plaque development. When the LDL receptor deficiency genotype is combined with a human apolipoprotein B transgenic genotype (TgN-hApoB +/+; LDLr −/−), atherosclerotic plaques develop rapidly. In accordance with the present invention, mice of this genetic background are used to investigate the ability of compounds to prevent atherosclerosis and plaque formation.

Male TgN-hApoB +/+;LDLr −/− mice are treated twice weekly with 10 or 20 mg/kg of human apolipoprotein B antisense oligonucleotides for 12 weeks. Control groups are treated with saline or control oligonucleotide. Serum total cholesterol, HDL-cholesterol, LDL-cholesterol and triglycerides are measured at 2, 4, 6, 8 and 12 weeks by routine clinical analysis using an Olympus Clinical Analyzer (Olympus America Inc., Melville, N.Y.). Serum human apolipoprotein B protein is measured at 2, 4, 6, 8 and 12 weeks using an ELISA kit (ALerCHEK Inc., Portland, Me.). Human and mouse apolipoprotein mRNA in liver is measured at 12 weeks. The results of the 12 week study serve to evaluate the pharmacological behavior of ISIS 301012 in a doubly transgenic model.

Additionally, a four month study is performed in TgN-hApoB +/+;LDLr −/− mice, with treatment conditions used in the 12 week study. Mice are treated for 4 months with antisense oligonucleotides targeted to human apolipoprotein B to evaluate the ability of such compounds to prevent atherosclerotic plaque formation. At the end of the 4 month treatment period, mice are anesthetized and perfused with 10% formalin. The perfused arterial tree is isolated and examined for the presence of atherosclerotic plaques. Sections of the arterial tree are embedded in paraffin and prepared for histological analysis using routine methods. Serum total cholesterol, HDL-cholesterol, LDL-cholesterol and triglycerides are measured at 2, 4, 6, 8, 12 and 16 weeks by routine clinical analysis using an Olympus Clinical Analyzer (Olympus America Inc., Melville, N.Y.). Serum human apolipoprotein B protein is measured at 2, 4, 6, 8, 12 and 16 weeks using an ELISA kit (ALerCHEK Inc., Portland, Me.). Human and mouse apolipoprotein mRNA in liver at 16 weeks is measured by real-time PCR.

Example 68

Rabbit Models for Study of Atherosclerotic Plaque Formation

The Watanabe heritable hyperlipidemic (WHHL) strain of rabbit is used as a model for atherosclerotic plaque formation. New Zealand white rabbits on a high-fat diet are also used as a model of atherosclerotic plaque formation. Treatment of WHHL or high fat fed New Zealand white rabbits with apolipoprotein B antisense compounds is used to test their potential as therapeutic or prophylactic treatments for atherosclerotic plaque disease. Rabbits are injected with 5, 10, 25 or 50 mg/kg of antisense oligonucleotides targeted to apolipoprotein B. Animals treated with saline alone or a control oligonucleotide serve as controls. Throughout the treatment, serum samples are collected and evaluated for apolipoprotein B protein levels by ELISA (kit from ALerCHEK Inc., Portland, Me.) and serum lipids (cholesterol, LDL-cholesterol, VLDL-cholesterol, HDL-cholesterol, triglycerides) by routine clinical analysis. Liver tissue triglyceride content is measured using a Triglyceride GPO Assay (Sigma-Aldrich, St. Louis, Mo.). Liver, kidney, heart, aorta and other tissues are procured and processed for histological analysis using routine procedures. Liver and kidney tissues are examined for evidence of basophilic granules and inflammatory infiltrates. Liver tissue is evaluated for steatosis using oil red 0 stain. Additionally, aortic sections stained with oil red 0 stain and hematoxylin are examined to evaluate the formation of atherosclerotic lesions.

Example 69

Oral Delivery of Apolipoprotein B Inhibitors

Oligonucleotides may be formulated for delivery in vivo in an acceptable dosage form, e.g. as parenteral or non-parenteral formulations. Parenteral formulations include intravenous (IV), subcutaneous (SC), intraperitoneal (IP), intravitreal and intramuscular (IM) formulations, as well as formulations for delivery via pulmonary inhalation, intranasal administration, topical administration, etc. Non-parenteral formulations include formulations for delivery via the alimentary canal, e.g. oral administration, rectal administration, intrajejunal instillation, etc. Rectal administration includes administration as an enema or a suppository. Oral administration includes administration as a capsule, a gel capsule, a pill, an elixir, etc.

In some embodiments, an oligonucleotide may be administered to a subject via an oral route of administration. The subject may began animal or a human (man). An animal subject may be a mammal, such as a mouse, rat, mouse, a rat, a dog, a guinea pig, a monkey, a non-human primate, a cat or a pig. Non-human primates include monkeys and chimpanzees. A suitable animal subject may be an experimental animal, such as a mouse, rat, mouse, a rat, a dog, a monkey, a non-human primate, a cat or a pig.

In some embodiments, the subject may be a human. In certain embodiments, the subject may be a human patient in need of therapeutic treatment as discussed in more detail herein. In certain embodiments, the subject may be in need of modulation of expression of one or more genes as discussed in more detail herein. In some particular embodiments, the subject may be in need of inhibition of expression of one or more genes as discussed in more detail herein. In particular embodiments, the subject may be in need of modulation, i.e. inhibition or enhancement, of apolipoprotein B in order to obtain therapeutic indications discussed in more detail herein.

In some embodiments, non-parenteral (e.g. oral) oligonucleotide formulations according to the present invention result in enhanced bioavailability of the oligonucleotide. In this context, the term "bioavailability" refers to a measurement of that portion of an administered drug which reaches the circulatory system (e.g. blood, especially blood plasma) when a particular mode of administration is used to deliver the drug. Enhanced bioavailability refers to a particular mode of administration's ability to deliver oligonucleotide to the peripheral blood plasma of a subject relative to another mode of administration. For example, when a non-parenteral mode of administration (e.g. an oral mode) is used to introduce the drug into a subject, the bioavailability for that mode of administration may be compared to a different mode of administration, e.g. an IV mode of administration. In some embodiments, the area under a compound's blood plasma concentration curve (AUCO) after non-parenteral (e.g. oral, rectal, intrajejunal) administration may be divided by the area under the drug's plasma concentration curve after intravenous (i.v.) administration ($AUC_{iv}$) to provide a dimensionless quotient (relative bioavailability, RB) that represents fraction of compound absorbed via the non-parenteral route as compared to the IV route. A composition's bioavailability is said to be enhanced in comparison to another composition's bioavailability when the first composition's relative bioavailability ($RB_1$) is greater than the second composition's relative bioavailability ($RB_2$).

In general, bioavailability correlates with therapeutic efficacy when a compound's therapeutic efficacy is related to the blood concentration achieved, even if the drug's ultimate site of action is intracellular (van Berge-Henegouwen et al., Gastroenterol., 1977, 73, 300). Bioavailability studies have been used to determine the degree of intestinal absorption of a drug by measuring the change in peripheral blood levels of the drug after an oral dose (DiSanto, Chapter 76 In: Remington=s Pharmaceutical Sciences, 18th Ed., Gennaro, ed., Mack Publishing Co., Easton, Pa., 1990, pages 1451-1458).

In general, an oral composition's bioavailability is said to be "enhanced" when its relative bioavailability is greater than the bioavailability of a composition substantially consisting of pure oligonucleotide, i.e. oligonucleotide in the absence of a penetration enhancer.

Organ bioavailability refers to the concentration of compound in an organ. Organ bioavailability may be measured in test subjects by a number of means, such as by whole-body radiography. Organ bioavailability may be modified, e.g. enhanced, by one or more modifications to the oligonucleotide, by use of one or more carrier compounds or excipients, etc. as discussed in more detail herein. In general, an increase in bioavailability will result in an increase in organ bioavailability.

Oral oligonucleotide compositions according to the present invention may comprise one or more "mucosal penetration enhancers," also known as "absorption enhancers" or simply as "penetration enhancers." Accordingly, some embodiments of the invention comprise at least one oligonucleotide in combination with at least one penetration enhancer. In general, a penetration enhancer is a substance that facilitates the transport of a drug across mucous membrane(s) associated with the desired mode of administration, e.g. intestinal epithelial membranes. Accordingly it is desirable to select one or more penetration enhancers that facilitate the uptake of an oligonucleotide, without interfering with the activity of the oligonucleotide, and in a such a manner the oligonucleotide can be introduced into the body of an animal without unacceptable side-effects such as toxicity, irritation or allergic response.

Embodiments of the present invention provide compositions comprising one or more pharmaceutically acceptable penetration enhancers, and methods of using such compositions, which result in the improved bioavailability of oligonucleotides administered via non-parenteral modes of administration. Heretofore, certain penetration enhancers have been used to improve the bioavailability of certain drugs. See Muranishi, Crit. Rev. Ther. Drug Carrier Systems, 1990, 7, 1 and Lee et al., Crit. Rev. Ther. Drug Carrier Systems, 1991, 8, 91. It has been found that the uptake and delivery of oligonucleotides, relatively complex molecules which are known to be difficult to administer to animals and man, can be greatly improved even when administered by non-parenteral means through the use of a number of different classes of penetration enhancers.

In some embodiments, compositions for non-parenteral administration include one or more modifications from naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property. Modifications may be made to the base, the linker, or the sugar, in general, as discussed in more detail herein with regards to oligonucleotide chemistry. In some embodiments of the invention, compositions for administration to a subject, and in particular oral compositions for administration to an animal or human subject, will comprise modified oligonucleotides having one or more modifications for enhancing affinity, stability, tissue distribution, or other biological property.

Suitable modified linkers include phosphorothioate linkers. In some embodiments according to the invention, the oligonucleotide has at least one phosphorothioate linker. Phosphorothioate linkers provide nuclease stability as well as plasma protein binding characteristics to the oligonucleotide. Nuclease stability is useful for increasing the in vivo lifetime of oligonucleotides, while plasma protein binding decreases the rate of first pass clearance of oligonucleotide via renal excretion. In some embodiments according to the present invention, the oligonucleotide has at least two phosphorothioate linkers. In some embodiments, wherein the oligonucleotide has exactly n nucleosides, the oligonucleotide has from one to n−1 phosphorothioate linkages. In some embodiments, wherein the oligonucleotide has exactly n nucleosides, the oligonucleotide has n−1 phosphorothioate linkages. In other embodiments wherein the oligonucleotide has exactly n nucleoside, and n is even, the oligonucleotide has from 1 to n/2 phosphorothioate linkages, or, when n is odd, from 1 to (n−1)/2 phosphorothioate linkages. In some embodiments, the oligonucleotide has alternating phosphodiester (PO) and phosphorothioate (PS) linkages. In other embodiments, the oligonucleotide has at least one stretch of two or more consecutive PO linkages and at least one stretch of two or more PS linkages. In other embodiments, the oligonucleotide has at least two stretches of PO linkages interrupted by at least on PS linkage.

In some embodiments, at least one of the nucleosides is modified on the ribosyl sugar unit by a modification that imparts nuclease stability, binding affinity or some other beneficial biological property to the sugar. In some cases, the sugar modification includes a 2'-modification, e.g. the 2'-OH of the ribosyl sugar is replaced or substituted. Suitable replacements for 2'-OH include 2'-F and 2'-arabino-F. Suitable substitutions for OH include 2'-O-alkyl, e.g. 2-O-methyl, and 2'-O-substituted alkyl, e.g. 2'-O-methoxyethyl, 2'-O-aminopropyl, etc. In some embodiments, the oligonucleotide contains at least one 2'-modification. In some embodiments, the oligonucleotide contains at least 2 2'-modifications. In some embodiments, the oligonucleotide has at least one 2'-modification at each of the termini (i.e. the 3'- and 5'-terminal nucleosides each have the same or different 2'-modifications). In some embodiments, the oligonucleotide has at least two sequential 2'-modifications at each end of the oligonucleotide. In some embodiments, oligonucleotides further comprise at least one deoxynucleoside. In particular embodiments, oligonucleotides comprise a stretch of deoxynucleosides such that the stretch is capable of activating RNase (e.g. RNase H) cleavage of an RNA to which the oligonucleotide is capable of hybridizing. In some embodiments, a stretch of deoxynucleosides capable of activating RNase-mediated cleavage of RNA comprises about 6 to about 16, e.g. about 8 to about 16 consecutive deoxynucleosides.

Oral compositions for administration of non-parenteral oligonucleotide compositions of the present invention may be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. A common requirement for these modes of administration is absorption over some portion or all of the alimentary tract and a need for efficient mucosal penetration of the nucleic acid(s) so administered.

Delivery of a drug via the oral mucosa, as in the case of buccal and sublingual administration, has several desirable features, including, in many instances, a more rapid rise in plasma concentration of the drug than via oral delivery (Harvey, Chapter 35 In: Remington=s Pharmaceutical Sciences, 18th Ed., Gennaro, ed., Mack Publishing Co., Easton, Pa., 1990, page 711).

Endoscopy may be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., Gan To Kagaku Ryoho, 1992, 19(10 Suppl.), 1591). Pharmaceutical compositions, including liposomal formulations, can be delivered directly into portions of the alimentary canal, such as, e.g., the duodenum (Somogyi et al., Pharm. Res., 1995, 12, 149) or the gastric submucosa (Akamo et al., Japanese J. Cancer Res., 1994, 85, 652) via endoscopic means. Gastric lavage devices (Inoue et al., Artif. Organs, 1997, 21, 28) and percutaneous endoscopic feeding devices (Pennington et al., Ailment Pharmacol. Ther., 1995, 9, 471) can also be used for direct alimentary delivery of pharmaceutical compositions.

In some embodiments, oligonucleotide formulations may be administered through the anus into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration can result in more prompt and higher blood levels than the oral route. (Harvey, Chapter 35 In: Remington=s Pharmaceutical Sciences, 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass metabolism (Benet et al., Chapter 1 In: Goodman & Gilman=s The Pharmacological Basis of Therapeutics, 9th Ed., Hardman et al., eds., McGraw-Hill, New York, N.Y., 1996).

One advantageous method of non-parenteral administration oligonucleotide compositions is oral delivery. Some embodiments employ various penetration enhancers in order to effect transport of oligonucleotides and other nucleic acids across mucosal and epithelial membranes. Penetration enhancers may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Accordingly, some embodiments comprise oral oligonucleotide compositions comprising at least one member of the group consisting of surfactants, fatty acids, bile salts, chelating agents, and non-chelating surfactants. Further embodiments comprise oral oligonucleotide comprising at least one fatty acid, e.g. capric or lauric acid, or combinations or salts thereof. Other embodiments comprise methods of enhancing the oral bioavailability of an oligonucleotide, the method comprising co-administering the oligonucleotide and at least one penetration enhancer.

Other excipients that may be added to oral oligonucleotide compositions include surfactants (or "surface-active agents"), which are chemical entities which, when dissolved in an aqueous solution, reduce the surface tension of the solution or the interfacial tension between the aqueous solution and another liquid, with the result that absorption of oligonucleotides through the alimentary mucosa and other epithelial membranes is enhanced. In addition to bile salts and fatty acids, surfactants include, for example, sodium lauryl sulfate, polyoxyethylene-9-lauryl ether and polyoxyethylene-20-cetyl ether (Lee et al., Critical Reviews in Therapeutic Drug Carrier Systems, 1991, page 92); and perfluorohemical emulsions, such as FC-43 (Takahashi et al., J. Pharm. Pharmacol., 1988, 40, 252).

Fatty acids and their derivatives which act as penetration enhancers and may be used in compositions of the present invention include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glyceryl 1-monocaprate, 1-dodecylazacycloheptan-2-one, acylcarnitines, acylcholines and mono- and di-glycerides thereof and/or physiologically acceptable salts thereof (i.e., oleate, laurate, caprate, myristate, palmitate, stearate, linoleate, etc.) (Lee et al., Critical Reviews in Therapeutic Drug Carrier Systems, 1991, page 92; Muranishi, Critical Reviews in Therapeutic Drug Carrier Systems, 1990, 7, 1; El-Hariri et al., J. Pharm. Pharmacol., 1992, 44, 651).

In some embodiments, oligonucleotide compositions for oral delivery comprise at least two discrete phases, which phases may comprise particles, capsules, gel-capsules, microspheres, etc. Each phase may contain one or more oligonucleotides, penetration enhancers, surfactants, bioadhesives, effervescent agents, or other adjuvant, excipient or diluent. In some embodiments, one phase comprises at least one oligonucleotide and at lease one penetration enhancer. In some embodiments, a first phase comprises at least one oligonucleotide and at least one penetration enhancer, while a second phase comprises at least one penetration enhancer. In some embodiments, a first phase comprises at least one oligonucleotide and at least one penetration enhancer, while a second phase comprises at least one penetration enhancer and substantially no oligonucleotide. In some embodiments, at least one phase is compounded with at least one degradation retardant, such as a coating or a matrix, which delays release of the contents of that phase. In some embodiments, at least one phase In some embodiments, a first phase comprises at least one oligonucleotide, at least one penetration enhancer, while a second phase comprises at least one penetration enhancer and a release-retardant. In particular embodiments, an oral oligonucleotide comprises a first phase comprising particles containing an oligonucleotide and a penetration enhancer, and a second phase comprising particles coated with a release-retarding agent and containing penetration enhancer.

A variety of bile salts also function as penetration enhancers to facilitate the uptake and bioavailability of drugs. The physiological roles of bile include the facilitation of dispersion and absorption of lipids and fat-soluble vitamins (Brunton, Chapter 38 In: Goodman & Gilman=s The Pharmacological Basis of Therapeutics, 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (CDCA, sodium chenodeoxycholate), ursodeoxycholic acid (UDCA), sodium tauro-24,25-dihydrofusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington=s Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1; Yamamoto et al., J. Pharm. Exp. Ther., 1992, 263, 25; Yamashita et al., J. Pharm. Sci., 1990, 79, 579).

In some embodiments, penetration enhancers useful in some embodiments of present invention are mixtures of penetration enhancing compounds. One such penetration enhancer is a mixture of UDCA (and/or CDCA) with capric and/or lauric acids or salts thereof e.g. sodium. Such mixtures are useful for enhancing the delivery of biologically active substances across mucosal membranes, in particular intestinal mucosa. Other penetration enhancer mixtures comprise about 5-95% of bile acid or salt(s) UDCA and/or CDCA with 5-95% capric and/or lauric acid. Particular penetration enhancers are mixtures of the sodium salts of UDCA, capric acid and lauric acid in a ratio of about 1:2:2 respectively. Anther such penetration enhancer is a mixture of capric and lauric acid (or salts thereof) in a 0.01:1 to 1:0.01 ratio (mole basis). In particular embodiments capric acid and lauric acid are present in molar ratios of e.g. about 0.1:1 to about 1:0.1, in particular about 0.5:1 to about 1:0.5.

Other excipients include chelating agents, i.e. compounds that remove metallic ions from solution by forming complexes therewith, with the result that absorption of oligonucleotides through the alimentary and other mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315). Chelating agents of the invention include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1; Buur et al., J. Control Rel., 1990, 14, 43).

As used herein, non-chelating non-surfactant penetration enhancers may be defined as compounds that demonstrate insignificant activity as chelating agents or as surfactants but that nonetheless enhance absorption of oligonucleotides through the alimentary and other mucosal membranes (Muranishi, Critical Reviews in Therapeutic Drug Carrier Systems, 1990, 7, 1). This class of penetration enhancers includes, but is not limited to, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), can be used.

Some oral oligonucleotide compositions also incorporate carrier compounds in the formulation. As used herein, "carrier compound" or "carrier" can refer to a nucleic acid, or analog thereof, which may be inert (i.e., does not possess biological activity per se) or may be necessary for transport, recognition or pathway activation or mediation, or is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., Antisense Res. Dev., 1995, 5, 115; Takakura et al., Antisense & Nucl. Acid Drug Dev., 1996, 6, 177).

A "pharmaceutical carrier" or "excipient" may be a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB); and wetting agents (e.g., sodium lauryl sulphate, etc.).

Oral oligonucleotide compositions may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the present invention.

SEQUENCE LISTING

<160> NUMBER OF SEQ ID NOS: 897

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1 tccgtcatcg ctcctcaggg 20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2 atgcattctg cccccaagga 20

<210> SEQ ID NO 3
<211> LENGTH: 14121
<212> TYPE: DNA
<213> ORGANISM: Homo sapiens
<220> FEATURE:
<221> NAME/KEY: CDS
<222> LOCATION: (129)..(13820)

<400> SEQUENCE: 3 attcccaccg ggacctgcgg ggctgagtgc ccttctcggt tgctgccgct gaggagcccg 60 cccagccagc cagggccgcg aggccgaggc caggccgcag cccaggagcc gccccaccgc 120 agctggcg atg gac ccg ccg agg ccc gcg ctg ctg gcg ctg ctg gcg ctg 170
Met Asp Pro Pro Arg Pro Ala Leu Leu Ala Leu Leu Ala Leu
1 5 10 cct gcg ctg ctg ctg ctg ctg ctg gcg ggc gcc agg gcc gaa gag gaa 218
Pro Ala Leu Leu Leu Leu Leu Leu Ala Gly Ala Arg Ala Glu Glu Glu
15 20 25 30 atg ctg gaa aat gtc agc ctg gtc tgt cca aaa gat gcg acc cga ttc 266
Met Leu Glu Asn Val Ser Leu Val Cys Pro Lys Asp Ala Thr Arg Phe
35 40 45 aag cac ctc cgg aag tac aca tac aac tat gag gct gag agt tcc agt 314
Lys His Leu Arg Lys Tyr Thr Tyr Asn Tyr Glu Ala Glu Ser Ser Ser
50 55 60 gga gtc cct ggg act gct gat tca aga agt gcc acc agg atc aac tgc 362
Gly Val Pro Gly Thr Ala Asp Ser Arg Ser Ala Thr Arg Ile Asn Cys
65 70 75 aag gtt gag ctg gag gtt ccc cag ctc tgc agc ttc atc ctg aag acc 410
Lys Val Glu Leu Glu Val Pro Gln Leu Cys Ser Phe Ile Leu Lys Thr
80 85 90 agc cag tgc acc ctg aaa gag gtg tat ggc ttc aac cct gag ggc aaa 458
Ser Gln Cys Thr Leu Lys Glu Val Tyr Gly Phe Asn Pro Glu Gly Lys
95 100 105 110 gcc ttg ctg aag aaa acc aag aac tct gag gag ttt gct gca gcc atg 506
Ala Leu Leu Lys Lys Thr Lys Asn Ser Glu Glu Phe Ala Ala Ala Met
115 120 125 tcc agg tat gag ctc aag ctg gcc att cca gaa ggg aag cag gtt ttc 554
Ser Arg Tyr Glu Leu Lys Leu Ala Ile Pro Glu Gly Lys Gln Val Phe
130 135 140 ctt tac ccg gag aaa gat gaa cct act tac atc ctg aac atc aag agg 602

```
Leu Tyr Pro Glu Lys Asp Glu Pro Thr Tyr Ile Leu Asn Ile Lys Arg
        145                 150                 155

ggc atc att tct gcc ctc ctg gtt ccc cca gag aca gaa gaa gcc aag      650
Gly Ile Ile Ser Ala Leu Leu Val Pro Pro Glu Thr Glu Glu Ala Lys
    160                 165                 170

caa gtg ttg ttt ctg gat acc gtg tat gga aac tgc tcc act cac ttt      698
Gln Val Leu Phe Leu Asp Thr Val Tyr Gly Asn Cys Ser Thr His Phe
175                 180                 185                 190

acc gtc aag acg agg aag ggc aat gtg gca aca gaa ata tcc act gaa      746
Thr Val Lys Thr Arg Lys Gly Asn Val Ala Thr Glu Ile Ser Thr Glu
                195                 200                 205

aga gac ctg ggg cag tgt gat cgc ttc aag ccc atc cgc aca ggc atc      794
Arg Asp Leu Gly Gln Cys Asp Arg Phe Lys Pro Ile Arg Thr Gly Ile
            210                 215                 220

agc cca ctt gct ctc atc aaa ggc atg acc cgc ccc ttg tca act ctg      842
Ser Pro Leu Ala Leu Ile Lys Gly Met Thr Arg Pro Leu Ser Thr Leu
        225                 230                 235

atc agc agc agc cag tcc tgt cag tac aca ctg gac gct aag agg aag      890
Ile Ser Ser Ser Gln Ser Cys Gln Tyr Thr Leu Asp Ala Lys Arg Lys
    240                 245                 250

cat gtg gca gaa gcc atc tgc aag gag caa cac ctc ttc ctg cct ttc      938
His Val Ala Glu Ala Ile Cys Lys Glu Gln His Leu Phe Leu Pro Phe
255                 260                 265                 270

tcc tac aac aat aag tat ggg atg gta gca caa gtg aca cag act ttg      986
Ser Tyr Asn Asn Lys Tyr Gly Met Val Ala Gln Val Thr Gln Thr Leu
                275                 280                 285

aaa ctt gaa gac aca cca aag atc aac agc cgc ttc ttt ggt gaa ggt     1034
Lys Leu Glu Asp Thr Pro Lys Ile Asn Ser Arg Phe Phe Gly Glu Gly
            290                 295                 300

act aag aag atg ggc ctc gca ttt gag agc acc aaa tcc aca tca cct     1082
Thr Lys Lys Met Gly Leu Ala Phe Glu Ser Thr Lys Ser Thr Ser Pro
        305                 310                 315

cca aag cag gcc gaa gct gtt ttg aag act ctc cag gaa ctg aaa aaa     1130
Pro Lys Gln Ala Glu Ala Val Leu Lys Thr Leu Gln Glu Leu Lys Lys
    320                 325                 330

cta acc atc tct gag caa aat atc cag aga gct aat ctc ttc aat aag     1178
Leu Thr Ile Ser Glu Gln Asn Ile Gln Arg Ala Asn Leu Phe Asn Lys
335                 340                 345                 350

ctg gtt act gag ctg aga ggc ctc agt gat gaa gca gtc aca tct ctc     1226
Leu Val Thr Glu Leu Arg Gly Leu Ser Asp Glu Ala Val Thr Ser Leu
                355                 360                 365

ttg cca cag ctg att gag gtg tcc agc ccc atc act tta caa gcc ttg     1274
Leu Pro Gln Leu Ile Glu Val Ser Ser Pro Ile Thr Leu Gln Ala Leu
            370                 375                 380

gtt cag tgt gga cag cct cag tgc tcc act cac atc ctc cag tgg ctg     1322
Val Gln Cys Gly Gln Pro Gln Cys Ser Thr His Ile Leu Gln Trp Leu
        385                 390                 395

aaa cgt gtg cat gcc aac ccc ctt ctg ata gat gtg gtc acc tac ctg     1370
Lys Arg Val His Ala Asn Pro Leu Leu Ile Asp Val Val Thr Tyr Leu
    400                 405                 410

gtg gcc ctg atc ccc gag ccc tca gca cag cag ctg cga gag atc ttc     1418
Val Ala Leu Ile Pro Glu Pro Ser Ala Gln Gln Leu Arg Glu Ile Phe
415                 420                 425                 430

aac atg gcg agg gat cag cgc agc cga gcc acc ttg tat gcg ctg agc     1466
Asn Met Ala Arg Asp Gln Arg Ser Arg Ala Thr Leu Tyr Ala Leu Ser
                435                 440                 445

cac gcg gtc aac aac tat cat aag aca aac cct aca ggg acc cag gag     1514
His Ala Val Asn Asn Tyr His Lys Thr Asn Pro Thr Gly Thr Gln Glu
            450                 455                 460

ctg ctg gac att gct aat tac ctg atg gaa cag att caa gat gac tgc     1562
```

```
Leu Leu Asp Ile Ala Asn Tyr Leu Met Glu Gln Ile Gln Asp Asp Cys
        465                 470                 475

act ggg gat gaa gat tac acc tat ttg att ctg cgg gtc att gga aat     1610
Thr Gly Asp Glu Asp Tyr Thr Tyr Leu Ile Leu Arg Val Ile Gly Asn
    480                 485                 490

atg ggc caa acc atg gag cag tta act cca gaa ctc aag tct tca atc     1658
Met Gly Gln Thr Met Glu Gln Leu Thr Pro Glu Leu Lys Ser Ser Ile
495                 500                 505                 510

ctc aaa tgt gtc caa agt aca aag cca tca ctg atg atc cag aaa gct     1706
Leu Lys Cys Val Gln Ser Thr Lys Pro Ser Leu Met Ile Gln Lys Ala
                515                 520                 525

gcc atc cag gct ctg cgg aaa atg gag cct aaa gac aag gac cag gag     1754
Ala Ile Gln Ala Leu Arg Lys Met Glu Pro Lys Asp Lys Asp Gln Glu
            530                 535                 540

gtt ctt ctt cag act ttc ctt gat gat gct tct ccg gga gat aag cga     1802
Val Leu Leu Gln Thr Phe Leu Asp Asp Ala Ser Pro Gly Asp Lys Arg
        545                 550                 555

ctg gct gcc tat ctt atg ttg atg agg agt cct tca cag gca gat att     1850
Leu Ala Ala Tyr Leu Met Leu Met Arg Ser Pro Ser Gln Ala Asp Ile
    560                 565                 570

aac aaa att gtc caa att cta cca tgg gaa cag aat gag caa gtg aag     1898
Asn Lys Ile Val Gln Ile Leu Pro Trp Glu Gln Asn Glu Gln Val Lys
575                 580                 585                 590

aac ttt gtg gct tcc cat att gcc aat atc ttg aac tca gaa gaa ttg     1946
Asn Phe Val Ala Ser His Ile Ala Asn Ile Leu Asn Ser Glu Glu Leu
                595                 600                 605

gat atc caa gat ctg aaa aag tta gtg aaa gaa gct ctg aaa gaa tct     1994
Asp Ile Gln Asp Leu Lys Lys Leu Val Lys Glu Ala Leu Lys Glu Ser
            610                 615                 620

caa ctt cca act gtc atg gac ttc aga aaa ttc tct cgg aac tat caa     2042
Gln Leu Pro Thr Val Met Asp Phe Arg Lys Phe Ser Arg Asn Tyr Gln
        625                 630                 635

ctc tac aaa tct gtt tct ctt cca tca ctt gac cca gcc tca gcc aaa     2090
Leu Tyr Lys Ser Val Ser Leu Pro Ser Leu Asp Pro Ala Ser Ala Lys
    640                 645                 650

ata gaa ggg aat ctt ata ttt gat cca aat aac tac ctt cct aaa gaa     2138
Ile Glu Gly Asn Leu Ile Phe Asp Pro Asn Asn Tyr Leu Pro Lys Glu
655                 660                 665                 670

agc atg ctg aaa act acc ctc act gcc ttt gga ttt gct tca gct gac     2186
Ser Met Leu Lys Thr Thr Leu Thr Ala Phe Gly Phe Ala Ser Ala Asp
                675                 680                 685

ctc atc gag att ggc ttg gaa gga aaa ggc ttt gag cca aca ttg gaa     2234
Leu Ile Glu Ile Gly Leu Glu Gly Lys Gly Phe Glu Pro Thr Leu Glu
            690                 695                 700

gct ctt ttt ggg aag caa gga ttt ttc cca gac agt gtc aac aaa gct     2282
Ala Leu Phe Gly Lys Gln Gly Phe Phe Pro Asp Ser Val Asn Lys Ala
        705                 710                 715

ttg tac tgg gtt aat ggt caa gtt cct gat ggt gtc tct aag gtc tta     2330
Leu Tyr Trp Val Asn Gly Gln Val Pro Asp Gly Val Ser Lys Val Leu
    720                 725                 730

gtg gac cac ttt ggc tat acc aaa gat gat aaa cat gag cag gat atg     2378
Val Asp His Phe Gly Tyr Thr Lys Asp Asp Lys His Glu Gln Asp Met
735                 740                 745                 750

gta aat gga ata atg ctc agt gtt gag aag ctg att aaa gat ttg aaa     2426
Val Asn Gly Ile Met Leu Ser Val Glu Lys Leu Ile Lys Asp Leu Lys
                755                 760                 765

tcc aaa gaa gtc ccg gaa gcc aga gcc tac ctc cgc atc ttg gga gag     2474
Ser Lys Glu Val Pro Glu Ala Arg Ala Tyr Leu Arg Ile Leu Gly Glu
            770                 775                 780

gag ctt ggt ttt gcc agt ctc cat gac ctc cag ctc ctg gga aag ctg     2522
```

```
Glu Leu Gly Phe Ala Ser Leu His Asp Leu Gln Leu Leu Gly Lys Leu
        785                 790                 795

ctt ctg atg ggt gcc cgc act ctg cag ggg atc ccc cag atg att gga     2570
Leu Leu Met Gly Ala Arg Thr Leu Gln Gly Ile Pro Gln Met Ile Gly
    800                 805                 810

gag gtc atc agg aag ggc tca aag aat gac ttt ttt ctt cac tac atc     2618
Glu Val Ile Arg Lys Gly Ser Lys Asn Asp Phe Phe Leu His Tyr Ile
815                 820                 825                 830

ttc atg gag aat gcc ttt gaa ctc ccc act gga gct gga tta cag ttg     2666
Phe Met Glu Asn Ala Phe Glu Leu Pro Thr Gly Ala Gly Leu Gln Leu
                835                 840                 845

caa ata tct tca tct gga gtc att gct ccc gga gcc aag gct gga gta     2714
Gln Ile Ser Ser Ser Gly Val Ile Ala Pro Gly Ala Lys Ala Gly Val
            850                 855                 860

aaa ctg gaa gta gcc aac atg cag gct gaa ctg gtg gca aaa ccc tcc     2762
Lys Leu Glu Val Ala Asn Met Gln Ala Glu Leu Val Ala Lys Pro Ser
        865                 870                 875

gtg tct gtg gag ttt gtg aca aat atg ggc atc atc att ccg gac ttc     2810
Val Ser Val Glu Phe Val Thr Asn Met Gly Ile Ile Pro Asp Phe
    880                 885                 890

gct agg agt ggg gtc cag atg aac acc aac ttc ttc cac gag tcg ggt     2858
Ala Arg Ser Gly Val Gln Met Asn Thr Asn Phe Phe His Glu Ser Gly
895                 900                 905                 910

ctg gag gct cat gtt gcc cta aaa gct ggg aag ctg aag ttt atc att     2906
Leu Glu Ala His Val Ala Leu Lys Ala Gly Lys Leu Lys Phe Ile Ile
                915                 920                 925

cct tcc cca aag aga cca gtc aag ctg ctc agt gga ggc aac aca tta     2954
Pro Ser Pro Lys Arg Pro Val Lys Leu Leu Ser Gly Gly Asn Thr Leu
            930                 935                 940

cat ttg gtc tct acc acc aaa acg gag gtg atc cca cct ctc att gag     3002
His Leu Val Ser Thr Thr Lys Thr Glu Val Ile Pro Pro Leu Ile Glu
        945                 950                 955

aac agg cag tcc tgg tca gtt tgc aag caa gtc ttt cct ggc ctg aat     3050
Asn Arg Gln Ser Trp Ser Val Cys Lys Gln Val Phe Pro Gly Leu Asn
    960                 965                 970

tac tgc acc tca ggc gct tac tcc aac gcc agc tcc aca gac tcc gcc     3098
Tyr Cys Thr Ser Gly Ala Tyr Ser Asn Ala Ser Ser Thr Asp Ser Ala
975                 980                 985                 990

tcc tac tat ccg ctg acc ggg gac acc aga tta gag ctg gaa ctg agg     3146
Ser Tyr Tyr Pro Leu Thr Gly Asp Thr Arg Leu Glu Leu Glu Leu Arg
                995                 1000                1005

cct aca gga gag att gag cag tat tct gtc agc gca acc tat gag ctc     3194
Pro Thr Gly Glu Ile Glu Gln Tyr Ser Val Ser Ala Thr Tyr Glu Leu
            1010                1015                1020

cag aga gag gac aga gcc ttg gtg gat acc ctg aag ttt gta act caa     3242
Gln Arg Glu Asp Arg Ala Leu Val Asp Thr Leu Lys Phe Val Thr Gln
        1025                1030                1035

gca gaa ggt gcg aag cag act gag gct acc atg aca ttc aaa tat aat     3290
Ala Glu Gly Ala Lys Gln Thr Glu Ala Thr Met Thr Phe Lys Tyr Asn
    1040                1045                1050

cgg cag agt atg acc ttg tcc agt gaa gtc caa att ccg gat ttt gat     3338
Arg Gln Ser Met Thr Leu Ser Ser Glu Val Gln Ile Pro Asp Phe Asp
1055                1060                1065                1070

gtt gac ctc gga aca atc ctc aga gtt aat gat gaa tct act gag ggc     3386
Val Asp Leu Gly Thr Ile Leu Arg Val Asn Asp Glu Ser Thr Glu Gly
                1075                1080                1085

aaa acg tct tac aga ctc acc ctg gac att cag aac aag aaa att act     3434
Lys Thr Ser Tyr Arg Leu Thr Leu Asp Ile Gln Asn Lys Lys Ile Thr
            1090                1095                1100

gag gtc gcc ctc atg ggc cac cta agt tgt gac aca aag gaa gaa aga     3482
```

```
Glu Val Ala Leu Met Gly His Leu Ser Cys Asp Thr Lys Glu Glu Arg
        1105                1110                1115

aaa atc aag ggt gtt att tcc ata ccc cgt ttg caa gca gaa gcc aga     3530
Lys Ile Lys Gly Val Ile Ser Ile Pro Arg Leu Gln Ala Glu Ala Arg
    1120                1125                1130

agt gag atc ctc gcc cac tgg tcg cct gcc aaa ctg ctt ctc caa atg     3578
Ser Glu Ile Leu Ala His Trp Ser Pro Ala Lys Leu Leu Leu Gln Met
1135                1140                1145                1150

gac tca tct gct aca gct tat ggc tcc aca gtt tcc aag agg gtg gca     3626
Asp Ser Ser Ala Thr Ala Tyr Gly Ser Thr Val Ser Lys Arg Val Ala
                1155                1160                1165

tgg cat tat gat gaa gag aag att gaa ttt gaa tgg aac aca ggc acc     3674
Trp His Tyr Asp Glu Glu Lys Ile Glu Phe Glu Trp Asn Thr Gly Thr
            1170                1175                1180

aat gta gat acc aaa aaa atg act tcc aat ttc cct gtg gat ctc tcc     3722
Asn Val Asp Thr Lys Lys Met Thr Ser Asn Phe Pro Val Asp Leu Ser
        1185                1190                1195

gat tat cct aag agc ttg cat atg tat gct aat aga ctc ctg gat cac     3770
Asp Tyr Pro Lys Ser Leu His Met Tyr Ala Asn Arg Leu Leu Asp His
    1200                1205                1210

aga gtc cct gaa aca gac atg act ttc cgg cac gtg ggt tcc aaa tta     3818
Arg Val Pro Glu Thr Asp Met Thr Phe Arg His Val Gly Ser Lys Leu
1215                1220                1225                1230

ata gtt gca atg agc tca tgg ctt cag aag gca tct ggg agt ctt cct     3866
Ile Val Ala Met Ser Ser Trp Leu Gln Lys Ala Ser Gly Ser Leu Pro
                1235                1240                1245

tat acc cag act ttg caa gac cac ctc aat agc ctg aag gag ttc aac     3914
Tyr Thr Gln Thr Leu Gln Asp His Leu Asn Ser Leu Lys Glu Phe Asn
            1250                1255                1260

ctc cag aac atg gga ttg cca gac ttc cac atc cca gaa aac ctc ttc     3962
Leu Gln Asn Met Gly Leu Pro Asp Phe His Ile Pro Glu Asn Leu Phe
        1265                1270                1275

tta aaa agc gat ggc cgg gtc aaa tat acc ttg aac aag aac agt ttg     4010
Leu Lys Ser Asp Gly Arg Val Lys Tyr Thr Leu Asn Lys Asn Ser Leu
    1280                1285                1290

aaa att gag att cct ttg cct ttt ggt ggc aaa tcc tcc aga gat cta     4058
Lys Ile Glu Ile Pro Leu Pro Phe Gly Gly Lys Ser Ser Arg Asp Leu
1295                1300                1305                1310

aag atg tta gag act gtt agg aca cca gcc ctc cac ttc aag tct gtg     4106
Lys Met Leu Glu Thr Val Arg Thr Pro Ala Leu His Phe Lys Ser Val
                1315                1320                1325

gga ttc cat ctg cca tct cga gag ttc caa gtc cct act ttt acc att     4154
Gly Phe His Leu Pro Ser Arg Glu Phe Gln Val Pro Thr Phe Thr Ile
            1330                1335                1340

ccc aag ttg tat caa ctg caa gtg cct ctc ctg ggt gtt cta gac ctc     4202
Pro Lys Leu Tyr Gln Leu Gln Val Pro Leu Leu Gly Val Leu Asp Leu
        1345                1350                1355

tcc acg aat gtc tac agc aac ttg tac aac tgg tcc gcc tcc tac agt     4250
Ser Thr Asn Val Tyr Ser Asn Leu Tyr Asn Trp Ser Ala Ser Tyr Ser
    1360                1365                1370

ggt ggc aac acc agc aca gac cat ttc agc ctt cgg gct cgt tac cac     4298
Gly Gly Asn Thr Ser Thr Asp His Phe Ser Leu Arg Ala Arg Tyr His
1375                1380                1385                1390

atg aag gct gac tct gtg gtt gac ctg ctt tcc tac aat gtg caa gga     4346
Met Lys Ala Asp Ser Val Val Asp Leu Leu Ser Tyr Asn Val Gln Gly
                1395                1400                1405

tct gga gaa aca aca tat gac cac aag aat acg ttc aca cta tca tgt     4394
Ser Gly Glu Thr Thr Tyr Asp His Lys Asn Thr Phe Thr Leu Ser Cys
            1410                1415                1420

gat ggg tct cta cgc cac aaa ttt cta gat tcg aat atc aaa ttc agt     4442
```

```
Asp Gly Ser Leu Arg His Lys Phe Leu Asp Ser Asn Ile Lys Phe Ser
        1425                1430                1435

cat gta gaa aaa ctt gga aac aac cca gtc tca aaa ggt tta cta ata     4490
His Val Glu Lys Leu Gly Asn Asn Pro Val Ser Lys Gly Leu Leu Ile
    1440                1445                1450

ttc gat gca tct agt tcc tgg gga cca cag atg tct gct tca gtt cat     4538
Phe Asp Ala Ser Ser Ser Trp Gly Pro Gln Met Ser Ala Ser Val His
1455                1460                1465                1470

ttg gac tcc aaa aag aaa cag cat ttg ttt gtc aaa gaa gtc aag att     4586
Leu Asp Ser Lys Lys Lys Gln His Leu Phe Val Lys Glu Val Lys Ile
                1475                1480                1485

gat ggg cag ttc aga gtc tct tcg ttc tat gct aaa ggc aca tat ggc     4634
Asp Gly Gln Phe Arg Val Ser Ser Phe Tyr Ala Lys Gly Thr Tyr Gly
            1490                1495                1500

ctg tct tgt cag agg gat cct aac act ggc cgg ctc aat gga gag tcc     4682
Leu Ser Cys Gln Arg Asp Pro Asn Thr Gly Arg Leu Asn Gly Glu Ser
        1505                1510                1515

aac ctg agg ttt aac tcc tcc tac ctc caa ggc acc aac cag ata aca     4730
Asn Leu Arg Phe Asn Ser Ser Tyr Leu Gln Gly Thr Asn Gln Ile Thr
    1520                1525                1530

gga aga tat gaa gat gga acc ctc tcc ctc acc tcc acc tct gat ctg     4778
Gly Arg Tyr Glu Asp Gly Thr Leu Ser Leu Thr Ser Thr Ser Asp Leu
1535                1540                1545                1550

caa agt ggc atc att aaa aat act gct tcc cta aag tat gag aac tac     4826
Gln Ser Gly Ile Ile Lys Asn Thr Ala Ser Leu Lys Tyr Glu Asn Tyr
                1555                1560                1565

gag ctg act tta aaa tct gac acc aat ggg aag tat aag aac ttt gcc     4874
Glu Leu Thr Leu Lys Ser Asp Thr Asn Gly Lys Tyr Lys Asn Phe Ala
            1570                1575                1580

act tct aac aag atg gat atg acc ttc tct aag caa aat gca ctg ctg     4922
Thr Ser Asn Lys Met Asp Met Thr Phe Ser Lys Gln Asn Ala Leu Leu
        1585                1590                1595

cgt tct gaa tat cag gct gat tac gag tca ttg agg ttc ttc agc ctg     4970
Arg Ser Glu Tyr Gln Ala Asp Tyr Glu Ser Leu Arg Phe Phe Ser Leu
    1600                1605                1610

ctt tct gga tca cta aat tcc cat ggt ctt gag tta aat gct gac atc     5018
Leu Ser Gly Ser Leu Asn Ser His Gly Leu Glu Leu Asn Ala Asp Ile
1615                1620                1625                1630

tta ggc act gac aaa att aat agt ggt gct cac aag gcg aca cta agg     5066
Leu Gly Thr Asp Lys Ile Asn Ser Gly Ala His Lys Ala Thr Leu Arg
                1635                1640                1645

att ggc caa gat gga ata tct acc agt gca acg acc aac ttg aag tgt     5114
Ile Gly Gln Asp Gly Ile Ser Thr Ser Ala Thr Thr Asn Leu Lys Cys
            1650                1655                1660

agt ctc ctg gtg ctg gag aat gag ctg aat gca gag ctt ggc ctc tct     5162
Ser Leu Leu Val Leu Glu Asn Glu Leu Asn Ala Glu Leu Gly Leu Ser
        1665                1670                1675

ggg gca tct atg aaa tta aca aca aat ggc cgc ttc agg gaa cac aat     5210
Gly Ala Ser Met Lys Leu Thr Thr Asn Gly Arg Phe Arg Glu His Asn
    1680                1685                1690

gca aaa ttc agt ctg gat ggg aaa gcc gcc ctc aca gag cta tca ctg     5258
Ala Lys Phe Ser Leu Asp Gly Lys Ala Ala Leu Thr Glu Leu Ser Leu
1695                1700                1705                1710

gga agt gct tat cag gcc atg att ctg ggt gtc gac agc aaa aac att     5306
Gly Ser Ala Tyr Gln Ala Met Ile Leu Gly Val Asp Ser Lys Asn Ile
                1715                1720                1725

ttc aac ttc aag gtc agt caa gaa gga ctt aag ctc tca aat gac atg     5354
Phe Asn Phe Lys Val Ser Gln Glu Gly Leu Lys Leu Ser Asn Asp Met
            1730                1735                1740

atg ggc tca tat gct gaa atg aaa ttt gac cac aca aac agt ctg aac     5402
```

```
Met Gly Ser Tyr Ala Glu Met Lys Phe Asp His Thr Asn Ser Leu Asn
        1745                1750                1755

att gca ggc tta tca ctg gac ttc tct tca aaa ctt gac aac att tac     5450
Ile Ala Gly Leu Ser Leu Asp Phe Ser Ser Lys Leu Asp Asn Ile Tyr
    1760                1765                1770

agc tct gac aag ttt tat aag caa act gtt aat tta cag cta cag ccc     5498
Ser Ser Asp Lys Phe Tyr Lys Gln Thr Val Asn Leu Gln Leu Gln Pro
1775                1780                1785                1790

tat tct ctg gta act act tta aac agt gac ctg aaa tac aat gct ctg     5546
Tyr Ser Leu Val Thr Thr Leu Asn Ser Asp Leu Lys Tyr Asn Ala Leu
                1795                1800                1805

gat ctc acc aac aat ggg aaa cta cgg cta gaa ccc ctg aag ctg cat     5594
Asp Leu Thr Asn Asn Gly Lys Leu Arg Leu Glu Pro Leu Lys Leu His
            1810                1815                1820

gtg gct ggt aac cta aaa gga gcc tac caa aat aat gaa ata aaa cac     5642
Val Ala Gly Asn Leu Lys Gly Ala Tyr Gln Asn Asn Glu Ile Lys His
        1825                1830                1835

atc tat gcc atc tct tct gct gcc tta tca gca agc tat aaa gca gac     5690
Ile Tyr Ala Ile Ser Ser Ala Ala Leu Ser Ala Ser Tyr Lys Ala Asp
    1840                1845                1850

act gtt gct aag gtt cag ggt gtg gag ttt agc cat cgg ctc aac aca     5738
Thr Val Ala Lys Val Gln Gly Val Glu Phe Ser His Arg Leu Asn Thr
1855                1860                1865                1870

gac atc gct ggg ctg gct tca gcc att gac atg agc aca aac tat aat     5786
Asp Ile Ala Gly Leu Ala Ser Ala Ile Asp Met Ser Thr Asn Tyr Asn
                1875                1880                1885

tca gac tca ctg cat ttc agc aat gtc ttc cgt tct gta atg gcc ccg     5834
Ser Asp Ser Leu His Phe Ser Asn Val Phe Arg Ser Val Met Ala Pro
            1890                1895                1900

ttt acc atg acc atc gat gca cat aca aat ggc aat ggg aaa ctc gct     5882
Phe Thr Met Thr Ile Asp Ala His Thr Asn Gly Asn Gly Lys Leu Ala
        1905                1910                1915

ctc tgg gga gaa cat act ggg cag ctg tat agc aaa ttc ctg ttg aaa     5930
Leu Trp Gly Glu His Thr Gly Gln Leu Tyr Ser Lys Phe Leu Leu Lys
    1920                1925                1930

gca gaa cct ctg gca ttt act ttc tct cat gat tac aaa ggc tcc aca     5978
Ala Glu Pro Leu Ala Phe Thr Phe Ser His Asp Tyr Lys Gly Ser Thr
1935                1940                1945                1950

agt cat cat ctc gtg tct agg aaa agc atc agt gca gct ctt gaa cac     6026
Ser His His Leu Val Ser Arg Lys Ser Ile Ser Ala Ala Leu Glu His
                1955                1960                1965

aaa gtc agt gcc ctg ctt act cca gct gag cag aca ggc acc tgg aaa     6074
Lys Val Ser Ala Leu Leu Thr Pro Ala Glu Gln Thr Gly Thr Trp Lys
            1970                1975                1980

ctc aag acc caa ttt aac aac aat gaa tac agc cag gac ttg gat gct     6122
Leu Lys Thr Gln Phe Asn Asn Asn Glu Tyr Ser Gln Asp Leu Asp Ala
        1985                1990                1995

tac aac act aaa gat aaa att ggc gtg gag ctt act gga cga act ctg     6170
Tyr Asn Thr Lys Asp Lys Ile Gly Val Glu Leu Thr Gly Arg Thr Leu
    2000                2005                2010

gct gac cta act cta cta gac tcc cca att aaa gtg cca ctt tta ctc     6218
Ala Asp Leu Thr Leu Leu Asp Ser Pro Ile Lys Val Pro Leu Leu Leu
2015                2020                2025                2030

agt gag ccc atc aat atc att gat gct tta gag atg aga gat gcc gtt     6266
Ser Glu Pro Ile Asn Ile Ile Asp Ala Leu Glu Met Arg Asp Ala Val
                2035                2040                2045

gag aag ccc caa gaa ttt aca att gtt gct ttt gta aag tat gat aaa     6314
Glu Lys Pro Gln Glu Phe Thr Ile Val Ala Phe Val Lys Tyr Asp Lys
            2050                2055                2060

aac caa gat gtt cac tcc att aac ctc cca ttt ttt gag acc ttg caa     6362
```

```
Asn Gln Asp Val His Ser Ile Asn Leu Pro Phe Phe Glu Thr Leu Gln
        2065                2070                2075

gaa tat ttt gag agg aat cga caa acc att ata gtt gta gtg gaa aac     6410
Glu Tyr Phe Glu Arg Asn Arg Gln Thr Ile Ile Val Val Val Glu Asn
    2080                2085                2090

gta cag aga aac ctg aag cac atc aat att gat caa ttt gta aga aaa     6458
Val Gln Arg Asn Leu Lys His Ile Asn Ile Asp Gln Phe Val Arg Lys
2095                2100                2105                2110

tac aga gca gcc ctg gga aaa ctc cca cag caa gct aat gat tat ctg     6506
Tyr Arg Ala Ala Leu Gly Lys Leu Pro Gln Gln Ala Asn Asp Tyr Leu
                2115                2120                2125

aat tca ttc aat tgg gag aga caa gtt tca cat gcc aag gag aaa ctg     6554
Asn Ser Phe Asn Trp Glu Arg Gln Val Ser His Ala Lys Glu Lys Leu
            2130                2135                2140

act gct ctc aca aaa aag tat aga att aca gaa aat gat ata caa att     6602
Thr Ala Leu Thr Lys Lys Tyr Arg Ile Thr Glu Asn Asp Ile Gln Ile
        2145                2150                2155

gca tta gat gat gcc aaa atc aac ttt aat gaa aaa cta tct caa ctg     6650
Ala Leu Asp Asp Ala Lys Ile Asn Phe Asn Glu Lys Leu Ser Gln Leu
    2160                2165                2170

cag aca tat atg ata caa ttt gat cag tat att aaa gat agt tat gat     6698
Gln Thr Tyr Met Ile Gln Phe Asp Gln Tyr Ile Lys Asp Ser Tyr Asp
2175                2180                2185                2190

tta cat gat ttg aaa ata gct att gct aat att att gat gaa atc att     6746
Leu His Asp Leu Lys Ile Ala Ile Ala Asn Ile Ile Asp Glu Ile Ile
                2195                2200                2205

gaa aaa tta aaa agt ctt gat gag cac tat cat atc cgt gta aat tta     6794
Glu Lys Leu Lys Ser Leu Asp Glu His Tyr His Ile Arg Val Asn Leu
            2210                2215                2220

gta aaa aca atc cat gat cta cat ttg ttt att gaa aat att gat ttt     6842
Val Lys Thr Ile His Asp Leu His Leu Phe Ile Glu Asn Ile Asp Phe
        2225                2230                2235

aac aaa agt gga agt agt act gca tcc tgg att caa aat gtg gat act     6890
Asn Lys Ser Gly Ser Ser Thr Ala Ser Trp Ile Gln Asn Val Asp Thr
    2240                2245                2250

aag tac caa atc aga atc cag ata caa gaa aaa ctg cag cag ctt aag     6938
Lys Tyr Gln Ile Arg Ile Gln Ile Gln Glu Lys Leu Gln Gln Leu Lys
2255                2260                2265                2270

aga cac ata cag aat ata gac atc cag cac cta gct gga aag tta aaa     6986
Arg His Ile Gln Asn Ile Asp Ile Gln His Leu Ala Gly Lys Leu Lys
                2275                2280                2285

caa cac att gag gct att gat gtt aga gtg ctt tta gat caa ttg gga     7034
Gln His Ile Glu Ala Ile Asp Val Arg Val Leu Leu Asp Gln Leu Gly
            2290                2295                2300

act aca att tca ttt gaa aga ata aat gat gtt ctt gag cat gtc aaa     7082
Thr Thr Ile Ser Phe Glu Arg Ile Asn Asp Val Leu Glu His Val Lys
        2305                2310                2315

cac ttt gtt ata aat ctt att ggg gat ttt gaa gta gct gag aaa atc     7130
His Phe Val Ile Asn Leu Ile Gly Asp Phe Glu Val Ala Glu Lys Ile
    2320                2325                2330

aat gcc ttc aga gcc aaa gtc cat gag tta atc gag agg tat gaa gta     7178
Asn Ala Phe Arg Ala Lys Val His Glu Leu Ile Glu Arg Tyr Glu Val
2335                2340                2345                2350

gac caa caa atc cag gtt tta atg gat aaa tta gta gag ttg acc cac     7226
Asp Gln Gln Ile Gln Val Leu Met Asp Lys Leu Val Glu Leu Thr His
                2355                2360                2365

caa tac aag ttg aag gag act att cag aag cta agc aat gtc cta caa     7274
Gln Tyr Lys Leu Lys Glu Thr Ile Gln Lys Leu Ser Asn Val Leu Gln
            2370                2375                2380

caa gtt aag ata aaa gat tac ttt gag aaa ttg gtt gga ttt att gat     7322
```

```
Gln Val Lys Ile Lys Asp Tyr Phe Glu Lys Leu Val Gly Phe Ile Asp
        2385                2390                2395

gat gct gtg aag aag ctt aat gaa tta tct ttt aaa aca ttc att gaa     7370
Asp Ala Val Lys Lys Leu Asn Glu Leu Ser Phe Lys Thr Phe Ile Glu
    2400                2405                2410

gat gtt aac aaa ttc ctt gac atg ttg ata aag aaa tta aag tca ttt     7418
Asp Val Asn Lys Phe Leu Asp Met Leu Ile Lys Lys Leu Lys Ser Phe
2415                2420                2425                2430

gat tac cac cag ttt gta gat gaa acc aat gac aaa atc cgt gag gtg     7466
Asp Tyr His Gln Phe Val Asp Glu Thr Asn Asp Lys Ile Arg Glu Val
                2435                2440                2445

act cag aga ctc aat ggt gaa att cag gct ctg gaa cta cca caa aaa     7514
Thr Gln Arg Leu Asn Gly Glu Ile Gln Ala Leu Glu Leu Pro Gln Lys
            2450                2455                2460

gct gaa gca tta aaa ctg ttt tta gag gaa acc aag gcc aca gtt gca     7562
Ala Glu Ala Leu Lys Leu Phe Leu Glu Glu Thr Lys Ala Thr Val Ala
        2465                2470                2475

gtg tat ctg gaa agc cta cag gac acc aaa ata acc tta atc atc aat     7610
Val Tyr Leu Glu Ser Leu Gln Asp Thr Lys Ile Thr Leu Ile Ile Asn
    2480                2485                2490

tgg tta cag gag gct tta agt tca gca tct ttg gct cac atg aag gcc     7658
Trp Leu Gln Glu Ala Leu Ser Ser Ala Ser Leu Ala His Met Lys Ala
2495                2500                2505                2510

aaa ttc cga gag act cta gaa gat aca cga gac cga atg tat caa atg     7706
Lys Phe Arg Glu Thr Leu Glu Asp Thr Arg Asp Arg Met Tyr Gln Met
                2515                2520                2525

gac att cag cag gaa ctt caa cga tac ctg tct ctg gta ggc cag gtt     7754
Asp Ile Gln Gln Glu Leu Gln Arg Tyr Leu Ser Leu Val Gly Gln Val
            2530                2535                2540

tat agc aca ctt gtc acc tac att tct gat tgg tgg act ctt gct gct     7802
Tyr Ser Thr Leu Val Thr Tyr Ile Ser Asp Trp Trp Thr Leu Ala Ala
        2545                2550                2555

aag aac ctt act gac ttt gca gag caa tat tct atc caa gat tgg gct     7850
Lys Asn Leu Thr Asp Phe Ala Glu Gln Tyr Ser Ile Gln Asp Trp Ala
    2560                2565                2570

aaa cgt atg aaa gca ttg gta gag caa ggg ttc act gtt cct gaa atc     7898
Lys Arg Met Lys Ala Leu Val Glu Gln Gly Phe Thr Val Pro Glu Ile
2575                2580                2585                2590

aag acc atc ctt ggg acc atg cct gcc ttt gaa gtc agt ctt cag gct     7946
Lys Thr Ile Leu Gly Thr Met Pro Ala Phe Glu Val Ser Leu Gln Ala
                2595                2600                2605

ctt cag aaa gct acc ttc cag aca cct gat ttt ata gtc ccc cta aca     7994
Leu Gln Lys Ala Thr Phe Gln Thr Pro Asp Phe Ile Val Pro Leu Thr
            2610                2615                2620

gat ttg agg att cca tca gtt cag ata aac ttc aaa gac tta aaa aat     8042
Asp Leu Arg Ile Pro Ser Val Gln Ile Asn Phe Lys Asp Leu Lys Asn
        2625                2630                2635

ata aaa atc cca tcc agg ttt tcc aca cca gaa ttt acc atc ctt aac     8090
Ile Lys Ile Pro Ser Arg Phe Ser Thr Pro Glu Phe Thr Ile Leu Asn
    2640                2645                2650

acc ttc cac att cct tcc ttt aca att gac ttt gtc gaa atg aaa gta     8138
Thr Phe His Ile Pro Ser Phe Thr Ile Asp Phe Val Glu Met Lys Val
2655                2660                2665                2670

aag atc atc aga acc att gac cag atg cag aac agt gag ctg cag tgg     8186
Lys Ile Ile Arg Thr Ile Asp Gln Met Gln Asn Ser Glu Leu Gln Trp
                2675                2680                2685

ccc gtt cca gat ata tat ctc agg gat ctg aag gtg gag gac att cct     8234
Pro Val Pro Asp Ile Tyr Leu Arg Asp Leu Lys Val Glu Asp Ile Pro
            2690                2695                2700

cta gcg aga atc acc ctg cca gac ttc cgt tta cca gaa atc gca att     8282
```

```
Leu Ala Arg Ile Thr Leu Pro Asp Phe Arg Leu Pro Glu Ile Ala Ile
        2705                2710                2715

cca gaa ttc ata atc cca act ctc aac ctt aat gat ttt caa gtt cct     8330
Pro Glu Phe Ile Ile Pro Thr Leu Asn Leu Asn Asp Phe Gln Val Pro
    2720                2725                2730

gac ctt cac ata cca gaa ttc cag ctt ccc cac atc tca cac aca att     8378
Asp Leu His Ile Pro Glu Phe Gln Leu Pro His Ile Ser His Thr Ile
2735                2740                2745                2750

gaa gta cct act ttt ggc aag cta tac agt att ctg aaa atc caa tct     8426
Glu Val Pro Thr Phe Gly Lys Leu Tyr Ser Ile Leu Lys Ile Gln Ser
                2755                2760                2765

cct ctt ttc aca tta gat gca aat gct gac ata ggg aat gga acc acc     8474
Pro Leu Phe Thr Leu Asp Ala Asn Ala Asp Ile Gly Asn Gly Thr Thr
            2770                2775                2780

tca gca aac gaa gca ggt atc gca gct tcc atc act gcc aaa gga gag     8522
Ser Ala Asn Glu Ala Gly Ile Ala Ala Ser Ile Thr Ala Lys Gly Glu
        2785                2790                2795

tcc aaa tta gaa gtt ctc aat ttt gat ttt caa gca aat gca caa ctc     8570
Ser Lys Leu Glu Val Leu Asn Phe Asp Phe Gln Ala Asn Ala Gln Leu
    2800                2805                2810

tca aac cct aag att aat ccg ctg gct ctg aag gag tca gtg aag ttc     8618
Ser Asn Pro Lys Ile Asn Pro Leu Ala Leu Lys Glu Ser Val Lys Phe
2815                2820                2825                2830

tcc agc aag tac ctg aga acg gag cat ggg agt gaa atg ctg ttt ttt     8666
Ser Ser Lys Tyr Leu Arg Thr Glu His Gly Ser Glu Met Leu Phe Phe
                2835                2840                2845

gga aat gct att gag gga aaa tca aac aca gtg gca agt tta cac aca     8714
Gly Asn Ala Ile Glu Gly Lys Ser Asn Thr Val Ala Ser Leu His Thr
            2850                2855                2860

gaa aaa aat aca ctg gag ctt agt aat gga gtg att gtc aag ata aac     8762
Glu Lys Asn Thr Leu Glu Leu Ser Asn Gly Val Ile Val Lys Ile Asn
        2865                2870                2875

aat cag ctt acc ctg gat agc aac act aaa tac ttc cac aaa ttg aac     8810
Asn Gln Leu Thr Leu Asp Ser Asn Thr Lys Tyr Phe His Lys Leu Asn
    2880                2885                2890

atc ccc aaa ctg gac ttc tct agt cag gct gac ctg cgc aac gag atc     8858
Ile Pro Lys Leu Asp Phe Ser Ser Gln Ala Asp Leu Arg Asn Glu Ile
2895                2900                2905                2910

aag aca ctg ttg aaa gct ggc cac ata gca tgg act tct tct gga aaa     8906
Lys Thr Leu Leu Lys Ala Gly His Ile Ala Trp Thr Ser Ser Gly Lys
                2915                2920                2925

ggg tca tgg aaa tgg gcc tgc ccc aga ttc tca gat gag gga aca cat     8954
Gly Ser Trp Lys Trp Ala Cys Pro Arg Phe Ser Asp Glu Gly Thr His
            2930                2935                2940

gaa tca caa att agt ttc acc ata gaa gga ccc ctc act tcc ttt gga     9002
Glu Ser Gln Ile Ser Phe Thr Ile Glu Gly Pro Leu Thr Ser Phe Gly
        2945                2950                2955

ctg tcc aat aag atc aat agc aaa cac cta aga gta aac caa aac ttg     9050
Leu Ser Asn Lys Ile Asn Ser Lys His Leu Arg Val Asn Gln Asn Leu
    2960                2965                2970

gtt tat gaa tct ggc tcc ctc aac ttt tct aaa ctt gaa att caa tca     9098
Val Tyr Glu Ser Gly Ser Leu Asn Phe Ser Lys Leu Glu Ile Gln Ser
2975                2980                2985                2990

caa gtc gat tcc cag cat gtg ggc cac agt gtt cta act gct aaa ggc     9146
Gln Val Asp Ser Gln His Val Gly His Ser Val Leu Thr Ala Lys Gly
                2995                3000                3005

atg gca ctg ttt gga gaa ggg aag gca gag ttt act ggg agg cat gat     9194
Met Ala Leu Phe Gly Glu Gly Lys Ala Glu Phe Thr Gly Arg His Asp
            3010                3015                3020

gct cat tta aat gga aag gtt att gga act ttg aaa aat tct ctt ttc     9242
```

```
Ala His Leu Asn Gly Lys Val Ile Gly Thr Leu Lys Asn Ser Leu Phe
        3025                3030                3035

ttt tca gcc cag cca ttt gag atc acg gca tcc aca aac aat gaa ggg     9290
Phe Ser Ala Gln Pro Phe Glu Ile Thr Ala Ser Thr Asn Asn Glu Gly
    3040                3045                3050

aat ttg aaa gtt cgt ttt cca tta agg tta aca ggg aag ata gac ttc     9338
Asn Leu Lys Val Arg Phe Pro Leu Arg Leu Thr Gly Lys Ile Asp Phe
3055                3060                3065                3070

ctg aat aac tat gca ctg ttt ctg agt ccc agt gcc cag caa gca agt     9386
Leu Asn Asn Tyr Ala Leu Phe Leu Ser Pro Ser Ala Gln Gln Ala Ser
                3075                3080                3085

tgg caa gta agt gct agg ttc aat cag tat aag tac aac caa aat ttc     9434
Trp Gln Val Ser Ala Arg Phe Asn Gln Tyr Lys Tyr Asn Gln Asn Phe
            3090                3095                3100

tct gct gga aac aac gag aac att atg gag gcc cat gta gga ata aat     9482
Ser Ala Gly Asn Asn Glu Asn Ile Met Glu Ala His Val Gly Ile Asn
        3105                3110                3115

gga gaa gca aat ctg gat ttc tta aac att cct tta aca att cct gaa     9530
Gly Glu Ala Asn Leu Asp Phe Leu Asn Ile Pro Leu Thr Ile Pro Glu
    3120                3125                3130

atg cgt cta cct tac aca ata atc aca act cct cca ctg aaa gat ttc     9578
Met Arg Leu Pro Tyr Thr Ile Ile Thr Thr Pro Pro Leu Lys Asp Phe
3135                3140                3145                3150

tct cta tgg gaa aaa aca ggc ttg aag gaa ttc ttg aaa acg aca aag     9626
Ser Leu Trp Glu Lys Thr Gly Leu Lys Glu Phe Leu Lys Thr Thr Lys
                3155                3160                3165

caa tca ttt gat tta agt gta aaa gct cag tat aag aaa aac aaa cac     9674
Gln Ser Phe Asp Leu Ser Val Lys Ala Gln Tyr Lys Lys Asn Lys His
            3170                3175                3180

agg cat tcc atc aca aat cct ttg gct gtg ctt tgt gag ttt atc agt     9722
Arg His Ser Ile Thr Asn Pro Leu Ala Val Leu Cys Glu Phe Ile Ser
        3185                3190                3195

cag agc atc aaa tcc ttt gac agg cat ttt gaa aaa aac aga aac aat     9770
Gln Ser Ile Lys Ser Phe Asp Arg His Phe Glu Lys Asn Arg Asn Asn
    3200                3205                3210

gca tta gat ttt gtc acc aaa tcc tat aat gaa aca aaa att aag ttt     9818
Ala Leu Asp Phe Val Thr Lys Ser Tyr Asn Glu Thr Lys Ile Lys Phe
3215                3220                3225                3230

gat aag tac aaa gct gaa aaa tct cac gac gag ctc ccc agg acc ttt     9866
Asp Lys Tyr Lys Ala Glu Lys Ser His Asp Glu Leu Pro Arg Thr Phe
                3235                3240                3245

caa att cct gga tac act gtt cca gtt gtc aat gtt gaa gtg tct cca     9914
Gln Ile Pro Gly Tyr Thr Val Pro Val Val Asn Val Glu Val Ser Pro
            3250                3255                3260

ttc acc ata gag atg tcg gca ttc ggc tat gtg ttc cca aaa gca gtc     9962
Phe Thr Ile Glu Met Ser Ala Phe Gly Tyr Val Phe Pro Lys Ala Val
        3265                3270                3275

agc atg cct agt ttc tcc atc cta ggt tct gac gtc cgt gtg cct tca    10010
Ser Met Pro Ser Phe Ser Ile Leu Gly Ser Asp Val Arg Val Pro Ser
    3280                3285                3290

tac aca tta atc ctg cca tca tta gag ctg cca gtc ctt cat gtc cct    10058
Tyr Thr Leu Ile Leu Pro Ser Leu Glu Leu Pro Val Leu His Val Pro
3295                3300                3305                3310

aga aat ctc aag ctt tct ctt cca cat ttc aag gaa ttg tgt acc ata    10106
Arg Asn Leu Lys Leu Ser Leu Pro His Phe Lys Glu Leu Cys Thr Ile
                3315                3320                3325

agc cat att ttt att cct gcc atg ggc aat att acc tat gat ttc tcc    10154
Ser His Ile Phe Ile Pro Ala Met Gly Asn Ile Thr Tyr Asp Phe Ser
            3330                3335                3340

ttt aaa tca agt gtc atc aca ctg aat acc aat gct gaa ctt ttt aac    10202
```

```
Phe Lys Ser Ser Val Ile Thr Leu Asn Thr Asn Ala Glu Leu Phe Asn
        3345                3350                3355

cag tca gat att gtt gct cat ctc ctt tct tca tct tca tct gtc att     10250
Gln Ser Asp Ile Val Ala His Leu Leu Ser Ser Ser Ser Ser Val Ile
    3360                3365                3370

gat gca ctg cag tac aaa tta gag ggc acc aca aga ttg aca aga aaa     10298
Asp Ala Leu Gln Tyr Lys Leu Glu Gly Thr Thr Arg Leu Thr Arg Lys
3375                3380                3385                3390

agg gga ttg aag tta gcc aca gct ctg tct ctg agc aac aaa ttt gtg     10346
Arg Gly Leu Lys Leu Ala Thr Ala Leu Ser Leu Ser Asn Lys Phe Val
                3395                3400                3405

gag ggt agt cat aac agt act gtg agc tta acc acg aaa aat atg gaa     10394
Glu Gly Ser His Asn Ser Thr Val Ser Leu Thr Thr Lys Asn Met Glu
            3410                3415                3420

gtg tca gtg gca aaa acc aca aaa gcc gaa att cca att ttg aga atg     10442
Val Ser Val Ala Lys Thr Thr Lys Ala Glu Ile Pro Ile Leu Arg Met
        3425                3430                3435

aat ttc aag caa gaa ctt aat gga aat acc aag tca aaa cct act gtc     10490
Asn Phe Lys Gln Glu Leu Asn Gly Asn Thr Lys Ser Lys Pro Thr Val
    3440                3445                3450

tct tcc tcc atg gaa ttt aag tat gat ttc aat tct tca atg ctg tac     10538
Ser Ser Ser Met Glu Phe Lys Tyr Asp Phe Asn Ser Ser Met Leu Tyr
3455                3460                3465                3470

tct acc gct aaa gga gca gtt gac cac aag ctt agc ttg gaa agc ctc     10586
Ser Thr Ala Lys Gly Ala Val Asp His Lys Leu Ser Leu Glu Ser Leu
                3475                3480                3485

acc tct tac ttt tcc att gag tca tct acc aaa gga gat gtc aag ggt     10634
Thr Ser Tyr Phe Ser Ile Glu Ser Ser Thr Lys Gly Asp Val Lys Gly
            3490                3495                3500

tcg gtt ctt tct cgg gaa tat tca gga act att gct agt gag gcc aac     10682
Ser Val Leu Ser Arg Glu Tyr Ser Gly Thr Ile Ala Ser Glu Ala Asn
        3505                3510                3515

act tac ttg aat tcc aag agc aca cgg tct tca gtg aag ctg cag ggc     10730
Thr Tyr Leu Asn Ser Lys Ser Thr Arg Ser Ser Val Lys Leu Gln Gly
    3520                3525                3530

act tcc aaa att gat gat atc tgg aac ctt gaa gta aaa gaa aat ttt     10778
Thr Ser Lys Ile Asp Asp Ile Trp Asn Leu Glu Val Lys Glu Asn Phe
3535                3540                3545                3550

gct gga gaa gcc aca ctc caa cgc ata tat tcc ctc tgg gag cac agt     10826
Ala Gly Glu Ala Thr Leu Gln Arg Ile Tyr Ser Leu Trp Glu His Ser
                3555                3560                3565

acg aaa aac cac tta cag cta gag ggc ctc ttt ttc acc aac gga gaa     10874
Thr Lys Asn His Leu Gln Leu Glu Gly Leu Phe Phe Thr Asn Gly Glu
            3570                3575                3580

cat aca agc aaa gcc acc ctg gaa ctc tct cca tgg caa atg tca gct     10922
His Thr Ser Lys Ala Thr Leu Glu Leu Ser Pro Trp Gln Met Ser Ala
        3585                3590                3595

ctt gtt cag gtc cat gca agt cag ccc agt tcc ttc cat gat ttc cct     10970
Leu Val Gln Val His Ala Ser Gln Pro Ser Ser Phe His Asp Phe Pro
    3600                3605                3610

gac ctt ggc cag gaa gtg gcc ctg aat gct aac act aag aac cag aag     11018
Asp Leu Gly Gln Glu Val Ala Leu Asn Ala Asn Thr Lys Asn Gln Lys
3615                3620                3625                3630

atc aga tgg aaa aat gaa gtc cgg att cat tct ggg tct ttc cag agc     11066
Ile Arg Trp Lys Asn Glu Val Arg Ile His Ser Gly Ser Phe Gln Ser
                3635                3640                3645

cag gtc gag ctt tcc aat gac caa gaa aag gca cac ctt gac att gca     11114
Gln Val Glu Leu Ser Asn Asp Gln Glu Lys Ala His Leu Asp Ile Ala
            3650                3655                3660

gga tcc tta gaa gga cac cta agg ttc ctc aaa aat atc atc cta cca     11162
```

```
Gly Ser Leu Glu Gly His Leu Arg Phe Leu Lys Asn Ile Ile Leu Pro
        3665                3670                3675

gtc tat gac aag agc tta tgg gat ttc cta aag ctg gat gta acc acc    11210
Val Tyr Asp Lys Ser Leu Trp Asp Phe Leu Lys Leu Asp Val Thr Thr
    3680                3685                3690

agc att ggt agg aga cag cat ctt cgt gtt tca act gcc ttt gtg tac    11258
Ser Ile Gly Arg Arg Gln His Leu Arg Val Ser Thr Ala Phe Val Tyr
3695                3700                3705                3710

acc aaa aac ccc aat ggc tat tca ttc tcc atc cct gta aaa gtt ttg    11306
Thr Lys Asn Pro Asn Gly Tyr Ser Phe Ser Ile Pro Val Lys Val Leu
                3715                3720                3725

gct gat aaa ttc att act cct ggg ctg aaa cta aat gat cta aat tca    11354
Ala Asp Lys Phe Ile Thr Pro Gly Leu Lys Leu Asn Asp Leu Asn Ser
            3730                3735                3740

gtt ctt gtc atg cct acg ttc cat gtc cca ttt aca gat ctt cag gtt    11402
Val Leu Val Met Pro Thr Phe His Val Pro Phe Thr Asp Leu Gln Val
        3745                3750                3755

cca tcg tgc aaa ctt gac ttc aga gaa ata caa atc tat aag aag ctg    11450
Pro Ser Cys Lys Leu Asp Phe Arg Glu Ile Gln Ile Tyr Lys Lys Leu
    3760                3765                3770

aga act tca tca ttt gcc ctc aac cta cca aca ctc ccc gag gta aaa    11498
Arg Thr Ser Ser Phe Ala Leu Asn Leu Pro Thr Leu Pro Glu Val Lys
3775                3780                3785                3790

ttc cct gaa gtt gat gtg tta aca aaa tat tct caa cca gaa gac tcc    11546
Phe Pro Glu Val Asp Val Leu Thr Lys Tyr Ser Gln Pro Glu Asp Ser
                3795                3800                3805

ttg att ccc ttt ttt gag ata acc gtg cct gaa tct cag tta act gtg    11594
Leu Ile Pro Phe Phe Glu Ile Thr Val Pro Glu Ser Gln Leu Thr Val
            3810                3815                3820

tcc cag ttc acg ctt cca aaa agt gtt tca gat ggc att gct gct ttg    11642
Ser Gln Phe Thr Leu Pro Lys Ser Val Ser Asp Gly Ile Ala Ala Leu
        3825                3830                3835

gat cta aat gca gta gcc aac aag atc gca gac ttt gag ttg ccc acc    11690
Asp Leu Asn Ala Val Ala Asn Lys Ile Ala Asp Phe Glu Leu Pro Thr
    3840                3845                3850

atc atc gtg cct gag cag acc att gag att ccc tcc att aag ttc tct    11738
Ile Ile Val Pro Glu Gln Thr Ile Glu Ile Pro Ser Ile Lys Phe Ser
3855                3860                3865                3870

gta cct gct gga att gtc att cct tcc ttt caa gca ctg act gca cgc    11786
Val Pro Ala Gly Ile Val Ile Pro Ser Phe Gln Ala Leu Thr Ala Arg
                3875                3880                3885

ttt gag gta gac tct ccc gtg tat aat gcc act tgg agt gcc agt ttg    11834
Phe Glu Val Asp Ser Pro Val Tyr Asn Ala Thr Trp Ser Ala Ser Leu
            3890                3895                3900

aaa aac aaa gca gat tat gtt gaa aca gtc ctg gat tcc aca tgc agc    11882
Lys Asn Lys Ala Asp Tyr Val Glu Thr Val Leu Asp Ser Thr Cys Ser
        3905                3910                3915

tca acc gta cag ttc cta gaa tat gaa cta aat gtt ttg gga aca cac    11930
Ser Thr Val Gln Phe Leu Glu Tyr Glu Leu Asn Val Leu Gly Thr His
    3920                3925                3930

aaa atc gaa gat ggt acg tta gcc tct aag act aaa gga aca ctt gca    11978
Lys Ile Glu Asp Gly Thr Leu Ala Ser Lys Thr Lys Gly Thr Leu Ala
3935                3940                3945                3950

cac cgt gac ttc agt gca gaa tat gaa gaa gat ggc aaa ttt gaa gga    12026
His Arg Asp Phe Ser Ala Glu Tyr Glu Glu Asp Gly Lys Phe Glu Gly
                3955                3960                3965

ctt cag gaa tgg gaa gga aaa gcg cac ctc aat atc aaa agc cca gcg    12074
Leu Gln Glu Trp Glu Gly Lys Ala His Leu Asn Ile Lys Ser Pro Ala
            3970                3975                3980

ttc acc gat ctc cat ctg cgc tac cag aaa gac aag aaa ggc atc tcc    12122
```

```
Phe Thr Asp Leu His Leu Arg Tyr Gln Lys Asp Lys Lys Gly Ile Ser
        3985                3990                3995

acc tca gca gcc tcc cca gcc gta ggc acc gtg ggc atg gat atg gat    12170
Thr Ser Ala Ala Ser Pro Ala Val Gly Thr Val Gly Met Asp Met Asp
    4000                4005                4010

gaa gat gac gac ttt tct aaa tgg aac ttc tac tac agc cct cag tcc    12218
Glu Asp Asp Asp Phe Ser Lys Trp Asn Phe Tyr Tyr Ser Pro Gln Ser
4015                4020                4025                4030

tct cca gat aaa aaa ctc acc ata ttc aaa act gag ttg agg gtc cgg    12266
Ser Pro Asp Lys Lys Leu Thr Ile Phe Lys Thr Glu Leu Arg Val Arg
                4035                4040                4045

gaa tct gat gag gaa act cag atc aaa gtt aat tgg gaa gaa gag gca    12314
Glu Ser Asp Glu Glu Thr Gln Ile Lys Val Asn Trp Glu Glu Glu Ala
            4050                4055                4060

gct tct ggc ttg cta acc tct ctg aaa gac aac gtg ccc aag gcc aca    12362
Ala Ser Gly Leu Leu Thr Ser Leu Lys Asp Asn Val Pro Lys Ala Thr
        4065                4070                4075

ggg gtc ctt tat gat tat gtc aac aag tac cac tgg gaa cac aca ggg    12410
Gly Val Leu Tyr Asp Tyr Val Asn Lys Tyr His Trp Glu His Thr Gly
    4080                4085                4090

ctc acc ctg aga gaa gtg tct tca aag ctg aga aga aat ctg cag aac    12458
Leu Thr Leu Arg Glu Val Ser Ser Lys Leu Arg Arg Asn Leu Gln Asn
4095                4100                4105                4110

aat gct gag tgg gtt tat caa ggg gcc att agg caa att gat gat atc    12506
Asn Ala Glu Trp Val Tyr Gln Gly Ala Ile Arg Gln Ile Asp Asp Ile
                4115                4120                4125

gac gtg agg ttc cag aaa gca gcc agt ggc acc act ggg acc tac caa    12554
Asp Val Arg Phe Gln Lys Ala Ala Ser Gly Thr Thr Gly Thr Tyr Gln
            4130                4135                4140

gag tgg aag gac aag gcc cag aat ctg tac cag gaa ctg ttg act cag    12602
Glu Trp Lys Asp Lys Ala Gln Asn Leu Tyr Gln Glu Leu Leu Thr Gln
        4145                4150                4155

gaa ggc caa gcc agt ttc cag gga ctc aag gat aac gtg ttt gat ggc    12650
Glu Gly Gln Ala Ser Phe Gln Gly Leu Lys Asp Asn Val Phe Asp Gly
    4160                4165                4170

ttg gta cga gtt act caa aaa ttc cat atg aaa gtc aag cat ctg att    12698
Leu Val Arg Val Thr Gln Lys Phe His Met Lys Val Lys His Leu Ile
4175                4180                4185                4190

gac tca ctc att gat ttt ctg aac ttc ccc aga ttc cag ttt ccg ggg    12746
Asp Ser Leu Ile Asp Phe Leu Asn Phe Pro Arg Phe Gln Phe Pro Gly
                4195                4200                4205

aaa cct ggg ata tac act agg gag gaa ctt tgc act atg ttc ata agg    12794
Lys Pro Gly Ile Tyr Thr Arg Glu Glu Leu Cys Thr Met Phe Ile Arg
            4210                4215                4220

gag gta ggg acg gta ctg tcc cag gta tat tcg aaa gtc cat aat ggt    12842
Glu Val Gly Thr Val Leu Ser Gln Val Tyr Ser Lys Val His Asn Gly
        4225                4230                4235

tca gaa ata ctg ttt tcc tat ttc caa gac cta gtg att aca ctt cct    12890
Ser Glu Ile Leu Phe Ser Tyr Phe Gln Asp Leu Val Ile Thr Leu Pro
    4240                4245                4250

ttc gag tta agg aaa cat aaa cta ata gat gta atc tcg atg tat agg    12938
Phe Glu Leu Arg Lys His Lys Leu Ile Asp Val Ile Ser Met Tyr Arg
4255                4260                4265                4270

gaa ctg ttg aaa gat tta tca aaa gaa gcc caa gag gta ttt aaa gcc    12986
Glu Leu Leu Lys Asp Leu Ser Lys Glu Ala Gln Glu Val Phe Lys Ala
                4275                4280                4285

att cag tct ctc aag acc aca gag gtg cta cgt aat ctt cag gac ctt    13034
Ile Gln Ser Leu Lys Thr Thr Glu Val Leu Arg Asn Leu Gln Asp Leu
            4290                4295                4300

tta caa ttc att ttc caa cta ata gaa gat aac att aaa cag ctg aaa    13082
```

```
Leu Gln Phe Ile Phe Gln Leu Ile Glu Asp Asn Ile Lys Gln Leu Lys
        4305                4310                4315

gag atg aaa ttt act tat ctt att aat tat atc caa gat gag atc aac    13130
Glu Met Lys Phe Thr Tyr Leu Ile Asn Tyr Ile Gln Asp Glu Ile Asn
    4320                4325                4330

aca atc ttc aat gat tat atc cca tat gtt ttt aaa ttg ttg aaa gaa    13178
Thr Ile Phe Asn Asp Tyr Ile Pro Tyr Val Phe Lys Leu Leu Lys Glu
4335                4340                4345                4350

aac cta tgc ctt aat ctt cat aag ttc aat gaa ttt att caa aac gag    13226
Asn Leu Cys Leu Asn Leu His Lys Phe Asn Glu Phe Ile Gln Asn Glu
                4355                4360                4365

ctt cag gaa gct tct caa gag tta cag cag atc cat caa tac att atg    13274
Leu Gln Glu Ala Ser Gln Glu Leu Gln Gln Ile His Gln Tyr Ile Met
            4370                4375                4380

gcc ctt cgt gaa gaa tat ttt gat cca agt ata gtt ggc tgg aca gtg    13322
Ala Leu Arg Glu Glu Tyr Phe Asp Pro Ser Ile Val Gly Trp Thr Val
        4385                4390                4395

aaa tat tat gaa ctt gaa gaa aag ata gtc agt ctg atc aag aac ctg    13370
Lys Tyr Tyr Glu Leu Glu Glu Lys Ile Val Ser Leu Ile Lys Asn Leu
    4400                4405                4410

tta gtt gct ctt aag gac ttc cat tct gaa tat att gtc agt gcc tct    13418
Leu Val Ala Leu Lys Asp Phe His Ser Glu Tyr Ile Val Ser Ala Ser
4415                4420                4425                4430

aac ttt act tcc caa ctc tca agt caa gtt gag caa ttt ctg cac aga    13466
Asn Phe Thr Ser Gln Leu Ser Ser Gln Val Glu Gln Phe Leu His Arg
                4435                4440                4445

aat att cag gaa tat ctt agc atc ctt acc gat cca gat gga aaa ggg    13514
Asn Ile Gln Glu Tyr Leu Ser Ile Leu Thr Asp Pro Asp Gly Lys Gly
            4450                4455                4460

aaa gag aag att gca gag ctt tct gcc act gct cag gaa ata att aaa    13562
Lys Glu Lys Ile Ala Glu Leu Ser Ala Thr Ala Gln Glu Ile Ile Lys
        4465                4470                4475

agc cag gcc att gcg acg aag aaa ata att tct gat tac cac cag cag    13610
Ser Gln Ala Ile Ala Thr Lys Lys Ile Ile Ser Asp Tyr His Gln Gln
    4480                4485                4490

ttt aga tat aaa ctg caa gat ttt tca gac caa ctc tct gat tac tat    13658
Phe Arg Tyr Lys Leu Gln Asp Phe Ser Asp Gln Leu Ser Asp Tyr Tyr
4495                4500                4505                4510

gaa aaa ttt att gct gaa tcc aaa aga ttg att gac ctg tcc att caa    13706
Glu Lys Phe Ile Ala Glu Ser Lys Arg Leu Ile Asp Leu Ser Ile Gln
                4515                4520                4525

aac tac cac aca ttt ctg ata tac atc acg gag tta ctg aaa aag ctg    13754
Asn Tyr His Thr Phe Leu Ile Tyr Ile Thr Glu Leu Leu Lys Lys Leu
            4530                4535                4540

caa tca acc aca gtc atg aac ccc tac atg aag ctt gct cca gga gaa    13802
Gln Ser Thr Thr Val Met Asn Pro Tyr Met Lys Leu Ala Pro Gly Glu
        4545                4550                4555

ctt act atc atc ctc taa ttttttaaaa gaaatcttca tttattcttc           13850
Leu Thr Ile Ile Leu  *
    4560

ttttccaatt gaactttcac atagcacaga aaaaattcaa actgcctata ttgataaaac  13910

catacagtga gccagccttg cagtaggcag tagactataa gcagaagcac atatgaactg  13970

gacctgcacc aaagctggca ccagggctcg gaaggtctct gaactcagaa ggatggcatt  14030

ttttgcaagt taaagaaaat caggatctga gttattttgc taaacttggg ggaggaggaa  14090

caaataaatg gagtctttat tgtgtatcat a                                 14121
```

<210> SEQ ID NO 4
<211> LENGTH: 21

<212> TYPE: DNA
<213> ORGANISM: Artificial Sequence
<220> FEATURE:
<223> OTHER INFORMATION: PCR Primer

<400> SEQUENCE: 4 tgctaaaggc acatatggcc t 21

<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5 ctcaggttgg actctccatt gag 23

<210> SEQ ID NO 6
<211> LENGTH: 28
<212> TYPE: DNA
<213> ORGANISM: Artificial Sequence
<220> FEATURE:
<223> OTHER INFORMATION: PCR Probe

<400> SEQUENCE: 6 cttgtcagag ggatcctaac actggccg 28

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7 gaaggtgaag gtcggagtc 19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8 gaagatggtg atgggatttc 20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9 caagcttccc gttctcagcc 20

<210> SEQ ID NO 10
<211> LENGTH: 2354
<212> TYPE: DNA
<213> ORGANISM: Mus musculus

<400> SEQUENCE: 10 gaattccaac ttcctcacct ctcacataca attgaaatac ctgcttttgg caaactgcat 60 agcatcctta agatccaatc tcctctcttt atattagatg ctaatgccaa catacagaat 120

```
gtaacaactt cagggaacaa agcagagatt gtggcttctg tcactgctaa aggagagtcc    180
caatttgaag ctctcaattt tgattttcaa gcacaagctc aattcctgga gttaaatcct    240
catcctccag tcctgaagga atccatgaac ttctccagta agcatgtgag aatggagcat    300
gagggtgaga tagtatttga tggaaaggcc attgagggga aatcagacac agtcgcaagt    360
ttacacacag agaaaaatga agtagagttt aataatggta tgactgtcaa agtaaacaat    420
cagctcaccc ttgacagtca cacaaagtac ttccacaagt tgagtgttcc taggctggac    480
ttctccagta aggcttctct taataatgaa atcaagacac tattagaagc tggacatgtg    540
gcattgacat cttcagggac agggtcatgg aactgggcct gtcccaactt ctcggatgaa    600
ggcatacatt cgtcccaaat tagctttact gtggatggtc ccattgcttt tgttggacta    660
tccaataaca taaatggcaa acacttacgg gtcatccaaa aactgactta tgaatctggc    720
ttcctcaact attctaagtt tgaagttgag tcaaaagttg aatctcagca cgtgggctcc    780
agcattctaa cagccaatgg tcgggcactg ctcaaggacg caaaggcaga aatgactggt    840
gagcacaatg ccaacttaaa tggaaaagtt attggaactt tgaaaaattc tctcttcttt    900
tcagcacaac catttgagat tactgcatcc acaaataatg aaggaaattt gaaagtgggt    960
tttccactaa agctgactgg gaaaatagac ttcctgaata actatgcatt gtttctgagt   1020
ccccgtgccc aacaagcaag ctggcaagcg agtaccagat tcaatcagta caaatacaat   1080
caaaactttt ctgctataaa caatgaacac aacatagaag ccagtatagg aatgaatgga   1140
gatgccaacc tggatttctt aaacatacct ttaacaattc ctgaaattaa cttgccttac   1200
acggagttca aaactccctt actgaaggat ttctccatat gggaagaaac aggcttgaaa   1260
gaatttttga agacaacaaa gcaatcattt gatttgagtg taaaggctca atataaaaag   1320
aacagtgaca agcattccat tgttgtccct ctgggtatgt tttatgaatt tattctcaac   1380
aatgtcaatt cgtgggacag aaaatttgag aaagtcagaa acaatgcttt acattttctt   1440
accacctcct ataatgaagc aaaaattaag gttgataagt acaaaactga aaattccctt   1500
aatcagccct ctgggacctt tcaaaatcat ggctacacta tcccagttgt caacattgaa   1560
gtatctccat ttgctgtaga gacactggct tccaggcatg tgatccccac agcaataagc   1620
accccaagtg tcacaatccc tggtcctaac atcatggtgc cttcatacaa gttagtgctg   1680
ccacccctgg agttgccagt tttccatggt cctgggaatc tattcaagtt tttcctccca   1740
gatttcaagg gattcaacac tattgacaat atttatattc cagccatggg caactttacc   1800
tatgactttt cttttaaatc aagtgtcatc acactgaata ccaatgctgg actttataac   1860
caatcagata tcgttgccca tttcctttct tcctcttcat ttgtcactga cgccctgcag   1920
tacaaattag agggaacatc acgtctgatg cgaaaaaggg gattgaaact agccacagct   1980
gtctctctaa ctaacaaatt tgtaaagggc agtcatgaca gcaccattag tttaaccaag   2040
aaaaacatgg aagcatcagt gagaacaact gccaacctcc atgctcccat attctcaatg   2100
aacttcaagc aggaacttaa tggaaatacc aagtcaaaac ccactgtttc atcatccatt   2160
gaactaaact atgacttcaa ttcctcaaag ctgcactcta ctgcaacagg aggcattgat   2220
cacaagttca gcttagaaag tctcacttcc tacttttcca ttgagtcatt caccaaagga   2280
aatatcaaga gttccttcct ttctcaggaa tattcaggaa gtgttgccaa tgaagccaat   2340
gtatatctga attc                                                     2354
```

<210> SEQ ID NO 11
<211> LENGTH: 19

<212> TYPE: DNA
<213> ORGANISM: Artificial Sequence
<220> FEATURE:
<223> OTHER INFORMATION: PCR Primer

<400> SEQUENCE: 11 cgtgggctcc agcattcta 19

<210> SEQ ID NO 12
<211> LENGTH: 21
<212> TYPE: DNA
<213> ORGANISM: Artificial Sequence
<220> FEATURE:
<223> OTHER INFORMATION: PCR Primer

<400> SEQUENCE: 12 agtcatttct gcctttgcgt c 21

<210> SEQ ID NO 13
<211> LENGTH: 22
<212> TYPE: DNA
<213> ORGANISM: Artificial Sequence
<220> FEATURE:
<223> OTHER INFORMATION: PCR Probe

<400> SEQUENCE: 13 ccaatggtcg ggcactgctc aa 22

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14 ggcaaattca acggcacagt 20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15 gggtctcgct cctggaagat 20

<210> SEQ ID NO 16
<211> LENGTH: 27
<212> TYPE: DNA
<213> ORGANISM: Artificial Sequence
<220> FEATURE:
<223> OTHER INFORMATION: PCR Probe

<400> SEQUENCE: 16 aaggccgaga atgggaagct tgtcatc 27

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17 ccgcaggtcc cggtgggaat 20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18 accgagaagg gcactcagcc 20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19 gcctcggcct cgcggccctg 20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20 tccatcgcca gctgcggtgg 20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21 cagcgccagc agcgccagca 20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22 gcccgccagc agcagcagca 20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23 cttgaatcag cagtcccagg 20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24 cttcagcaag gctttgccct 20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25 tttctgttgc cacattgccc 20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26 ggaagaggtg ttgctccttg 20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27 tgtgctacca tcccatactt 20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28 tcaaatgcga ggcccatctt 20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29 ggacacctca atcagctgtg 20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30 tcagggccac caggtaggtg 20

<210> SEQ ID NO 31
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 31 gtaatcttca tccccagtgc 20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32 tgctccatgg tttggcccat 20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33 gcagccagtc gcttatctcc 20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34 gtatagccaa agtggtccac 20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35 cccaggagct ggaggtcatg 20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36 ttgagccctt cctgatgacc 20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37 atctggaccc cactcctagc 20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38 cagacccgac tcgtggaaga 20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39 gccctcagta gattcatcat 20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40 gccatgccac cctcttggaa 20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41 aacccacgtg ccggaaagtc 20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42 actcccagat gccttctgaa 20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43 atgtggtaac gagcccgaag 20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44 ggcgtagaga cccatcacat 20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45 gtgttaggat ccctctgaca 20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46 cccagtgata gctctgtgag 20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47 atttcagcat atgagcccat 20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48 ccctgaacct tagcaacagt 20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49 gctgaagcca gcccagcgat 20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50 acagctgccc agtatgttct 20

<210> SEQ ID NO 51
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 51 cccaataaga tttataacaa 20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52 tggcctacca gagacaggta 20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53 tcatacgttt agcccaatct 20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54 gcatggtccc aaggatggtc 20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55 agtgatggaa gctgcgatac 20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56 atgagcatca tgcctcccag 20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57 gaacacatag ccgaatgccg 20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58 gtggtgccct ctaatttgta 20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59 cccgagaaag aaccgaaccc 20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60 tgccctgcag cttcactgaa 20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61 gaaatcccat aagctcttgt 20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62 agaagctgcc tcttcttccc 20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63 tcagggtgag ccctgtgtgt 20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64 ctaatggccc cttgataaac 20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65 acgttatcct tgagtccctg 20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66 tatatcccag gtttccccgg 20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67 acctgggaca gtaccgtccc 20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68 ctgcctactg caaggctggc 20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69 agagaccttc cgagccctgg 20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70 atgatacaca ataaagactc 20

<210> SEQ ID NO 71
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 71 attgtatgtg agaggtgagg 20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72 gaggagattg gatcttaagg 20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73 cttcaaattg ggactctcct 20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74 tccaggaatt gagcttgtgc 20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75 ttcaggactg gaggatgagg 20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76 tctcaccctc atgctccatt 20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77 tgactgtcaa gggtgagctg 20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78 gtccagccta ggaacactca 20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79 atgtcaatgc cacatgtcca 20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80 ttcatccgag aagttgggac 20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81 atttgggacg aatgtatgcc 20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82 agttgaggaa gccagattca 20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83 ttcccagtca gctttagtgg 20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84 agcttgcttg ttgggcacgg 20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85 cctatactgg cttctatgtt 20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86 tgaactccgt gtaaggcaag 20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87 gagaaatcct tcagtaaggg 20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88 caatggaatg cttgtcactg 20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89 gcttcattat aggaggtggt 20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90 acaactggga tagtgtagcc 20

<210> SEQ ID NO 91
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 91 gttaggacca gggattgtga 20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92 accatggaaa actggcaact 20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93 tgggaggaaa aacttgaata 20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94 tgggcaacga tatctgattg 20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95 ctgcagggcg tcagtgacaa 20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96 gcatcagacg tgatgttccc 20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97 cttggttaaa ctaatggtgc 20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98 atgggagcat ggaggttggc 20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99 aatggatgat gaaacagtgg 20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100 atcaatgcct cctgttgcag 20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101 ggaagtgaga ctttctaagc 20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102 aggaaggaac tcttgatatt 20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103 attggcttca ttggcaacac 20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104 aggtgaggaa gttggaattc 20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105 ttgttccctg aagttgttac 20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106 gttcatggat tccttcagga 20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107 atgctccatt ctcacatgct 20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108 tgcgactgtg tctgatttcc 20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109 gtccctgaag atgtcaatgc 20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110 aggcccagtt ccatgaccct 20

<210> SEQ ID NO 111
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 111 ggagcccacg tgctgagatt 20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112 cgtccttgag cagtgcccga 20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113 cccatatgga gaaatccttc 20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114 catgcctgga agccagtgtc 20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115 gtgttgaatc ccttgaaatc 20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116 ggtaaagttg cccatggctg 20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117 gttataaagt ccagcattgg 20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118 catcagacgt gatgttccct 20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119 tggctagttt caatcccctt 20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120 ctgtcatgac tgccctttac 20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121 gcttgaagtt cattgagaat 20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122 ttcctgagaa aggaaggaac 20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123 tcagatatac attggcttca 20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124 ttcctcttcg gccctggcgc 20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125 ctccactgga actctcagcc 20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126 cctccagctc aaccttgcag 20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127 gggttgaagc catacacctc 20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128 ccagcttgag ctcatacctg 20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129 ccctcttgat gttcaggatg 20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130 gagcagtttc catacacggt 20

<210> SEQ ID NO 131
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 131 cccttcctcg tcttgacggt 20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132 ttgaagcgat cacactgccc 20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133 gcctttgatg agagcaagtg 20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134 tcctcttagc gtccagtgtg 20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135 cctctcagct cagtaaccag 20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136 gcactgaggc tgtccacact 20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137 cgctgatccc tcgccatgtt 20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138 gttgaccgcg tggctcagcg 20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139 gcagctcctg ggtccctgta 20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140 cccatggtag aatttggaca 20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141 aatctcgatg aggtcagctg 20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142 gacaccatca ggaacttgac 20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143 gctcctctcc caagatgcgg 20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144 ggcacccatc agaagcagct 20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145 agtccggaat gatgatgccc 20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146 ctgagcagct tgactggtct 20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147 cccggtcagc ggatagtagg 20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148 tgtcacaact taggtggccc 20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149 gtctggcaat cccatgttct 20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150 cccacagact tgaagtggag 20

<210> SEQ ID NO 151
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 151 gaactgccca tcaatcttga 20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152 cccagagagg ccaagctctg 20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153 tgtgttccct gaagcggcca 20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154 acccagaatc atggcctgat 20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155 ggtgcctgtc tgctcagctg 20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156 atgtgaaact tgtctctccc 20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157 tatgtctgca gttgagatag 20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158 ttgaatccag gatgcagtac 20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159 gagtctctga gtcacctcac 20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160 gatagaatat tgctctgcaa 20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161 cccttgctct accaatgctt 20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162 tccattccct atgtcagcat 20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163 gactccttca gagccagcgg 20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164 cccatgctcc gttctcaggt 20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165 cgcaggtcag cctgactaga 20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166 cagttagaac actgtggccc 20

<210> SEQ ID NO 167
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167 cagtgtgatg acacttgatt 20

<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 168 ctgtggctaa cttcaatccc 20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169 cagtactgtt atgactaccc 20

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 170 cactgaagac cgtgtgctct 20

<210> SEQ ID NO 171
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 171 tcgtactgtg ctcccagagg 20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172 aagaggccct ctagctgtaa 20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173 aagacccaga atgaatccgg 20

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174 gtctacctca aagcgtgcag 20

<210> SEQ ID NO 175
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 175 tagaggctaa cgtaccatct 20

<210> SEQ ID NO 176
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 176 ccatatccat gcccacggtg 20

<210> SEQ ID NO 177
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 177 agtttcctca tcagattccc 20

<210> SEQ ID NO 178
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 178 cccagtggta cttgttgaca 20

<210> SEQ ID NO 179
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 179 cccagtggtg ccactggctg 20

<210> SEQ ID NO 180
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 180 gtcaacagtt cctggtacag 20

<210> SEQ ID NO 181
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 181 ccctagtgta tatcccaggt 20

<210> SEQ ID NO 182
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 182 ctgaagatta cgtagcacct 20

<210> SEQ ID NO 183
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 183 gtccagccaa ctatacttgg 20

<210> SEQ ID NO 184
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 184 cctggagcaa gcttcatgta 20

<210> SEQ ID NO 185
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 185 tggacagacc aggctgacat 20

<210> SEQ ID NO 186
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 186 atgtgtactt ccggaggtgc 20

<210> SEQ ID NO 187
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 187 tcttcaggat gaagctgcag 20

<210> SEQ ID NO 188
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 188 tcagcaaggc tttgccctca 20

<210> SEQ ID NO 189
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 189 ctgcttccct tctggaatgg 20

<210> SEQ ID NO 190
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 190 tgccacattg cccttcctcg 20

<210> SEQ ID NO 191
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 191 gctgatcaga gttgacaagg 20

<210> SEQ ID NO 192
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 192 tactgacagg actggctgct 20

<210> SEQ ID NO 193
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 193 gatggcttct gccacatgct 20

<210> SEQ ID NO 194
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 194 gatgtggatt tggtgctctc 20

<210> SEQ ID NO 195
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 195 tgactgcttc atcactgagg 20

<210> SEQ ID NO 196
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 196 ggtaggtgac cacatctatc 20

<210> SEQ ID NO 197
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 197 tcgcagctgc tgtgctgagg 20

<210> SEQ ID NO 198
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 198 ttccaatgac ccgcagaatc 20

<210> SEQ ID NO 199
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 199 gatcatcagt gatggctttg 20

<210> SEQ ID NO 200
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 200 agcctggatg gcagctttct 20

<210> SEQ ID NO 201
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 201 gtctgaagaa gaacctcctg 20

<210> SEQ ID NO 202
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 202 tatctgcctg tgaaggactc 20

<210> SEQ ID NO 203
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 203 ctgagttcaa gatattggca 20

<210> SEQ ID NO 204
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 204 cttccaagcc aatctcgatg 20

<210> SEQ ID NO 205
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 205 tgcaactgta atccagctcc 20

<210> SEQ ID NO 206
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 206 ccagttcagc ctgcatgttg 20

<210> SEQ ID NO 207
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 207 gtagagacca aatgtaatgt 20

<210> SEQ ID NO 208
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 208 cgttggagta agcgcctgag 20

<210> SEQ ID NO 209
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 209 cagctctaat ctggtgtccc 20

<210> SEQ ID NO 210
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 210 ctgtcctctc tctggagctc 20

<210> SEQ ID NO 211
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 211 caaggtcata ctctgccgat 20

<210> SEQ ID NO 212
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 212 gtatggaaat aacacccttg 20

<210> SEQ ID NO 213
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 213 taagctgtag cagatgagtc 20

<210> SEQ ID NO 214
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 214 tagatctctg gaggatttgc 20

<210> SEQ ID NO 215
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 215 gtctagaaca cccaggagag 20

<210> SEQ ID NO 216
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 216 accacagagt cagccttcat 20

<210> SEQ ID NO 217
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 217 aagcagacat ctgtggtccc 20

<210> SEQ ID NO 218
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 218 ctctccattg agccggccag 20

<210> SEQ ID NO 219
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 219 cctgatattc agaacgcagc 20

<210> SEQ ID NO 220
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 220 cagtgcctaa gatgtcagca 20

<210> SEQ ID NO 221
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 221 agcaccagga gactacactt 20

<210> SEQ ID NO 222
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 222 cccatccaga ctgaattttg 20

<210> SEQ ID NO 223
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 223 ggttctagcc gtagtttccc 20

<210> SEQ ID NO 224
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 224 aggttaccag ccacatgcag 20

<210> SEQ ID NO 225
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 225 atgtgcatcg atggtcatgg 20

<210> SEQ ID NO 226
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 226 ccagagagcg agtttcccat 20

<210> SEQ ID NO 227
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 227 ctagacacga gatgatgact 20

<210> SEQ ID NO 228
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 228 tccaagtcct ggctgtattc 20

<210> SEQ ID NO 229
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 229 cgtccagtaa gctccacgcc 20

<210> SEQ ID NO 230
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 230 tcaacggcat ctctcatctc 20

<210> SEQ ID NO 231
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 231 tgatagtgct catcaagact 20

<210> SEQ ID NO 232
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 232 gattctgatt tggtacttag 20

<210> SEQ ID NO 233
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 233 ctctcgatta actcatggac 20

<210> SEQ ID NO 234
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 234 atacactgca actgtggcct 20

<210> SEQ ID NO 235
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 235 gcaagagtcc accaatcaga 20

<210> SEQ ID NO 236
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 236 agagcctgaa gactgacttc 20

<210> SEQ ID NO 237
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 237 tccctcatct gagaatctgg 20

<210> SEQ ID NO 238
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 238 cagtgcatca atgacagatg 20

<210> SEQ ID NO 239
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 239 ccgaaccctt gacatctcct 20

<210> SEQ ID NO 240
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 240 gcctcactag caatagttcc 20

<210> SEQ ID NO 241
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 241 gacatttgcc atggagagag 20

<210> SEQ ID NO 242
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 242 ctgtctccta ccaatgctgg 20

<210> SEQ ID NO 243
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 243 tctgcactga agtcacggtg 20

<210> SEQ ID NO 244
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 244 tcccggaccc tcaactcagt 20

<210> SEQ ID NO 245
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 245 gcaggtccag ttcatatgtg 20

<210> SEQ ID NO 246
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 246 gccatccttc tgagttcaga 20

<210> SEQ ID NO 247
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 247 gcctcagtct gcttcgcacc 20

<210> SEQ ID NO 248
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 248 ccccgcaggt cccggtggga 20

<210> SEQ ID NO 249
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 249 cagccccgca ggtcccggtg 20

<210> SEQ ID NO 250
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 250 caaccgagaa gggcactcag 20

<210> SEQ ID NO 251
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 251 cctcagcggc agcaaccgag 20

<210> SEQ ID NO 252
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 252 tcctcagcgg cagcaaccga 20

<210> SEQ ID NO 253
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 253 ctcctcagcg gcagcaaccg 20

<210> SEQ ID NO 254
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 254 ggctcctcag cggcagcaac 20

<210> SEQ ID NO 255
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 255 ggcgggctcc tcagcggcag 20

<210> SEQ ID NO 256
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 256 ggtccatcgc cagctgcggt 20

<210> SEQ ID NO 257
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 257 ggcgggtcca tcgccagctg 20

<210> SEQ ID NO 258
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 258 tagaggatga tagtaagttc 20

<210> SEQ ID NO 259
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 259 aaatgaagat ttcttttaaa 20

<210> SEQ ID NO 260
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 260 tatgtgaaag ttcaattgga 20

<210> SEQ ID NO 261
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 261 atataggcag tttgaatttt 20

<210> SEQ ID NO 262
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 262 gctcactgta tggttttatc 20

<210> SEQ ID NO 263
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 263 ggctcactgt atggttttat 20

<210> SEQ ID NO 264
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 264 ggctggctca ctgtatggtt 20

<210> SEQ ID NO 265
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 265 aggctggctc actgtatggt 20

<210> SEQ ID NO 266
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 266 aaggctggct cactgtatgg 20

<210> SEQ ID NO 267
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 267 ctactgcaag gctggctcac 20

<210> SEQ ID NO 268
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 268 actgcctact gcaaggctgg 20

<210> SEQ ID NO 269
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 269 tgcttatagt ctactgccta 20

<210> SEQ ID NO 270
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 270 ttctgcttat agtctactgc 20

<210> SEQ ID NO 271
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 271 tttggtgcag gtccagttca 20

<210> SEQ ID NO 272
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 272 cagctttggt gcaggtccag 20

<210> SEQ ID NO 273
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 273 gccagctttg gtgcaggtcc 20

<210> SEQ ID NO 274
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 274 tggtgccagc tttggtgcag 20

<210> SEQ ID NO 275
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 275 gccctggtgc cagctttggt 20

<210> SEQ ID NO 276
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 276 gagttcagag accttccgag 20

<210> SEQ ID NO 277
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 277 aaatgccatc cttctgagtt 20

<210> SEQ ID NO 278
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 278 aaaaatgcca tccttctgag 20

<210> SEQ ID NO 279
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 279 aaaataactc agatcctgat 20

<210> SEQ ID NO 280
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 280 agcaaaataa ctcagatcct 20

<210> SEQ ID NO 281
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 281 agtttagcaa aataactcag 20

<210> SEQ ID NO 282
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 282 tcccccaagt ttagcaaaat 20

<210> SEQ ID NO 283
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 283 ttcctcctcc cccaagttta 20

<210> SEQ ID NO 284
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 284 agactccatt tatttgttcc 20

<210> SEQ ID NO 285
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 285 cttctgcttg agttacaaac 20

<210> SEQ ID NO 286
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 286 accttctgct tgagttacaa 20

<210> SEQ ID NO 287
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 287 gcaccttctg cttgagttac 20

<210> SEQ ID NO 288
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 288 tcgcaccttc tgcttgagtt 20

<210> SEQ ID NO 289
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 289 cttcgcacct tctgcttgag 20

<210> SEQ ID NO 290
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 290 tgcttcgcac cttctgcttg 20

<210> SEQ ID NO 291
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 291 tctgcttcgc accttctgct 20

<210> SEQ ID NO 292
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 292 agtctgcttc gcaccttctg 20

<210> SEQ ID NO 293
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 293 tcagtctgct tcgcaccttc 20

<210> SEQ ID NO 294
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 294 cctcagtctg cttcgcacct 20

<210> SEQ ID NO 295
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 295 agcctcagtc tgcttcgcac 20

<210> SEQ ID NO 296
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 296 gtagcctcag tctgcttcgc 20

<210> SEQ ID NO 297
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 297 tggtagcctc agtctgcttc 20

<210> SEQ ID NO 298
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 298 catggtagcc tcagtctgct 20

<210> SEQ ID NO 299
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 299 gtcatggtag cctcagtctg 20

<210> SEQ ID NO 300
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 300 atgtcatggt agcctcagtc 20

<210> SEQ ID NO 301
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 301 gaatgtcatg gtagcctcag 20

<210> SEQ ID NO 302
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 302 ttgaatgtca tggtagcctc 20

<210> SEQ ID NO 303
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 303 atttgaatgt catggtagcc 20

<210> SEQ ID NO 304
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 304 atatttgaat gtcatggtag 20

<210> SEQ ID NO 305
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 305 cagccacatg cagcttcagg 20

<210> SEQ ID NO 306
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 306 accagccaca tgcagcttca 20

<210> SEQ ID NO 307
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 307 ttaccagcca catgcagctt 20

<210> SEQ ID NO 308
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 308 ggttaccagc cacatgcagc 20

<210> SEQ ID NO 309
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 309 taggttacca gccacatgca 20

<210> SEQ ID NO 310
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 310 tttaggttac cagccacatg 20

<210> SEQ ID NO 311
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 311 cttttaggtt accagccaca 20

<210> SEQ ID NO 312
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 312 tccttttagg ttaccagcca 20

<210> SEQ ID NO 313
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 313 gctcctttta ggttaccagc 20

<210> SEQ ID NO 314
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 314 aggctccttt taggttacca 20

<210> SEQ ID NO 315
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 315 gtaggctcct tttaggttac 20

<210> SEQ ID NO 316
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 316 tggtaggctc cttttaggtt 20

<210> SEQ ID NO 317
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 317 tttggtaggc tccttttagg 20

<210> SEQ ID NO 318
<211> LENGTH: 13993
<212> TYPE: DNA
<213> ORGANISM: H. sapiens
<220> FEATURE:
<221> NAME/KEY: CDS
<222> LOCATION: (1).. (13692)

<400> SEQUENCE: 318

```
atg gac ccg ccg agg ccc gcg ctg ctg gcg ctg ctg gcg ctg cct gcg       48
Met Asp Pro Pro Arg Pro Ala Leu Leu Ala Leu Leu Ala Leu Pro Ala
 1               5                  10                  15

ctg ctg ctg ctg ctg ctg gcg ggc gcc agg gcc gaa gag gaa atg ctg       96
Leu Leu Leu Leu Leu Leu Ala Gly Ala Arg Ala Glu Glu Glu Met Leu
            20                  25                  30

gaa aat gtc agc ctg gtc tgt cca aaa gat gcg acc cga ttc aag cac      144
Glu Asn Val Ser Leu Val Cys Pro Lys Asp Ala Thr Arg Phe Lys His
        35                  40                  45

ctc cgg aag tac aca tac aac tat gag gct gag agt tcc agt gga gtc      192
Leu Arg Lys Tyr Thr Tyr Asn Tyr Glu Ala Glu Ser Ser Ser Gly Val
    50                  55                  60

cct ggg act gct gat tca aga agt gcc acc agg atc aac tgc aag gtt      240
Pro Gly Thr Ala Asp Ser Arg Ser Ala Thr Arg Ile Asn Cys Lys Val
65                  70                  75                  80

gag ctg gag gtt ccc cag ctc tgc agc ttc atc ctg aag acc agc cag      288
Glu Leu Glu Val Pro Gln Leu Cys Ser Phe Ile Leu Lys Thr Ser Gln
                85                  90                  95

tgc acc ctg aaa gag gtg tat ggc ttc aac cct gag ggc aaa gcc ttg      336
Cys Thr Leu Lys Glu Val Tyr Gly Phe Asn Pro Glu Gly Lys Ala Leu
            100                 105                 110

ctg aag aaa acc aag aac tct gag gag ttt gct gca gcc atg tcc agg      384
Leu Lys Lys Thr Lys Asn Ser Glu Glu Phe Ala Ala Ala Met Ser Arg
        115                 120                 125

tat gag ctc aag ctg gcc att cca gaa ggg aag cag gtt ttc ctt tac      432
Tyr Glu Leu Lys Leu Ala Ile Pro Glu Gly Lys Gln Val Phe Leu Tyr
    130                 135                 140

ccg gag aaa gat gaa cct act tac atc ctg aac atc aag agg ggc atc      480
Pro Glu Lys Asp Glu Pro Thr Tyr Ile Leu Asn Ile Lys Arg Gly Ile
145                 150                 155                 160

att tct gcc ctc ctg gtt ccc cca gag aca gaa gaa gcc aag caa gtg      528
Ile Ser Ala Leu Leu Val Pro Pro Glu Thr Glu Glu Ala Lys Gln Val
                165                 170                 175

ttg ttt ctg gat acc gtg tat gga aac tgc tcc act cac ttt acc gtc      576
Leu Phe Leu Asp Thr Val Tyr Gly Asn Cys Ser Thr His Phe Thr Val
            180                 185                 190

aag acg agg aag ggc aat gtg gca aca gaa ata tcc act gaa aga gac      624
Lys Thr Arg Lys Gly Asn Val Ala Thr Glu Ile Ser Thr Glu Arg Asp
        195                 200                 205

ctg ggg cag tgt gat cgc ttc aag ccc atc cgc aca ggc atc agc cca      672
Leu Gly Gln Cys Asp Arg Phe Lys Pro Ile Arg Thr Gly Ile Ser Pro
    210                 215                 220

ctt gct ctc atc aaa ggc atg acc cgc ccc ttg tca act ctg atc agc      720
Leu Ala Leu Ile Lys Gly Met Thr Arg Pro Leu Ser Thr Leu Ile Ser
225                 230                 235                 240

agc agc cag tcc tgt cag tac aca ctg gac gct aag agg aag cat gtg      768
Ser Ser Gln Ser Cys Gln Tyr Thr Leu Asp Ala Lys Arg Lys His Val
                245                 250                 255

gca gaa gcc atc tgc aag gag caa cac ctc ttc ctg cct ttc tcc tac      816
Ala Glu Ala Ile Cys Lys Glu Gln His Leu Phe Leu Pro Phe Ser Tyr
            260                 265                 270
```

```
aag aat aag tat ggg atg gta gca caa gtg aca cag act ttg aaa ctt      864
Lys Asn Lys Tyr Gly Met Val Ala Gln Val Thr Gln Thr Leu Lys Leu
        275                 280                 285

gaa gac aca cca aag atc aac agc cgc ttc ttt ggt gaa ggt act aag      912
Glu Asp Thr Pro Lys Ile Asn Ser Arg Phe Phe Gly Glu Gly Thr Lys
    290                 295                 300

aag atg ggc ctc gca ttt gag agc acc aaa tcc aca tca cct cca aag      960
Lys Met Gly Leu Ala Phe Glu Ser Thr Lys Ser Thr Ser Pro Pro Lys
305                 310                 315                 320

cag gcc gaa gct gtt ttg aag act ctc cag gaa ctg aaa aaa cta acc     1008
Gln Ala Glu Ala Val Leu Lys Thr Leu Gln Glu Leu Lys Lys Leu Thr
                325                 330                 335

atc tct gag caa aat atc cag aga gct aat ctc ttc aat aag ctg gtt     1056
Ile Ser Glu Gln Asn Ile Gln Arg Ala Asn Leu Phe Asn Lys Leu Val
            340                 345                 350

act gag ctg aga ggc ctc agt gat gaa gca gtc aca tct ctc ttg cca     1104
Thr Glu Leu Arg Gly Leu Ser Asp Glu Ala Val Thr Ser Leu Leu Pro
        355                 360                 365

cag ctg att gag gtg tcc agc ccc atc act tta caa gcc ttg gtt cag     1152
Gln Leu Ile Glu Val Ser Ser Pro Ile Thr Leu Gln Ala Leu Val Gln
    370                 375                 380

tgt gga cag cct cag tgc tcc act cac atc ctc cag tgg ctg aaa cgt     1200
Cys Gly Gln Pro Gln Cys Ser Thr His Ile Leu Gln Trp Leu Lys Arg
385                 390                 395                 400

gtg cat gcc aac ccc ctt ctg ata gat gtg gtc acc tac ctg gtg gcc     1248
Val His Ala Asn Pro Leu Leu Ile Asp Val Val Thr Tyr Leu Val Ala
                405                 410                 415

ctg atc ccc gag ccc tca gca cag cag ctg cga gag atc ttc aac atg     1296
Leu Ile Pro Glu Pro Ser Ala Gln Gln Leu Arg Glu Ile Phe Asn Met
            420                 425                 430

gcg agg gat cag cgc agc cga gcc acc ttg tat gcg ctg agc cac gcg     1344
Ala Arg Asp Gln Arg Ser Arg Ala Thr Leu Tyr Ala Leu Ser His Ala
        435                 440                 445

gtc aac aac tat cat aag aca aac cct aca ggg acc cag gag ctg ctg     1392
Val Asn Asn Tyr His Lys Thr Asn Pro Thr Gly Thr Gln Glu Leu Leu
    450                 455                 460

gac att gct aat tac ctg atg gaa cag att caa gat gac tgc act ggg     1440
Asp Ile Ala Asn Tyr Leu Met Glu Gln Ile Gln Asp Asp Cys Thr Gly
465                 470                 475                 480

gat gaa gat tac acc tat ttg att ctg cgg gtc att gga aat atg ggc     1488
Asp Glu Asp Tyr Thr Tyr Leu Ile Leu Arg Val Ile Gly Asn Met Gly
                485                 490                 495

caa acc atg gag cag tta act cca gaa ctc aag tct tca atc ctg aaa     1536
Gln Thr Met Glu Gln Leu Thr Pro Glu Leu Lys Ser Ser Ile Leu Lys
            500                 505                 510

tgt gtc caa agt aca aag cca tca ctg atg atc cag aaa gct gcc atc     1584
Cys Val Gln Ser Thr Lys Pro Ser Leu Met Ile Gln Lys Ala Ala Ile
        515                 520                 525

cag gct ctg cgg aaa atg gag cct aaa gac aag gac cag gag gtt ctt     1632
Gln Ala Leu Arg Lys Met Glu Pro Lys Asp Lys Asp Gln Glu Val Leu
    530                 535                 540

ctt cag act ttc ctt gat gat gct tct ccg gga gat aag cga ctg gct     1680
Leu Gln Thr Phe Leu Asp Asp Ala Ser Pro Gly Asp Lys Arg Leu Ala
545                 550                 555                 560

gcc tat ctt atg ttg atg agg agt cct tca cag gca gat att aac aaa     1728
Ala Tyr Leu Met Leu Met Arg Ser Pro Ser Gln Ala Asp Ile Asn Lys
                565                 570                 575

att gtc caa att cta cca tgg gaa cag aat gag caa gtg aag aac ttt     1776
Ile Val Gln Ile Leu Pro Trp Glu Gln Asn Glu Gln Val Lys Asn Phe
            580                 585                 590
```

```
gtg gct tcc cat att gcc aat atc ttg aac tca gaa gaa ttg gat atc     1824
Val Ala Ser His Ile Ala Asn Ile Leu Asn Ser Glu Glu Leu Asp Ile
        595                 600                 605

caa gat ctg aaa aag tta gtg aaa gaa gct ctg aaa gaa tct caa ctt     1872
Gln Asp Leu Lys Lys Leu Val Lys Glu Ala Leu Lys Glu Ser Gln Leu
    610                 615                 620

cca act gtc atg gac ttc aga aaa ttc tct cgg aac tat caa ctc tac     1920
Pro Thr Val Met Asp Phe Arg Lys Phe Ser Arg Asn Tyr Gln Leu Tyr
625                 630                 635                 640

aaa tct gtt tct ctt cca tca ctt gac cca gcc tca gcc aaa ata gaa     1968
Lys Ser Val Ser Leu Pro Ser Leu Asp Pro Ala Ser Ala Lys Ile Glu
                645                 650                 655

ggg aat ctt ata ttt gat cca aat aac tac ctt cct aaa gaa agc atg     2016
Gly Asn Leu Ile Phe Asp Pro Asn Asn Tyr Leu Pro Lys Glu Ser Met
            660                 665                 670

ctg aaa act acc ctc act gcc ttt gga ttt gct tca gct gac ctc atc     2064
Leu Lys Thr Thr Leu Thr Ala Phe Gly Phe Ala Ser Ala Asp Leu Ile
        675                 680                 685

gag att ggc ttg gaa gga aaa ggc ttt gag cca aca ttg gag gct cct     2112
Glu Ile Gly Leu Glu Gly Lys Gly Phe Glu Pro Thr Leu Glu Ala Pro
    690                 695                 700

ttt ggg aag caa gga ttt ttc cca gac agt gtc aac aaa gct ttg tac     2160
Phe Gly Lys Gln Gly Phe Phe Pro Asp Ser Val Asn Lys Ala Leu Tyr
705                 710                 715                 720

tgg gtt aat ggt caa gtt cct gat ggt gtc tct aag gtc tta gtg gac     2208
Trp Val Asn Gly Gln Val Pro Asp Gly Val Ser Lys Val Leu Val Asp
                725                 730                 735

cac ttt ggc tat acc aaa gat gat aaa cat gag cag gat atg gta aat     2256
His Phe Gly Tyr Thr Lys Asp Asp Lys His Glu Gln Asp Met Val Asn
            740                 745                 750

gga ata atg ctc agt gtt gag aag ctg att aaa gat ttg aaa tcc aaa     2304
Gly Ile Met Leu Ser Val Glu Lys Leu Ile Lys Asp Leu Lys Ser Lys
        755                 760                 765

gaa gtc ccg gaa gcc aga gcc tac ctc cgc atc ttg gga gag gag ctt     2352
Glu Val Pro Glu Ala Arg Ala Tyr Leu Arg Ile Leu Gly Glu Glu Leu
    770                 775                 780

ggt ttt gcc agt ctc cat gac ctc cga ctc ctg gga aag ctg ctt ctg     2400
Gly Phe Ala Ser Leu His Asp Leu Arg Leu Leu Gly Lys Leu Leu Leu
785                 790                 795                 800

atg ggt gcc cgc act ctg cag ggg atc ccc cag atg att gga gag gtc     2448
Met Gly Ala Arg Thr Leu Gln Gly Ile Pro Gln Met Ile Gly Glu Val
                805                 810                 815

atc agg aag ggc tca aag aat gac ttt ttt ctt cac tac atc ttc atg     2496
Ile Arg Lys Gly Ser Lys Asn Asp Phe Phe Leu His Tyr Ile Phe Met
            820                 825                 830

gag aat gcc ttt gaa ctc ccc act gga gct gga tta cag ttg caa ata     2544
Glu Asn Ala Phe Glu Leu Pro Thr Gly Ala Gly Leu Gln Leu Gln Ile
        835                 840                 845

tct tca tct gga gtc att gct ccc gga gcc aag gct gga gta aaa ctg     2592
Ser Ser Ser Gly Val Ile Ala Pro Gly Ala Lys Ala Gly Val Lys Leu
    850                 855                 860

gaa gta gcc aac atg cag gct gaa ctg gtg gca aaa ccc tcc gtg tct     2640
Glu Val Ala Asn Met Gln Ala Glu Leu Val Ala Lys Pro Ser Val Ser
865                 870                 875                 880

gtg gag ttt gtg aca aat atg ggc atc atc att ccg gac ttc gct agg     2688
Val Glu Phe Val Thr Asn Met Gly Ile Ile Ile Pro Asp Phe Ala Arg
                885                 890                 895

agt ggg gtc cag atg aac acc aac ttc ttc cac gag tcg ggt ctg gag     2736
Ser Gly Val Gln Met Asn Thr Asn Phe Phe His Glu Ser Gly Leu Glu
            900                 905                 910
```

```
gct cat gtt gcc cta aaa gct ggg aag ctg aag ttt atc att cct tcc     2784
Ala His Val Ala Leu Lys Ala Gly Lys Leu Lys Phe Ile Ile Pro Ser
        915                 920                 925

cca aag aga cca gtc aag ctg ctc agt gga ggc aac aca tta cat ttg     2832
Pro Lys Arg Pro Val Lys Leu Leu Ser Gly Gly Asn Thr Leu His Leu
    930                 935                 940

gtc tct acc acc aaa acg gag gtc atc cca cct ctc att gag aac agg     2880
Val Ser Thr Thr Lys Thr Glu Val Ile Pro Pro Leu Ile Glu Asn Arg
945                 950                 955                 960

cag tcc tgg tca gtt tgc aag caa gtc ttt cct ggc ctg aat tac tgc     2928
Gln Ser Trp Ser Val Cys Lys Gln Val Phe Pro Gly Leu Asn Tyr Cys
                965                 970                 975

acc tca ggc gct tac tcc aac gcc agc tcc aca gac tcc gcc tcc tac     2976
Thr Ser Gly Ala Tyr Ser Asn Ala Ser Ser Thr Asp Ser Ala Ser Tyr
            980                 985                 990

tat ccg ctg acc ggg gac acc aga tta gag ctg gaa ctg agg cct aca     3024
Tyr Pro Leu Thr Gly Asp Thr Arg Leu Glu Leu Glu Leu Arg Pro  Thr
        995                 1000                1005

gga gag att gag cag tat tct gtc agc gca acc tat gag ctc cag aga     3072
Gly Glu Ile Glu Gln Tyr Ser Val Ser Ala Thr Tyr Glu Leu Gln  Arg
   1010                1015                1020

gag gac aga gcc ttg gtg gat acc ctg aag ttt gta act caa gca gaa     3120
Glu Asp Arg Ala Leu Val Asp Thr Leu Lys Phe Val Thr Gln Ala Glu
1025                1030                1035                1040

ggc gcg aag cag act gag gct acc atg aca ttc aaa tat aat cgg cag     3168
Gly Ala Lys Gln Thr Glu Ala Thr Met Thr Phe Lys Tyr Asn Arg Gln
                1045                1050                1055

agt atg acc ttg tcc agt gaa gtc caa att ccg gat ttt gat gtt gac     3216
Ser Met Thr Leu Ser Ser Glu Val Gln Ile Pro Asp Phe Asp Val Asp
            1060                1065                1070

ctc gga aca atc ctc aga gtt aat gat gaa tct act gag ggc aaa acg     3264
Leu Gly Thr Ile Leu Arg Val Asn Asp Glu Ser Thr Glu Gly Lys Thr
        1075                1080                1085

tct tac aga ctc acc ctg gac att cag aac aag aaa att act gag gtc     3312
Ser Tyr Arg Leu Thr Leu Asp Ile Gln Asn Lys Lys Ile Thr Glu Val
    1090                1095                1100

gcc ctc atg ggc cac cta agt tgt gac aca aag gaa gaa aga aaa atc     3360
Ala Leu Met Gly His Leu Ser Cys Asp Thr Lys Glu Glu Arg Lys Ile
1105                1110                1115                1120

aag ggt gtt att tcc ata ccc cgt ttg caa gca gaa gcc aga agt gag     3408
Lys Gly Val Ile Ser Ile Pro Arg Leu Gln Ala Glu Ala Arg Ser Glu
                1125                1130                1135

atc ctc gcc cac tgg tcg cct gcc aaa ctg ctt ctc caa atg gac tca     3456
Ile Leu Ala His Trp Ser Pro Ala Lys Leu Leu Leu Gln Met Asp Ser
            1140                1145                1150

tct gct aca gct tat ggc tcc aca gtt tcc aag agg gtg gca tgg cat     3504
Ser Ala Thr Ala Tyr Gly Ser Thr Val Ser Lys Arg Val Ala Trp His
        1155                1160                1165

tat gat gaa gag aag att gaa ttt gaa tgg aac aca ggc acc aat gta     3552
Tyr Asp Glu Glu Lys Ile Glu Phe Glu Trp Asn Thr Gly Thr Asn Val
    1170                1175                1180

gat acc aaa aaa atg act tcc aat ttc cct gtg gat ctc tcc gat tat     3600
Asp Thr Lys Lys Met Thr Ser Asn Phe Pro Val Asp Leu Ser Asp Tyr
1185                1190                1195                1200

cct aag agc ttg cat atg tat gct aat aga ctc ctg gat cac aga gtc     3648
Pro Lys Ser Leu His Met Tyr Ala Asn Arg Leu Leu Asp His Arg Val
                1205                1210                1215

cct caa aca gac atg act ttc cgg cac gtg ggt tcc aaa tta ata gtt     3696
Pro Gln Thr Asp Met Thr Phe Arg His Val Gly Ser Lys Leu Ile Val
            1220                1225                1230
```

```
gca atg agc tca tgg ctt cag aag gca tct ggg agt ctt cct tat acc     3744
Ala Met Ser Ser Trp Leu Gln Lys Ala Ser Gly Ser Leu Pro Tyr Thr
        1235                1240                1245

cag act ttg caa gac cac ctc aat agc ctg aag gag ttc aac ctc cag     3792
Gln Thr Leu Gln Asp His Leu Asn Ser Leu Lys Glu Phe Asn Leu Gln
    1250                1255                1260

aac atg gga ttg cca gac tcc cac atc cca gaa aac ctc ttc tta aaa     3840
Asn Met Gly Leu Pro Asp Ser His Ile Pro Glu Asn Leu Phe Leu Lys
1265                1270                1275                1280

agc gat ggc cgc gtc aaa tat acc ttg aac aag aac agt ttg aaa att     3888
Ser Asp Gly Arg Val Lys Tyr Thr Leu Asn Lys Asn Ser Leu Lys Ile
                1285                1290                1295

gag att cct ttg cct ttt ggt ggc aaa tcc tcc aga gat cta aag atg     3936
Glu Ile Pro Leu Pro Phe Gly Gly Lys Ser Ser Arg Asp Leu Lys Met
            1300                1305                1310

tta gag act gtt agg aca cca gcc ctc cac ttc aag tct gtg gga ttc     3984
Leu Glu Thr Val Arg Thr Pro Ala Leu His Phe Lys Ser Val Gly Phe
        1315                1320                1325

cat ctg cca tct cga gag ttc caa gtc cct act ttt acc att ccc aag     4032
His Leu Pro Ser Arg Glu Phe Gln Val Pro Thr Phe Thr Ile Pro Lys
    1330                1335                1340

ttg tat caa ctg caa gtg cct ctc ctg ggt gtt cta gac ctc tcc acg     4080
Leu Tyr Gln Leu Gln Val Pro Leu Leu Gly Val Leu Asp Leu Ser Thr
1345                1350                1355                1360

aat gtc tac agc aac ttg tac aac tgg tcc gcc tcc tac agt ggt ggc     4128
Asn Val Tyr Ser Asn Leu Tyr Asn Trp Ser Ala Ser Tyr Ser Gly Gly
                1365                1370                1375

aac acc agc aca gac cat ttc agc ctt cgg gct cgt tac cac atg aag     4176
Asn Thr Ser Thr Asp His Phe Ser Leu Arg Ala Arg Tyr His Met Lys
            1380                1385                1390

gct gac tct gtg gtt gac ctg ctt tcc tac aat gtg caa gga tct gga     4224
Ala Asp Ser Val Val Asp Leu Leu Ser Tyr Asn Val Gln Gly Ser Gly
        1395                1400                1405

gaa aca aca tat gac cac aag aat acg ttc aca cta tca tgt gat ggg     4272
Glu Thr Thr Tyr Asp His Lys Asn Thr Phe Thr Leu Ser Cys Asp Gly
    1410                1415                1420

tct cta cgc cac aaa ttt cta gat tcg aat atc aaa ttc agt cat gta     4320
Ser Leu Arg His Lys Phe Leu Asp Ser Asn Ile Lys Phe Ser His Val
1425                1430                1435                1440

gaa aaa ctt gga aac aac cca gtc tca aaa ggt tta cta ata ttc gat     4368
Glu Lys Leu Gly Asn Asn Pro Val Ser Lys Gly Leu Leu Ile Phe Asp
                1445                1450                1455

gca tct agt tcc tgg gga cca cag atg tct gct tca gtt cat ttg gac     4416
Ala Ser Ser Ser Trp Gly Pro Gln Met Ser Ala Ser Val His Leu Asp
            1460                1465                1470

tcc aaa aag aaa cag cat ttg ttt gtc aaa gaa gtc aag att gat ggg     4464
Ser Lys Lys Lys Gln His Leu Phe Val Lys Glu Val Lys Ile Asp Gly
        1475                1480                1485

cag ttc aga gtc tct tcg ttc tat gct aaa ggc aca tat ggc ctg tct     4512
Gln Phe Arg Val Ser Ser Phe Tyr Ala Lys Gly Thr Tyr Gly Leu Ser
    1490                1495                1500

tgt cag agg gat cct aac act ggc cgg ctc aat gga gag tcc aac ctg     4560
Cys Gln Arg Asp Pro Asn Thr Gly Arg Leu Asn Gly Glu Ser Asn Leu
1505                1510                1515                1520

agg ttt aac tcc tcc tac ctc caa ggc acc aac cag ata aca gga aga     4608
Arg Phe Asn Ser Ser Tyr Leu Gln Gly Thr Asn Gln Ile Thr Gly Arg
                1525                1530                1535

tat gaa gat gga acc ctc tcc ctc acc tcc acc tct gat ctg caa agt     4656
Tyr Glu Asp Gly Thr Leu Ser Leu Thr Ser Thr Ser Asp Leu Gln Ser
            1540                1545                1550
```

```
ggc atc att aaa aat act gct tcc cta aag tat gag aac tac gag ctg     4704
Gly Ile Ile Lys Asn Thr Ala Ser Leu Lys Tyr Glu Asn Tyr Glu Leu
        1555                1560                1565

act tta aaa tct gac acc aat ggg aag tat aag aac ttt gcc act tct     4752
Thr Leu Lys Ser Asp Thr Asn Gly Lys Tyr Lys Asn Phe Ala Thr Ser
    1570                1575                1580

aac aag atg gat atg acc ttc tct aag caa aat gca ctg ctg cgt tct     4800
Asn Lys Met Asp Met Thr Phe Ser Lys Gln Asn Ala Leu Leu Arg Ser
1585                1590                1595                1600

gaa tat cag gct gat tac gag tca ttg agg ttc ttc agc ctg ctt tct     4848
Glu Tyr Gln Ala Asp Tyr Glu Ser Leu Arg Phe Phe Ser Leu Leu Ser
                1605                1610                1615

gga tca cta aat tcc cat ggt ctt gag tta aat gct gac atc tta ggc     4896
Gly Ser Leu Asn Ser His Gly Leu Glu Leu Asn Ala Asp Ile Leu Gly
            1620                1625                1630

act gac aaa att aat agt ggt gct cac aag gcg aca cta agg att ggc     4944
Thr Asp Lys Ile Asn Ser Gly Ala His Lys Ala Thr Leu Arg Ile Gly
        1635                1640                1645

caa gat gga ata tct acc agt gca acg acc aac ttg aag tgt agt ctc     4992
Gln Asp Gly Ile Ser Thr Ser Ala Thr Thr Asn Leu Lys Cys Ser Leu
    1650                1655                1660

ctg gtg ctg gag aat gag ctg aat gca gag ctt ggc ctc tct ggg gca     5040
Leu Val Leu Glu Asn Glu Leu Asn Ala Glu Leu Gly Leu Ser Gly Ala
1665                1670                1675                1680

tct atg aaa tta aca aca aat ggc cgc ttc agg gaa cac aat gca aaa     5088
Ser Met Lys Leu Thr Thr Asn Gly Arg Phe Arg Glu His Asn Ala Lys
                1685                1690                1695

ttc agt ctg gat ggg aaa gcc gcc ctc aca gag cta tca ctg gga agt     5136
Phe Ser Leu Asp Gly Lys Ala Ala Leu Thr Glu Leu Ser Leu Gly Ser
            1700                1705                1710

gct tat cag gcc atg att ctg ggt gtc gac agc aaa aac att ttc aac     5184
Ala Tyr Gln Ala Met Ile Leu Gly Val Asp Ser Lys Asn Ile Phe Asn
        1715                1720                1725

ttc aag gtc agt caa gaa gga ctt aag ctc tca aat gac atg atg ggc     5232
Phe Lys Val Ser Gln Glu Gly Leu Lys Leu Ser Asn Asp Met Met Gly
    1730                1735                1740

tca tat gct gaa atg aaa ttt gac cac aca aac agt ctg aac att gca     5280
Ser Tyr Ala Glu Met Lys Phe Asp His Thr Asn Ser Leu Asn Ile Ala
1745                1750                1755                1760

ggc tta tca ctg gac ttc tct tca aaa ctt gac aac att tac agc tct     5328
Gly Leu Ser Leu Asp Phe Ser Ser Lys Leu Asp Asn Ile Tyr Ser Ser
                1765                1770                1775

gac aag ttt tat aag caa act gtt aat tta cag cta cag ccc tat tct     5376
Asp Lys Phe Tyr Lys Gln Thr Val Asn Leu Gln Leu Gln Pro Tyr Ser
            1780                1785                1790

ctg gta act act tta aac agt gac ctg aaa tac aat gct ctg gat ctc     5424
Leu Val Thr Thr Leu Asn Ser Asp Leu Lys Tyr Asn Ala Leu Asp Leu
        1795                1800                1805

acc aac aat ggg aaa cta cgg cta gaa ccc ctg aag ctg cat gtg gct     5472
Thr Asn Asn Gly Lys Leu Arg Leu Glu Pro Leu Lys Leu His Val Ala
    1810                1815                1820

ggt aac cta aaa gga gcc tac caa aat aat gaa ata aaa cac atc tat     5520
Gly Asn Leu Lys Gly Ala Tyr Gln Asn Asn Glu Ile Lys His Ile Tyr
1825                1830                1835                1840

gcc atc tct tct gct gcc tta tca gca agc tat aaa gca gac act gtt     5568
Ala Ile Ser Ser Ala Ala Leu Ser Ala Ser Tyr Lys Ala Asp Thr Val
                1845                1850                1855

gct aag gtt cag ggt gtg gag ttt agc cat ggg ctc aac aca gac atc     5616
Ala Lys Val Gln Gly Val Glu Phe Ser His Gly Leu Asn Thr Asp Ile
            1860                1865                1870
```

```
gct ggg ctg gct tca gcc att gac atg agc aca aac tat aat tca gac     5664
Ala Gly Leu Ala Ser Ala Ile Asp Met Ser Thr Asn Tyr Asn Ser Asp
        1875                1880                1885

tca ctg cat ttc agc aat gtc ttc cgt tct gta atg gcc ccg ttt acc     5712
Ser Leu His Phe Ser Asn Val Phe Arg Ser Val Met Ala Pro Phe Thr
    1890                1895                1900

atg acc atc gat gca cat aca aat ggc aat ggg aaa ctc gct ctc tgg     5760
Met Thr Ile Asp Ala His Thr Asn Gly Asn Gly Lys Leu Ala Leu Trp
1905                1910                1915                1920

gga gaa cat act ggg cag ctg tat agc aaa ttc ctg ttg aaa gca gaa     5808
Gly Glu His Thr Gly Gln Leu Tyr Ser Lys Phe Leu Leu Lys Ala Glu
                1925                1930                1935

cct ctg gca ttt act ttc tct cat gat tac aaa ggc tcc aca agt cat     5856
Pro Leu Ala Phe Thr Phe Ser His Asp Tyr Lys Gly Ser Thr Ser His
            1940                1945                1950

cat ctc gtg tct agg aaa agc atc agt gca gct ctt gaa cac aaa gtc     5904
His Leu Val Ser Arg Lys Ser Ile Ser Ala Ala Leu Glu His Lys Val
        1955                1960                1965

agt gcc ctg ctt act cca gct gag cag aca ggc acc tgg aaa ctc aag     5952
Ser Ala Leu Leu Thr Pro Ala Glu Gln Thr Gly Thr Trp Lys Leu Lys
    1970                1975                1980

acc caa ttt aac aac aat gaa tac agc cag gac ttg gat gct tac aac     6000
Thr Gln Phe Asn Asn Asn Glu Tyr Ser Gln Asp Leu Asp Ala Tyr Asn
1985                1990                1995                2000

act aaa gat aaa att ggc gtg gag ctt act gga cga act ctg gct gac     6048
Thr Lys Asp Lys Ile Gly Val Glu Leu Thr Gly Arg Thr Leu Ala Asp
                2005                2010                2015

cta act cta cta gac tcc cca att aaa gtg cca ctt tta ctc agt gag     6096
Leu Thr Leu Leu Asp Ser Pro Ile Lys Val Pro Leu Leu Leu Ser Glu
            2020                2025                2030

ccc atc aat atc aat gat gct tta gag atg aga gat gcc gtt gag aag     6144
Pro Ile Asn Ile Asn Asp Ala Leu Glu Met Arg Asp Ala Val Glu Lys
        2035                2040                2045

ccc caa gaa ttt aca att gtt gct ttt gta aag tat gat aaa aac caa     6192
Pro Gln Glu Phe Thr Ile Val Ala Phe Val Lys Tyr Asp Lys Asn Gln
    2050                2055                2060

gat gtt cac tcc att aac ctc cca ttt ttt gag acc ttg caa gaa tat     6240
Asp Val His Ser Ile Asn Leu Pro Phe Phe Glu Thr Leu Gln Glu Tyr
2065                2070                2075                2080

ttt gag agg aat cga caa acc att ata gtt gta ctg gaa aac gta cag     6288
Phe Glu Arg Asn Arg Gln Thr Ile Ile Val Val Leu Glu Asn Val Gln
                2085                2090                2095

aga aac ctg aag cac atc aat att gat caa ttt gta aga aaa tac aga     6336
Arg Asn Leu Lys His Ile Asn Ile Asp Gln Phe Val Arg Lys Tyr Arg
            2100                2105                2110

gca gcc ctg gga aaa ctc cca cag caa gct aat gat tat ctg aat tca     6384
Ala Ala Leu Gly Lys Leu Pro Gln Gln Ala Asn Asp Tyr Leu Asn Ser
        2115                2120                2125

ttc aat tgg gag aga caa gtt tca cat gcc aag gag aaa ctg act gct     6432
Phe Asn Trp Glu Arg Gln Val Ser His Ala Lys Glu Lys Leu Thr Ala
    2130                2135                2140

ctc aca aaa aag tat aga att aca gaa aat gat ata caa att gca tta     6480
Leu Thr Lys Lys Tyr Arg Ile Thr Glu Asn Asp Ile Gln Ile Ala Leu
2145                2150                2155                2160

gat gat gcc aaa atc aac ttt aat gaa aaa cta tct caa ctg cag aca     6528
Asp Asp Ala Lys Ile Asn Phe Asn Glu Lys Leu Ser Gln Leu Gln Thr
                2165                2170                2175

tat atg ata caa ttt gat cag tat att aaa gat agt tat gat tta cat     6576
Tyr Met Ile Gln Phe Asp Gln Tyr Ile Lys Asp Ser Tyr Asp Leu His
            2180                2185                2190
```

```
gat ttg aaa ata gct att gct aat att att gat gaa atc att gaa aaa     6624
Asp Leu Lys Ile Ala Ile Ala Asn Ile Ile Asp Glu Ile Ile Glu Lys
        2195                2200                2205

tta aaa agt ctt gat gag cac tat cat acc cgt gta aat tta gta aaa     6672
Leu Lys Ser Leu Asp Glu His Tyr His Thr Arg Val Asn Leu Val Lys
    2210                2215                2220

aca atc cat gat cta cat ttg ttt att gaa aat att gat ttt aac aaa     6720
Thr Ile His Asp Leu His Leu Phe Ile Glu Asn Ile Asp Phe Asn Lys
2225                2230                2235                2240

agt gga agt agt act gca tcc tgg att caa aat gtg gat act aag tac     6768
Ser Gly Ser Ser Thr Ala Ser Trp Ile Gln Asn Val Asp Thr Lys Tyr
                2245                2250                2255

caa atc aga atc cag ata caa gaa aaa ctg cag cag ctt aag aga cac     6816
Gln Ile Arg Ile Gln Ile Gln Glu Lys Leu Gln Gln Leu Lys Arg His
            2260                2265                2270

ata cag aat ata gac atc cag cac cta gct gga aag tta aaa caa cac     6864
Ile Gln Asn Ile Asp Ile Gln His Leu Ala Gly Lys Leu Lys Gln His
        2275                2280                2285

att gag gct att gat gtt aga gtg ctt tta gat caa ttg gga act aca     6912
Ile Glu Ala Ile Asp Val Arg Val Leu Leu Asp Gln Leu Gly Thr Thr
    2290                2295                2300

att tca ttt gaa aga ata aat gat gtt ctt gag cat gtc aaa cac ttt     6960
Ile Ser Phe Glu Arg Ile Asn Asp Val Leu Glu His Val Lys His Phe
2305                2310                2315                2320

gtt ata aat ctt att ggg gat ttt gaa gta gct gag aaa atc aat gcc     7008
Val Ile Asn Leu Ile Gly Asp Phe Glu Val Ala Glu Lys Ile Asn Ala
                2325                2330                2335

ttc aga gcc aaa gtc cat gag tta atc gag agg tat gaa gta gac caa     7056
Phe Arg Ala Lys Val His Glu Leu Ile Glu Arg Tyr Glu Val Asp Gln
            2340                2345                2350

caa atc cag gtt tta atg gat aaa tta gta gag ttg gcc cac caa tac     7104
Gln Ile Gln Val Leu Met Asp Lys Leu Val Glu Leu Ala His Gln Tyr
        2355                2360                2365

aag ttg aag gag act att cag aag cta agc aat gtc cta caa caa gtt     7152
Lys Leu Lys Glu Thr Ile Gln Lys Leu Ser Asn Val Leu Gln Gln Val
    2370                2375                2380

aag ata aaa gat tac ttt gag aaa ttg gtt gga ttt att gat gat gct     7200
Lys Ile Lys Asp Tyr Phe Glu Lys Leu Val Gly Phe Ile Asp Asp Ala
2385                2390                2395                2400

gtc aag aag ctt aat gaa tta tct ttt aaa aca ttc att gaa gat gtt     7248
Val Lys Lys Leu Asn Glu Leu Ser Phe Lys Thr Phe Ile Glu Asp Val
                2405                2410                2415

aac aaa ttc ctt gac atg ttg ata aag aaa tta aag tca ttt gat tac     7296
Asn Lys Phe Leu Asp Met Leu Ile Lys Lys Leu Lys Ser Phe Asp Tyr
            2420                2425                2430

cac cag ttt gta gat gaa acc aat gac aaa atc cgt gag gtg act cag     7344
His Gln Phe Val Asp Glu Thr Asn Asp Lys Ile Arg Glu Val Thr Gln
        2435                2440                2445

aga ctc aat ggt gaa att cag gct ctg gaa cta cca caa aaa gct gaa     7392
Arg Leu Asn Gly Glu Ile Gln Ala Leu Glu Leu Pro Gln Lys Ala Glu
    2450                2455                2460

gca tta aaa ctg ttt tta gag gaa acc aag gcc aca gtt gca gtg tat     7440
Ala Leu Lys Leu Phe Leu Glu Glu Thr Lys Ala Thr Val Ala Val Tyr
2465                2470                2475                2480

ctg gaa agc cta cag gac acc aaa ata acc tta atc atc aat tgg tta     7488
Leu Glu Ser Leu Gln Asp Thr Lys Ile Thr Leu Ile Ile Asn Trp Leu
                2485                2490                2495

cag gag gct tta agt tca gca tct ttg gct cac atg aag gcc aaa ttc     7536
Gln Glu Ala Leu Ser Ser Ala Ser Leu Ala His Met Lys Ala Lys Phe
            2500                2505                2510
```

```
cga gag act cta gaa gat aca cga gac cga atg tat caa atg gac att     7584
Arg Glu Thr Leu Glu Asp Thr Arg Asp Arg Met Tyr Gln Met Asp Ile
        2515                2520                2525

cag cag gaa ctt caa cga tac ctg tct ctg gta ggc cag gtt tat agc     7632
Gln Gln Glu Leu Gln Arg Tyr Leu Ser Leu Val Gly Gln Val Tyr Ser
    2530                2535                2540

aca ctt gtc acc tac att tct gat tgg tgg act ctt gct gct aag aac     7680
Thr Leu Val Thr Tyr Ile Ser Asp Trp Trp Thr Leu Ala Ala Lys Asn
2545                2550                2555                2560

ctt act gac ttt gca gag caa tat tct atc caa gat tgg gct aaa cgt     7728
Leu Thr Asp Phe Ala Glu Gln Tyr Ser Ile Gln Asp Trp Ala Lys Arg
                2565                2570                2575

atg aaa gca ttg gta gag caa ggg ttc act gtt cct gaa atc aag acc     7776
Met Lys Ala Leu Val Glu Gln Gly Phe Thr Val Pro Glu Ile Lys Thr
            2580                2585                2590

atc ctt ggg acc atg cct gcc ttt gaa gtc agt ctt cag gct ctt cag     7824
Ile Leu Gly Thr Met Pro Ala Phe Glu Val Ser Leu Gln Ala Leu Gln
        2595                2600                2605

aaa gct acc ttc cag aca cct gat ttt ata gtc ccc cta aca gat ttg     7872
Lys Ala Thr Phe Gln Thr Pro Asp Phe Ile Val Pro Leu Thr Asp Leu
    2610                2615                2620

agg att cca tca gtt cag ata aac ttc aaa gac tta aaa aat ata aaa     7920
Arg Ile Pro Ser Val Gln Ile Asn Phe Lys Asp Leu Lys Asn Ile Lys
2625                2630                2635                2640

atc cca tcc agg ttt tcc aca cca gaa ttt acc atc ctt aac acc ttc     7968
Ile Pro Ser Arg Phe Ser Thr Pro Glu Phe Thr Ile Leu Asn Thr Phe
                2645                2650                2655

cac att cct tcc ttt aca att gac ttt gta gaa atg aaa gta aag atc     8016
His Ile Pro Ser Phe Thr Ile Asp Phe Val Glu Met Lys Val Lys Ile
            2660                2665                2670

atc aga acc att gac cag atg ctg aac agt gag ctg cag tgg ccc gtt     8064
Ile Arg Thr Ile Asp Gln Met Leu Asn Ser Glu Leu Gln Trp Pro Val
        2675                2680                2685

cca gat ata tat ctc agg gat ctg aag gtg gag gac att cct cta gcg     8112
Pro Asp Ile Tyr Leu Arg Asp Leu Lys Val Glu Asp Ile Pro Leu Ala
    2690                2695                2700

aga atc acc ctg cca gac ttc cgt tta cca gaa atc gca att cca gaa     8160
Arg Ile Thr Leu Pro Asp Phe Arg Leu Pro Glu Ile Ala Ile Pro Glu
2705                2710                2715                2720

ttc ata atc cca act ctc aac ctt aat gat ttt caa gtt cct gac ctt     8208
Phe Ile Ile Pro Thr Leu Asn Leu Asn Asp Phe Gln Val Pro Asp Leu
                2725                2730                2735

cac ata cca gaa ttc cag ctt ccc cac atc tca cac aca att gaa gta     8256
His Ile Pro Glu Phe Gln Leu Pro His Ile Ser His Thr Ile Glu Val
            2740                2745                2750

cct act ttt ggc aag cta tac agt att ctg aaa atc caa tct cct ctt     8304
Pro Thr Phe Gly Lys Leu Tyr Ser Ile Leu Lys Ile Gln Ser Pro Leu
        2755                2760                2765

ttc aca tta gat gca aat gct gac ata ggg aat gga acc acc tca gca     8352
Phe Thr Leu Asp Ala Asn Ala Asp Ile Gly Asn Gly Thr Thr Ser Ala
    2770                2775                2780

aac gaa gca ggt atc gca gct tcc atc act gcc aaa gga gag tcc aaa     8400
Asn Glu Ala Gly Ile Ala Ala Ser Ile Thr Ala Lys Gly Glu Ser Lys
2785                2790                2795                2800

tta gaa gtt ctc aat ttt gat ttt caa gca aat gca caa ctc tca aac     8448
Leu Glu Val Leu Asn Phe Asp Phe Gln Ala Asn Ala Gln Leu Ser Asn
                2805                2810                2815

cct aag att aat ccg ctg gct ctg aag gag tca gtg aag ttc tcc agc     8496
Pro Lys Ile Asn Pro Leu Ala Leu Lys Glu Ser Val Lys Phe Ser Ser
            2820                2825                2830
```

```
aag tac ctg aga acg gag cat ggg agt gaa atg ctg ttt ttt gga aat     8544
Lys Tyr Leu Arg Thr Glu His Gly Ser Glu Met Leu Phe Phe Gly Asn
        2835                2840                2845

gct att gag gga aaa tca aac aca gtg gca agt tta cac aca gaa aaa     8592
Ala Ile Glu Gly Lys Ser Asn Thr Val Ala Ser Leu His Thr Glu Lys
    2850                2855                2860

aat aca ctg gag ctt agt aat gga gtg att gtc aag ata aac aat cag     8640
Asn Thr Leu Glu Leu Ser Asn Gly Val Ile Val Lys Ile Asn Asn Gln
2865                2870                2875                2880

ctt acc ctg gat agc aac act aaa tac ttc cac aaa ttg aac atc ccc     8688
Leu Thr Leu Asp Ser Asn Thr Lys Tyr Phe His Lys Leu Asn Ile Pro
                2885                2890                2895

aaa ctg gac ttc tct agt cag gct gac ctg cgc aac gag atc aag aca     8736
Lys Leu Asp Phe Ser Ser Gln Ala Asp Leu Arg Asn Glu Ile Lys Thr
            2900                2905                2910

ctg ttg aaa gct ggc cac ata gca tgg act tct tct gga aaa ggg tca     8784
Leu Leu Lys Ala Gly His Ile Ala Trp Thr Ser Ser Gly Lys Gly Ser
        2915                2920                2925

tgg aaa tgg gcc tcg ccc aga ttc tca gat gag gga aca cat gaa tca     8832
Trp Lys Trp Ala Ser Pro Arg Phe Ser Asp Glu Gly Thr His Glu Ser
    2930                2935                2940

caa att agt ttc acc ata gaa gga ccc ctc act tcc ttt gga ctg tcc     8880
Gln Ile Ser Phe Thr Ile Glu Gly Pro Leu Thr Ser Phe Gly Leu Ser
2945                2950                2955                2960

aat aag atc aat agc aaa cac cta aga gta aac caa aac ttg gtt tat     8928
Asn Lys Ile Asn Ser Lys His Leu Arg Val Asn Gln Asn Leu Val Tyr
                2965                2970                2975

gaa tct ggc tcc ctc aac ttt tct aaa ctt gaa att caa tca caa gtc     8976
Glu Ser Gly Ser Leu Asn Phe Ser Lys Leu Glu Ile Gln Ser Gln Val
            2980                2985                2990

gat tcc cag cat gtg ggc cac agt gtt cta act gct aaa ggc atg gca     9024
Asp Ser Gln His Val Gly His Ser Val Leu Thr Ala Lys Gly Met Ala
        2995                3000                3005

ctg ttt gga gaa ggg aag gca gag ttt act ggg agg cat gat gct cat     9072
Leu Phe Gly Glu Gly Lys Ala Glu Phe Thr Gly Arg His Asp Ala His
    3010                3015                3020

tta aat gga aag gtt att gga act ttg aaa aat tct ctt ttc ttt tca     9120
Leu Asn Gly Lys Val Ile Gly Thr Leu Lys Asn Ser Leu Phe Phe Ser
3025                3030                3035                3040

gcc cag cca ttt gag atc acg gca tcc aca aac aat gaa ggg aat ttg     9168
Ala Gln Pro Phe Glu Ile Thr Ala Ser Thr Asn Asn Glu Gly Asn Leu
                3045                3050                3055

aaa gtt cgt ttt cca tta agg tta aca ggg aag ata gac ttc ctg aat     9216
Lys Val Arg Phe Pro Leu Arg Leu Thr Gly Lys Ile Asp Phe Leu Asn
            3060                3065                3070

aac tat gca ctg ttt ctg agt ccc agt gcc cag caa gca agt tgg caa     9264
Asn Tyr Ala Leu Phe Leu Ser Pro Ser Ala Gln Gln Ala Ser Trp Gln
        3075                3080                3085

gta agt gct agg ttc aat cag tat aag tac aac caa aat ttc tct gct     9312
Val Ser Ala Arg Phe Asn Gln Tyr Lys Tyr Asn Gln Asn Phe Ser Ala
    3090                3095                3100

gga aac aac gag aac att atg gag gcc cat gta gga ata aat gga gaa     9360
Gly Asn Asn Glu Asn Ile Met Glu Ala His Val Gly Ile Asn Gly Glu
3105                3110                3115                3120

gca aat ctg gat ttc tta aac att cct tta aca att cct gaa atg cgt     9408
Ala Asn Leu Asp Phe Leu Asn Ile Pro Leu Thr Ile Pro Glu Met Arg
                3125                3130                3135

cta cct tac aca ata atc aca act cct cca ctg aaa gat ttc tct cta     9456
Leu Pro Tyr Thr Ile Ile Thr Thr Pro Pro Leu Lys Asp Phe Ser Leu
            3140                3145                3150
```

```
tgg gaa aaa aca ggc ttg aag gaa ttc ttg aaa acg aca aag caa tca      9504
Trp Glu Lys Thr Gly Leu Lys Glu Phe Leu Lys Thr Thr Lys Gln Ser
        3155                3160                3165

ttt gat tta agt gta aaa gct cag tat aag aaa aac aaa cac agg cat      9552
Phe Asp Leu Ser Val Lys Ala Gln Tyr Lys Lys Asn Lys His Arg His
    3170                3175                3180

tcc atc aca aat cct ttg gct gtg ctt tgt gag ttt atc agt cag agc      9600
Ser Ile Thr Asn Pro Leu Ala Val Leu Cys Glu Phe Ile Ser Gln Ser
3185                3190                3195                3200

atc aaa tcc ttt gac agg cat ttt gaa aaa aac aga aac aat gca tta      9648
Ile Lys Ser Phe Asp Arg His Phe Glu Lys Asn Arg Asn Asn Ala Leu
                3205                3210                3215

gat ttt gtc acc aaa tcc tat aat gaa aca aaa att aag ttt gat aag      9696
Asp Phe Val Thr Lys Ser Tyr Asn Glu Thr Lys Ile Lys Phe Asp Lys
            3220                3225                3230

tac aaa gct gaa aaa tct cac gac gag ctc ccc agg acc ttt caa att      9744
Tyr Lys Ala Glu Lys Ser His Asp Glu Leu Pro Arg Thr Phe Gln Ile
        3235                3240                3245

cct gga tac act gtt cca gtt gtc aat gtt gaa gtg tct cca ttc acc      9792
Pro Gly Tyr Thr Val Pro Val Val Asn Val Glu Val Ser Pro Phe Thr
    3250                3255                3260

ata gag atg tcg gca ttc ggc tat gtg ttc cca aaa gca gtc agc atg      9840
Ile Glu Met Ser Ala Phe Gly Tyr Val Phe Pro Lys Ala Val Ser Met
3265                3270                3275                3280

cct agt ttc tcc atc ata ggt tct gac gtc cgt gtg cct tca tac aca      9888
Pro Ser Phe Ser Ile Ile Gly Ser Asp Val Arg Val Pro Ser Tyr Thr
                3285                3290                3295

tta atc ctg cca tca tta gag ctg cca gtc ctt cat gtc cct aga aat      9936
Leu Ile Leu Pro Ser Leu Glu Leu Pro Val Leu His Val Pro Arg Asn
            3300                3305                3310

ctc aag ctt tct ctt cca gat ttc aag gaa ttg tgt acc ata agc cat      9984
Leu Lys Leu Ser Leu Pro Asp Phe Lys Glu Leu Cys Thr Ile Ser His
        3315                3320                3325

att ttt att cct gcc atg ggc aat att acc tat gat ttc tcc ttt aaa     10032
Ile Phe Ile Pro Ala Met Gly Asn Ile Thr Tyr Asp Phe Ser Phe Lys
    3330                3335                3340

tca agt gtc atc aca ctg aat acc aat gct gaa ctt ttt aac cag tca     10080
Ser Ser Val Ile Thr Leu Asn Thr Asn Ala Glu Leu Phe Asn Gln Ser
3345                3350                3355                3360

gat att gtt gct cat ctc ctt tct tca tct tca tct gtc att gat gca     10128
Asp Ile Val Ala His Leu Leu Ser Ser Ser Ser Ser Val Ile Asp Ala
                3365                3370                3375

ctg cag tac aaa tta gag ggc acc aca aga ttg aca aga aaa agg gga     10176
Leu Gln Tyr Lys Leu Glu Gly Thr Thr Arg Leu Thr Arg Lys Arg Gly
            3380                3385                3390

ttg aag tta gcc aca gct ctg tct ctg agc aac aaa ttt gtg gag ggt     10224
Leu Lys Leu Ala Thr Ala Leu Ser Leu Ser Asn Lys Phe Val Glu Gly
        3395                3400                3405

agt cat aac agt act gtg agc tta acc acg aaa aat atg gaa gtg tca     10272
Ser His Asn Ser Thr Val Ser Leu Thr Thr Lys Asn Met Glu Val Ser
    3410                3415                3420

gtg gca aaa acc aca aaa ccg gaa att cca att ttg aga atg aat ttc     10320
Val Ala Lys Thr Thr Lys Pro Glu Ile Pro Ile Leu Arg Met Asn Phe
3425                3430                3435                3440

aag caa gaa ctt aat gga aat acc aag tca aaa cct act gtc tct tcc     10368
Lys Gln Glu Leu Asn Gly Asn Thr Lys Ser Lys Pro Thr Val Ser Ser
                3445                3450                3455

tcc atg gaa ttt aag tat gat ttc aat tct tca atg ctg tac tct acc     10416
Ser Met Glu Phe Lys Tyr Asp Phe Asn Ser Ser Met Leu Tyr Ser Thr
            3460                3465                3470
```

```
gct aaa gga gca gtt gac cac aag ctt agc ttg gaa agc ctc acc tct    10464
Ala Lys Gly Ala Val Asp His Lys Leu Ser Leu Glu Ser Leu Thr Ser
        3475                3480                3485

tac ttt tcc att gag tca tct acc aaa gga gat gtc aag ggt tcg gtt    10512
Tyr Phe Ser Ile Glu Ser Ser Thr Lys Gly Asp Val Lys Gly Ser Val
    3490                3495                3500

ctt tct cgg gaa tat tca gga act att gct agt gag gcc aac act tac    10560
Leu Ser Arg Glu Tyr Ser Gly Thr Ile Ala Ser Glu Ala Asn Thr Tyr
3505                3510                3515                3520

ttg aat tcc aag agc aca cgg tct tca gtg aag ctg cag ggc act tcc    10608
Leu Asn Ser Lys Ser Thr Arg Ser Ser Val Lys Leu Gln Gly Thr Ser
                3525                3530                3535

aaa att gat gat atc tgg aac ctt gaa gta aaa gaa aat ttt gct gga    10656
Lys Ile Asp Asp Ile Trp Asn Leu Glu Val Lys Glu Asn Phe Ala Gly
            3540                3545                3550

gaa gcc aca ctc caa cgc ata tat tcc ctc tgg gag cac agt acg aaa    10704
Glu Ala Thr Leu Gln Arg Ile Tyr Ser Leu Trp Glu His Ser Thr Lys
        3555                3560                3565

aac cac tta cag cta gag ggc ctc ttt ttc acc aac gga gaa cat aca    10752
Asn His Leu Gln Leu Glu Gly Leu Phe Phe Thr Asn Gly Glu His Thr
    3570                3575                3580

agc aaa gcc acc ctg gaa ctc tct cca tgg caa atg tca gct ctt gtt    10800
Ser Lys Ala Thr Leu Glu Leu Ser Pro Trp Gln Met Ser Ala Leu Val
3585                3590                3595                3600

cag gtc cat gca agt cag ccc agt tcc ttc cat gat ttc cct gac ctt    10848
Gln Val His Ala Ser Gln Pro Ser Ser Phe His Asp Phe Pro Asp Leu
                3605                3610                3615

ggc cag gaa gtg gcc ctg aat gct aac act aag aac cag aag atc aga    10896
Gly Gln Glu Val Ala Leu Asn Ala Asn Thr Lys Asn Gln Lys Ile Arg
            3620                3625                3630

tgg aaa aat gaa gtc cgg att cat tct ggg tct ttc cag agc cag gtc    10944
Trp Lys Asn Glu Val Arg Ile His Ser Gly Ser Phe Gln Ser Gln Val
        3635                3640                3645

gag ctt tcc aat gac caa gaa aag gca cac ctt gac att gca gga tcc    10992
Glu Leu Ser Asn Asp Gln Glu Lys Ala His Leu Asp Ile Ala Gly Ser
    3650                3655                3660

tta gaa gga cac cta agg ttc ctc aaa aat atc atc cta cca gtc tat    11040
Leu Glu Gly His Leu Arg Phe Leu Lys Asn Ile Ile Leu Pro Val Tyr
3665                3670                3675                3680

gac aag agc tta tgg gat ttc cta aag ctg gat gtc acc acc agc att    11088
Asp Lys Ser Leu Trp Asp Phe Leu Lys Leu Asp Val Thr Thr Ser Ile
                3685                3690                3695

ggt agg aga cag cat ctt cgt gtt tca act gcc ttt gtg tac acc aaa    11136
Gly Arg Arg Gln His Leu Arg Val Ser Thr Ala Phe Val Tyr Thr Lys
            3700                3705                3710

aac ccc aat ggc tat tca ttc tcc atc cct gta aaa gtt ttg gct gat    11184
Asn Pro Asn Gly Tyr Ser Phe Ser Ile Pro Val Lys Val Leu Ala Asp
        3715                3720                3725

aaa ttc att att cct ggg ctg aaa cta aat gat cta aat tca gtt ctt    11232
Lys Phe Ile Ile Pro Gly Leu Lys Leu Asn Asp Leu Asn Ser Val Leu
    3730                3735                3740

gtc atg cct acg ttc cat gtc cca ttt aca gat ctt cag gtt cca tcg    11280
Val Met Pro Thr Phe His Val Pro Phe Thr Asp Leu Gln Val Pro Ser
3745                3750                3755                3760

tgc aaa ctt gac ttc aga gaa ata caa atc tat aag aag ctg aga act    11328
Cys Lys Leu Asp Phe Arg Glu Ile Gln Ile Tyr Lys Lys Leu Arg Thr
                3765                3770                3775

tca tca ttt gcc ctc acc cta cca aca ctc ccc gag gta aaa ttc cct    11376
Ser Ser Phe Ala Leu Thr Leu Pro Thr Leu Pro Glu Val Lys Phe Pro
            3780                3785                3790
```

```
gaa gtt gat gtg tta aca aaa tat tct caa cca gaa gac tcc ttg att    11424
Glu Val Asp Val Leu Thr Lys Tyr Ser Gln Pro Glu Asp Ser Leu Ile
        3795                3800                3805

ccc ttt ttt gag ata acc gtg cct gaa tct cag tta act gtg tcc cag    11472
Pro Phe Phe Glu Ile Thr Val Pro Glu Ser Gln Leu Thr Val Ser Gln
    3810                3815                3820

ttc acg ctt cca aaa agt gtt tca gat ggc att gct gct ttg gat cta    11520
Phe Thr Leu Pro Lys Ser Val Ser Asp Gly Ile Ala Ala Leu Asp Leu
3825                3830                3835                3840

aat gca gta gcc aac aag atc gca gac ttt gag ttg ccc acc atc atc    11568
Asn Ala Val Ala Asn Lys Ile Ala Asp Phe Glu Leu Pro Thr Ile Ile
                3845                3850                3855

gtg cct gag cag acc att gag att ccc tcc att aag ttc tct gta cct    11616
Val Pro Glu Gln Thr Ile Glu Ile Pro Ser Ile Lys Phe Ser Val Pro
            3860                3865                3870

gct gga att gtc att cct tcc ttt caa gca ctg act gca cgc ttt gag    11664
Ala Gly Ile Val Ile Pro Ser Phe Gln Ala Leu Thr Ala Arg Phe Glu
        3875                3880                3885

gta gac tct ccc gtg tat aat gcc act tgg agt gcc agt ttg aaa aac    11712
Val Asp Ser Pro Val Tyr Asn Ala Thr Trp Ser Ala Ser Leu Lys Asn
    3890                3895                3900

aaa gca gat tat gtt gaa aca gtc ctg gat tcc aca tgc agc tca acc    11760
Lys Ala Asp Tyr Val Glu Thr Val Leu Asp Ser Thr Cys Ser Ser Thr
3905                3910                3915                3920

gta cag ttc cta gaa tat gaa cta aat gtt ttg gga aca cac aaa atc    11808
Val Gln Phe Leu Glu Tyr Glu Leu Asn Val Leu Gly Thr His Lys Ile
                3925                3930                3935

gaa gat ggt acg tta gcc tct aag act aaa gga aca ctt gca cac cgt    11856
Glu Asp Gly Thr Leu Ala Ser Lys Thr Lys Gly Thr Leu Ala His Arg
            3940                3945                3950

gac ttc agt gca gaa tat gaa gaa gat ggc aaa tat gaa gga ctt cag    11904
Asp Phe Ser Ala Glu Tyr Glu Glu Asp Gly Lys Tyr Glu Gly Leu Gln
        3955                3960                3965

gaa tgg gaa gga aaa gcg cac ctc aat atc aaa agc cca gcg ttc acc    11952
Glu Trp Glu Gly Lys Ala His Leu Asn Ile Lys Ser Pro Ala Phe Thr
    3970                3975                3980

gat ctc cat ctg cgc tac cag aaa gac aag aaa ggc atc tcc acc tca    12000
Asp Leu His Leu Arg Tyr Gln Lys Asp Lys Lys Gly Ile Ser Thr Ser
3985                3990                3995                4000

gca gcc tcc cca gcc gta ggc acc gtg ggc atg gat atg gat gaa gat    12048
Ala Ala Ser Pro Ala Val Gly Thr Val Gly Met Asp Met Asp Glu Asp
                4005                4010                4015

gac gac ttt tct aaa tgg aac ttc tac tac agc cct cag tcc tct cca    12096
Asp Asp Phe Ser Lys Trp Asn Phe Tyr Tyr Ser Pro Gln Ser Ser Pro
            4020                4025                4030

gat aaa aaa ctc acc ata ttc aaa act gag ttg agg gtc cgg gaa tct    12144
Asp Lys Lys Leu Thr Ile Phe Lys Thr Glu Leu Arg Val Arg Glu Ser
        4035                4040                4045

gat gag gaa act cag atc aaa gtt aat tgg gaa gaa gag gca gct tct    12192
Asp Glu Glu Thr Gln Ile Lys Val Asn Trp Glu Glu Glu Ala Ala Ser
    4050                4055                4060

ggc ttg cta acc tct ctg aaa gac aac gtg ccc aag gcc aca ggg gtc    12240
Gly Leu Leu Thr Ser Leu Lys Asp Asn Val Pro Lys Ala Thr Gly Val
4065                4070                4075                4080

ctt tat gat tat gtc aac aag tac cac tgg gaa cac aca ggg ctc acc    12288
Leu Tyr Asp Tyr Val Asn Lys Tyr His Trp Glu His Thr Gly Leu Thr
                4085                4090                4095

ctg aga gaa gtg tct tca aag ctg aga aga aat ctg cag aac aat gct    12336
Leu Arg Glu Val Ser Ser Lys Leu Arg Arg Asn Leu Gln Asn Asn Ala
            4100                4105                4110
```

```
gag tgg gtt tat caa ggg gcc att agg caa att gat gat atc gac gtg    12384
Glu Trp Val Tyr Gln Gly Ala Ile Arg Gln Ile Asp Asp Ile Asp Val
        4115                4120                4125

agg ttc cag aaa gca gcc agt ggc acc act ggg acc tac caa gag tgg    12432
Arg Phe Gln Lys Ala Ala Ser Gly Thr Thr Gly Thr Tyr Gln Glu Trp
    4130                4135                4140

aag gac aag gcc cag aat ctg tac cag gaa ctg ttg act cag gaa ggc    12480
Lys Asp Lys Ala Gln Asn Leu Tyr Gln Glu Leu Leu Thr Gln Glu Gly
4145                4150                4155                4160

caa gcc agt ttc cag gga ctc aag gat aac gtg ttt gat ggc ttg gta    12528
Gln Ala Ser Phe Gln Gly Leu Lys Asp Asn Val Phe Asp Gly Leu Val
                4165                4170                4175

cga gtt act caa aaa ttc cat atg aaa gtc aag aag ctg att gac tca    12576
Arg Val Thr Gln Lys Phe His Met Lys Val Lys Lys Leu Ile Asp Ser
            4180                4185                4190

ctc att gat ttt ctg aac ttc ccc aga ttc cag ttt ccg ggg aaa cct    12624
Leu Ile Asp Phe Leu Asn Phe Pro Arg Phe Gln Phe Pro Gly Lys Pro
        4195                4200                4205

ggg ata tac act agg gag gaa ctt tgc act atg ttc atg agg gag gta    12672
Gly Ile Tyr Thr Arg Glu Glu Leu Cys Thr Met Phe Met Arg Glu Val
    4210                4215                4220

ggg acg gta ctg tcc cag gta tat tcg aaa gtc cat aat ggt tca gaa    12720
Gly Thr Val Leu Ser Gln Val Tyr Ser Lys Val His Asn Gly Ser Glu
4225                4230                4235                4240

ata ctg ttt tcc tat ttc caa gac cta gtg att aca ctt cct ttc gag    12768
Ile Leu Phe Ser Tyr Phe Gln Asp Leu Val Ile Thr Leu Pro Phe Glu
                4245                4250                4255

tta agg aaa cat aaa cta ata gat gta atc tcg atg tat agg gaa ctg    12816
Leu Arg Lys His Lys Leu Ile Asp Val Ile Ser Met Tyr Arg Glu Leu
            4260                4265                4270

ttg aaa gat tta tca aaa gaa gcc caa gag gta ttt aaa gcc att cag    12864
Leu Lys Asp Leu Ser Lys Glu Ala Gln Glu Val Phe Lys Ala Ile Gln
        4275                4280                4285

tct ctc aag acc aca gag gtg cta cgt aat ctt cag gac ctt tta caa    12912
Ser Leu Lys Thr Thr Glu Val Leu Arg Asn Leu Gln Asp Leu Leu Gln
    4290                4295                4300

ttc att ttc caa cta ata gaa gat aac att aaa cag ctg aaa gag atg    12960
Phe Ile Phe Gln Leu Ile Glu Asp Asn Ile Lys Gln Leu Lys Glu Met
4305                4310                4315                4320

aaa ttt act tat ctt att aat tat atc caa gat gag atc aac aca atc    13008
Lys Phe Thr Tyr Leu Ile Asn Tyr Ile Gln Asp Glu Ile Asn Thr Ile
                4325                4330                4335

ttc aat gat tat atc cca tat gtt ttt aaa ttg ttg aaa gaa aac cta    13056
Phe Asn Asp Tyr Ile Pro Tyr Val Phe Lys Leu Leu Lys Glu Asn Leu
            4340                4345                4350

tgc ctt aat ctt cat aag ttc aat gaa ttt att caa aac gag ctt cag    13104
Cys Leu Asn Leu His Lys Phe Asn Glu Phe Ile Gln Asn Glu Leu Gln
        4355                4360                4365

gaa gct tct caa gag tta cag cag atc cat caa tac att atg gcc ctt    13152
Glu Ala Ser Gln Glu Leu Gln Gln Ile His Gln Tyr Ile Met Ala Leu
    4370                4375                4380

cgt gaa gaa tat ttt gat cca agt ata gtt ggc tgg aca gtg aaa tat    13200
Arg Glu Glu Tyr Phe Asp Pro Ser Ile Val Gly Trp Thr Val Lys Tyr
4385                4390                4395                4400

tat gaa ctt gaa gaa aag ata gtc agt ctg atc aag aac ctg tta gtt    13248
Tyr Glu Leu Glu Glu Lys Ile Val Ser Leu Ile Lys Asn Leu Leu Val
                4405                4410                4415

gct ctt aag gac ttc cat tct gaa tat att gtc agt gcc tct aac ttt    13296
Ala Leu Lys Asp Phe His Ser Glu Tyr Ile Val Ser Ala Ser Asn Phe
            4420                4425                4430
```

```
act tcc caa ctc tca agt caa gtt gag caa ttt ctg cac aga aat att    13344
Thr Ser Gln Leu Ser Ser Gln Val Glu Gln Phe Leu His Arg Asn Ile
        4435                4440                4445

cag gaa tat ctt agc atc ctt acc gat cca gat gga aaa ggg aaa gag    13392
Gln Glu Tyr Leu Ser Ile Leu Thr Asp Pro Asp Gly Lys Gly Lys Glu
    4450                4455                4460

aag att gca gag ctt tct gcc act gct cag gaa ata att aaa agc cag    13440
Lys Ile Ala Glu Leu Ser Ala Thr Ala Gln Glu Ile Ile Lys Ser Gln
4465                4470                4475                4480

gcc att gcg acg aag aaa ata att tct gat tac cac cag cag ttt aga    13488
Ala Ile Ala Thr Lys Lys Ile Ile Ser Asp Tyr His Gln Gln Phe Arg
                4485                4490                4495

tat aaa ctg caa gat ttt tca gac caa ctc tct gat tac tat gaa aaa    13536
Tyr Lys Leu Gln Asp Phe Ser Asp Gln Leu Ser Asp Tyr Tyr Glu Lys
            4500                4505                4510

ttt att gct gaa tcc aaa aga ttg att gac ctg tcc att caa aac tac    13584
Phe Ile Ala Glu Ser Lys Arg Leu Ile Asp Leu Ser Ile Gln Asn Tyr
        4515                4520                4525

cac aca ttt ctg ata tac atc acg gag tta ctg aaa aag ctg caa tca    13632
His Thr Phe Leu Ile Tyr Ile Thr Glu Leu Leu Lys Lys Leu Gln Ser
    4530                4535                4540

acc aca gtc atg aac ccc tac atg aag ctt gct cca gga gaa ctt act    13680
Thr Thr Val Met Asn Pro Tyr Met Lys Leu Ala Pro Gly Glu Leu Thr
4545                4550                4555                4560

atc atc ctc taa ttttttaaa agaaatcttc atttattctt cttttccaat        13732
Ile Ile Leu  *

tgaactttca catagcacag aaaaaattca aactgcctat attgataaaa ccatacagtg  13792

agccagcctt gcagtaggca gtagactata agcagaagca catatgaact ggacctgcac  13852

caaagctggc accagggctc ggaaggtctc tgaactcaga aggatggcat tttttgcaag  13912

ttaaagaaaa tcaggatctg agttattttg ctaaacttgg gggaggagga acaaataaat  13972

ggagtcttta ttgtgtatca t                                            13993
```

<210> SEQ ID NO 319
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 319 gcctcagtct gcttcgcgcc 20

<210> SEQ ID NO 320
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 320 gctcactgtt cagcatctgg 20

<210> SEQ ID NO 321
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 321 tgagaatctg ggcgaggccc 20

<210> SEQ ID NO 322
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 322 gtccttcata tttgccatct 20

<210> SEQ ID NO 323
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 323 cctccctcat gaacatagtg 20

<210> SEQ ID NO 324
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 324 gacgtcagaa cctatgatgg 20

<210> SEQ ID NO 325
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 325 tgagtgagtc aatcagcttc 20

<210> SEQ ID NO 326
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 326 gccttctgct tgagttacaa 20

<210> SEQ ID NO 327
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 327 gcgccttctg cttgagttac 20

<210> SEQ ID NO 328
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 328 tcgcgccttc tgcttgagtt 20

<210> SEQ ID NO 329
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 329 cttcgcgcct tctgcttgag 20

<210> SEQ ID NO 330
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 330 agtctgcttc gcgccttctg 20

<210> SEQ ID NO 331
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 331 tcagtctgct tcgcgccttc 20

<210> SEQ ID NO 332
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 332 cctcagtctg cttcgcgcct 20

<210> SEQ ID NO 333
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 333 agcctcagtc tgcttcgcgc 20

<210> SEQ ID NO 334
<211> LENGTH: 43445
<212> TYPE: DNA
<213> ORGANISM: H. sapiens

<400> SEQUENCE: 334 accaagacag cgctcaggac tggttctcct cgtggctccc aattcagtcc aggagaagca 60 gagattttgt ccccatggtg ggtcatctga agaaggcacc cctggtcagg gcaggcttct 120 cagaccctga ggcgctggcc atggccccac tgagacacag gaagggccgc gccagagcac 180 tgaagacgct tggggaaggg aacccacctg ggacccagcc cctggtggct gcggctgcat 240

```
cccaggtggg ccccctcccc gaggctcttc aaggctcaaa gagaagccag tgtagaaaag    300
caaacaggtc aggcccggga ggcgcccttt ggaccttttg caatcctggc gctcttgcag    360
cctgggcttc ctataaatgg ggtgcgggcg ccggccgcgc attcccaccg ggacctgcgg    420
ggctgagtgc ccttctcggt tgctgccgct gaggagcccg cccagccagc cagggccgcg    480
aggccgaggc caggccgcag cccaggagcc gccccaccgc agctggcgat ggacccgccg    540
aggcccgcgc tgctggcgct gctggcgctg cctgcgctgc tgctgctgct gctggcgggc    600
gccagggccg gtgagtgcgc ggccgctctg cgggcgcaga gggagcggga gggagccggc    660
ggcacgaggt tggccggggc agcctgggcc taggccagag ggagggcagc cacagggtcc    720
agggcgagtg gggggattgg accagctggc ggcccctgca ggctcaggat ggggggcgcg    780
ggatggaggg gctgaggagg gggtctccgg agcctgcctc cctcctgaaa ggtgaaacct    840
gtgccggtgg tccccctgtc gggccctagc acccgctggg aagacgtggg aagctcacag    900
atttctttct cctgtcttac agaagaggaa atgctggaaa atgtcagcct ggtctgtcca    960
agtaaggcat ctgcgcatgg ggcgtggaag ggcgcccagc cccgtgcact ctcctacacc   1020
cgggtccctg agggcctccc actctacagg gctgagatgg catcgtggtg tgccttgctc   1080
tgaccccagg aagcaagttc cctgagcctc tgcccacacc caagggatgc caactctctt   1140
ctacctggcc ttctgttctg tcccaaaagt tcagcctggg ggcgggggag ggaagggatt   1200
gtctctccgc tggcctgtgc acactttgaa gaaacatcac tgtcctgttt atcagtgact   1260
agtcattgat tcgaagcatg tgagggtgag gaaatactga ctttaacctt tgtgaagaaa   1320
tcgaacctcc acccccttcc tatttacctg acccctgggg gttaaaggaa ctggcctcca   1380
agcgcgaccc tgtgtgctgg agccgcgggg cggacttctg atggggcagc accgccatct   1440
agtggccgtc tgtcatcact gcagctggac tcaggaccca gatgttcttt ttcttcaatt   1500
gttcagaaaa ttcctctcaa ctacagtgga aacctccaga aattcttttc taggagtttg   1560
ttaagttagt tacgcttaat gcttaatgaa ctttgcctta agtatttggt agtcttagag   1620
tcacggaatt acggcgtgtt caagctaaaa aagcattaga gatagtacta tttgcgtaat   1680
gttgtcatct cttaatttgc cagagggtct ctcatgcaga ttttctgagc cccattactt   1740
gacacttgtc actcccttcc ctgtgcctca gatgagatat tcaagacatg ccagccaatt   1800
taaacattag cctcagcaaa aacataatgg agaagtcaaa tctataaagg aaaattaagt   1860
ataaagtcaa ttaaaaaata atttgagttg aattaccatt tttaattctc tatgccactg   1920
cccctctctg cccagaattg gctgtccttg ggagagctat ttctgctatg tggctgacgt   1980
atttctcccc acgttagaag atgcgacccg attcaagcac ctccggaagt acacatacaa   2040
ctatgaggct gagagttcca gtggagtccc tgggactgct gattcaagaa gtgccaccag   2100
gatcaactgc aaggtatgga ggatgcaggc aggagggacc tagagcccac agctttcccc   2160
cagccctgtt ccagcgggcg cccaacacgc gaccttcccg gagggtgtgt actgagcaaa   2220
cgcagaacat cccagaactg ttgtaatctg atcaaagcac tgggactttg cctctgtttg   2280
taagtcagcc acattgctga gatgtggtct gcccccacca aatttcgcaa gtcagaagta   2340
ttttcccgtt aacttcccag atgcaatagg aatccatgat ctagattagc agcagtgtgg   2400
gtctgtagat ttcagcgtga gagaggccca gtaggtgagc tatgggaggc aggcaactcg   2460
gaatcgcact gtgaaatgca gtttttataa tttaagtcaa acagaatctg ttgctgaaaa   2520
atgaatggaa agaagaaaaa aatataaaca tacagtttgt tctaaaataa aactttgctt   2580
attattgaga ctggttgtac tcatgttaca tacatgtgga gcagatctac aggctgctat   2640
```

```
tggggtttgg gtggggaaga gaagtcaagc tgagcagtca cctttttta gagagtaccg   2700
tagctcttgt atgtgctgtc caatatggta gacatgagcc acattgggct atttaaatgg   2760
aatgaaatta aaaattcata ttcgttgtca cattagctgc atttcaactg ctcaacagcc   2820
accctggcta ctggctccca tattgaacag cacacatgta caacatttct ataaagttat   2880
ttgaatagtg ctggataata agtaggaatc cgttgaaact ccagctatat gcaaagctct   2940
aaataggccc taatagatat aaccagtttt ttgggtgaca ttaaggagac atttgctgtg   3000
gaaacgaagg atggccctct tcctgctttc tgtttttctt cttcactttc actcctagtc   3060
tgcagcgctt ctatttaacc acagctcttt ataattaaag tgagtaactt tagaaccaat   3120
aaaaggacat cctccttccc atgcctaggg gcaaacttaa gaaatgtgtt acccgggagg   3180
gggaaaacgt cagcaatagg actaagtcta ggttggtgca cagagaaccc aggaggcatg   3240
ttgataaggc atgtggtgtt gaggcgcagg cagtggtgtt cccagcacca ttccctttgg   3300
tgctctgatt agagattaag ccctgggctt caggggccac ctctcattct tgatagacaa   3360
cctcaatgct ctgctaccct gaattctcag gttgagctgg aggttcccca gctctgcagc   3420
ttcatcctga agaccagcca gtgcaccctg aaagaggtgt atggcttcaa ccctgagggc   3480
aaagccttgc tgaagaaaac caagaactct gaggagtttg ctgcagccat gtccaggtaa   3540
gtcatgttgt acatgagcac acgcatgtgt gtgtgtccgc tgaggtatga acttgtgtgt   3600
ttgcaccagg cacggatgtg actgtaagta tttgtattcc gtatccatcg tggatcaggg   3660
aattactgag ttttcacaat catcaaaaag agagaagcat tagttaacct tccctagtta   3720
ggttccttta attatcattt tcatgtgttt ctaaaaatct catgctttaa acttcttgag   3780
attataaaac tgagatgctt tgtttaaaca agtgaattct tatttaaaga actagtcaag   3840
actagtgctt ggtggtcttt ggtgtggggt cccagaggca ctggctgctg tggccggcac   3900
atggcggggc agggtctgtt caccgcaggg cagaggagca ccaaggcttc ggtggctccc   3960
cctcctaggc tggcattcag ccactgcacg ctgatcggcc actgcagctg catctctgct   4020
gactggtcag ggcccatgtc gcacccattg taaatatttt caacatcacc cctgcctcat   4080
cctcaatcac agtttgtagg gtcctaggtg tgtatgaata caggcaggat agagttgtta   4140
acttggtagc atcagaaaac tctgtctgta ttagtctgtt ttcatgctgc tgataaagac   4200
atacctgaga ctgggcaatt tacaaaagaa aggtttattg gactcacagt tccacgtggc   4260
tggggaggtc tcacaatcat ggcggaaggt gagggacagc aagtcacatc ttatgtagat   4320
ggtggctggc aaagagagct tgtgcagaga aactcctgtt tttagaacca tcagatctcc   4380
cgacacccat ctgcaatcac gagaacagca cgggaaagac ctgcccccat gattcaatca   4440
cctcccccccg ggtccctccc acaacacgtg ggaattatga gagctacgag acgaaatttg   4500
ggtggggacg cagagccaaa ccatatcacc atccttgccc atttttcagt tttgctaaac   4560
attagattca gatgccagtc ctttcttgcc aaaataggct gtgaggcttc tttctttcct   4620
atgctttatt ttctccaaga cttaactgta tatgagggag aggggtatgg tggcaggagg   4680
aaagagtggt ttatttttg gtccttggtc ttctccaaat acagaagaga ctcctgttct   4740
tgaaaaggag ggctttccat gtttgcatct tcatgacttt aactgtcttt tttaaaaatt   4800
gacatacaat aattatacat atttattgag aacatagtga tattttgata catgtaatgt   4860
atggtgatca gatcagagta attagcatac ccatcatctc aaacatttat catttcttcg   4920
tgttgggaac tttctgagag agtgtaggct gtgggagata agtccgtcac cttttcctcc   4980
tgatgtaacc agagtggctg cagccaggtc ctcagaaact cagagagtac ccagtgggaa   5040
```

```
atccctaaga ccaaagtcag catgggcttc agccatggcc tgacaccata caaaagaatg   5100
actgtccaac aagtgtatga aaataagctc caattcactg gtagtcaaga aatgcgaatt   5160
aatgtaacaa caagatattt atctgctttt acccatcata ctgcaaaact ggaaaacagt   5220
gatagcacct gttgctggca ggccagtgag gaaaagtgtg ctgtcctgag ctgctggtgg   5280
aaacgagagc catcaggcaa tatctactgt aatttaaaat acttaatacc ctttgacaca   5340
gatattttag tctttgggac tctagcccat gaaaataaaa gcagtaatgt gtgaagatag   5400
gcacataagg atgtttgttt tggtattgtt tgtgtggttt aaaaaaaatc cagaaagaga   5460
gagggcaaat gccatcaaat ggggcaatgt gtgaataaat tatatttagc catggaatgg   5520
aatgttctgc atgcagcttt taaaaaaatc tgttagagct gtaccaagtg actcagaagg   5580
atttttgtga agtataatta agtgagaaaa acaagataaa agtatgcata atacaatgcc   5640
acttgtataa aacaaacaat ggcaaaatct ttgtatgact ctgtttgcac tcacccatgt   5700
ttacagagga ttgtatgagt gtgcagaaac aaatggaaca accactcggg tgtccgtatg   5760
gggaggatgg gcaaagagac tgatatgggt ggagaacaga gcagggctgg atgagccaag   5820
caaaaaaagt taaaacacag ctggacctgg tggctcatgc ctgtagtccc agcactttgg   5880
gaggccgagg agggagaatc acctgaggtc aggagtttga gaccagcctg gccaacatgg   5940
tgaaaactgt ctctactaaa aatacaaaaa ttagctgggt gtgatggcac atgccagtag   6000
tcctagctac tccggaggct gaggcaggag aatcacttga tcccaggagg tggaggttgc   6060
agtgagctga ggttgcgcca ttgcactcca gcccgggcga ccgagcgaga ctccatttca   6120
aaaaaagaaa aagaaaaaag aaaaaaagaa aaaaaaagaa tcaccaaaac ttatgtatat   6180
gtgcatactt ttttgaaaat gtatgtctat gtgtagctat attctatatt tacaaataaa   6240
tgatgtcaga agaacaattg gttaaaaaaa tatgagaaaa gaaacttcag tgccacccag   6300
cttacttcca gcaagttgta atggagaagg acatttccgt gaccatcctc tctctgggac   6360
aggtatgagc tcaagctggc cattccagaa gggaagcagg ttttccttta cccggagaaa   6420
gatgaaccta cttacatcct gaacatcaag aggggcatca tttctgccct cctggttccc   6480
ccagagacag aagaagccaa gcaagtgttg tttctggtga ggatttagaa agctgatagc   6540
agtggccctt gaaactcatc ttcatgtgtt agagaccagt cctaccatat acaaagcaga   6600
tcactgagtc agctccatga ctagttacat aggaagccct ggattggcgt gaaatactgg   6660
tgcccgaggt tcctcctgcc ccttaggctc actgacagat catcccaagc aggcttatca   6720
ggttgggtct aattttaaaa cagtcattga ggagtcctgg ccaccccacc cctgcttttg   6780
tttgatgctt cacctgtgtt tgctgggtta tggtgtacac agtaaatcct gtgtgtattt   6840
taaacaccaa aaataatggg atctgttgct ggtctctttt acgaatttca ggtttcactg   6900
tgagacagaa ttcatttcac ctcagtccca tgagcacttt tgtgtgttct aatttctcta   6960
cgacaccata atgggagaag acaccgatgc aacctgcgga ggcctttctg cagacccacc   7020
tttaactggt tttctctctc ccaacttggg ctggccaggc actagcaaga ccacactctg   7080
cataggaaga aaaagaaagt ccctcccaaa gctagattcc ttctgctttt tctttcacga   7140
tccccacccc atccctccca agtacccaag gatgttgccc gtgttgaata catgtggttg   7200
catcttcttc ctccatagga taccgtgtat ggaaactgct ccactcactt taccgtcaag   7260
acgaggaagg gcaatgtggc aacagaaata tccactgaaa gagacctggg gcagtgtgat   7320
cgcttcaagc ccatccgcac aggcatcagc ccacttgctc tcatcaaagg catggtaagt   7380
cccatgtcag cactgtcgtg cacagcaagg agcatcctct tattaataca attccagaac   7440
```

```
ttttgagcta gtgggcacct ttgaggacag cctgccctgg ctgtttttta tacagactag   7500
agataggacc ctgagcaggc acgggaaggt ctgcccaggc ttcacggcct gggatcagtt   7560
gagccaaggc ttgagtcagg ctcctccctc ccagcccaga gctctgtctt tcctcctgtc   7620
cttctgtcac tggcaccaaa ctgcctctaa tctcatcact tgagagtaat gactactcac   7680
ctctgagaag gttccgggga tggatgtagg gcagcaaaac caccttctgt tcttttctgc   7740
acaaggactc cttgtgccag ctccaagcct ctggcctttg aagaagtccc aagacctgtg   7800
ttctccccct ctccctcatc ccatgaagtg gagtgactta gagtgctcca gcttcttgtc   7860
cttccacccc cagtaccacc ctgaccaaac atggccccac tgccaccggc ctggagcacc   7920
ctctcctctc tgttaactgg ggccatggag caccatatta cctgagcctg cctgacccct   7980
gcaacatctt ccctgatatg agccccagcc tgtctcagtg aacatgaata acttgggcaa   8040
tcactgtcat gctgggcgct gttcctggtc attgtcctta gggttgaaaa cagggagtct   8100
gatgaccatg agtgccacag tcagaagagg ataatgcact ggcttagggg tcttttctga   8160
gcatctgctg tttgctcaac cccactctgg gcagcaccaa ggaagggaca gtggcagatg   8220
aaccatggac cttcccctca ggatgcttcc agtctaatgc aggagccagg tcaataaagt   8280
atacgtggta tactcaataa ggtgataagc tgaacagtgc agacaagaag tcctgggcct   8340
gaccaggaag gagaaagaat tattcatgta gctcagcggg caacatttca tggaagatgt   8400
ggagcaggaa cccaaaaaat gcaaagaata tgtaaatgaa agagacatgt aagaatgggc   8460
ttttgggcaa agaaaagtta ctgagcaggt gtgtgagggg ctatgtggtg ggatgggcat   8520
gtggaggata caaagtttag acattgtcca gtgagggtgg aaaaagagga gtctacagct   8580
tgactcagct ttggggatgc cgacttgttg cacccccctgg tctaaatgtc aagtacccag   8640
ttatcttctt tctctgagtt tatctagtgg tacaggactc ctgctccctt ctaccttgaa   8700
ggtaaatgct tttaacagaa gatacaggga ctgatcaaaa tgctcgtctc caatctcttt   8760
catagacccg ccccttgtca actctgatca gcagcagcca gtcctgtcag tacacactgg   8820
acgctaagag gaagcatgtg gcagaagcca tctgcaagga gcaacacctc ttcctgcctt   8880
tctcctacaa gtaggtcatg tgatgcaccc ctgatttgtc atttaatggg tcagtgtgaa   8940
ctgaacactt ctcaagtgct ctgttccagg caaacctgtg cctgggaggg aggaatggag   9000
agggataaaa tgccgcccct ccctgtcccc ctttttaagc gaacaggcca tttggcagaa   9060
aagtcctagg catgcaaaac aatccaagac caacaaaaga tatctaagac ccattcttta   9120
agggctgtag atccagaaaa cctgaggatc actgcagggt accctggtta gaaaaggttt   9180
catggaagat ttgggatact gactggaaac ttgtgtatcc aaatccactt tgaaaactga   9240
taatcaatga atatatattg agtaactgcc atattcttgg ctctatgttg tggaagatac   9300
gaaagaattt tgagacattg cactagttcc tacctctggc cactccagac tagtggagag   9360
tataaggcac gcatgtcttt ttgatgggag gataactagc gtgaccagga agaggtggat   9420
gttattcatt cagggccaac aatggctgga tttacccatg ctttgaaaga tgggcaggac   9480
ttgggtagat gcagagacag ggaaaacctt caacatggaa agaatagtat gttctggcca   9540
tccgtgacat ggtgtgcttc cttggttacc aggaataagt atgggatggt agcacaagtg   9600
acacagactt tgaaacttga agacacacca aagatcaaca gccgcttctt tggtgaaggt   9660
aagagtttct gtccacatag ttgctggaaa atctactcaa gatgtgccta tcatggctta   9720
gccacttgct gagccctgtt aaatgtctgc tgactaacaa gtgatacaga cactggtgtt   9780
ctggctacct ctagtgagaa agcaaactca tttcatgatg tcaagttgca atggcataaa   9840
```

```
ggaaaagaag ttcccaaagc tacttaggca tttgtaaata gaaaactgga atcctaagtt   9900
taacatgaca tatttgatag aactgacatc acccatcctg tgataagatc cagagctgtc   9960
ccagacgagg tggaccaagt gggagagaac cttcagagtc tggccagata gtaacctcag  10020
gagtcagtct ttagaggtag aaggaactct aacaatctca agtccaaccc ttacccagta  10080
ttgtattgta tttatatctg tccaaattcc ttcttgtaca ttacctcatt gtccttttg  10140
ctcatagcaa cctgtgatgt caggtggtag agatgtgatt ttatacctat tctacagagg  10200
agacagtgac acagagaggc ttagagtttg atgtagtcaa ggccgcagaa tattagaggg  10260
gggaaaataa gtgccaggtt gtaatctaag ccaggactat tctcattaca ccacatttcc  10320
atgatgactt ttacctctct tcctggcata ggtcacagta ggtggtggag aggatacaaa  10380
agtgtctccc ctccccacaa gctgctggta gacccaatta gaagaaatgg tgataagcac  10440
ccatgtgcct ggtcccagtt gtaaccatgt caacagtagc acctcctcac caattatttc  10500
aagctaaggg taacctgatg atagactcag acaagtctgg attccacttt agctctacct  10560
cttagaccct gagagctctt gggaaaccta agttgctcat ctctgggtca cacttcctca  10620
tctctgggtc tcatctcttt gtctcatctc tgggactcag agctgagatc cagggatgag  10680
caatttacat ggcccaaaaa ctctgtgggt ctcagaagca gggctgaatt tatcattaaa  10740
ttgaacaata atgccacccc acagggatag gatgatgagt cagtgaaaac aagtcaatca  10800
cctatggcag agccagatct agcaggcatt gaatacagga tagtttcttt ccctttccc  10860
ctgtgctgat actccacaat ttccagcttc cagtagacaa agatatggtt gagatgaaga  10920
aagctagagt tcctttgaca ctttccatct tccaggtact aagaagatgg gcctcgcatt  10980
tgagagcacc aaatccacat cacctccaaa gcaggccgaa gctgttttga agactctcca  11040
ggaactgaaa aaactaacca tctctgagca aaatatccag agagctaatc tcttcaataa  11100
gctggttact gagctgagag gcctcagtga tgaagcagtc acatctctct tgccacagct  11160
gattgaggtg tccaggtatc taatggttac agctcaactt tttataaaac tgatggtaac  11220
tgactgaact ttcaaacctt ggccaaatgg agaatctcag ggaccatttg gatatcaatc  11280
cagttaatca attagtcaat cagttcatga ttgctggata gagaactatc agctgctgcg  11340
ctgagttcca tgaaacacac acgcgcatac tgtgttcaag gcagctatgt atttgtgtgt  11400
taaaacagaa ggagaatagt tcccacattt tgatgggtaa cttttaattc ctaggtctat  11460
tgcaggtgct ctccagaagc ttataggctg gtggagagag aactcagacg aaaaatataa  11520
tatgatttct ctacccttca aggcactggc tttaagtgct atgaaggtga gagaagggac  11580
tgaggccagg aatgagaccc agctaatgtt ggccaggcat attctgtgtg ctggccaaag  11640
gactgtgata acagtcttct tgttgctaca gatccacagt cccctcttgg aacttttctc  11700
gattgggctt cttctgtggg taatattcct aaggaaagca tcatggttct gagctccaag  11760
ttgggttttg aagttagatt tgaatagtga atgaggtgat taagggctct cctggcagag  11820
gacacaccat gagcaatatt ttatgtgccc tgaaggtggt ctgtataact ttatccatgt  11880
ctttcttctc agccccatca ctttacaagc cttggttcag tgtggacagc ctcagtgctc  11940
cactcacatc ctccagtggc tgaaacgtgt gcatgccaac ccccttctga tagatgtggt  12000
cacctacctg gtggccctga tccccgagcc ctcagcacag cagctgcgag agatcttcaa  12060
catggcgagg gatcagcgca gccgagccac cttgtatgcg ctgagccacg cggtcaacaa  12120
gtgagtttcc acactgtatt tctcctccta ggagcagagg aacatcttgc acctctgtgc  12180
atctctgtat taaaactgaa cccctccttc cactttcaaa ctctgctcct tactcttgtg  12240
```

```
ttttttcttg atcatttttg gggtaatgac ttgaaataag aaatcagcaa acacaaattg  12300
aatttttaaa aatattttct ctacattata ttataaaagt ttttgaacat agcaaagttg  12360
acagaatttc acagggaaaa cccctagaaa accagctatc tcctactatt taagtgttat  12420
tatatttgct ttatcacata tacatccatc cattaattca tcttattttc tgaagcattt  12480
caaagtaaat tgcaaacatc aacacacttt cccctaagta ttacagcttg catattatta  12540
acttcagttc aatattagtt agcagttttt tcctctgaat ttttttgttt gtttgttttg  12600
tttttttttg ttgttgttgt ttttttgaga tggtctcact gtgtcaccca ggctggagtg  12660
cagtgatgca gtcacggctc actgaagcct caaattcctg ggctgaagtg atcctcccac  12720
ctcagcctcc tgagtagctg ggaccacagg tgcatgctac catgccctgg ctaatttttg  12780
tattcttggt agatacaggg tttcaccatg ttgctcaggc tagcaggttt ttcctttgat  12840
gaaatttttt ggctttttct tttttacatt tttatataaa tttatgtgga acaagtgtaa  12900
ttttgttaca tgaatagatt gtgcagtagt taagtcaggg ctttcagggt atccatcacc  12960
cagacaacat atagtgtacc cactaagtaa tttctcacca tccatctccc tccacttcca  13020
caccttctga gtctcaattg tctatcattc cacacactat gtccttgtgt gcacattatt  13080
tcactcccac ttataaatga caacacgcaa tatttgtctt tctgtgactg tcctgtttca  13140
cttaagacaa tgacctccag ttccatccat gttgctgcaa atgacatgat tttattcttt  13200
ttatggccga atagtatttt attgcctata catttcacat ttttaatcca atcgtccatt  13260
gatagacact taggttgatt ccatgtcttt gctattgtga atagtgctgt gataaacata  13320
tgggtgcagg tttcctttgg atataatgat ttcttttcct ttaggtatat acccagtaat  13380
gggattgttg gatttattgg tagttctatt tttagttctt tgagaaatct ctgtattgtt  13440
ttccatagtg gttgtactta tttacaatcc catcaacagt gattaactgt ttccttttct  13500
ctgtatcctc accaacaact gttatttttt gtcttttgaa taatggccct cctgactctt  13560
gtaagatgtt atctcattgt ggttttaatt tacatttctc taatgattag taatgttatg  13620
catttttca tatgcctatt gccatttgta tgtcttcttt tgaaaaaaat gtctattcat  13680
gtcctttgcc tactttttaa tgggattatt tgggggattt ttttgttgag ttgtttgaat  13740
tgcttgtaca ttccggatat tagtacccca ttggatgaat agtttgcaaa tattttctcc  13800
cattctgcag gttaccaccc tgttgattat ttgttttact gtgcagaaac tttttacttt  13860
aattaagttc tatttgtcta ttttttgttt ttgttgtctt tgcctttgag gtcttattca  13920
cgaattcttt gtctaggcca atgtccagag aagttttccc taggttttct tcttgcattt  13980
ttatagtctc aggtcttata tttaagtctt tgatccatct tgagttgatt tttttatatg  14040
gtgacagata ggagtccagt tttattcttc tgcatatggc aatccatctt tcccagcacc  14100
acttattgaa aagggtgtcc tttccctagt gtatgttttt gtcaattttg tcaaagatcc  14160
gttgactgta agtatgtgac tttatttctg ggttcagtat tctgttccat tgatctatgt  14220
gtctattttt atgccagtac catgctgttt agattactat agccttgttg tataatctga  14280
agtcaggtaa tgtgatgcct ccagctatgt tctttttgct taaaattgct tcagctattc  14340
aggctctttt tggattccat atgaatttta taattatttt ttctaattca caagtttggg  14400
ttttaagaca aacctaactg gggttaccaa gtcctgactc tcttctctta ttctgtagct  14460
atcataagac aaaccctaca gggacccagg agctgctgga cattgctaat tacctgatgg  14520
aacagattca agatgactgc actggggatg aagattacac ctatttgatt ctgcgggtaa  14580
tctcagtctt ttatatgaca tacatcattt cagaagcact tttcctggac accttttact  14640
```

```
tccctctcct gcaccctgat gggttcttgt ttcttttctt caatgcaggt cattggaaat  14700
atgggccaaa ccatggagca gttaactcca gaactcaagt cttcaatcct gaaatgtgtc  14760
caaagtacaa agccatcact gatgatccag aaagctgcca tccaggctct gcggaaaatg  14820
gagcctaaag acaaggtaaa gtccacaaga agaggtctga aagtgaaagt ttattaacaa  14880
ggatttggaa ggtactaggg gaatgagact ctagatttca tctactgact ttattctgct  14940
gtttctttcc tttccttcct tccttccttc cttccttcct ccctccctcc ctttcttctt  15000
tccttccttc cttccttctt tcgagatgga atctcactct attgcccagg ctggagtgca  15060
gtggcatgat ctcggctcac tgcaacttct gcctcctggg ttcaagcaat tctctctgcc  15120
tcagcctcct gagtaactgg gattacaggc atgtgccatt acacccagct aatttttgta  15180
ttttttagta gagatggagt tttgccatgt tggccaggct ggtcttgagc tcctgacctc  15240
aggtgatccg cctgcctcag ccttgcaaag tgctgggatt acaggcgtga gccactgcac  15300
ctggcctcta ctgttttcta attgcaaatt tcaacaagcc tattgacttg actgcctagc  15360
agtatgtgac gtgagagaaa tacttgactt tgctgctatg tcaacatgca gaacgtgaga  15420
tgtttttgct tcctaccgtc cacctaccag attgaccatc cctctcatca tggaaaaaca  15480
tgcttaattt tcccccaata agcttaggct aggatagcca acttggcccc ctcttaggtg  15540
caaagactcc agaactttgg aaactaccct atttattagc cccaaactct tactacccct  15600
tctcatcttt atcctcacat taaaataact tacgttaaaa caacttgatt ttcacttagt  15660
ggtggatctc caaacaaatc acaacttggc cataatttat gtgttttaat ggaattgaat  15720
tcaacaggca ttccacaggc tttttctggg aacccttact tgatagtgct ctaggaaaca  15780
ctggcaagaa gattcaatac cagcatttga agaacgatta cagagaaatt agacctgtgc  15840
ttaagaaaga gctagcagac aatgccagtg tttgccaggc atgttctgtg ttctgaccac  15900
aggacagtga taaccatctc ctcttttgac tgcaggacca ggaggttctt cttcagactt  15960
tccttgatga tgcttctccg ggagataagc gactggctgc ctatcttatg ttgatgagga  16020
gtccttcaca ggcagatatt aacaaaattg tccaaattct accatgggaa cagaatgagc  16080
aagtgaagaa ctttgtggct tcccatattg ccaatatctt gaactcagaa gaattggata  16140
tccaagagta agtaagagct attcacccca tataccactg agggccctga gctggaattc  16200
caaccctagg ttttggcata gccactgtct gcccttgctt ctgaaacaaa cacttgtgca  16260
aatgtgtagc agatctagac ccaaagactt agggtcaatg aaatcaagac attttggtag  16320
tgattggaaa tccatattta cttggggtgc aagagtcaaa ggataataac atggtgtgtc  16380
agctcaaaat atacttcttc ttatctagtc tgaaaaagtt agtgaaagaa gctctgaaag  16440
aatctcaact tccaactgtc atggacttca gaaaattctc tcggaactat caactctaca  16500
aatctgtttc tcttccatca cttgacccag cctcagccaa aatagaaggg aatcttatat  16560
ttgatccaaa taactacctt cctaaagaaa gcatgctgaa aactaccctc actgcctttg  16620
gatttgcttc agctgacctc atcgaggtaa gtgtgaagag tttgaggttc tctagcccat  16680
tttgtacagc atcataaaca gagagtccct gggagccagg agctacccag aggaaaacta  16740
agaaccacca ggcacttcct accatgattc tgaggctttc ttctttccct ccttccccgc  16800
cttcctctct ccccgctagg ggtcacctga agcatgactt cttaacatta atagaaatgc  16860
aggcctggcg aggtggctca ctcctgtaat cccagcactt tgggaggccg aggcgggtgg  16920
atcatgaggt caggatatcg acaccatcct ggctaacacg gtgaaagccc atctctacta  16980
aaaatacaaa aaattagccg ggcgtggtgg caggcacctg tagtcccagc tacttgggag  17040
```

gatgaggcag gagaatggcg tgaacccagg aggctgagct tgcagtgagc cgagagattg 17100
cgccactgcg ctccagcctg ggcgacagag caagactcca tctcaaaaaa aaaaaaaaaa 17160
aaaaaaattg aaatgcaaat gtctcgtctt taagtcccaa agccaaggaa gcatatgtgc 17220
tgcctagtca gatctgcttc aaatctcaaa tcactcccaa ctctgaatcc tttgttgaat 17280
tatttgtcct atctgaacct tagctgcctc ttctagaaaa aagcaagtaa taaggtcaag 17340
attctagtga gattttaata aagcagctcc tgtgaaatgc taaggtcagc tcctggcctg 17400
tggtattcaa atacttgttt agataaatgg acatcaagag tggggactac taggctggca 17460
tacaacaaag aaacctgatg ccattttctt gtctgatttt ctttctcaga ttggcttgga 17520
aggaaaaggc tttgagccaa cattggaagc tctttttggg aagcaaggat ttttcccaga 17580
cagtgtcaac aaagctttgt actgggttaa tggtcaagtt cctgatggtg tctctaaggt 17640
cttagtggac cactttggct ataccaaaga tgataaacat gagcaggtgt gtatttgtga 17700
agtatcttct taaggaaagc tttgggtctc aatgcaaaaa caattctttt ctaagcatgg 17760
aagtcctcaa aatactatct aactgaaggg ataactatgg tttttatcaa ccagacctgc 17820
tggggtaagg gccagtatcc tctgcagtta aagatctcct gaattcagtg tgcccagaaa 17880
ccagactcac aataagtact ctaggataac aagagtatga actctgggct gggtgtggtg 17940
gttcatgcct gtaatcccag cactttggga ggccaaggtg ggcagatcac aaggtcagga 18000
atttgagacc agcctggcca acatactgaa accccgtctc tactaaaaat acaaaaaaac 18060
tagctgggca tggtagtggg tgcctgtaat cctagctact cgggaggctg agacaggaga 18120
attgcttgaa cccgggaggt ggaggttgca gtgagccgag atcacgccgt tacactccag 18180
cccgggtgac agtgtgagac tgtatcttaa aaaaaaaaaa agtatgaact ctgggcatag 18240
atttaattct aacttccctg tcttgaagct gtgcgcactt ggggaagttg gttgatatta 18300
tgtgtatctg tttctgtctg tatcccagac tactaataac agtccaaacc tcacaaggtt 18360
atttaaagac aatgaaataa ggcatctaaa atgccaagca cagtgcctga tgctggcatt 18420
ggttgttcaa taagcagaca ctattacgag ttctaaatta atattttcat tattattaac 18480
tgctgtcttt ggctctcact cccatcagtg cactagcaaa tgagaccaaa cttccacttt 18540
gaagctagca atgagccccc atttaaggag ggaaataggt tgtatgatct ggagcttatt 18600
cttgaatttt ttgctaccca aagtgtggtc tggtcagaaa tacagcttct catgcttcac 18660
ccacaatcta ctgaatcaga agcgcatttt agcaagacct catgtgactt gtatgcacat 18720
tcaactttgc agagcaaggc agtaatttac ccctccaggc tcactgttga gcacgagctc 18780
catcttctaa tttcctgacc cccacttgag gccgaggatc tttgatctgc tttgagtctg 18840
tcagtttcac attttttttt tcccaatgcc tgggcatcca tctctgagat tcttcttctc 18900
tctgagaaga acttgtctag gatcaagtgt ttttcaaact tctggtgaat ttatataaca 18960
gctacatttt cttaagaaac accttgtagt cttcactggt caaagaagag aaggctaagc 19020
agggaacggg tgggggatag aggatcttct aatcttgagg atcctggcat actggagaat 19080
agggacccct cctctcatcc caccacatct tactatgtct acagattttt taattaagaa 19140
tagctttagg agtgccacta tccctgacaa gaccttagtt ctttaatctc tgcttagagg 19200
aattagcctg gacttcagtg tctccctgtt cctcacctgg agcatttttt aggcccatcc 19260
tggctgcatc agacaggtcc cacattggga actgaaaggt gtttgacatt gctgacatct 19320
cactggccat tttattacta aactctcagg atatggtaaa tggaataatg ctcagtgttg 19380
agaagctgat taaagatttg aaatccaaag aagtcccgga agccagagcc tacctccgca 19440

```
tcttgggaga ggagcttggt tttgccagtc tccatgacct ccagctcctg ggaaagctgc  19500
ttctgatggg tgcccgcact ctgcagggga tcccccagat ggtaagtcag caggccccac  19560
tgggggccca tgagaccaga cgttggtttt tttttagatc gcccagactc ccttacgatc  19620
ccagctgcac aagcccgaaa agatgcttgt actttcttca gagatggagg tttgccttga  19680
atttcactga agatgactct tggatcacat ggaaatgtta acatttagaa attaagctat  19740
tcataatgtt agctgtattt ttaagagcat taatttattc atctggaaaa caatgttcgg  19800
tataccttcc tctacctttg ctgaaggtcc ttttattttt atttttattt ttttaatttt  19860
ttgagatgga gtcttgctcc caggctggag tgcagtgata caatctcggc tcactgcaac  19920
tctgccttcc gggttcaagc aattctcctg cctcagcctc ccaagtagct gggactgtgg  19980
acgtgcacca gcatgcccgg ctaatttgtg tatctttagt agagacaagc ctgttgacaa  20040
ccatgtcagg ctggtttcga actcctgacc tcaagtgatc ctccagcctg ggcctcccac  20100
agtgctggaa taacaggtgt gagccactgc acctgacctg aaggtccttt taagattgaa  20160
atgatacaat gattataaaa gaaagtattt ggcaaactat aattcactat ctaaatatgc  20220
tataattttt attattaatt cataaaagga aatatataaa tgtactccta tggcttgatt  20280
aaaaaaatgt tgactttaag aaaacaggtc tcaagctatt ttattgaaat attatttaaa  20340
aaataaaacc caatgcaaat tgatatgtac atcatctcaa taggcctttg gtttcaaaaa  20400
attgatttta tcataatata atacatttca agtacacctt cacttacagt cagactccag  20460
aacaccagaa ttaagccatg gcatatatga tacttaaagt ccataaagct ctgaggccca  20520
gcaatattct taagagcctt ctgagtccac ttgaaaatga catgatatct atctagtgaa  20580
atttcttata tcctgattca ctgaaaacgg taaaaacatc agtttgatct ttatttatca  20640
aactattcag ctcatcaaaa tatgctagtc cttcctttcc agataaagag gaattactct  20700
ccaatgtatg ggaggttgta attaacaaaa ccgactttaa aaagacttac ttttatttgc  20760
tctcccttgt tgggtctaca gattggagag gtcatcagga agggctcaaa gaatgacttt  20820
tttcttcact acatcttcat ggagaatgcc tttgaactcc ccactggagc tggattacag  20880
ttgcaaatat cttcatctgg agtcattgct cccggagcca aggctggagt aaaactggaa  20940
gtagccaacg taagattctg tttgcctttt gatttcttag gttattactt tcttccaggg  21000
tgcatttctt gttaaaacat atttaaaaat gtgtttccac ttcaagacaa aatgcttcat  21060
cattgtaatc acctcattat ttttttatga aaaacttcaa gcttccacca gaatgcacta  21120
cctcactagc tccagtagtg gtatggccat aagacaagaa ctcagttctc tcaacaaatg  21180
agtattccta tcatcttttt aatctggttt tgcctcacgt taactcaggt gctttctagt  21240
tctgggtagt atactccaac tctagagaac tgagaactcg ctttccttct tccaaacaaa  21300
tcccagtaat gtttccaaag gtctgagtta tccaggaaat ctttgcccgg aggtgagaaa  21360
gggtggttga tctgactgac aggggactga agtatttaat gaatctgaat aggttgtttt  21420
ctgacttata gatgcaggct gaactggtgg caaaaccctc cgtgtctgtg gagtttgtga  21480
caaatatggg catcatcatt ccggacttcg ctaggagtgg ggtccagatg aacaccaact  21540
tcttccacga gtcgggtctg gaggctcatg ttgccctaaa agctgggaag ctgaagttta  21600
tcattccttc cccaaagaga ccagtcaagc tgctcagtgg agggtaattc tttcagccaa  21660
gtctgcctag ccagtttgaa agagagaaca gagaatgtac ctgcagaatt ttgccaggct  21720
aaacagttga ttgagatcat tcaggtcctg aggaagcagg agaggagtag aaaggaaaga  21780
ttccgggtta cctattttaa ttctagccta gacttactac ataactacat aattaccttt  21840
```

```
cttctacttt tcacatttta ctaaactgtc ctttatcttt ctgctttgag acttattaag  21900
acctactgct taattagttt ttattaagtt gtgatttttt gttatctatt tgttttgaga  21960
atgaagaaac aatagctctg gagagatcat ctttggaaaa ttaatatttt ccccccccaaa  22020
aaatacctaa gaacatattg atttgaggta gctaggtagg taaagcatga aactcctaac  22080
ctcgtgataa tggaatacag cctcttttgg agagttccat tttaagtggc accctcaacc  22140
attgatttgc cttagttttc atattttaga cacattcatg tgttcattca aaaataatat  22200
ttaattggcc agccacggtg gttcatgcct gtaatcctag cactttggga gccccaggtg  22260
gatggatcgc ttgagccctg gtgtttggat accagcctgg gcaacatggc aaaaccccat  22320
ctctacaaaa aaaattaaat aaataacaaa attagccagt cgtggtggca catgcctgta  22380
gctccagcta ctcagaaggc tgagatggga ggatcaactg agcccaagag ttcaagcctt  22440
cagtgaacca tgcttgcacc actgcactcc agcctgggag acagagcaag atcctgtctc  22500
acaaaaaaca aaaaatagta tatttaattg cctaatatat accacgtatg ttgagtgaga  22560
cacacaaggt ccctgacctt tgaacgctta cattttataa gggagacaca caattaagca  22620
agcagtaatc atagagtaag ggctaagtta tagaaagtat tagagtacca tgaaatttta  22680
tatcatgtag cctgtgctag tcagggaatg cattctgaag caagtgtact tgacctgata  22740
actgaggact gtgtcagagt catttaggca aaggagaaag gagtgagtgt tccaggcaaa  22800
aggaaaagca tgtaatggcc tgaaggtaaa ggaatatggt tcaaggaact ggaagaagtg  22860
cagaatggta aggggctcag agatgatggg gagaggtagg caggggagag agcatgccca  22920
gctgcgaaag ccatcctaag gagtttggac tcttttgaag gcacaggagt tgaaaagggg  22980
agcagaaata agataggggt gatgttttag aagaaatact ctgactctag tgtggaagat  23040
gggtgagaag gaggcacagc tggacacgaa gagaccattg gacatctctt acgatcctat  23100
gtggctaaga gctgataatg gcctgcagtg gagaaaagcc aggtatagaa aggagtgagc  23160
agattctaca actttctaag aggcagaatc ataagtactg ggtgattaac tgggtatggg  23220
gacaaggcaa aagaaagaag aaaagaggaa ggaggcgccc ttcattttaa taagaactac  23280
agtgggagag cttctggttt caaggaaagt gacaaattca gttttggatg tgctgtattt  23340
gatgtcctcc tatgaaacaa ccagtttaga aatctagctg tcaaatagac ctatggatct  23400
gagcccagta aagaggcttg ggctccacat atggatttgg gaatcattag tatacagagg  23460
ttgttgtggt taaacagcaa ctggtataga gtgagacatg agagatgagg acagaaatat  23520
ggagaagaca aacatataaa ggaagaaggg gaataaccag caatgagtta gaagaagtga  23580
ccagagaagc agaaggagaa ccaaagccat aaaaggtcac agaagccaaa gagcagccac  23640
aggggagatc accccatggg taggcgaaag ctggcattag gactccagca catcagcaaa  23700
gcttggtctt gtggcacccc caacttggag aaacaatact tggaggaaaa tgtgctattt  23760
caaagaaagc atccttagaa aaaaccaggc caatgttgaa ctttcttaca tgtactaagt  23820
ttttaagtac acacttggaa ggaaggtgcc atcatctctt cagatgtgag aggctccagc  23880
gtcttagtct ggtcatgagt gcgcaactct atggaaggct tctgggaggt caaggaagat  23940
gaaacctaaa tatgcccatt ggatgtagga gcaaggaggg cattagagac attgatgaaa  24000
gcattttcag gagatggagt gagcagtcag agcacattgg gaggaagtag agactgcaaa  24060
ggcagacaac tcttgatggt gaggaagatg agaaagcaag aaaagaaaga aaggagcata  24120
ggggaggggc acaggggaag agacttgagc gtgcttaatg caggtggaag gaagcaggta  24180
gagagtagga gatttcatat gaaagagaca gtttctcttg ccctgcattg taggaaggaa  24240
```

```
ggggcacact gaagttcagc cccagtgatc agctatttaa catctctgag cctctgcttc  24300
tgtaaaatga gaaccataag cctactgttg tggggattac aggtaacaga tggaaagaac  24360
tcagccagaa gcttcagagt cactctcatg gcttgtcatg ttgatgttct ttctaatatt  24420
atttgtttct cagtaaatta aatagttaga gataggtgtg gactgaggga agacaggagg  24480
ataagggggt atttgcaccc tgagaatttg tgatgtccat tttgattcat gacttggcaa  24540
taactcaggt atttttgttc ttcaccagca acacattaca tttggtctct accaccaaaa  24600
cggaggtgat cccacctctc attgagaaca ggcagtcctg gtcagtttgc aagcaagtct  24660
ttcctggcct gaattactgc acctcaggcg cttactccaa cgccagctcc acagactccg  24720
cctcctacta tccgctgacc ggggacacca ggttagagat gctcagtgcc tgacccagca  24780
ttttctcacc ttccacatca tggccaccta gcatggcaca ggaaaaaata ctctgtgttg  24840
taagaccctg tcactagcct tctgggtttg caccatcttt gggtatttaa agcagggtcc  24900
tctggccaac acattgggtg tcaccttttg cttccttgtg catgggatgg gatcacagca  24960
cagatcccaa tttgctccta attcagtgtc catgtttctg agcctccaga cccatcgcta  25020
tgagcttcct ggagcccacc aatgtgcttg aagccttcac cgtacttagg tggctccctg  25080
tcttcagccc ccaagttcca gtgcttgttc tcagctttgc tgaaacaacc agccaactcc  25140
tgctctgctt gtccaaagtc ttgggaatcc tggtgtctgc ccttgccttg ggttcttgta  25200
ggactgaggg atcaaaaaga tcatcttagt taagggcaag agacaatgtt aaaataagga  25260
ccatattttt gttgcatttg aggctgaatt gttttgggaa cataatcacc atccttgaaa  25320
gctctaacat tatgcactgt cttcattgta atgtctttag attagagctg gaactgaggc  25380
ctacaggaga gattgagcag tattctgtca gcgcaaccta tgagctccag agagaggaca  25440
gagccttggt ggataccctg aagtttgtaa ctcaagcaga aggtgagtat tcaaaacaca  25500
gctgcctcat ctctgctcgc agtctcaggt tcagaattca tgaggagaag acatgtaatt  25560
taacctattt aacaaatagg ttaactgagt acccactaag cggcaggcct attctaagac  25620
ctgggttaac tgagtaccca ataagcggca ggcctattct aagacctggg gctagaacag  25680
tgaacaatgg agtctctgcc ttcatggaag ttacagtgaa caaccaaaca agttaatatt  25740
tggaatatca gataagtact gaggaggaaa acagagcgta gactggtcta tggagggcta  25800
ggagtaggag ggaggaagaa gggcagggaa agcagtgcat ttggaataat aagggaaagt  25860
ctccctggta aagtgagcat aaggagacct atcagaaata agaggagaag ccgtgtggta  25920
agactgttaa caggcagagg gaccagcaag tgcaaaggcc ctgaggctga cacactacta  25980
ccatgtttca aggaaaggaa ggaagacagt atggctggag cagaaagacc agggagaaaa  26040
gaggtagaag atgaggacag agagatatgg agaggtgaag gaaggataat ctcataggcc  26100
atggtaagaa ctttggcttt ttctatgaat taaacgaaag ccattgggga gtcctcatga  26160
tttgatttat gtttatgttg agaaaagact atgggcagac aagggcagag aaactaatat  26220
gtaggttatc acaataatcc aggcaggaat cagtgttgtt ttggatcagg gcaatggcag  26280
aagagatatg agaaggggat ggattctggc catattttga agattaggct gacaagattt  26340
gctgatacag tggatgttga gtgtaagagg aaaaggggaa tgaagacaaa cctaaggttt  26400
ttggcccggg caactgaaaa atggaacttc catttattga gatggaaagg gctactggag  26460
gagcaggttt tagggaatgg gagaaattta ggtgttcact ttggaaaaaa aattatatag  26520
ggatagcgag gagcaggttt tagggaatgg ggcacattta ggtgttcact ttggaaaaat  26580
ttttatatag ggatagcata tcacagaatt aaactaggaa gaaaatccca tgatagaaag  26640
```

```
cactggagga gcagggcacg ctggggaaat agtgtttggt aaacattgtt ttacgaagga  26700
tataaaatgg accagcctat ggattgaagg acgcccggga atcttgttac aaagaaaggg  26760
ggagttgggg agatggagcc cagggcaagg gcagcaagga accaggacag gcatcttggg  26820
tagaaagtaa tatagagatg tcgtgtcttc ctggcccaga agggctgcga gcctttgctg  26880
ttccacaaac aagctaagtg ctccccattt cagggccttt gcattcctga ccttctgcct  26940
ggaatgtgct cctcccagaa ctcagcgtgg ctccaacctc ttttcattct ggtctctgcc  27000
cacatgtgcc cttatcagag agaatttctc tgaccaccaa gtatgaaata acacttcttc  27060
tatccctttc ttttatcctt gtatccagtt ttactcttct tcataacatt cattaccatc  27120
tgacatgagc aagttacttg tttattgcct gtacacctcc cccactagaa ggtaagcccc  27180
atgaaagcaa ggattcccca gtaccaagag cagtgcccag cacacaatag gctcataaca  27240
ggcaatccat aaagacttgc atacatgaac acaactgagt ttaaaattat cagtaaatga  27300
gacccattaa aaaattttaa tgagaaaaaa aaaattcagt aaaatcctga actgtgtttt  27360
tgtttaagca cattgattcc ttggagtttc tctacctttt cctctctttc cttccaaaac  27420
atagcttctt tatttattta tttatttatt tgtttgttta tttatttatt tatttattta  27480
tttatttttt gagatggagt ctcgctcttt tgcccaggct gcagtgcagt ggtgccatct  27540
cggctcactg caagccccgc ctcccgggtt catgccattc tcctgcctca gcctcctgag  27600
tagctgggac tacaggcacc caccaacgcg cccggctaat tttttgtatt tttagtagag  27660
acggggtttc accatgttag ccagaatggt cttgatctcc tgacctcatg atctgcccgc  27720
cttggcctcc caaagtgctg ggattacagg tgtgagccac cgcacccggc ccaaaacata  27780
gcttcttacc acacatctct tgattctctt atacactcgt ccaggtgcga agcagactga  27840
ggctaccatg acattcaaat ataatcggca gagtatgacc ttgtccagtg aagtccaaat  27900
tccggatttt gatgttgacc tcggaacaat cctcagagtt aatgatgaat ctactgaggg  27960
caaaacgtct tacagactca ccctggacat tcagaacaag aaaattactg aggtcgccct  28020
catgggccac ctaaggtaaa gaaggccgag ggtcatctga cctgcactgc aggcctgggt  28080
ggttcttttc attattcctc ttccacttca tacctgacca agccatgttc tcccctagtc  28140
tacaatcaga gtggcagaga gagccctcaa caattttttt ttttttgag atggagtctc  28200
actctgtcac caggctggag tgcagtggca caatctcggc tcactgcaac ctccgcctcc  28260
cgagttcaag tgattctcct gcttaagcct cccaaggagc tggaactata ggtgcatgcc  28320
accacaccca gctaattttt atatttttag tagagacagg gtttcaccat attgaccagg  28380
atggtctcga tctcctgacc tcgtgatcca cctgccttgg cctcccaaag tgctgggatt  28440
acaggtgtaa gccactgcac ccggccaagc tctcaacatt ttaaccctct gcgcatgtcc  28500
agttggattt tcctaccatt tatcaggcac ttactattca tgtatcaagc acagtgctgg  28560
gtgctttaaa gaaattatct cggtcctcac aataaactgc gaggtcactg tgagttttcc  28620
tgtttcatgg ataaggaaat ggtagctcag aggggttaaa tcatttggtc aaaatcacag  28680
agctagtaaa tagcagagca ggattcaaac agttttcaaa aaacttctct ttctcctaaa  28740
cctgtttgca aagtccttaa tttgtgctga atgttggctt tagaagttga tgagtttgat  28800
ctgtggctgt ttctctgaac catccttgta tctggttttg atcaccacaa atggaacttc  28860
tgtttaatcc tgcatatctc cattgaaagg acaaaatcat tggtgccaac tgattttctt  28920
taccatagtt gtgacacaaa ggaagaaaga aaaatcaagg gtgttatttc catacccccgt  28980
ttgcaagcag aagccagaag tgagatcctc gcccactggt cgcctgccaa actgcttctc  29040
```

caaatggact catctgctac agcttatggc tccacagttt ccaagagggt ggcatggcat 29100
tatggtatgt gtctcttccc ctgtgtgagc acttccaaag taatgcaggt gttgagacct 29160
gtggttacag gctgaactag taccattcac aactatttcc tacgtatttt cagatgaaga 29220
gaagattgaa tttgaatgga acacaggcac caatgtagat accaaaaaaa tgacttccaa 29280
tttccctgtg gatctctccg attatcctaa gagcttgcat atgtatgcta atagactcct 29340
ggatcacaga gtccctcaaa cagacatgac tttccggcac gtgggttcca aattaatagt 29400
tgtaagtatg agtctgccag tcaataaata catggatata agtgctaatt acatcctcaa 29460
ctctgagcta ggtgcaggaa ggtttccaaa gatgtataag gcatgcttcc ttccccccag 29520
ggaattcttg gggagaaaaa aaaactttca caagtgtgta gttacccagt tacacaaagc 29580
tgaatgtgat acatatcaaa gagatgctac taagtagaac agttctttgc ctagtggtat 29640
caaaggaagc ttcaggacac cagctaggag gctgactatg ttagacattc cttttataaa 29700
tatggacagt gatcagtgac tggcaacgaa gattcataat tttctgttat ttatttttaa 29760
ctttcagtgc attgtccagc ttaataatta acttgtcaaa tcggtatttt tgcctaatgt 29820
tcattgctct ttgaggctca tccaagccca ttaccttaaa aatctcctgt cattttgtag 29880
gcaatgagct catggcttca gaaggcatct gggagtcttc cttataccca gactttgcaa 29940
gaccacctca atagcctgaa ggagttcaac ctccagaaca tgggattgcc agacttccac 30000
atcccagaaa acctcttctt aaaaaggtaa aagaagaaag cagcaaggct tcttgaacca 30060
tgcaaagtaa atgaaagatt ttacatagca tgatttagac atttttttaa atttttaaag 30120
gaaataattt aagcatttta aggagattaa taactatagc acaaacactg tggcatcttt 30180
gcattagtaa acatgagaac accaaccctg tcaggaagaa tctaagaaag tcattagagg 30240
attctggtac tttcacccta agatatttta ttcagtacaa cctgttataa gcaaattctc 30300
cctctgactg tgaagaattc agaatggcta gaggcgttat tgactacagg cttgctgtta 30360
agctagagag agtcagaaca gccattgagc actaaatgga ggcagcattc tgagaaaata 30420
ctttaaccca ggcttactga cttccatacc tatgttcttt ccacaaatca agttgtctca 30480
attcagttta gcaaatttgt atcaagtatc ccctatgtgc aaaatgctag actaggtaca 30540
gtgagaagat agaaactggg taaggtatag ccttttcttt caagaagata ccatggagac 30600
atcaacaaat gagaaataat taattatata agcaaaatta tgacatgctc tttgagaaag 30660
gtgcaaggga ctatgtaact gtaagaatga gacaaattgg ctatgactta ggtgggatgg 30720
taatgataag gagtggccct tagaagagct ttgtcaggat ttgagtgttt gacaggtgga 30780
ggtaaaagca aaggggtcca ggcataggag tagcacaaag aaaagtgcag agtggctttg 30840
ggaatggggc aagtacaata ttgttgtgaa ggtcagaggc agagaacttt gaatgactga 30900
tgtctgactg tggggatgtt atctttgttg ttcatttcag cgatggccgg gtcaaatata 30960
ccttgaacaa gaacagtttg aaaattgaga ttcctttgcc ttttggtggc aaatcctcca 31020
gagatctaaa gatgttagag actgttagga caccagccct ccacttcaag tctgtgggat 31080
tccatctgcc atctcgagag ttccaagtcc ctacttttac cattcccaag ttgtatcaac 31140
tgcaagtgcc tctcctgggt gttctagacc tctccacgaa tgtctacagc aacttgtaca 31200
actggtccgc ctcctacagt ggtggcaaca ccagcacaga ccatttcagc cttcgggctc 31260
gttaccacat gaaggctgac tctgtggttg acctgctttc ctacaatgtg caaggtgagc 31320
tatgctcagg taaagggtgc accgggctag ttcatggcag gctctaagag gagagcctcc 31380
tccagggagg aaaggacttt ggctttctag cagataatct tccttgctac ttggaagtct 31440

```
tttattttat tcaacaaata gaaatattta ttaaacatat cacgtgtatt aaatattcta  31500
gtaggcagta acagaaagta gacagataag ccagcaatta taattcagtg tgagaggtgc  31560
tatgataaag tgtagtatat aagtataagg tagagtggaa gcactcaaca agggaaccta  31620
aacaaagcct gtggtggtca ggcaaggctt cctggaggaa tgccttttgc tatcagattt  31680
tatctttgca ttacagatgg aggagtctat tgcacaattg gcccagaaaa atggggcttt  31740
attattgaaa gactttcaac atagagattg ctctggaaat gtactgctta atttaaccaa  31800
tgtcttttca tttttatgtt aggatctgga gaaacaacat atgaccacaa gaatacgttc  31860
acactatcat atgatgggtc tctacgccac aaatttctag attcgaatat caaattcagt  31920
catgtagaaa aacttggaaa caacccagtc tcaaaaggtt tactaatatt cgatgcatct  31980
agttcctggg gaccacagat gtctgcttca gttcatttgg actccaaaaa gaaacagcat  32040
ttgtttgtca aagaagtcaa gattgatggg cagttcagag tctcttcgtt ctatgctaaa  32100
ggcacatatg gcctgtcttg tcagagggat cctaacactg gccggctcaa tggagagtcc  32160
aacctgaggt ttaactcctc ctacctccaa ggcaccaacc agataacagg aagatatgaa  32220
gatggaaccc tctccctcac ctccacctct gatctgcaaa gtggcatcat taaaaatact  32280
gcttccctaa agtatgagaa ctacgagctg actttaaaat ctgacaccaa tgggaagtat  32340
aagaactttg ccacttctaa caagatggat atgaccttct ctaagcaaaa tgcactgctg  32400
cgttctgaat atcaggctga ttacgagtca ttgaggttct tcagcctgct ttctggatca  32460
ctaaattccc atggtcttga gttaaatgct gacatcttag gcactgacaa aattaatagt  32520
ggtgctcaca aggcgacact aaggattggc caagatggaa tatctaccag tgcaacgacc  32580
aacttgaagt gtagtctcct ggtgctggag aatgagctga atgcagagct tggcctctct  32640
ggggcatcta tgaaattaac aacaaatggc cgcttcaggg aacacaatgc aaaattcagt  32700
ctggatggga aagccgccct cacagagcta tcactgggaa gtgcttatca ggccatgatt  32760
ctgggtgtcg acagcaaaaa cattttcaac ttcaaggtca gtcaagaagg acttaagctc  32820
tcaaatgaca tgatgggctc atatgctgaa atgaaatttg accacacaaa cagtctgaac  32880
attgcaggct tatcactgga cttctcttca aaacttgaca acatttacag ctctgacaag  32940
ttttataagc aaactgttaa tttacagcta cagccctatt ctctggtaac tactttaaac  33000
agtgacctga aatacaatgc tctggatctc accaacaatg ggaaactacg gctagaaccc  33060
ctgaagctgc atgtggctgg taacctaaaa ggagcctacc aaaataatga aataaaacac  33120
atctatgcca tctcttctgc tgccttatca gcaagctata aagcagacac tgttgctaag  33180
gttcagggtg tggagtttag ccatcggctc aacacagaca tcgctgggct ggcttcagcc  33240
attgacatga gcacaaacta taattcagac tcactgcatt tcagcaatgt cttccgttct  33300
gtaatggccc cgtttaccat gaccatcgat gcacatacaa atggcaatgg gaaactcgct  33360
ctctggggag aacatactgg gcagctgtat agcaaattcc tgttgaaagc agaacctctg  33420
gcatttactt tctctcatga ttacaaaggc tccacaagtc atcatctcgt gtctaggaaa  33480
agcatcagtg cagctcttga acacaaagtc agtgccctgc ttactccagc tgagcagaca  33540
ggcacctgga aactcaagac ccaatttaac aacaatgaat acagccagga cttggatgct  33600
tacaacacta aagataaaat tggcgtggag cttactggac gaactctggc tgacctaact  33660
ctactagact ccccaattaa agtgccactt ttactcagtg agcccatcaa tatcattgat  33720
gctttagaga tgagagatgc cgttgagaag ccccaagaat ttacaattgt tgcttttgta  33780
aagtatgata aaaaccaaga tgttcactcc attaacctcc catttttga gaccttgcaa  33840
```

gaatattttg agaggaatcg acaaaccatt atagttgtac tggaaaacgt acagagaaac 33900
ctgaagcaca tcaatattga tcaatttgta agaaaataca gagcagccct gggaaaactc 33960
ccacagcaag ctaatgatta tctgaattca ttcaattggg agagacaagt ttcacatgcc 34020
aaggagaaac tgactgctct cacaaaaaag tatagaatta cagaaaatga tatacaaatt 34080
gcattagatg atgccaaaat caactttaat gaaaaactat ctcaactgca gacatatatg 34140
atacaatttg atcagtatat taaagatagt tatgatttac atgatttgaa aatagctatt 34200
gctaatatta ttgatgaaat cattgaaaaa ttaaaaagtc ttgatgagca ctatcatatc 34260
cgtgtaaatt tagtaaaaac aatccatgat ctacatttgt ttattgaaaa tattgatttt 34320
aacaaaagtg gaagtagtac tgcatcctgg attcaaaatg tggatactaa gtaccaaatc 34380
agaatccaga tacaagaaaa actgcagcag cttaagagac acatacagaa tatagacatc 34440
cagcacctag ctggaaagtt aaaacaacac attgaggcta ttgatgttag agtgctttta 34500
gatcaattgg gaactacaat ttcatttgaa agaataaatg acattcttga gcatgtcaaa 34560
cactttgtta taaatcttat tggggatttt gaagtagctg agaaaatcaa tgccttcaga 34620
gccaaagtcc atgagttaat cgagaggtat gaagtagacc aacaaatcca ggttttaatg 34680
gataaattag tagagttggc ccaccaatac aagttgaagg agactattca gaagctaagc 34740
aatgtcctac aacaagttaa gataaaagat tactttgaga aattggttgg atttattgat 34800
gatgctgtca agaagcttaa tgaattatct tttaaaacat tcattgaaga tgttaacaaa 34860
ttccttgaca tgttgataaa gaaattaaag tcatttgatt accaccagtt tgtagatgaa 34920
accaatgaca aaatccgtga ggtgactcag agactcaatg gtgaaattca ggctctggaa 34980
ctaccacaaa aagctgaagc attaaaactg tttttagagg aaaccaaggc cacagttgca 35040
gtgtatctgg aaagcctaca ggacaccaaa ataaccttaa tcatcaattg gttacaggag 35100
gctttaagtt cagcatcttt ggctcacatg aaggccaaat tccgagagac cctagaagat 35160
acacgagacc gaatgtatca aatggacatt cagcaggaac ttcaacgata cctgtctctg 35220
gtaggccagg tttatagcac acttgtcacc tacatttctg attggtggac tcttgctgct 35280
aagaacctta ctgactttgc agagcaatat tctatccaag attgggctaa acgtatgaaa 35340
gcattggtag agcaagggtt cactgttcct gaaatcaaga ccatccttgg gaccatgcct 35400
gcctttgaag tcagtcttca ggctcttcag aaagctacct tccagacacc tgattttata 35460
gtccccctaa cagatttgag gattccatca gttcagataa acttcaaaga cttaaaaaat 35520
ataaaaatcc catccaggtt ttccacacca gaatttacca tccttaacac cttccacatt 35580
ccttccttta caattgactt tgtagaaatg aaagtaaaga tcatcagaac cattgaccag 35640
atgctgaaca gtgagctgca gtggcccgtt ccagatatat atctcaggga tctgaaggtg 35700
gaggacattc ctctagcgag aatcaccctg ccagacttcc gtttaccaga aatcgcaatt 35760
ccagaattca taatcccaac tctcaacctt aatgattttc aagttcctga ccttcacata 35820
ccagaattcc agcttcccca catctcacac acaattgaag tacctacttt tggcaagcta 35880
tacagtattc tgaaaatcca atctcctctt ttcacattag atgcaaatgc tgacataggg 35940
aatggaacca cctcagcaaa cgaagcaggt atcgcagctt ccatcactgc caaaggagag 36000
tccaaattag aagttctcaa ttttgatttt caagcaaatg cacaactctc aaaccctaag 36060
attaatccgc tggctctgaa ggagtcagtg aagttctcca gcaagtacct gagaacggag 36120
catgggagtg aaatgctgtt ttttggaaat gctattgagg gaaaatcaaa cacagtggca 36180
agtttacaca cagaaaaaaa tacactggag cttagtaatg gagtgattgt caagataaac 36240 aatcagctta ccctggatag caacactaaa tacttccaca aattgaacat ccccaaactg 36300
gacttctcta gtcaggctga cctgcgcaac gagatcaaga cactgttgaa agctggccac 36360
atagcatgga cttcttctgg aaaagggtca tggaaatggg cctgccccag attctcagat 36420
gagggaacac atgaatcaca aattagtttc accatagaag gacccctcac ttcctttgga 36480
ctgtccaata agatcaatag caaacaccta agagtaaacc aaaacttggt ttatgaatct 36540
ggctccctca acttttctaa acttgaaatt caatcacaag tcgattccca gcatgtgggc 36600
cacagtgttc taactgctaa aggcatggca ctgtttggag aagggaaggc agagtttact 36660
gggaggcatg atgctcattt aaatggaaag gttattggaa ctttgaaaaa ttctcttttc 36720
ttttcagccc agccatttga gatcacggca tccacaaaca atgaagggaa tttgaaagtt 36780
cgttttccat taaggttaac agggaagata gacttcctga ataactatgc actgtttctg 36840
agtcccagtg cccagcaagc aagttggcaa gtaagtgcta ggttcaatca gtataagtac 36900
aaccaaaatt tctctgctgg aaacaacgag aacattatgg aggcccatgt aggaataaat 36960
ggagaagcaa atctggattt cttaaacatt cctttaacaa ttcctgaaat gcgtctacct 37020
tacacaataa tcacaactcc tccactgaaa gatttctctc tatgggaaaa aacaggcttg 37080
aaggaattct tgaaaacgac aaagcaatca tttgatttaa gtgtaaaagc tcagtataag 37140
aaaaacaaac acaggcattc catcacaaat cctttggctg tgctttgtga gtttatcagt 37200
cagagcatca aatcctttga caggcatttt gaaaaaaaca gaaacaatgc attagatttt 37260
gtcaccaaat cctataatga aacaaaaatt aagtttgata agtacaaagc tgaaaaatct 37320
cacgacgagc tccccaggac ctttcaaatt cctggataca ctgttccagt tgtcaatgtt 37380
gaagtgtctc cattcaccat agagatgtcg gcattcggct atgtgttccc aaaagcagtc 37440
agcatgccta gtttctccat cctaggttct gacgtccgtg tgccttcata cacattaatc 37500
ctgccatcat tagagctgcc agtccttcat gtccctagaa atctcaagct ttctcttcca 37560
gatttcaagg aattgtgtac cataagccat atttttattc ctgccatggg caatattacc 37620
tatgatttct cctttaaatc aagtgtcatc acactgaata ccaatgctga actttttaac 37680
cagtcagata ttgttgctca tctcctttct tcatcttcat ctgtcattga tgcactgcag 37740
tacaaattag agggcaccac aagattgaca agaaaaaggg gattgaagtt agccacagct 37800
ctgtctctga gcaacaaatt tgtggagggt agtcataaca gtactgtgag cttaaccacg 37860
aaaaatatgg aagtgtcagt ggcaacaacc acaaaagccc aaattccaat tttgagaatg 37920
aatttcaagc aagaacttaa tggaaatacc aagtcaaaac ctactgtctc ttcctccatg 37980
gaatttaagt atgatttcaa ttcttcaatg ctgtactcta ccgctaaagg agcagttgac 38040
cacaagctta gcttggaaag cctcacctct tacttttcca ttgagtcatc taccaaagga 38100
gatgtcaagg gttcggttct ttctcgggaa tattcaggaa ctattgctag tgaggccaac 38160
acttacttga attccaagag cacacggtct tcagtgaagc tgcagggcac ttccaaaatt 38220
gatgatatct ggaaccttga agtaaaagaa aattttgctg gagaagccac actccaacgc 38280
atatattccc tctgggagca cagtacgaaa aaccacttac agctagaggg cctctttttc 38340
accaacggag aacatacaag caaagccacc ctggaactct ctccatggca aatgtcagct 38400
cttgttcagg tccatgcaag tcagcccagt tccttccatg atttccctga ccttggccag 38460
gaagtggccc tgaatgctaa cactaagaac cagaagatca gatggaaaaa tgaagtccgg 38520
attcattctg ggtctttcca gagccaggtc gagctttcca atgaccaaga aaaggcacac 38580
cttgacattg caggatcctt agaaggacac ctaaggttcc tcaaaaatat catcctacca 38640 gtctatgaca agagcttatg ggatttccta aagctggatg taaccaccag cattggtagg 38700
agacagcatc ttcgtgtttc aactgccttt gtgtacacca aaaaccccaa tggctattca 38760
ttctccatcc ctgtaaaagt tttggctgat aaattcatta ttcctgggct gaaactaaat 38820
gatctaaatt cagttcttgt catgcctacg ttccatgtcc catttacaga tcttcaggtt 38880
ccatcgtgca aacttgactt cagagaaata caaatctata agaagctgag aacttcatca 38940
tttgccctca acctaccaac actccccgag gtaaaattcc ctgaagttga tgtgttaaca 39000
aaatattctc aaccagaaga ctccttgatt cccttttttg agataaccgt gcctgaatct 39060
cagttaactg tgtcccagtt cacgcttcca aaaagtgttt cagatggcat tgctgctttg 39120
gatctaaatg cagtagccaa caagatcgca gactttgagt tgcccaccat catcgtgcct 39180
gagcagacca ttgagattcc ctccattaag ttctctgtac ctgctggaat tgtcattcct 39240
tcctttcaag cactgactgc acgctttgag gtagactctc ccgtgtataa tgccacttgg 39300
agtgccagtt tgaaaaacaa agcagattat gttgaaacag tcctggattc cacatgcagc 39360
tcaaccgtac agttcctaga atatgaacta aatggtaaga aatatcctgc ctcctctcct 39420
agatactgta tattttcaat gagagttatg agtaaataat tatgtattta gttgtgagta 39480
gatgtacaat tactcaatgt cacaaaattt taagtaagaa aagagataca tgtataccct 39540
acacgtaaaa accaaactgt agaaaatcta gtgtcattca agacaaacag ctttaaagaa 39600
aatggatttt tctgtaatta ttttaggact aacaatgtct tttaactatt tattttaaaa 39660
taagtgtgag ctgtacattg catattttaa acacaagtga aatatctggt taggatagaa 39720
ttctcccagt tttcacaatg aaaacatcaa cgtcctactg ttatgaatct aataaaatac 39780
aaaatctctc ctatacagtt ttgggaacac acaaaatcga agatggtacg ttagcctcta 39840
agactaaagg aacatttgca caccgtgact tcagtgcaga atatgaagaa gatggcaaat 39900
atgaaggact tcagtatgga gcttttattg aattgaaacc ttataccttt tgaaaactca 39960
ttgtgatttt cttcatctcc ataccccttt cgtgatagct catctgtttt tctgctttca 40020
gggaatggga aggaaaagcg cacctcaata tcaaaagccc agcgttcacc gatctccatc 40080
tgcgctacca gaaagacaag aaaggcatct ccacctcagc agcctcccca gccgtaggca 40140
ccgtgggcat ggatatggat gaagatgacg acttttctaa atggaacttc tactacagcc 40200
ctcaggtaaa taccacctaa tgagtgacac gcccccaaga gcgagtggag aattggggca 40260
gatacattta attcaggacc aaatattcag agattcccca aactaggtga aagacaggcg 40320
gtaagcaact tcttctctga ggaaatattc tctagaaagt attacaatga gtccttgatt 40380
gattttaatg tttagatgca cacatgacat cccatcagca ctattattta ttaattctgg 40440
gcaaatccag gaagatgagg gttatacctc atcatctaaa tcataggcaa gctcagccat 40500
aggcagggta tatttttcag agaggactgg tttctgtagt atttaaaact ttaaaattct 40560
tccccacaat agaattgcta gatgagatac atcaaattcc tctcatgtca tttacaagct 40620
ctgccagggc caaatcaagg gtgacattac cagaggagaa gaccaaacat ggttctatga 40680
ctgttactaa aagtttgtca tgggcttgga gaatgcgtac tgatgttggg attctgggtc 40740
tctgcagggt gggctccaac ttgccttttt tgctatttct tcttttccta tctgtcattt 40800
cctgactctt cttctctctc ctcttctttc tcttcccccc actcctcttc cagttttcag 40860
tcctaggaag gctttaattt taagtgtcac aatgtaaatg acaaacagca agcgtttttg 40920
ttaaatcctt tctggggcat gtgataaaga gaaattaaca acagtagact tatttaacca 40980
taaaacaaac acatgaactg acatatgaaa gataaatccc tttcagtata tgaaagattc 41040

```
tctgatcttt atttttaact gctaatgaag ttttagtgta ctatattgtg taattggagt  41100
aattgaaaac atgttatttt tttttttctc tctgtttagt cctctccaga taaaaaactc  41160
accatattca aaactgagtt gagggtccgg gaatctgatg aggaaactca gatcaaagtt  41220
aattgggaag aagaggcagc ttctggcttg ctaacctctc tgaaagacaa cgtgcccaag  41280
gccacagggg tcctttatga ttatgtcaac aagtaccact gggaacacac agggctcacc  41340
ctgagagaag tgtcttcaaa gctgagaaga aatctgcaga acaatgctga gtgggtttat  41400
caaggggcca ttaggcaaat tgatgatatc gacgtgaggt tccagaaagc agccagtggc  41460
accactggga cctaccaaga gtggaaggac aaggcccaga atctgtacca ggaactgttg  41520
actcaggaag gccaagccag tttccaggga ctcaaggata acgtgtttga tggcttggta  41580
cgagttactc aagaattcca tatgaaagtc aagcatctga ttgactcact cattgatttt  41640
ctgaacttcc ccagattcca gtttccgggg aaacctggga tatacactag ggaggaactt  41700
tgcactatgt tcataaggga ggtagggacg gtactgtccc aggtatattc gaaagtccat  41760
aatggttcag aaatactgtt ttcctatttc caagacctag tgattacact tcctttcgag  41820
ttaaggaaac ataaactaat agatgtaatc tcgatgtata gggaactgtt gaaagattta  41880
tcaaaagaag cccaagaggt atttaaagcc attcagtctc tcaagaccac agaggtgcta  41940
cgtaatcttc aggacctttt acaattcatt ttccaactaa tagaagataa cattaaacag  42000
ctgaaagaga tgaaatttac ttatcttatt aattatatcc aagatgagat caacacaatc  42060
ttcagtgatt atatcccata tgtttttaaa ttgttgaaag aaaacctatg ccttaatctt  42120
cataagttca atgaatttat tcaaaacgag cttcaggaag cttctcaaga gttacagcag  42180
atccatcaat acattatggc ccttcgtgaa gaatattttg atccaagtat agttggctgg  42240
acagtgaaat attatgaact tgaagaaaag atagtcagtc tgatcaagaa cctgttagtt  42300
gctcttaagg acttccattc tgaatatatt gtcagtgcct ctaactttac ttcccaactc  42360
tcaagtcaag ttgagcaatt tctgcacaga aatattcagg aatatcttag catccttacc  42420
gatccagatg gaaaagggaa agagaagatt gcagagcttt ctgccactgc tcaggaaata  42480
attaaaagcc aggccattgc gacgaagaaa ataatttctg attaccacca gcagtttaga  42540
tataaactgc aagatttttc agaccaactc tctgattact atgaaaaatt tattgctgaa  42600
tccaaaagat tgattgacct gtccattcaa aactaccaca catttctgat atacatcacg  42660
gagttactga aaaagctgca atcaaccaca gtcatgaacc cctacatgaa gcttgctcca  42720
ggagaactta ctatcatcct ctaatttttt aaaagaaatc ttcatttatt cttcttttcc  42780
aattgaactt tcacatagca cagaaaaaat tcaaactgcc tatattgata aaaccataca  42840
gtgagccagc cttgcagtag gcagtagact ataagcagaa gcacatatga actggacctg  42900
caccaaagct ggcaccaggg ctcggaaggt ctctgaactc agaaggatgg catttttttgc  42960
aagttaaaga aaatcaggat ctgagttatt ttgctaaact tgggggagga ggaacaaata  43020
aatggagtct ttattgtgta tcataccact gaatgtggct catttgtatt gaaagacagt  43080
gaaacgaggg cattgataaa atgttctggc acagcaaaac ctctagaaca catagtgtga  43140
tttaagtaac agaataaaaa tggaaacgga gaaattatgg agggaaatat tttgcaaaaa  43200
tatttaaaaa gatgaggtaa ttgtgttttt ataattaaat attttataat taaaatattt  43260
ataattaaaa tatttataat taaatatttt ataattaaaa tatttataat taaatatttt  43320
ataattaaag tatttataat taaatatttt ataattaaaa tatttataat taaatatttt  43380
ataattaaaa tatttataat taaatatttt ataattaaaa tatttataat taaatatttt  43440
```

ataat 43445

<210> SEQ ID NO 335
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 335 tctgtaagac aggagaaaga 20

<210> SEQ ID NO 336
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 336 atttcctctt ctgtaagaca 20

<210> SEQ ID NO 337
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 337 gatgccttac ttggacagac 20

<210> SEQ ID NO 338
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 338 agaaatagct ctcccaagga 20

<210> SEQ ID NO 339
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 339 gtcgcatctt ctaacgtggg 20

<210> SEQ ID NO 340
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 340 tcctccatac cttgcagttg 20

<210> SEQ ID NO 341
<211> LENGTH: 20
<212> TYPE: DNA
<213> ORGANISM: Artificial Sequence <220> FEATURE:
<223> OTHER INFORMATION: Antisense Oligonucleotide

<400> SEQUENCE: 341 tggctcatgt ctaccatatt 20

<210> SEQ ID NO 342
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 342 cagttgaaat gcagctaatg 20

<210> SEQ ID NO 343
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 343 tgcagactag gagtgaaagt 20

<210> SEQ ID NO 344
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 344 aggaggatgt ccttttattg 20

<210> SEQ ID NO 345
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 345 atcagagcac caaagggaat 20

<210> SEQ ID NO 346
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 346 ccagctcaac ctgagaattc 20

<210> SEQ ID NO 347
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 347 catgacttac ctggacatgg 20

<210> SEQ ID NO 348
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 348 cctcagcgga cacacacaca 20

<210> SEQ ID NO 349
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 349 gtcacatccg tgcctggtgc 20

<210> SEQ ID NO 350
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 350 cagtgcctct gggaccccac 20

<210> SEQ ID NO 351
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 351 agctgcagtg gccgatcagc 20

<210> SEQ ID NO 352
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 352 gacctcccca gccacgtgga 20

<210> SEQ ID NO 353
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 353 tctgatcacc atacattaca 20

<210> SEQ ID NO 354
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 354 atttcccact gggtactctc 20

<210> SEQ ID NO 355
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 355 ggctgaagcc catgctgact 20

<210> SEQ ID NO 356
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 356 gttggacagt cattcttttg 20

<210> SEQ ID NO 357
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 357 cacttgttgg acagtcattc 20

<210> SEQ ID NO 358
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 358 attttaaatt acagtagata 20

<210> SEQ ID NO 359
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 359 ctgttctcca cccatatcag 20

<210> SEQ ID NO 360
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 360 gagctcatac ctgtcccaga 20

<210> SEQ ID NO 361
<211> LENGTH: 20
<212> TYPE: DNA
<213> ORGANISM: Artificial Sequence <220> FEATURE:
<223> OTHER INFORMATION: Antisense Oligonucleotide

<400> SEQUENCE: 361 ttcaagggcc actgctatca 20

<210> SEQ ID NO 362
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 362 ccagtatttc acgccaatcc 20

<210> SEQ ID NO 363
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 363 ggcaggagga acctcgggca 20

<210> SEQ ID NO 364
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 364 ttttaaaatt agacccaacc 20

<210> SEQ ID NO 365
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 365 tgactgtttt aaaattagac 20

<210> SEQ ID NO 366
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 366 cccagcaaac acaggtgaag 20

<210> SEQ ID NO 367
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 367 gagtgtggtc ttgctagtgc 20

<210> SEQ ID NO 368
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 368 ctatgcagag tgtggtcttg 20

<210> SEQ ID NO 369
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 369 agaagatgca accacatgta 20

<210> SEQ ID NO 370
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 370 acacggtatc ctatggagga 20

<210> SEQ ID NO 371
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 371 tgggacttac catgcctttg 20

<210> SEQ ID NO 372
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 372 ggttttgctg ccctacatcc 20

<210> SEQ ID NO 373
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 373 acaaggagtc cttgtgcaga 20

<210> SEQ ID NO 374
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 374 atgttcactg agacaggctg 20

<210> SEQ ID NO 375
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 375 gaaggtccat ggttcatctg 20

<210> SEQ ID NO 376
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 376 attagactgg aagcatcctg 20

<210> SEQ ID NO 377
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 377 gagattggag acgagcattt 20

<210> SEQ ID NO 378
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 378 catgacctac ttgtaggaga 20

<210> SEQ ID NO 379
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 379 tggatttgga tacacaagtt 20

<210> SEQ ID NO 380
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 380 actcaatata tattcattga 20

<210> SEQ ID NO 381
<211> LENGTH: 20
<212> TYPE: DNA
<213> ORGANISM: Artificial Sequence <220> FEATURE:
<223> OTHER INFORMATION: Antisense Oligonucleotide

<400> SEQUENCE: 381 caaggaagca caccatgtca 20

<210> SEQ ID NO 382
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 382 atacttattc ctggtaacca 20

<210> SEQ ID NO 383
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 383 ggtagccaga acaccagtgt 20

<210> SEQ ID NO 384
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 384 actagaggta gccagaacac 20

<210> SEQ ID NO 385
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 385 accacctgac atcacaggtt 20

<210> SEQ ID NO 386
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 386 tactgtgacc tatgccagga 20

<210> SEQ ID NO 387
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 387 ggaggtgcta ctgttgacat 20

<210> SEQ ID NO 388
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 388 tccagacttg tctgagtcta 20

<210> SEQ ID NO 389
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 389 tctaagaggt agagctaaag 20

<210> SEQ ID NO 390
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 390 ccagagatga gcaacttagg 20

<210> SEQ ID NO 391
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 391 ggccatgtaa attgctcatc 20

<210> SEQ ID NO 392
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 392 aaagaaacta tcctgtattc 20

<210> SEQ ID NO 393
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 393 ttcttagtac ctggaagatg 20

<210> SEQ ID NO 394
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 394 cattagatac ctggacacct 20

<210> SEQ ID NO 395
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 395 gtttcatgga actcagcgca 20

<210> SEQ ID NO 396
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 396 ctggagagca cctgcaatag 20

<210> SEQ ID NO 397
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 397 tgaagggtag agaaatcata 20

<210> SEQ ID NO 398
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 398 ggaaactcac ttgttgaccg 20

<210> SEQ ID NO 399
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 399 aggtgcaaga tgttcctctg 20

<210> SEQ ID NO 400
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 400 tgcacagagg tgcaagatgt 20

<210> SEQ ID NO 401
<211> LENGTH: 20
<212> TYPE: DNA
<213> ORGANISM: Artificial Sequence <220> FEATURE:
<223> OTHER INFORMATION: Antisense Oligonucleotide

<400> SEQUENCE: 401 cacaagagta aggagcagag 20

<210> SEQ ID NO 402
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 402 gatggatggt gagaaattac 20

<210> SEQ ID NO 403
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 403 tagacaattg agactcagaa 20

<210> SEQ ID NO 404
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 404 atgtgcacac aaggacatag 20

<210> SEQ ID NO 405
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 405 acatacaaat ggcaataggc 20

<210> SEQ ID NO 406
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 406 taggcaaagg acatgaatag 20

<210> SEQ ID NO 407
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 407 ttatgatagc tacagaataa 20

<210> SEQ ID NO 408
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 408 ctgagattac ccgcagaatc 20

<210> SEQ ID NO 409
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 409 gatgtatgtc atataaaaga 20

<210> SEQ ID NO 410
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 410 tttccaatga cctgcattga 20

<210> SEQ ID NO 411
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 411 agggatggtc aatctggtag 20

<210> SEQ ID NO 412
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 412 ggctaataaa tagggtagtt 20

<210> SEQ ID NO 413
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 413 tcctagagca ctatcaagta 20

<210> SEQ ID NO 414
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 414 cctcctggtc ctgcagtcaa 20

<210> SEQ ID NO 415
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 415 catttgcaca agtgtttgtt 20

<210> SEQ ID NO 416
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 416 ctgacacacc atgttattat 20

<210> SEQ ID NO 417
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 417 ctttttcaga ctagataaga 20

<210> SEQ ID NO 418
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 418 tcacacttac ctcgatgagg 20

<210> SEQ ID NO 419
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 419 aagaaaatgg catcaggttt 20

<210> SEQ ID NO 420
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 420 ccaagccaat ctgagaaaga 20

<210> SEQ ID NO 421
<211> LENGTH: 20
<212> TYPE: DNA
<213> ORGANISM: Artificial Sequence <220> FEATURE:
<223> OTHER INFORMATION: Antisense Oligonucleotide

<400> SEQUENCE: 421 aaatacacac ctgctcatgt 20

<210> SEQ ID NO 422
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 422 cttcacaaat acacacctgc 20

<210> SEQ ID NO 423
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 423 agtggaagtt tggtctcatt 20

<210> SEQ ID NO 424
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 424 ttgctagctt caaagtggaa 20

<210> SEQ ID NO 425
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 425 tcaagaataa gctccagatc 20

<210> SEQ ID NO 426
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 426 gcatacaagt cacatgaggt 20

<210> SEQ ID NO 427
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 427 tacaaggtgt ttcttaagaa 20

<210> SEQ ID NO 428
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 428 atgcagccag gatgggccta 20

<210> SEQ ID NO 429
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 429 ttaccatatc ctgagagttt 20

<210> SEQ ID NO 430
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 430 gcaaaggtag aggaaggtat 20

<210> SEQ ID NO 431
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 431 aaggaccttc agcaaaggta 20

<210> SEQ ID NO 432
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 432 cataggagta catttatata 20

<210> SEQ ID NO 433
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 433 attatgataa aatcaatttt 20

<210> SEQ ID NO 434
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 434 agaaatttca ctagatagat 20

<210> SEQ ID NO 435
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 435 agcatatttt gatgagctga 20

<210> SEQ ID NO 436
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 436 gaaaggaagg actagcatat 20

<210> SEQ ID NO 437
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 437 cctctccaat ctgtagaccc 20

<210> SEQ ID NO 438
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 438 ctggataact cagacctttg 20

<210> SEQ ID NO 439
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 439 agtcagaaaa caacctattc 20

<210> SEQ ID NO 440
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 440 cagcctgcat ctataagtca 20

<210> SEQ ID NO 441
<211> LENGTH: 20
<212> TYPE: DNA
<213> ORGANISM: Artificial Sequence <220> FEATURE:
<223> OTHER INFORMATION: Antisense Oligonucleotide

<400> SEQUENCE: 441 aaagaattac cctccactga 20

<210> SEQ ID NO 442
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 442 tctttcaaac tggctaggca 20

<210> SEQ ID NO 443
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 443 gcctggcaaa attctgcagg 20

<210> SEQ ID NO 444
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 444 ctacctcaaa tcaatatgtt 20

<210> SEQ ID NO 445
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 445 tgctttacct acctagctac 20

<210> SEQ ID NO 446
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 446 accttgtgtg tctcactcaa 20

<210> SEQ ID NO 447
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 447 atgcattccc tgactagcac 20

<210> SEQ ID NO 448
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 448 catctctgag ccccttacca 20

<210> SEQ ID NO 449
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 449 gctgggcatg ctctctcccc 20

<210> SEQ ID NO 450
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 450 gctttcgcag ctgggcatgc 20

<210> SEQ ID NO 451
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 451 actcctttct atacctggct 20

<210> SEQ ID NO 452
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 452 attctgcctc ttagaaagtt 20

<210> SEQ ID NO 453
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 453 ccaagcctct ttactgggct 20

<210> SEQ ID NO 454
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 454 cactcatgac cagactaaga 20

<210> SEQ ID NO 455
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 455 acctcccaga agccttccat 20

<210> SEQ ID NO 456
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 456 ttcatatgaa atctcctact 20

<210> SEQ ID NO 457
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 457 tatttaattt actgagaaac 20

<210> SEQ ID NO 458
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 458 taatgtgttg ctggtgaaga 20

<210> SEQ ID NO 459
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 459 catctctaac ctggtgtccc 20

<210> SEQ ID NO 460
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 460 gtgccatgct aggtggccat 20

<210> SEQ ID NO 461
<211> LENGTH: 20
<212> TYPE: DNA
<213> ORGANISM: Artificial Sequence <220> FEATURE:
<223> OTHER INFORMATION: Antisense Oligonucleotide

<400> SEQUENCE: 461 agcaaattgg gatctgtgct 20

<210> SEQ ID NO 462
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 462 tctggaggct cagaaacatg 20

<210> SEQ ID NO 463
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 463 tgaagacagg gagccaccta 20

<210> SEQ ID NO 464
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 464 aggattccca agactttgga 20

<210> SEQ ID NO 465
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 465 cagctctaat ctaaagacat 20

<210> SEQ ID NO 466
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 466 gaatactcac cttctgcttg 20

<210> SEQ ID NO 467
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 467 atctctctgt cctcatcttc 20

<210> SEQ ID NO 468
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 468 ccaactcccc ctttctttgt 20

<210> SEQ ID NO 469
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 469 tctgggccag gaagacacga 20

<210> SEQ ID NO 470
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 470 tattgtgtgc tgggcactgc 20

<210> SEQ ID NO 471
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 471 tgcttcgcac ctggacgagt 20

<210> SEQ ID NO 472
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 472 ccttctttac cttaggtggc 20

<210> SEQ ID NO 473
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 473 gctctctctg ccactctgat 20

<210> SEQ ID NO 474
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 474 aacttctaaa gccaacattc 20

<210> SEQ ID NO 475
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 475 tgtgtcacaa ctatggtaaa 20

<210> SEQ ID NO 476
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 476 agacacatac cataatgcca 20

<210> SEQ ID NO 477
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 477 ttctcttcat ctgaaaatac 20

<210> SEQ ID NO 478
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 478 tgaggatgta attagcactt 20

<210> SEQ ID NO 479
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 479 agctcattgc ctacaaaatg 20

<210> SEQ ID NO 480
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 480 gttctcatgt ttactaatgc 20

<210> SEQ ID NO 481
<211> LENGTH: 20
<212> TYPE: DNA
<213> ORGANISM: Artificial Sequence <220> FEATURE:
<223> OTHER INFORMATION: Antisense Oligonucleotide

<400> SEQUENCE: 481 gaattgagac aacttgattt 20

<210> SEQ ID NO 482
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 482 ccggccatcg ctgaaatgaa 20

<210> SEQ ID NO 483
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 483 catagctcac cttgcacatt 20

<210> SEQ ID NO 484
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 484 cggtgcaccc tttacctgag 20

<210> SEQ ID NO 485
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 485 tctccagatc ctaacataaa 20

<210> SEQ ID NO 486
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 486 ttgaatgaca ctagattttc 20

<210> SEQ ID NO 487
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 487 aaaatccatt ttctttaaag 20

<210> SEQ ID NO 488
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 488 cagctcacac ttattttaaa 20

<210> SEQ ID NO 489
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 489 gttcccaaaa ctgtatagga 20

<210> SEQ ID NO 490
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 490 agctccatac tgaagtcctt 20

<210> SEQ ID NO 491
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 491 caattcaata aaagctccat 20

<210> SEQ ID NO 492
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 492 gttttcaaaa ggtataaggt 20

<210> SEQ ID NO 493
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 493 ttcccattcc ctgaaagcag 20

<210> SEQ ID NO 494
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 494 tggtatttac ctgagggctg 20

<210> SEQ ID NO 495
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 495 ataaataata gtgctgatgg 20

<210> SEQ ID NO 496
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 496 ctatggctga gcttgcctat 20

<210> SEQ ID NO 497
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 497 ctctctgaaa aatataccct 20

<210> SEQ ID NO 498
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 498 ttgatgtatc tcatctagca 20

<210> SEQ ID NO 499
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 499 tagaaccatg tttggtcttc 20

<210> SEQ ID NO 500
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 500 tttctcttta tcacatgccc 20

<210> SEQ ID NO 501
<211> LENGTH: 20
<212> TYPE: DNA
<213> ORGANISM: Artificial Sequence <220> FEATURE:
<223> OTHER INFORMATION: Antisense Oligonucleotide

<400> SEQUENCE: 501 tatagtacac taaaacttca 20

<210> SEQ ID NO 502
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 502 ctggagagga ctaaacagag 20

<210> SEQ ID NO 503
<211> LENGTH: 568
<212> TYPE: DNA
<213> ORGANISM: H. sapiens
<220> FEATURE:
<221> NAME/KEY: misc_feature
<222> LOCATION: 44, 99, 156, 468
<223> OTHER INFORMATION: n = A,T,C or G

<400> SEQUENCE: 503 ccaaaagatt gattgactgt ccattcaaag ctacacgcaa tttntgatat acatcacgta 60 gttactgaaa aagctgcaat caacacagtt catggaccnc taccatgaag cttgctccag 120 gagaacttct atcattcctc taatttttta aaaganatct tcatttattc ttcttttcca 180 attgaacttt cacatagcac agaaaaaatt caaactgcct atattgataa aaccatacag 240 tgagccagcc ttgcagtagg cagtagacta taagcagaag cacatatgaa ctggacctgc 300 accaaagctg gcaccagggc tcggaaggtc tctgaactca gaaggatggc atttttttgca 360 agttaaagaa aatcaggatc tgagttattt tgctaaactt gggggaggag gaacaaataa 420 atggagtctt tattgtgtat cataccactg aatgtggctc atttgtanta aaagacagtg 480 aaacgagggc attgataaaa tgttctggca cagcaaaacc tctagaacac atagtgtgat 540 ttaagtaaca gaataaaaat ggaaacgg 568

<210> SEQ ID NO 504
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 504 acattttatc aatgccctcg 20

<210> SEQ ID NO 505
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 505 gccagaacat tttatcaatg 20

<210> SEQ ID NO 506
<211> LENGTH: 20
<212> TYPE: DNA
<213> ORGANISM: Artificial Sequence <220> FEATURE:
<223> OTHER INFORMATION: Antisense Oligonucleotide

<400> SEQUENCE: 506 agaggttttg ctgtgccaga 20

<210> SEQ ID NO 507
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 507 ctagaggttt tgctgtgcca 20

<210> SEQ ID NO 508
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 508 tctagaggtt ttgctgtgcc 20

<210> SEQ ID NO 509
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 509 aatcacacta tgtgttctag 20

<210> SEQ ID NO 510
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 510 aaatcacact atgtgttcta 20

<210> SEQ ID NO 511
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 511 taaatcacac tatgtgttct 20

<210> SEQ ID NO 512
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 512 cttaaatcac actatgtgtt 20

<210> SEQ ID NO 513
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 513 tattctgtta cttaaatcac 20

<210> SEQ ID NO 514
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 514 tggtagcctc agtctgcttc 20

<210> SEQ ID NO 515
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 515 agtctgcttc gcgccttctg 20

<210> SEQ ID NO 516
<211> LENGTH: 20
<212> TYPE: DNA
<213> ORGANISM: H. sapiens

<400> SEQUENCE: 516 gcgccagggc cgaagaggaa 20

<210> SEQ ID NO 517
<211> LENGTH: 20
<212> TYPE: DNA
<213> ORGANISM: H. sapiens

<400> SEQUENCE: 517 caggtatgag ctcaagctgg 20

<210> SEQ ID NO 518
<211> LENGTH: 20
<212> TYPE: DNA
<213> ORGANISM: H. sapiens

<400> SEQUENCE: 518 catcctgaac atcaagaggg 20

<210> SEQ ID NO 519
<211> LENGTH: 20
<212> TYPE: DNA
<213> ORGANISM: H. sapiens

<400> SEQUENCE: 519 gggcagtgtg atcgcttcaa 20

<210> SEQ ID NO 520
<211> LENGTH: 20
<212> TYPE: DNA
<213> ORGANISM: H. sapiens

<400> SEQUENCE: 520 cacttgctct catcaaaggc 20

<210> SEQ ID NO 521
<211> LENGTH: 20
<212> TYPE: DNA
<213> ORGANISM: H. sapiens

<400> SEQUENCE: 521 cacactggac gctaagagga 20

<210> SEQ ID NO 522
<211> LENGTH: 20
<212> TYPE: DNA
<213> ORGANISM: H. sapiens

<400> SEQUENCE: 522 cgctgagcca cgcggtcaac 20

<210> SEQ ID NO 523
<211> LENGTH: 20
<212> TYPE: DNA
<213> ORGANISM: H. sapiens

<400> SEQUENCE: 523 tgtccaaatt ctaccatggg 20

<210> SEQ ID NO 524
<211> LENGTH: 20
<212> TYPE: DNA
<213> ORGANISM: H. sapiens

<400> SEQUENCE: 524 cagctgacct catcgagatt 20

<210> SEQ ID NO 525
<211> LENGTH: 20
<212> TYPE: DNA
<213> ORGANISM: H. sapiens

<400> SEQUENCE: 525 gtcaagttcc tgatggtgtc 20

<210> SEQ ID NO 526
<211> LENGTH: 20
<212> TYPE: DNA
<213> ORGANISM: H. sapiens

<400> SEQUENCE: 526 agctgcttct gatgggtgcc 20

<210> SEQ ID NO 527
<211> LENGTH: 20
<212> TYPE: DNA
<213> ORGANISM: H. sapiens

<400> SEQUENCE: 527 gggcatcatc attccggact 20

<210> SEQ ID NO 528
<211> LENGTH: 20
<212> TYPE: DNA
<213> ORGANISM: H. sapiens

<400> SEQUENCE: 528 cctactatcc gctgaccggg 20

<210> SEQ ID NO 529
<211> LENGTH: 20
<212> TYPE: DNA
<213> ORGANISM: H. sapiens

<400> SEQUENCE: 529 gggccaccta agttgtgaca 20

<210> SEQ ID NO 530
<211> LENGTH: 20
<212> TYPE: DNA
<213> ORGANISM: H. sapiens

<400> SEQUENCE: 530 agaacatggg attgccagac 20

<210> SEQ ID NO 531
<211> LENGTH: 20
<212> TYPE: DNA
<213> ORGANISM: H. sapiens

<400> SEQUENCE: 531 ctccacttca agtctgtggg 20

<210> SEQ ID NO 532
<211> LENGTH: 20
<212> TYPE: DNA
<213> ORGANISM: H. sapiens

<400> SEQUENCE: 532 cagagcttgg cctctctggg 20

<210> SEQ ID NO 533
<211> LENGTH: 20
<212> TYPE: DNA
<213> ORGANISM: H. sapiens

<400> SEQUENCE: 533 tggccgcttc agggaacaca 20

<210> SEQ ID NO 534
<211> LENGTH: 20
<212> TYPE: DNA
<213> ORGANISM: H. sapiens

<400> SEQUENCE: 534 cagctgagca gacaggcacc 20

<210> SEQ ID NO 535
<211> LENGTH: 20
<212> TYPE: DNA
<213> ORGANISM: H. sapiens

<400> SEQUENCE: 535 gggagagaca agtttcacat 20

<210> SEQ ID NO 536
<211> LENGTH: 20
<212> TYPE: DNA
<213> ORGANISM: H. sapiens

<400> SEQUENCE: 536 gtactgcatc ctggattcaa 20

<210> SEQ ID NO 537
<211> LENGTH: 20
<212> TYPE: DNA
<213> ORGANISM: H. sapiens

<400> SEQUENCE: 537 gtgaggtgac tcagagactc 20

<210> SEQ ID NO 538
<211> LENGTH: 20
<212> TYPE: DNA
<213> ORGANISM: H. sapiens

<400> SEQUENCE: 538 ttgcagagca atattctatc 20

<210> SEQ ID NO 539
<211> LENGTH: 20
<212> TYPE: DNA
<213> ORGANISM: H. sapiens

<400> SEQUENCE: 539 aagcattggt agagcaaggg 20

<210> SEQ ID NO 540
<211> LENGTH: 20
<212> TYPE: DNA
<213> ORGANISM: H. sapiens

<400> SEQUENCE: 540 ccgctggctc tgaaggagtc 20

<210> SEQ ID NO 541
<211> LENGTH: 20
<212> TYPE: DNA
<213> ORGANISM: H. sapiens

<400> SEQUENCE: 541 tctagtcagg ctgacctgcg 20

<210> SEQ ID NO 542
<211> LENGTH: 20
<212> TYPE: DNA
<213> ORGANISM: H. sapiens

<400> SEQUENCE: 542 gggccacagt gttctaactg 20

<210> SEQ ID NO 543
<211> LENGTH: 20
<212> TYPE: DNA
<213> ORGANISM: H. sapiens

<400> SEQUENCE: 543 aatcaagtgt catcacactg 20

<210> SEQ ID NO 544
<211> LENGTH: 20
<212> TYPE: DNA
<213> ORGANISM: H. sapiens

<400> SEQUENCE: 544 gggtagtcat aacagtactg 20

<210> SEQ ID NO 545
<211> LENGTH: 20
<212> TYPE: DNA
<213> ORGANISM: H. sapiens

<400> SEQUENCE: 545 agagcacacg gtcttcagtg 20

<210> SEQ ID NO 546
<211> LENGTH: 20
<212> TYPE: DNA
<213> ORGANISM: H. sapiens

<400> SEQUENCE: 546 ttacagctag agggcctctt 20

<210> SEQ ID NO 547
<211> LENGTH: 20
<212> TYPE: DNA
<213> ORGANISM: H. sapiens

<400> SEQUENCE: 547 caccgtgggc atggatatgg 20

<210> SEQ ID NO 548
<211> LENGTH: 20
<212> TYPE: DNA
<213> ORGANISM: H. sapiens

<400> SEQUENCE: 548 gggaatctga tgaggaaact 20

<210> SEQ ID NO 549
<211> LENGTH: 20
<212> TYPE: DNA
<213> ORGANISM: H. sapiens

<400> SEQUENCE: 549 tgtcaacaag taccactggg 20

<210> SEQ ID NO 550
<211> LENGTH: 20
<212> TYPE: DNA
<213> ORGANISM: H. sapiens

<400> SEQUENCE: 550 acctgggata tacactaggg 20

<210> SEQ ID NO 551
<211> LENGTH: 20
<212> TYPE: DNA
<213> ORGANISM: H. sapiens

<400> SEQUENCE: 551 ccaagtatag ttggctggac 20

<210> SEQ ID NO 552
<211> LENGTH: 20
<212> TYPE: DNA
<213> ORGANISM: H. sapiens

<400> SEQUENCE: 552 tacatgaagc ttgctccagg 20

<210> SEQ ID NO 553
<211> LENGTH: 20
<212> TYPE: DNA
<213> ORGANISM: H. sapiens

<400> SEQUENCE: 553 atgtcagcct ggtctgtcca 20

<210> SEQ ID NO 554
<211> LENGTH: 20
<212> TYPE: DNA
<213> ORGANISM: H. sapiens

<400> SEQUENCE: 554 gcacctccgg aagtacacat 20

<210> SEQ ID NO 555
<211> LENGTH: 20
<212> TYPE: DNA
<213> ORGANISM: H. sapiens

<400> SEQUENCE: 555 ctgcagcttc atcctgaaga 20

<210> SEQ ID NO 556
<211> LENGTH: 20
<212> TYPE: DNA
<213> ORGANISM: H. sapiens

<400> SEQUENCE: 556 tgagggcaaa gccttgctga 20

<210> SEQ ID NO 557
<211> LENGTH: 20
<212> TYPE: DNA
<213> ORGANISM: H. sapiens

<400> SEQUENCE: 557 ccattccaga agggaagcag 20

<210> SEQ ID NO 558
<211> LENGTH: 20
<212> TYPE: DNA
<213> ORGANISM: H. sapiens

<400> SEQUENCE: 558 cgaggaaggg caatgtggca 20

<210> SEQ ID NO 559
<211> LENGTH: 20
<212> TYPE: DNA
<213> ORGANISM: H. sapiens

<400> SEQUENCE: 559 ccttgtcaac tctgatcagc 20

<210> SEQ ID NO 560
<211> LENGTH: 20
<212> TYPE: DNA
<213> ORGANISM: H. sapiens

<400> SEQUENCE: 560 agcagccagt cctgtcagta 20

<210> SEQ ID NO 561
<211> LENGTH: 20
<212> TYPE: DNA
<213> ORGANISM: H. sapiens

<400> SEQUENCE: 561 agcatgtggc agaagccatc 20

<210> SEQ ID NO 562
<211> LENGTH: 20
<212> TYPE: DNA
<213> ORGANISM: H. sapiens

<400> SEQUENCE: 562 gagagcacca aatccacatc 20

<210> SEQ ID NO 563
<211> LENGTH: 20
<212> TYPE: DNA
<213> ORGANISM: H. sapiens

<400> SEQUENCE: 563 cctcagtgat gaagcagtca 20

<210> SEQ ID NO 564
<211> LENGTH: 20
<212> TYPE: DNA
<213> ORGANISM: H. sapiens

<400> SEQUENCE: 564 gatagatgtg gtcacctacc 20

<210> SEQ ID NO 565
<211> LENGTH: 20
<212> TYPE: DNA
<213> ORGANISM: H. sapiens

<400> SEQUENCE: 565 cctcagcaca gcagctgcga 20

<210> SEQ ID NO 566
<211> LENGTH: 20
<212> TYPE: DNA
<213> ORGANISM: H. sapiens

<400> SEQUENCE: 566 gattctgcgg gtcattggaa 20

<210> SEQ ID NO 567
<211> LENGTH: 20
<212> TYPE: DNA
<213> ORGANISM: H. sapiens

<400> SEQUENCE: 567 caaagccatc actgatgatc 20

<210> SEQ ID NO 568
<211> LENGTH: 20
<212> TYPE: DNA
<213> ORGANISM: H. sapiens

<400> SEQUENCE: 568 agaaagctgc catccaggct 20

<210> SEQ ID NO 569
<211> LENGTH: 20
<212> TYPE: DNA
<213> ORGANISM: H. sapiens

<400> SEQUENCE: 569 caggaggttc ttcttcagac 20

<210> SEQ ID NO 570
<211> LENGTH: 20
<212> TYPE: DNA
<213> ORGANISM: H. sapiens

<400> SEQUENCE: 570 gagtccttca caggcagata 20

<210> SEQ ID NO 571
<211> LENGTH: 20
<212> TYPE: DNA
<213> ORGANISM: H. sapiens

<400> SEQUENCE: 571 tgccaatatc ttgaactcag 20

<210> SEQ ID NO 572
<211> LENGTH: 20
<212> TYPE: DNA
<213> ORGANISM: H. sapiens

<400> SEQUENCE: 572 catcgagatt ggcttggaag 20

<210> SEQ ID NO 573
<211> LENGTH: 20
<212> TYPE: DNA
<213> ORGANISM: H. sapiens

<400> SEQUENCE: 573 ggagctggat tacagttgca 20

<210> SEQ ID NO 574
<211> LENGTH: 20
<212> TYPE: DNA
<213> ORGANISM: H. sapiens

<400> SEQUENCE: 574 caacatgcag gctgaactgg 20

<210> SEQ ID NO 575
<211> LENGTH: 20
<212> TYPE: DNA
<213> ORGANISM: H. sapiens

<400> SEQUENCE: 575 acattacatt tggtctctac 20

<210> SEQ ID NO 576
<211> LENGTH: 20
<212> TYPE: DNA
<213> ORGANISM: H. sapiens

<400> SEQUENCE: 576 ctcaggcgct tactccaacg 20

<210> SEQ ID NO 577
<211> LENGTH: 20
<212> TYPE: DNA
<213> ORGANISM: H. sapiens

<400> SEQUENCE: 577 gggacaccag attagagctg 20

<210> SEQ ID NO 578
<211> LENGTH: 20
<212> TYPE: DNA
<213> ORGANISM: H. sapiens

<400> SEQUENCE: 578 gagctccaga gagaggacag 20

<210> SEQ ID NO 579
<211> LENGTH: 20
<212> TYPE: DNA
<213> ORGANISM: H. sapiens

<400> SEQUENCE: 579 atcggcagag tatgaccttg 20

<210> SEQ ID NO 580
<211> LENGTH: 20
<212> TYPE: DNA
<213> ORGANISM: H. sapiens

<400> SEQUENCE: 580 caagggtgtt atttccatac 20

<210> SEQ ID NO 581
<211> LENGTH: 20
<212> TYPE: DNA
<213> ORGANISM: H. sapiens

<400> SEQUENCE: 581 gactcatctg ctacagctta 20

<210> SEQ ID NO 582
<211> LENGTH: 20
<212> TYPE: DNA
<213> ORGANISM: H. sapiens

<400> SEQUENCE: 582 gcaaatcctc cagagatcta 20

<210> SEQ ID NO 583
<211> LENGTH: 20
<212> TYPE: DNA
<213> ORGANISM: H. sapiens

<400> SEQUENCE: 583 ctctcctggg tgttctagac 20

<210> SEQ ID NO 584
<211> LENGTH: 20
<212> TYPE: DNA
<213> ORGANISM: H. sapiens

<400> SEQUENCE: 584 atgaaggctg actctgtggt 20

<210> SEQ ID NO 585
<211> LENGTH: 20
<212> TYPE: DNA
<213> ORGANISM: H. sapiens

<400> SEQUENCE: 585 gggaccacag atgtctgctt 20

<210> SEQ ID NO 586
<211> LENGTH: 20
<212> TYPE: DNA
<213> ORGANISM: H. sapiens

<400> SEQUENCE: 586 ctggccggct caatggagag 20

<210> SEQ ID NO 587
<211> LENGTH: 20
<212> TYPE: DNA
<213> ORGANISM: H. sapiens

<400> SEQUENCE: 587 gctgcgttct gaatatcagg 20

<210> SEQ ID NO 588
<211> LENGTH: 20
<212> TYPE: DNA
<213> ORGANISM: H. sapiens

<400> SEQUENCE: 588 tgctgacatc ttaggcactg 20

<210> SEQ ID NO 589
<211> LENGTH: 20
<212> TYPE: DNA
<213> ORGANISM: H. sapiens

<400> SEQUENCE: 589 aagtgtagtc tcctggtgct 20

<210> SEQ ID NO 590
<211> LENGTH: 20
<212> TYPE: DNA
<213> ORGANISM: H. sapiens

<400> SEQUENCE: 590 caaaattcag tctggatggg 20

<210> SEQ ID NO 591
<211> LENGTH: 20
<212> TYPE: DNA
<213> ORGANISM: H. sapiens

<400> SEQUENCE: 591 gggaaactac ggctagaacc 20

<210> SEQ ID NO 592
<211> LENGTH: 20
<212> TYPE: DNA
<213> ORGANISM: H. sapiens

<400> SEQUENCE: 592 ctgcatgtgg ctggtaacct 20

<210> SEQ ID NO 593
<211> LENGTH: 20
<212> TYPE: DNA
<213> ORGANISM: H. sapiens

<400> SEQUENCE: 593 ccatgaccat cgatgcacat 20

<210> SEQ ID NO 594
<211> LENGTH: 20
<212> TYPE: DNA
<213> ORGANISM: H. sapiens

<400> SEQUENCE: 594 atgggaaact cgctctctgg 20

<210> SEQ ID NO 595
<211> LENGTH: 20
<212> TYPE: DNA
<213> ORGANISM: H. sapiens

<400> SEQUENCE: 595 agtcatcatc tcgtgtctag 20

<210> SEQ ID NO 596
<211> LENGTH: 20
<212> TYPE: DNA
<213> ORGANISM: H. sapiens

<400> SEQUENCE: 596 gaatacagcc aggacttgga 20

<210> SEQ ID NO 597
<211> LENGTH: 20
<212> TYPE: DNA
<213> ORGANISM: H. sapiens

<400> SEQUENCE: 597 ggcgtggagc ttactggacg 20

<210> SEQ ID NO 598
<211> LENGTH: 20
<212> TYPE: DNA
<213> ORGANISM: H. sapiens

<400> SEQUENCE: 598 gagatgagag atgccgttga 20

<210> SEQ ID NO 599
<211> LENGTH: 20
<212> TYPE: DNA
<213> ORGANISM: H. sapiens

<400> SEQUENCE: 599 agtcttgatg agcactatca 20

<210> SEQ ID NO 600
<211> LENGTH: 20
<212> TYPE: DNA
<213> ORGANISM: H. sapiens

<400> SEQUENCE: 600 ctaagtacca aatcagaatc 20

<210> SEQ ID NO 601
<211> LENGTH: 20
<212> TYPE: DNA
<213> ORGANISM: H. sapiens

<400> SEQUENCE: 601 gtccatgagt taatcgagag 20

<210> SEQ ID NO 602
<211> LENGTH: 20
<212> TYPE: DNA
<213> ORGANISM: H. sapiens

<400> SEQUENCE: 602 aggccacagt tgcagtgtat 20

<210> SEQ ID NO 603
<211> LENGTH: 20
<212> TYPE: DNA
<213> ORGANISM: H. sapiens

<400> SEQUENCE: 603 tctgattggt ggactcttgc 20

<210> SEQ ID NO 604
<211> LENGTH: 20
<212> TYPE: DNA
<213> ORGANISM: H. sapiens

<400> SEQUENCE: 604 gaagtcagtc ttcaggctct 20

<210> SEQ ID NO 605
<211> LENGTH: 20
<212> TYPE: DNA
<213> ORGANISM: H. sapiens

<400> SEQUENCE: 605 ccagattctc agatgaggga 20

<210> SEQ ID NO 606
<211> LENGTH: 20
<212> TYPE: DNA
<213> ORGANISM: H. sapiens

<400> SEQUENCE: 606 catctgtcat tgatgcactg 20

<210> SEQ ID NO 607
<211> LENGTH: 20
<212> TYPE: DNA
<213> ORGANISM: H. sapiens

<400> SEQUENCE: 607 aggagatgtc aagggttcgg 20

<210> SEQ ID NO 608
<211> LENGTH: 20
<212> TYPE: DNA
<213> ORGANISM: H. sapiens

<400> SEQUENCE: 608 ggaactattg ctagtgaggc 20

<210> SEQ ID NO 609
<211> LENGTH: 20
<212> TYPE: DNA
<213> ORGANISM: H. sapiens

<400> SEQUENCE: 609 ctctctccat ggcaaatgtc 20

<210> SEQ ID NO 610
<211> LENGTH: 20
<212> TYPE: DNA
<213> ORGANISM: H. sapiens

<400> SEQUENCE: 610 caccgtgact tcagtgcaga 20

<210> SEQ ID NO 611
<211> LENGTH: 20
<212> TYPE: DNA
<213> ORGANISM: H. sapiens

<400> SEQUENCE: 611 actgagttga gggtccggga 20

<210> SEQ ID NO 612
<211> LENGTH: 20
<212> TYPE: DNA
<213> ORGANISM: H. sapiens

<400> SEQUENCE: 612 cacatatgaa ctggacctgc 20

<210> SEQ ID NO 613
<211> LENGTH: 20
<212> TYPE: DNA
<213> ORGANISM: H. sapiens

<400> SEQUENCE: 613 tctgaactca gaaggatggc 20

<210> SEQ ID NO 614
<211> LENGTH: 20
<212> TYPE: DNA
<213> ORGANISM: H. sapiens

<400> SEQUENCE: 614 ggtgcgaagc agactgaggc 20

<210> SEQ ID NO 615
<211> LENGTH: 20
<212> TYPE: DNA
<213> ORGANISM: H. sapiens

<400> SEQUENCE: 615 tcccaccggg acctgcgggg 20

<210> SEQ ID NO 616
<211> LENGTH: 20
<212> TYPE: DNA
<213> ORGANISM: H. sapiens

<400> SEQUENCE: 616 caccgggacc tgcggggctg 20

<210> SEQ ID NO 617
<211> LENGTH: 20
<212> TYPE: DNA
<213> ORGANISM: H. sapiens

<400> SEQUENCE: 617 ctgagtgccc ttctcggttg 20

<210> SEQ ID NO 618
<211> LENGTH: 20
<212> TYPE: DNA
<213> ORGANISM: H. sapiens

<400> SEQUENCE: 618 ctcggttgct gccgctgagg 20

<210> SEQ ID NO 619
<211> LENGTH: 20
<212> TYPE: DNA
<213> ORGANISM: H. sapiens

<400> SEQUENCE: 619 tcggttgctg ccgctgagga 20

<210> SEQ ID NO 620
<211> LENGTH: 20
<212> TYPE: DNA
<213> ORGANISM: H. sapiens

<400> SEQUENCE: 620 cggttgctgc cgctgaggag 20

<210> SEQ ID NO 621
<211> LENGTH: 20
<212> TYPE: DNA
<213> ORGANISM: H. sapiens

<400> SEQUENCE: 621 gttgctgccg ctgaggagcc 20

<210> SEQ ID NO 622
<211> LENGTH: 20
<212> TYPE: DNA
<213> ORGANISM: H. sapiens

<400> SEQUENCE: 622 ctgccgctga ggagcccgcc 20

<210> SEQ ID NO 623
<211> LENGTH: 20
<212> TYPE: DNA
<213> ORGANISM: H. sapiens

<400> SEQUENCE: 623 accgcagctg gcgatggacc 20

<210> SEQ ID NO 624
<211> LENGTH: 20
<212> TYPE: DNA
<213> ORGANISM: H. sapiens

<400> SEQUENCE: 624 cagctggcga tggacccgcc 20

<210> SEQ ID NO 625
<211> LENGTH: 20
<212> TYPE: DNA
<213> ORGANISM: H. sapiens

<400> SEQUENCE: 625 gaacttacta tcatcctcta 20

<210> SEQ ID NO 626
<211> LENGTH: 20
<212> TYPE: DNA
<213> ORGANISM: H. sapiens

<400> SEQUENCE: 626 tccaattgaa ctttcacata 20

<210> SEQ ID NO 627
<211> LENGTH: 20
<212> TYPE: DNA
<213> ORGANISM: H. sapiens

<400> SEQUENCE: 627 aaaattcaaa ctgcctatat 20

<210> SEQ ID NO 628
<211> LENGTH: 20
<212> TYPE: DNA
<213> ORGANISM: H. sapiens

<400> SEQUENCE: 628 gataaaacca tacagtgagc 20

<210> SEQ ID NO 629
<211> LENGTH: 20
<212> TYPE: DNA
<213> ORGANISM: H. sapiens

<400> SEQUENCE: 629 ataaaaccat acagtgagcc 20

<210> SEQ ID NO 630
<211> LENGTH: 20
<212> TYPE: DNA
<213> ORGANISM: H. sapiens

<400> SEQUENCE: 630 aaccatacag tgagccagcc 20

<210> SEQ ID NO 631
<211> LENGTH: 20
<212> TYPE: DNA
<213> ORGANISM: H. sapiens

<400> SEQUENCE: 631 accatacagt gagccagcct 20

<210> SEQ ID NO 632
<211> LENGTH: 20
<212> TYPE: DNA
<213> ORGANISM: H. sapiens

<400> SEQUENCE: 632 ccatacagtg agccagcctt 20

<210> SEQ ID NO 633
<211> LENGTH: 20
<212> TYPE: DNA
<213> ORGANISM: H. sapiens

<400> SEQUENCE: 633 gtgagccagc cttgcagtag 20

<210> SEQ ID NO 634
<211> LENGTH: 20
<212> TYPE: DNA
<213> ORGANISM: H. sapiens

<400> SEQUENCE: 634 ccagccttgc agtaggcagt 20

<210> SEQ ID NO 635
<211> LENGTH: 20
<212> TYPE: DNA
<213> ORGANISM: H. sapiens

<400> SEQUENCE: 635 taggcagtag actataagca 20

<210> SEQ ID NO 636
<211> LENGTH: 20
<212> TYPE: DNA
<213> ORGANISM: H. sapiens

<400> SEQUENCE: 636 gcagtagact ataagcagaa 20

<210> SEQ ID NO 637
<211> LENGTH: 20
<212> TYPE: DNA
<213> ORGANISM: H. sapiens

<400> SEQUENCE: 637 tgaactggac ctgcaccaaa 20

<210> SEQ ID NO 638
<211> LENGTH: 20
<212> TYPE: DNA
<213> ORGANISM: H. sapiens

<400> SEQUENCE: 638 ctggacctgc accaaagctg 20

<210> SEQ ID NO 639
<211> LENGTH: 20
<212> TYPE: DNA
<213> ORGANISM: H. sapiens

<400> SEQUENCE: 639 ggacctgcac caaagctggc 20

<210> SEQ ID NO 640
<211> LENGTH: 20
<212> TYPE: DNA
<213> ORGANISM: H. sapiens

<400> SEQUENCE: 640 ctgcaccaaa gctggcacca 20

<210> SEQ ID NO 641
<211> LENGTH: 20
<212> TYPE: DNA
<213> ORGANISM: H. sapiens

<400> SEQUENCE: 641 accaaagctg gcaccagggc 20

<210> SEQ ID NO 642
<211> LENGTH: 20
<212> TYPE: DNA
<213> ORGANISM: H. sapiens

<400> SEQUENCE: 642 ctcggaaggt ctctgaactc 20

<210> SEQ ID NO 643
<211> LENGTH: 20
<212> TYPE: DNA
<213> ORGANISM: H. sapiens

<400> SEQUENCE: 643 aactcagaag gatggcattt 20

<210> SEQ ID NO 644
<211> LENGTH: 20
<212> TYPE: DNA
<213> ORGANISM: H. sapiens

<400> SEQUENCE: 644 ctcagaagga tggcattttt 20

<210> SEQ ID NO 645
<211> LENGTH: 20
<212> TYPE: DNA
<213> ORGANISM: H. sapiens

<400> SEQUENCE: 645 atcaggatct gagttatttt 20

<210> SEQ ID NO 646
<211> LENGTH: 20
<212> TYPE: DNA
<213> ORGANISM: H. sapiens

<400> SEQUENCE: 646 aggatctgag ttattttgct 20

<210> SEQ ID NO 647
<211> LENGTH: 20
<212> TYPE: DNA
<213> ORGANISM: H. sapiens

<400> SEQUENCE: 647 ctgagttatt ttgctaaact 20

<210> SEQ ID NO 648
<211> LENGTH: 20
<212> TYPE: DNA
<213> ORGANISM: H. sapiens

<400> SEQUENCE: 648 attttgctaa acttggggga 20

<210> SEQ ID NO 649
<211> LENGTH: 20
<212> TYPE: DNA
<213> ORGANISM: H. sapiens

<400> SEQUENCE: 649 taaacttggg ggaggaggaa 20

<210> SEQ ID NO 650
<211> LENGTH: 20
<212> TYPE: DNA
<213> ORGANISM: H. sapiens

<400> SEQUENCE: 650 ggaacaaata aatggagtct 20

<210> SEQ ID NO 651
<211> LENGTH: 20
<212> TYPE: DNA
<213> ORGANISM: H. sapiens

<400> SEQUENCE: 651 gtttgtaact caagcagaag 20

<210> SEQ ID NO 652
<211> LENGTH: 20
<212> TYPE: DNA
<213> ORGANISM: H. sapiens

<400> SEQUENCE: 652 ttgtaactca agcagaaggt 20

<210> SEQ ID NO 653
<211> LENGTH: 20
<212> TYPE: DNA
<213> ORGANISM: H. sapiens

<400> SEQUENCE: 653 gtaactcaag cagaaggtgc 20

<210> SEQ ID NO 654
<211> LENGTH: 20
<212> TYPE: DNA
<213> ORGANISM: H. sapiens

<400> SEQUENCE: 654 aactcaagca gaaggtgcga 20

<210> SEQ ID NO 655
<211> LENGTH: 20
<212> TYPE: DNA
<213> ORGANISM: H. sapiens

<400> SEQUENCE: 655 ctcaagcaga aggtgcgaag 20

<210> SEQ ID NO 656
<211> LENGTH: 20
<212> TYPE: DNA
<213> ORGANISM: H. sapiens

<400> SEQUENCE: 656 caagcagaag gtgcgaagca 20

<210> SEQ ID NO 657
<211> LENGTH: 20
<212> TYPE: DNA
<213> ORGANISM: H. sapiens

<400> SEQUENCE: 657 agcagaaggt gcgaagcaga 20

<210> SEQ ID NO 658
<211> LENGTH: 20
<212> TYPE: DNA
<213> ORGANISM: H. sapiens

<400> SEQUENCE: 658 cagaaggtgc gaagcagact 20

<210> SEQ ID NO 659
<211> LENGTH: 20
<212> TYPE: DNA
<213> ORGANISM: H. sapiens

<400> SEQUENCE: 659 gaaggtgcga agcagactga 20

<210> SEQ ID NO 660
<211> LENGTH: 20
<212> TYPE: DNA
<213> ORGANISM: H. sapiens

<400> SEQUENCE: 660 aggtgcgaag cagactgagg 20

<210> SEQ ID NO 661
<211> LENGTH: 20
<212> TYPE: DNA
<213> ORGANISM: H. sapiens

<400> SEQUENCE: 661 gtgcgaagca gactgaggct 20

<210> SEQ ID NO 662
<211> LENGTH: 20
<212> TYPE: DNA
<213> ORGANISM: H. sapiens

<400> SEQUENCE: 662 gcgaagcaga ctgaggctac 20

<210> SEQ ID NO 663
<211> LENGTH: 20
<212> TYPE: DNA
<213> ORGANISM: H. sapiens

<400> SEQUENCE: 663 gaagcagact gaggctacca 20

<210> SEQ ID NO 664
<211> LENGTH: 20
<212> TYPE: DNA
<213> ORGANISM: H. sapiens

<400> SEQUENCE: 664 agcagactga ggctaccatg 20

<210> SEQ ID NO 665
<211> LENGTH: 20
<212> TYPE: DNA
<213> ORGANISM: H. sapiens

<400> SEQUENCE: 665 cagactgagg ctaccatgac 20

<210> SEQ ID NO 666
<211> LENGTH: 20
<212> TYPE: DNA
<213> ORGANISM: H. sapiens

<400> SEQUENCE: 666 gactgaggct accatgacat 20

<210> SEQ ID NO 667
<211> LENGTH: 20
<212> TYPE: DNA
<213> ORGANISM: H. sapiens

<400> SEQUENCE: 667 ctgaggctac catgacattc 20

<210> SEQ ID NO 668
<211> LENGTH: 20
<212> TYPE: DNA
<213> ORGANISM: H. sapiens

<400> SEQUENCE: 668 gaggctacca tgacattcaa 20

<210> SEQ ID NO 669
<211> LENGTH: 20
<212> TYPE: DNA
<213> ORGANISM: H. sapiens

<400> SEQUENCE: 669 ggctaccatg acattcaaat 20

<210> SEQ ID NO 670
<211> LENGTH: 20
<212> TYPE: DNA
<213> ORGANISM: H. sapiens

<400> SEQUENCE: 670 ctaccatgac attcaaatat 20

<210> SEQ ID NO 671
<211> LENGTH: 20
<212> TYPE: DNA
<213> ORGANISM: H. sapiens

<400> SEQUENCE: 671 cctgaagctg catgtggctg 20

<210> SEQ ID NO 672
<211> LENGTH: 20
<212> TYPE: DNA
<213> ORGANISM: H. sapiens

<400> SEQUENCE: 672 tgaagctgca tgtggctggt 20

<210> SEQ ID NO 673
<211> LENGTH: 20
<212> TYPE: DNA
<213> ORGANISM: H. sapiens

<400> SEQUENCE: 673 aagctgcatg tggctggtaa 20

<210> SEQ ID NO 674
<211> LENGTH: 20
<212> TYPE: DNA
<213> ORGANISM: H. sapiens

<400> SEQUENCE: 674 gctgcatgtg gctggtaacc 20

<210> SEQ ID NO 675
<211> LENGTH: 20
<212> TYPE: DNA
<213> ORGANISM: H. sapiens

<400> SEQUENCE: 675 tgcatgtggc tggtaaccta 20

<210> SEQ ID NO 676
<211> LENGTH: 20
<212> TYPE: DNA
<213> ORGANISM: H. sapiens

<400> SEQUENCE: 676 catgtggctg gtaacctaaa 20

<210> SEQ ID NO 677
<211> LENGTH: 20
<212> TYPE: DNA
<213> ORGANISM: H. sapiens

<400> SEQUENCE: 677 tgtggctggt aacctaaaag 20

<210> SEQ ID NO 678
<211> LENGTH: 20
<212> TYPE: DNA
<213> ORGANISM: H. sapiens

<400> SEQUENCE: 678 tggctggtaa cctaaaagga 20

<210> SEQ ID NO 679
<211> LENGTH: 20
<212> TYPE: DNA
<213> ORGANISM: H. sapiens

<400> SEQUENCE: 679 gctggtaacc taaaaggagc 20

<210> SEQ ID NO 680
<211> LENGTH: 20
<212> TYPE: DNA
<213> ORGANISM: H. sapiens

<400> SEQUENCE: 680 tggtaaccta aaaggagcct 20

<210> SEQ ID NO 681
<211> LENGTH: 20
<212> TYPE: DNA
<213> ORGANISM: H. sapiens

<400> SEQUENCE: 681 gtaacctaaa aggagcctac 20

<210> SEQ ID NO 682
<211> LENGTH: 20
<212> TYPE: DNA
<213> ORGANISM: H. sapiens

<400> SEQUENCE: 682 aacctaaaag gagcctacca 20

<210> SEQ ID NO 683
<211> LENGTH: 20
<212> TYPE: DNA
<213> ORGANISM: H. sapiens

<400> SEQUENCE: 683 cctaaaagga gcctaccaaa 20

<210> SEQ ID NO 684
<211> LENGTH: 20
<212> TYPE: DNA
<213> ORGANISM: H. sapiens

<400> SEQUENCE: 684 ggcgcgaagc agactgaggc 20

<210> SEQ ID NO 685
<211> LENGTH: 20
<212> TYPE: DNA
<213> ORGANISM: H. sapiens

<400> SEQUENCE: 685 cactatgttc atgagggagg 20

<210> SEQ ID NO 686
<211> LENGTH: 20
<212> TYPE: DNA
<213> ORGANISM: H. sapiens

<400> SEQUENCE: 686 ccatcatagg ttctgacgtc 20

<210> SEQ ID NO 687
<211> LENGTH: 20
<212> TYPE: DNA
<213> ORGANISM: H. sapiens

<400> SEQUENCE: 687 gaagctgatt gactcactca 20

<210> SEQ ID NO 688
<211> LENGTH: 20
<212> TYPE: DNA
<213> ORGANISM: H. sapiens

<400> SEQUENCE: 688 ttgtaactca agcagaaggc 20

<210> SEQ ID NO 689
<211> LENGTH: 20
<212> TYPE: DNA
<213> ORGANISM: H. sapiens

<400> SEQUENCE: 689 gtaactcaag cagaaggcgc 20

<210> SEQ ID NO 690
<211> LENGTH: 20
<212> TYPE: DNA
<213> ORGANISM: H. sapiens

<400> SEQUENCE: 690 aactcaagca gaaggcgcga 20

<210> SEQ ID NO 691
<211> LENGTH: 20
<212> TYPE: DNA
<213> ORGANISM: H. sapiens

<400> SEQUENCE: 691 ctcaagcaga aggcgcgaag 20

<210> SEQ ID NO 692
<211> LENGTH: 20
<212> TYPE: DNA
<213> ORGANISM: H. sapiens

<400> SEQUENCE: 692 cagaaggcgc gaagcagact 20

<210> SEQ ID NO 693
<211> LENGTH: 20
<212> TYPE: DNA
<213> ORGANISM: H. sapiens

<400> SEQUENCE: 693 gaaggcgcga agcagactga 20

<210> SEQ ID NO 694
<211> LENGTH: 20
<212> TYPE: DNA
<213> ORGANISM: H. sapiens

<400> SEQUENCE: 694 aggcgcgaag cagactgagg 20

<210> SEQ ID NO 695
<211> LENGTH: 20
<212> TYPE: DNA
<213> ORGANISM: H. sapiens

<400> SEQUENCE: 695 gcgcgaagca gactgaggct 20

<210> SEQ ID NO 696
<211> LENGTH: 20
<212> TYPE: DNA
<213> ORGANISM: H. sapiens

<400> SEQUENCE: 696 gaagcagact gaggctacca 20

<210> SEQ ID NO 697
<211> LENGTH: 20
<212> TYPE: DNA
<213> ORGANISM: H. sapiens

<400> SEQUENCE: 697 cagaaggcgc gaagcagact 20

<210> SEQ ID NO 698
<211> LENGTH: 20
<212> TYPE: DNA
<213> ORGANISM: H. sapiens

<400> SEQUENCE: 698 tctttctcct gtcttacaga 20

<210> SEQ ID NO 699
<211> LENGTH: 20
<212> TYPE: DNA
<213> ORGANISM: H. sapiens

<400> SEQUENCE: 699 cccacgttag aagatgcgac 20

<210> SEQ ID NO 700
<211> LENGTH: 20
<212> TYPE: DNA
<213> ORGANISM: H. sapiens

<400> SEQUENCE: 700 aatatggtag acatgagcca 20

<210> SEQ ID NO 701
<211> LENGTH: 20
<212> TYPE: DNA
<213> ORGANISM: H. sapiens

<400> SEQUENCE: 701 cattagctgc atttcaactg 20

<210> SEQ ID NO 702
<211> LENGTH: 20
<212> TYPE: DNA
<213> ORGANISM: H. sapiens

<400> SEQUENCE: 702 actttcactc ctagtctgca 20

<210> SEQ ID NO 703
<211> LENGTH: 20
<212> TYPE: DNA
<213> ORGANISM: H. sapiens

<400> SEQUENCE: 703 ccatgtccag gtaagtcatg 20

<210> SEQ ID NO 704
<211> LENGTH: 20
<212> TYPE: DNA
<213> ORGANISM: H. sapiens

<400> SEQUENCE: 704 gcaccaggca cggatgtgac 20

<210> SEQ ID NO 705
<211> LENGTH: 20
<212> TYPE: DNA
<213> ORGANISM: H. sapiens

<400> SEQUENCE: 705 gtggggtccc agaggcactg 20

<210> SEQ ID NO 706
<211> LENGTH: 20
<212> TYPE: DNA
<213> ORGANISM: H. sapiens

<400> SEQUENCE: 706 gctgatcggc cactgcagct 20

<210> SEQ ID NO 707
<211> LENGTH: 20
<212> TYPE: DNA
<213> ORGANISM: H. sapiens

<400> SEQUENCE: 707 tccacgtggc tggggaggtc 20

<210> SEQ ID NO 708
<211> LENGTH: 20
<212> TYPE: DNA
<213> ORGANISM: H. sapiens

<400> SEQUENCE: 708 tgtaatgtat ggtgatcaga 20

<210> SEQ ID NO 709
<211> LENGTH: 20
<212> TYPE: DNA
<213> ORGANISM: H. sapiens

<400> SEQUENCE: 709 gagagtaccc agtgggaaat 20

<210> SEQ ID NO 710
<211> LENGTH: 20
<212> TYPE: DNA
<213> ORGANISM: H. sapiens

<400> SEQUENCE: 710 agtcagcatg ggcttcagcc 20

<210> SEQ ID NO 711
<211> LENGTH: 20
<212> TYPE: DNA
<213> ORGANISM: H. sapiens

<400> SEQUENCE: 711 caaaagaatg actgtccaac 20

<210> SEQ ID NO 712
<211> LENGTH: 20
<212> TYPE: DNA
<213> ORGANISM: H. sapiens

<400> SEQUENCE: 712 gaatgactgt ccaacaagtg 20

<210> SEQ ID NO 713
<211> LENGTH: 20
<212> TYPE: DNA
<213> ORGANISM: H. sapiens

<400> SEQUENCE: 713 tatctactgt aatttaaaat 20

<210> SEQ ID NO 714
<211> LENGTH: 20
<212> TYPE: DNA
<213> ORGANISM: H. sapiens

<400> SEQUENCE: 714 ctgatatggg tggagaacag 20

<210> SEQ ID NO 715
<211> LENGTH: 20
<212> TYPE: DNA
<213> ORGANISM: H. sapiens

<400> SEQUENCE: 715 tctgggacag gtatgagctc 20

<210> SEQ ID NO 716
<211> LENGTH: 20
<212> TYPE: DNA
<213> ORGANISM: H. sapiens

<400> SEQUENCE: 716 tgatagcagt ggcccttgaa 20

<210> SEQ ID NO 717
<211> LENGTH: 20
<212> TYPE: DNA
<213> ORGANISM: H. sapiens

<400> SEQUENCE: 717 ggattggcgt gaaatactgg 20

<210> SEQ ID NO 718
<211> LENGTH: 20
<212> TYPE: DNA
<213> ORGANISM: H. sapiens

<400> SEQUENCE: 718 tgcccgaggt tcctcctgcc 20

<210> SEQ ID NO 719
<211> LENGTH: 20
<212> TYPE: DNA
<213> ORGANISM: H. sapiens

<400> SEQUENCE: 719 gcactagcaa gaccacactc 20

<210> SEQ ID NO 720
<211> LENGTH: 20
<212> TYPE: DNA
<213> ORGANISM: H. sapiens

<400> SEQUENCE: 720 caagaccaca ctctgcatag 20

<210> SEQ ID NO 721
<211> LENGTH: 20
<212> TYPE: DNA
<213> ORGANISM: H. sapiens

<400> SEQUENCE: 721 tcctccatag gataccgtgt 20

<210> SEQ ID NO 722
<211> LENGTH: 20
<212> TYPE: DNA
<213> ORGANISM: H. sapiens

<400> SEQUENCE: 722 ggatgtaggg cagcaaaacc 20

<210> SEQ ID NO 723
<211> LENGTH: 20
<212> TYPE: DNA
<213> ORGANISM: H. sapiens

<400> SEQUENCE: 723 tctgcacaag gactccttgt 20

<210> SEQ ID NO 724
<211> LENGTH: 20
<212> TYPE: DNA
<213> ORGANISM: H. sapiens

<400> SEQUENCE: 724 cagcctgtct cagtgaacat 20

<210> SEQ ID NO 725
<211> LENGTH: 20
<212> TYPE: DNA
<213> ORGANISM: H. sapiens

<400> SEQUENCE: 725 caggatgctt ccagtctaat 20

<210> SEQ ID NO 726
<211> LENGTH: 20
<212> TYPE: DNA
<213> ORGANISM: H. sapiens

<400> SEQUENCE: 726 aaatgctcgt ctccaatctc 20

<210> SEQ ID NO 727
<211> LENGTH: 20
<212> TYPE: DNA
<213> ORGANISM: H. sapiens

<400> SEQUENCE: 727 aacttgtgta tccaaatcca 20

<210> SEQ ID NO 728
<211> LENGTH: 20
<212> TYPE: DNA
<213> ORGANISM: H. sapiens

<400> SEQUENCE: 728 tgacatggtg tgcttccttg 20

<210> SEQ ID NO 729
<211> LENGTH: 20
<212> TYPE: DNA
<213> ORGANISM: H. sapiens

<400> SEQUENCE: 729 acactggtgt tctggctacc 20

<210> SEQ ID NO 730
<211> LENGTH: 20
<212> TYPE: DNA
<213> ORGANISM: H. sapiens

<400> SEQUENCE: 730 gtgttctggc tacctctagt 20

<210> SEQ ID NO 731
<211> LENGTH: 20
<212> TYPE: DNA
<213> ORGANISM: H. sapiens

<400> SEQUENCE: 731 tcctggcata ggtcacagta 20

<210> SEQ ID NO 732
<211> LENGTH: 20
<212> TYPE: DNA
<213> ORGANISM: H. sapiens

<400> SEQUENCE: 732 atgtcaacag tagcacctcc 20

<210> SEQ ID NO 733
<211> LENGTH: 20
<212> TYPE: DNA
<213> ORGANISM: H. sapiens

<400> SEQUENCE: 733 tagactcaga caagtctgga 20

<210> SEQ ID NO 734
<211> LENGTH: 20
<212> TYPE: DNA
<213> ORGANISM: H. sapiens

<400> SEQUENCE: 734 cctaagttgc tcatctctgg 20

<210> SEQ ID NO 735
<211> LENGTH: 20
<212> TYPE: DNA
<213> ORGANISM: H. sapiens

<400> SEQUENCE: 735 tgcgctgagt tccatgaaac 20

<210> SEQ ID NO 736
<211> LENGTH: 20
<212> TYPE: DNA
<213> ORGANISM: H. sapiens

<400> SEQUENCE: 736 ctattgcagg tgctctccag 20

<210> SEQ ID NO 737
<211> LENGTH: 20
<212> TYPE: DNA
<213> ORGANISM: H. sapiens

<400> SEQUENCE: 737 cagaggaaca tcttgcacct 20

<210> SEQ ID NO 738
<211> LENGTH: 20
<212> TYPE: DNA
<213> ORGANISM: H. sapiens

<400> SEQUENCE: 738 ctctgctcct tactcttgtg 20

<210> SEQ ID NO 739
<211> LENGTH: 20
<212> TYPE: DNA
<213> ORGANISM: H. sapiens

<400> SEQUENCE: 739 gtaatttctc accatccatc 20

<210> SEQ ID NO 740
<211> LENGTH: 20
<212> TYPE: DNA
<213> ORGANISM: H. sapiens

<400> SEQUENCE: 740 ttctgagtct caattgtcta 20

<210> SEQ ID NO 741
<211> LENGTH: 20
<212> TYPE: DNA
<213> ORGANISM: H. sapiens

<400> SEQUENCE: 741 ctatgtcctt gtgtgcacat 20

<210> SEQ ID NO 742
<211> LENGTH: 20
<212> TYPE: DNA
<213> ORGANISM: H. sapiens

<400> SEQUENCE: 742 gcctattgcc atttgtatgt 20

<210> SEQ ID NO 743
<211> LENGTH: 20
<212> TYPE: DNA
<213> ORGANISM: H. sapiens

<400> SEQUENCE: 743 ctattcatgt cctttgccta 20

<210> SEQ ID NO 744
<211> LENGTH: 20
<212> TYPE: DNA
<213> ORGANISM: H. sapiens

<400> SEQUENCE: 744 gattctgcgg gtaatctcag 20

<210> SEQ ID NO 745
<211> LENGTH: 20
<212> TYPE: DNA
<213> ORGANISM: H. sapiens

<400> SEQUENCE: 745 tcaatgcagg tcattggaaa 20

<210> SEQ ID NO 746
<211> LENGTH: 20
<212> TYPE: DNA
<213> ORGANISM: H. sapiens

<400> SEQUENCE: 746 ctaccagatt gaccatccct 20

<210> SEQ ID NO 747
<211> LENGTH: 20
<212> TYPE: DNA
<213> ORGANISM: H. sapiens

<400> SEQUENCE: 747 tacttgatag tgctctagga 20

<210> SEQ ID NO 748
<211> LENGTH: 20
<212> TYPE: DNA
<213> ORGANISM: H. sapiens

<400> SEQUENCE: 748 ttgactgcag gaccaggagg 20

<210> SEQ ID NO 749
<211> LENGTH: 20
<212> TYPE: DNA
<213> ORGANISM: H. sapiens

<400> SEQUENCE: 749 aacaaacact tgtgcaaatg 20

<210> SEQ ID NO 750
<211> LENGTH: 20
<212> TYPE: DNA
<213> ORGANISM: H. sapiens

<400> SEQUENCE: 750 aatgagacca aacttccact 20

<210> SEQ ID NO 751
<211> LENGTH: 20
<212> TYPE: DNA
<213> ORGANISM: H. sapiens

<400> SEQUENCE: 751 ttccactttg aagctagcaa 20

<210> SEQ ID NO 752
<211> LENGTH: 20
<212> TYPE: DNA
<213> ORGANISM: H. sapiens

<400> SEQUENCE: 752 gatctggagc ttattcttga 20

<210> SEQ ID NO 753
<211> LENGTH: 20
<212> TYPE: DNA
<213> ORGANISM: H. sapiens

<400> SEQUENCE: 753 acctcatgtg acttgtatgc 20

<210> SEQ ID NO 754
<211> LENGTH: 20
<212> TYPE: DNA
<213> ORGANISM: H. sapiens

<400> SEQUENCE: 754 ttcttaagaa acaccttgta 20

<210> SEQ ID NO 755
<211> LENGTH: 20
<212> TYPE: DNA
<213> ORGANISM: H. sapiens

<400> SEQUENCE: 755 taggcccatc ctggctgcat 20

<210> SEQ ID NO 756
<211> LENGTH: 20
<212> TYPE: DNA
<213> ORGANISM: H. sapiens

<400> SEQUENCE: 756 aaactctcag gatatggtaa 20

<210> SEQ ID NO 757
<211> LENGTH: 20
<212> TYPE: DNA
<213> ORGANISM: H. sapiens

<400> SEQUENCE: 757 ataccttcct ctacctttgc 20

<210> SEQ ID NO 758
<211> LENGTH: 20
<212> TYPE: DNA
<213> ORGANISM: H. sapiens

<400> SEQUENCE: 758 taccttttgct gaaggtcctt 20

<210> SEQ ID NO 759
<211> LENGTH: 20
<212> TYPE: DNA
<213> ORGANISM: H. sapiens

<400> SEQUENCE: 759 atctatctag tgaaatttct 20

<210> SEQ ID NO 760
<211> LENGTH: 20
<212> TYPE: DNA
<213> ORGANISM: H. sapiens

<400> SEQUENCE: 760 tcagctcatc aaaatatgct 20

<210> SEQ ID NO 761
<211> LENGTH: 20
<212> TYPE: DNA
<213> ORGANISM: H. sapiens

<400> SEQUENCE: 761 atatgctagt ccttcctttc 20

<210> SEQ ID NO 762
<211> LENGTH: 20
<212> TYPE: DNA
<213> ORGANISM: H. sapiens

<400> SEQUENCE: 762 caaaggtctg agttatccag 20

<210> SEQ ID NO 763
<211> LENGTH: 20
<212> TYPE: DNA
<213> ORGANISM: H. sapiens

<400> SEQUENCE: 763 tgacttatag atgcaggctg 20

<210> SEQ ID NO 764
<211> LENGTH: 20
<212> TYPE: DNA
<213> ORGANISM: H. sapiens

<400> SEQUENCE: 764 tcagtggagg gtaattcttt 20

<210> SEQ ID NO 765
<211> LENGTH: 20
<212> TYPE: DNA
<213> ORGANISM: H. sapiens

<400> SEQUENCE: 765 tgcctagcca gtttgaaaga 20

<210> SEQ ID NO 766
<211> LENGTH: 20
<212> TYPE: DNA
<213> ORGANISM: H. sapiens

<400> SEQUENCE: 766 cctgcagaat tttgccaggc 20

<210> SEQ ID NO 767
<211> LENGTH: 20
<212> TYPE: DNA
<213> ORGANISM: H. sapiens

<400> SEQUENCE: 767 gtagctaggt aggtaaagca 20

<210> SEQ ID NO 768
<211> LENGTH: 20
<212> TYPE: DNA
<213> ORGANISM: H. sapiens

<400> SEQUENCE: 768 ttgagtgaga cacacaaggt 20

<210> SEQ ID NO 769
<211> LENGTH: 20
<212> TYPE: DNA
<213> ORGANISM: H. sapiens

<400> SEQUENCE: 769 gtgctagtca gggaatgcat 20

<210> SEQ ID NO 770
<211> LENGTH: 20
<212> TYPE: DNA
<213> ORGANISM: H. sapiens

<400> SEQUENCE: 770 ggggagagag catgcccagc 20

<210> SEQ ID NO 771
<211> LENGTH: 20
<212> TYPE: DNA
<213> ORGANISM: H. sapiens

<400> SEQUENCE: 771 gcatgcccag ctgcgaaagc 20

<210> SEQ ID NO 772
<211> LENGTH: 20
<212> TYPE: DNA
<213> ORGANISM: H. sapiens

<400> SEQUENCE: 772 agccaggtat agaaaggagt 20

<210> SEQ ID NO 773
<211> LENGTH: 20
<212> TYPE: DNA
<213> ORGANISM: H. sapiens

<400> SEQUENCE: 773 aactttctaa gaggcagaat 20

<210> SEQ ID NO 774
<211> LENGTH: 20
<212> TYPE: DNA
<213> ORGANISM: H. sapiens

<400> SEQUENCE: 774 tcttagtctg gtcatgagtg 20

<210> SEQ ID NO 775
<211> LENGTH: 20
<212> TYPE: DNA
<213> ORGANISM: H. sapiens

<400> SEQUENCE: 775 agtaggagat ttcatatgaa 20

<210> SEQ ID NO 776
<211> LENGTH: 20
<212> TYPE: DNA
<213> ORGANISM: H. sapiens

<400> SEQUENCE: 776 tcttcaccag caacacatta 20

<210> SEQ ID NO 777
<211> LENGTH: 20
<212> TYPE: DNA
<213> ORGANISM: H. sapiens

<400> SEQUENCE: 777 atggccacct agcatggcac 20

<210> SEQ ID NO 778
<211> LENGTH: 20
<212> TYPE: DNA
<213> ORGANISM: H. sapiens

<400> SEQUENCE: 778 catgtttctg agcctccaga 20

<210> SEQ ID NO 779
<211> LENGTH: 20
<212> TYPE: DNA
<213> ORGANISM: H. sapiens

<400> SEQUENCE: 779 taggtggctc cctgtcttca 20

<210> SEQ ID NO 780
<211> LENGTH: 20
<212> TYPE: DNA
<213> ORGANISM: H. sapiens

<400> SEQUENCE: 780 tccaaagtct tgggaatcct 20

<210> SEQ ID NO 781
<211> LENGTH: 20
<212> TYPE: DNA
<213> ORGANISM: H. sapiens

<400> SEQUENCE: 781 acaaagaaag ggggagttgg 20

<210> SEQ ID NO 782
<211> LENGTH: 20
<212> TYPE: DNA
<213> ORGANISM: H. sapiens

<400> SEQUENCE: 782 tcgtgtcttc ctggcccaga 20

<210> SEQ ID NO 783
<211> LENGTH: 20
<212> TYPE: DNA
<213> ORGANISM: H. sapiens

<400> SEQUENCE: 783 gcagtgccca gcacacaata 20

<210> SEQ ID NO 784
<211> LENGTH: 20
<212> TYPE: DNA
<213> ORGANISM: H. sapiens

<400> SEQUENCE: 784 actcgtccag gtgcgaagca 20

<210> SEQ ID NO 785
<211> LENGTH: 20
<212> TYPE: DNA
<213> ORGANISM: H. sapiens

<400> SEQUENCE: 785 gccacctaag gtaaagaagg 20

<210> SEQ ID NO 786
<211> LENGTH: 20
<212> TYPE: DNA
<213> ORGANISM: H. sapiens

<400> SEQUENCE: 786 atcagagtgg cagagagagc 20

<210> SEQ ID NO 787
<211> LENGTH: 20
<212> TYPE: DNA
<213> ORGANISM: H. sapiens

<400> SEQUENCE: 787 tttaccatag ttgtgacaca 20

<210> SEQ ID NO 788
<211> LENGTH: 20
<212> TYPE: DNA
<213> ORGANISM: H. sapiens

<400> SEQUENCE: 788 cattttgtag gcaatgagct 20

<210> SEQ ID NO 789
<211> LENGTH: 20
<212> TYPE: DNA
<213> ORGANISM: H. sapiens

<400> SEQUENCE: 789 gcattagtaa acatgagaac 20

<210> SEQ ID NO 790
<211> LENGTH: 20
<212> TYPE: DNA
<213> ORGANISM: H. sapiens

<400> SEQUENCE: 790 ttcatttcag cgatggccgg 20

<210> SEQ ID NO 791
<211> LENGTH: 20
<212> TYPE: DNA
<213> ORGANISM: H. sapiens

<400> SEQUENCE: 791 gaaaatctag tgtcattcaa 20

<210> SEQ ID NO 792
<211> LENGTH: 20
<212> TYPE: DNA
<213> ORGANISM: H. sapiens

<400> SEQUENCE: 792 tcctatacag ttttgggaac 20

<210> SEQ ID NO 793
<211> LENGTH: 20
<212> TYPE: DNA
<213> ORGANISM: H. sapiens

<400> SEQUENCE: 793 aaggacttca gtatggagct 20

<210> SEQ ID NO 794
<211> LENGTH: 20
<212> TYPE: DNA
<213> ORGANISM: H. sapiens

<400> SEQUENCE: 794 atggagcttt tattgaattg 20

<210> SEQ ID NO 795
<211> LENGTH: 20
<212> TYPE: DNA
<213> ORGANISM: H. sapiens

<400> SEQUENCE: 795 ccatcagcac tattatttat 20

<210> SEQ ID NO 796
<211> LENGTH: 20
<212> TYPE: DNA
<213> ORGANISM: H. sapiens

<400> SEQUENCE: 796 ataggcaagc tcagccatag 20

<210> SEQ ID NO 797
<211> LENGTH: 20
<212> TYPE: DNA
<213> ORGANISM: H. sapiens

<400> SEQUENCE: 797 tgctagatga gatacatcaa 20

<210> SEQ ID NO 798
<211> LENGTH: 20
<212> TYPE: DNA
<213> ORGANISM: H. sapiens

<400> SEQUENCE: 798 gaagaccaaa catggttcta 20

<210> SEQ ID NO 799
<211> LENGTH: 20
<212> TYPE: DNA
<213> ORGANISM: H. sapiens

<400> SEQUENCE: 799 ctctgtttag tcctctccag 20

<210> SEQ ID NO 800
<211> LENGTH: 20
<212> TYPE: DNA
<213> ORGANISM: H. sapiens

<400> SEQUENCE: 800 cattgataaa atgttctggc 20

<210> SEQ ID NO 801
<211> LENGTH: 20
<212> TYPE: DNA
<213> ORGANISM: H. sapiens

<400> SEQUENCE: 801 tctggcacag caaaacctct 20

<210> SEQ ID NO 802
<211> LENGTH: 20
<212> TYPE: DNA
<213> ORGANISM: H. sapiens

<400> SEQUENCE: 802 tggcacagca aaacctctag 20

<210> SEQ ID NO 803
<211> LENGTH: 20
<212> TYPE: DNA
<213> ORGANISM: H. sapiens

<400> SEQUENCE: 803 tagaacacat agtgtgattt 20

<210> SEQ ID NO 804
<211> LENGTH: 20
<212> TYPE: DNA
<213> ORGANISM: H. sapiens

<400> SEQUENCE: 804 aacacatagt gtgatttaag 20

<210> SEQ ID NO 805
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 805 ctttccgttg gacccctggg 20

<210> SEQ ID NO 806
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 806 tcccgcctgt gacatgcatt 20

<210> SEQ ID NO 807
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 807 ttctacctcg cgcgatttac 20

<210> SEQ ID NO 808
<211> LENGTH: 432
<212> TYPE: DNA
<213> ORGANISM: O. cuniculus

<400> SEQUENCE: 808 gatcttacct tctccaagca aaatgcattg ctacgtgctg agtatcaggc tgattacaag 60 tcactgaggt tcttcaccct gctttctggg ttgttgaata cccatggtct tgaattaaat 120 gctgacatct tgggcactga caaaatgaat actgctgctc acaaggcaac tctaagaatt 180 ggccaaaatg gagtatctac cagtgcaaca accagcttga ggtacagtcc cctgatgctg 240 gagaatgagc tgaacgcaga gcttgccctt tctggggcat ctatgaaatt agcaacaaat 300 ggccgcttca aggaacacaa tgcaaaattc agcctagatg ggaaagctac cctcacagag 360 ttatccctgg gaagcgctta ccaggccatg attctgggtg ctgacagcaa gaacattttc 420 aacttcaaga tc 432

<210> SEQ ID NO 809
<211> LENGTH: 660
<212> TYPE: DNA
<213> ORGANISM: O. cuniculus

<400> SEQUENCE: 809 ctgggaaaac tcccacagca agttaatgat tatctgagta cattcaattg ggagagacaa 60 gtttccagtg ccaaggagaa actaactact ttcacaaaaa attataaaat tacagagaat 120 gatatacaaa ctgcattgga taatgccaaa atcaacttaa atgaaaaact gtctcaactt 180 cagacatatg tgatataatt tgatcagtat attaaagata attttgatct acatgatttt 240 aaaatagcta tagctagtat tatagatcaa atcatggaaa aattaaaaat tcttgatgaa 300 cgttatcata tccgtgcaca tttaattaaa tcaatccata atttatattt gtttattgaa 360 gctattgatt ttaacaaaat tggaagtagt actgcatctt ggattcaaaa tgtggatacc 420 aagtatcaag tcagaatctg gatacaagaa atattgcaac agtttaagac acagattcag 480 aatacaaaca tcccatacct ggctgaaaaa ctgaaacaac agattgaggc tattgatgtc 540 agagtgcttt tagatcaatt gagaactaca attccatttc gtataataaa ggacattatt 600 gaacatttca aatactttgt tataaatatt attgaaaatt ttgaagtaat tgacaaaatc 660

<210> SEQ ID NO 810
<211> LENGTH: 543
<212> TYPE: DNA
<213> ORGANISM: O. cuniculus
<220> FEATURE:
<221> NAME/KEY: misc_feature
<222> LOCATION: (45)
<223> OTHER INFORMATION: n = a, c, g, or t
<220> FEATURE:
<221> NAME/KEY: misc_feature
<222> LOCATION: (118)
<223> OTHER INFORMATION: n = a, c, g, or t
<220> FEATURE:
<221> NAME/KEY: misc_feature
<222> LOCATION: (148)
<223> OTHER INFORMATION: n = a, c, g, or t
<220> FEATURE:
<221> NAME/KEY: misc_feature
<222> LOCATION: (173)
<223> OTHER INFORMATION: n = a, c, g, or t
<220> FEATURE:
<221> NAME/KEY: misc_feature
<222> LOCATION: (180)
<223> OTHER INFORMATION: n = a, c, g, or t

<400> SEQUENCE: 810 cagaacatcg gagacaacgc attggatttt ctcactaaat cttanaatga agcaaaaatt 60 aagtttgata agtacaaagt tgaaaaatcg ctcaacaggc tccccaggac ctttcagnct 120 cctggataca ttattccaat tttcaatntt gaagtatctc cactcacaat agnagacgtn 180 agcattcagt catgtgatcc caaaatcaat aagcaccccc aatgtcacca tcctggattc 240 aagcttctat gtgccttcat atacattggc tctgccatcc ctagagctgc cagtcttcca 300 tgtccccagg aatctactca aggtctctct tccagatttc aaggaattga aaaccattaa 360 caatattttt attccagcca tgggcaacat tacctatgaa ttttccttca aatcaacgat 420 cattacactg aataccaatg ctggacttta taaccaatca gacattgttg cccatatcct 480 ttcttcctct tcatctgtca ttgatgcact acagtacaaa ttagagggca cgctcaagtt 540 tga 543

<210> SEQ ID NO 811
<211> LENGTH: 19
<212> TYPE: DNA
<213> ORGANISM: Artificial Sequence
<220> FEATURE:
<223> OTHER INFORMATION: Primer

<400> SEQUENCE: 811 aagcaccccc aatgtcacc 19

<210> SEQ ID NO 812
<211> LENGTH: 20
<212> TYPE: DNA
<213> ORGANISM: Artificial Sequence
<220> FEATURE:
<223> OTHER INFORMATION: Primer

<400> SEQUENCE: 812 gggatggcag agccaatgta 20

<210> SEQ ID NO 813
<211> LENGTH: 29
<212> TYPE: DNA
<213> ORGANISM: Artificial Sequence
<220> FEATURE:
<223> OTHER INFORMATION: Probe

<400> SEQUENCE: 813 tcctggattc aagcttctat gtgccttca 29

<210> SEQ ID NO 814
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 814 tgcttggaga aggtaagatc 20

<210> SEQ ID NO 815
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 815 gcgttgtctc cgatgttctg 20

<210> SEQ ID NO 816
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 816 taatcattaa cttgctgtgg 20

<210> SEQ ID NO 817
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 817 tcagcacgta gcaatgcatt 20

<210> SEQ ID NO 818
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 818 gcctgatact cagcacgtag 20

<210> SEQ ID NO 819
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 819 caattgaatg tactcagata 20

<210> SEQ ID NO 820
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 820 acctcagtga cttgtaatca 20

<210> SEQ ID NO 821
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 821 cactggaaac ttgtctctcc 20

<210> SEQ ID NO 822
<211> LENGTH: 20
<212> TYPE: DNA
<213> ORGANISM: Artificial Sequence <220> FEATURE:
<223> OTHER INFORMATION: Antisense Oligonucleotide

<400> SEQUENCE: 822 agtagttagt ttctccttgg 20

<210> SEQ ID NO 823
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 823 tcagtgccca agatgtcagc 20

<210> SEQ ID NO 824
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 824 attggaataa tgtatccagg 20

<210> SEQ ID NO 825
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 825 ttggcattat ccaatgcagt 20

<210> SEQ ID NO 826
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 826 gttgccttgt gagcagcagt 20

<210> SEQ ID NO 827
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 827 attgtgagtg gagatacttc 20

<210> SEQ ID NO 828
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 828 catatgtctg aagttgagac 20

<210> SEQ ID NO 829
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 829 gtagatactc cattttggcc 20

<210> SEQ ID NO 830
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 830 ggatcacatg actgaatgct 20

<210> SEQ ID NO 831
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 831 tcaagctggt tgttgcactg 20

<210> SEQ ID NO 832
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 832 ggactgtacc tcaagctggt 20

<210> SEQ ID NO 833
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 833 gctcattctc cagcatcagg 20

<210> SEQ ID NO 834
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 834 ttgatctata atactagcta 20

<210> SEQ ID NO 835
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 835 atggaagact ggcagctcta 20

<210> SEQ ID NO 836
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 836 ttgtgttcct tgaagcggcc 20

<210> SEQ ID NO 837
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 837 tgtgcacgga tatgataacg 20

<210> SEQ ID NO 838
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 838 gaccttgagt agattcctgg 20

<210> SEQ ID NO 839
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 839 gaaatctgga agagagacct 20

<210> SEQ ID NO 840
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 840 gtagctttcc catctaggct 20

<210> SEQ ID NO 841
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 841 gataactctg tgagggtagc 20

<210> SEQ ID NO 842
<211> LENGTH: 20
<212> TYPE: DNA
<213> ORGANISM: Artificial Sequence <220> FEATURE:
<223> OTHER INFORMATION: Antisense Oligonucleotide

<400> SEQUENCE: 842 atgttgccca tggctggaat 20

<210> SEQ ID NO 843
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 843 aagatgcagt actacttcca 20

<210> SEQ ID NO 844
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 844 gcacccagaa tcatggcctg 20

<210> SEQ ID NO 845
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 845 cttgatactt ggtatccaca 20

<210> SEQ ID NO 846
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 846 cagtgtaatg atcgttgatt 20

<210> SEQ ID NO 847
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 847 taaagtccag cattggtatt 20

<210> SEQ ID NO 848
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 848 caacaatgtc tgattggtta 20

<210> SEQ ID NO 849
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 849 gaagaggaag aaaggatatg 20

<210> SEQ ID NO 850
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 850 tgacagatga agaggaagaa 20

<210> SEQ ID NO 851
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 851 ttgtactgta gtgcatcaat 20

<210> SEQ ID NO 852
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 852 gcctcaatct gttgtttcag 20

<210> SEQ ID NO 853
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 853 acttgagcgt gccctctaat 20

<210> SEQ ID NO 854
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 854 gaaatggaat tgtagttctc 20

<210> SEQ ID NO 855
<211> LENGTH: 479
<212> TYPE: DNA
<213> ORGANISM: M. fascicularis
<220> FEATURE:
<221> NAME/KEY: misc_feature
<222> LOCATION: (7)
<223> OTHER INFORMATION: n = A,T,C or G <220> FEATURE:
<221> NAME/KEY: misc_feature
<222> LOCATION: (469)..(474)
<223> OTHER INFORMATION: n = A,T,C or G
<220> FEATURE:
<221> NAME/KEY: misc_feature
<222> LOCATION: (476)..( 479)
<223> OTHER INFORMATION: n = A,T,C or G

<400> SEQUENCE: 855 tgcgtcnaga ctccgccccc tactatccgc tgaccgggga caccagatta gagctggaac 60 tgaggcctac aggagaagtt gagcagtatt ctgtcagtgc aacctatgag ctccagagag 120 aggacagagc cttggtggac accctgaagt ttgtaactca agcagaaggt gtaaagcaga 180 ctgaggctac catgacattc aaatataatc ggcagagtat gaccttgtcc agtgaagtcc 240 aaattccgga ttttgaggtt gaccttggaa caatcctcag agttaatgat gaatctactg 300 agggcagaaa gtcttacaga ctcaccctgg acattcagaa ccagaaaatt actgaggtca 360 ccctcatggg ccacctaagt tgtgacacaa aggaagaagg aaaaatcaaa ggtgttattt 420 ccgtaccccg tttgcaagca gaagccagaa gtgagatcct cgcccacann nnnnannnn 479

<210> SEQ ID NO 856
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 856 gtccctcaac atctgaatgc 20

<210> SEQ ID NO 857
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 857 ctgctagcct ctggatttga 20

<210> SEQ ID NO 858
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 858 ccttccctga aggttcctcc 20

<210> SEQ ID NO 859
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 859 ctcttactgt gctgtggaca 20

<210> SEQ ID NO 860
<211> LENGTH: 13938
<212> TYPE: DNA
<213> ORGANISM: H. sapiens

<400> SEQUENCE: 860 ctgggattgg gacacacttt ctggacactg ctggccagtc ccaaaatgga acataaggaa 60 gtggttcttc tacttctttt atttctgaaa tcagcagcac ctgagcaaag ccatgtggtc 120 caggattgct accatggtga tggacagagt tatcgaggca cgtactccac cactgtcaca 180 ggaaggacct gccaagcttg gtcatctatg acaccacatc aacataatag gaccacagaa 240 aactacccaa atgctggctt gatcatgaac tactgcagga atccagatgc tgtggcagct 300 ccttattgtt atacgaggga tcccggtgtc aggtgggagt actgcaacct gacgcaatgc 360 tcagacgcag aagggactgc cgtcgcgcct ccgactgtta ccccggttcc aagcctagag 420 gctccttccg aacaagcacc gactgagcaa aggcctgggg tgcaggagtg ctaccatggt 480 aatggacaga gttatcgagg cacatactcc accactgtca caggaagaac ctgccaagct 540 tggtcatcta tgacaccaca ctcgcatagt cggaccccag aatactaccc aaatgctggc 600 ttgatcatga actactgcag gaatccagat gctgtggcag ctccttattg ttatacgagg 660 gatcccggtg tcaggtggga gtactgcaac ctgacgcaat gctcagacgc agaagggact 720 gccgtcgcgc ctccgactgt taccccggtt ccaagcctag aggctccttc cgaacaagca 780 ccgactgagc aaaggcctgg ggtgcaggag tgctaccatg gtaatggaca gagttatcga 840 ggcacatact ccaccactgt cacaggaaga acctgccaag cttggtcatc tatgacacca 900 cactcgcata gtcggacccc agaatactac ccaaatgctg gcttgatcat gaactactgc 960 aggaatccag atgctgtggc agctccttat tgttatacga gggatcccgg tgtcaggtgg 1020 gagtactgca acctgacgca atgctcagac gcagaaggga ctgccgtcgc gcctccgact 1080 gttaccccgg ttccaagcct agaggctcct tccgaacaag caccgactga gcaaaggcct 1140 ggggtgcagg agtgctacca tggtaatgga cagagttatc gaggcacata ctccaccact 1200 gtcacaggaa gaacctgcca agcttggtca tctatgacac cacactcgca tagtcggacc 1260 ccagaatact acccaaatgc tggcttgatc atgaactact gcaggaatcc agatgctgtg 1320 gcagctcctt attgttatac gagggatccc ggtgtcaggt gggagtactg caacctgacg 1380 caatgctcag acgcagaagg gactgccgtc gcgcctccga ctgttacccc ggttccaagc 1440 ctagaggctc cttccgaaca agcaccgact gagcaaaggc ctggggtgca ggagtgctac 1500 catggtaatg gacagagtta tcgaggcaca tactccacca ctgtcacagg aagaacctgc 1560 caagcttggt catctatgac accacactcg catagtcgga ccccagaata ctacccaaat 1620 gctggcttga tcatgaacta ctgcaggaat ccagatgctg tggcagctcc ttattgttat 1680 acgagggatc ccggtgtcag gtgggagtac tgcaacctga cgcaatgctc agacgcagaa 1740 gggactgccg tcgcgcctcc gactgttacc ccggttccaa gcctagaggc tccttccgaa 1800 caagcaccga ctgagcaaag gcctggggtg caggagtgct accatggtaa tggacagagt 1860 tatcgaggca catactccac cactgtcaca ggaagaacct gccaagcttg gtcatctatg 1920 acaccacact cgcatagtcg gaccccagaa tactacccaa atgctggctt gatcatgaac 1980 tactgcagga atccagatgc tgtggcagct ccttattgtt atacgaggga tcccggtgtc 2040 aggtgggagt actgcaacct gacgcaatgc tcagacgcag aagggactgc cgtcgcgcct 2100 ccgactgtta ccccggttcc aagcctagag gctccttccg aacaagcacc gactgagcaa 2160 aggcctgggg tgcaggagtg ctaccatggt aatggacaga gttatcgagg cacatactcc 2220 accactgtca caggaagaac ctgccaagct tggtcatcta tgacaccaca ctcgcatagt 2280 cggaccccag aatactaccc aaatgctggc ttgatcatga actactgcag gaatccagat 2340

```
gctgtggcag ctccttattg ttatacgagg gatcccggtg tcaggtggga gtactgcaac   2400
ctgacgcaat gctcagacgc agaagggact gccgtcgcgc ctccgactgt taccccggtt   2460
ccaagcctag aggctccttc cgaacaagca ccgactgagc aaaggcctgg ggtgcaggag   2520
tgctaccatg gtaatggaca gagttatcga ggcacatact ccaccactgt cacaggaaga   2580
acctgccaag cttggtcatc tatgacacca cactcgcata gtcggacccc agaatactac   2640
ccaaatgctg gcttgatcat gaactactgc aggaatccag atgctgtggc agctccttat   2700
tgttatacga gggatcccgg tgtcaggtgg gagtactgca acctgacgca atgctcagac   2760
gcagaaggga ctgccgtcgc gcctccgact gttaccccgg ttccaagcct agaggctcct   2820
tccgaacaag caccgactga gcaaaggcct ggggtgcagg agtgctacca tggtaatgga   2880
cagagttatc gaggcacata ctccaccact gtcacaggaa gaacctgcca agcttggtca   2940
tctatgacac cacactcgca tagtcggacc ccagaatact acccaaatgc tggcttgatc   3000
atgaactact gcaggaatcc agatgctgtg gcagctcctt attgttatac gagggatccc   3060
ggtgtcaggt gggagtactg caacctgacg caatgctcag acgcagaagg gactgccgtc   3120
gcgcctccga ctgttacccc ggttccaagc ctagaggctc cttccgaaca agcaccgact   3180
gagcaaaggc ctggggtgca ggagtgctac catggtaatg gacagagtta tcgaggcaca   3240
tactccacca ctgtcacagg aagaacctgc caagcttggt catctatgac accacactcg   3300
catagtcgga ccccagaata ctacccaaat gctggcttga tcatgaacta ctgcaggaat   3360
ccagatgctg tggcagctcc ttattgttat acgagggatc ccggtgtcag gtgggagtac   3420
tgcaacctga cgcaatgctc agacgcagaa gggactgccg tcgcgcctcc gactgttacc   3480
ccggttccaa gcctagaggc tccttccgaa caagcaccga ctgagcaaag gcctggggtg   3540
caggagtgct accatggtaa tggacagagt tatcgaggca catactccac cactgtcaca   3600
ggaagaacct gccaagcttg gtcatctatg acaccacact cgcatagtcg gaccccagaa   3660
tactacccaa atgctggctt gatcatgaac tactgcagga atccagatgc tgtggcagct   3720
ccttattgtt atacgaggga tcccggtgtc aggtgggagt actgcaacct gacgcaatgc   3780
tcagacgcag aagggactgc cgtcgcgcct ccgactgtta ccccggttcc aagcctagag   3840
gctccttccg aacaagcacc gactgagcaa aggcctgggg tgcaggagtg ctaccatggt   3900
aatggacaga gttatcgagg cacatactcc accactgtca caggaagaac ctgccaagct   3960
tggtcatcta tgacaccaca ctcgcatagt cggaccccag aatactaccc aaatgctggc   4020
ttgatcatga actactgcag gaatccagat gctgtggcag ctccttattg ttatacgagg   4080
gatcccggtg tcaggtggga gtactgcaac ctgacgcaat gctcagacgc agaagggact   4140
gccgtcgcgc ctccgactgt taccccggtt ccaagcctag aggctccttc cgaacaagca   4200
ccgactgagc aaaggcctgg ggtgcaggag tgctaccatg gtaatggaca gagttatcga   4260
ggcacatact ccaccactgt cacaggaaga acctgccaag cttggtcatc tatgacacca   4320
cactcgcata gtcggacccc agaatactac ccaaatgctg gcttgatcat gaactactgc   4380
aggaatccag atgctgtggc agctccttat tgttatacga gggatcccgg tgtcaggtgg   4440
gagtactgca acctgacgca atgctcagac gcagaaggga ctgccgtcgc gcctccgact   4500
gttaccccgg ttccaagcct agaggctcct tccgaacaag caccgactga gcaaaggcct   4560
ggggtgcagg agtgctacca tggtaatgga cagagttatc gaggcacata ctccaccact   4620
gtcacaggaa gaacctgcca agcttggtca tctatgacac cacactcgca tagtcggacc   4680
ccagaatact acccaaatgc tggcttgatc atgaactact gcaggaatcc agatgctgtg   4740
```

```
gcagctcctt attgttatac gagggatccc ggtgtcaggt gggagtactg caacctgacg   4800
caatgctcag acgcagaagg gactgccgtc gcgcctccga ctgttacccc ggttccaagc   4860
ctagaggctc cttccgaaca agcaccgact gagcaaaggc ctggggtgca ggagtgctac   4920
catggtaatg gacagagtta tcgaggcaca tactccacca ctgtcacagg aagaacctgc   4980
caagcttggt catctatgac accacactcg catagtcgga ccccagaata ctacccaaat   5040
gctggcttga tcatgaacta ctgcaggaat ccagatgctg tggcagctcc ttattgttat   5100
acgagggatc ccggtgtcag gtgggagtac tgcaacctga cgcaatgctc agacgcagaa   5160
gggactgccg tcgcgcctcc gactgttacc ccggttccaa gcctagaggc tccttccgaa   5220
caagcaccga ctgagcaaag gcctggggtg caggagtgct accatggtaa tggacagagt   5280
tatcgaggca catactccac cactgtcaca ggaagaacct gccaagcttg gtcatctatg   5340
acaccacact cgcatagtcg gaccccagaa tactacccaa atgctggctt gatcatgaac   5400
tactgcagga atccagatgc tgtggcagct ccttattgtt atacgaggga tcccggtgtc   5460
aggtgggagt actgcaacct gacgcaatgc tcagacgcag aagggactgc cgtcgcgcct   5520
ccgactgtta ccccggttcc aagcctagag gctccttccg aacaagcacc gactgagcaa   5580
aggcctgggg tgcaggagtg ctaccatggt aatggacaga gttatcgagg cacatactcc   5640
accactgtca caggaagaac ctgccaagct tggtcatcta tgacaccaca ctcgcatagt   5700
cggaccccag aatactaccc aaatgctggc ttgatcatga actactgcag gaatccagat   5760
gctgtggcag ctccttattg ttatacgagg gatcccggtg tcaggtggga gtactgcaac   5820
ctgacgcaat gctcagacgc agaagggact gccgtcgcgc ctccgactgt taccccggtt   5880
ccaagcctag aggctccttc cgaacaagca ccgactgagc aaaggcctgg ggtgcaggag   5940
tgctaccatg gtaatggaca gagttatcga ggcacatact ccaccactgt cacaggaaga   6000
acctgccaag cttggtcatc tatgacacca cactcgcata gtcggacccc agaatactac   6060
ccaaatgctg gcttgatcat gaactactgc aggaatccag atgctgtggc agctccttat   6120
tgttatacga gggatcccgg tgtcaggtgg gagtactgca acctgacgca atgctcagac   6180
gcagaaggga ctgccgtcgc gcctccgact gttaccccgg ttccaagcct agaggctcct   6240
tccgaacaag caccgactga gcaaaggcct ggggtgcagg agtgctacca tggtaatgga   6300
cagagttatc gaggcacata ctccaccact gtcacaggaa gaacctgcca agcttggtca   6360
tctatgacac cacactcgca tagtcggacc ccagaatact acccaaatgc tggcttgatc   6420
atgaactact gcaggaatcc agatgctgtg gcagctcctt attgttatac gagggatccc   6480
ggtgtcaggt gggagtactg caacctgacg caatgctcag acgcagaagg gactgccgtc   6540
gcgcctccga ctgttacccc ggttccaagc ctagaggctc cttccgaaca agcaccgact   6600
gagcaaaggc ctggggtgca ggagtgctac catggtaatg gacagagtta tcgaggcaca   6660
tactccacca ctgtcacagg aagaacctgc caagcttggt catctatgac accacactcg   6720
catagtcgga ccccagaata ctacccaaat gctggcttga tcatgaacta ctgcaggaat   6780
ccagatgctg tggcagctcc ttattgttat acgagggatc ccggtgtcag gtgggagtac   6840
tgcaacctga cgcaatgctc agacgcagaa gggactgccg tcgcgcctcc gactgttacc   6900
ccggttccaa gcctagaggc tccttccgaa caagcaccga ctgagcaaag gcctggggtg   6960
caggagtgct accatggtaa tggacagagt tatcgaggca catactccac cactgtcaca   7020
ggaagaacct gccaagcttg gtcatctatg acaccacact cgcatagtcg gaccccagaa   7080
tactacccaa atgctggctt gatcatgaac tactgcagga atccagatgc tgtggcagct   7140
```

```
ccttattgtt atacgaggga tcccggtgtc aggtgggagt actgcaacct gacgcaatgc   7200
tcagacgcag aagggactgc cgtcgcgcct ccgactgtta ccccggttcc aagcctagag   7260
gctccttccg aacaagcacc gactgagcaa aggcctgggg tgcaggagtg ctaccatggt   7320
aatggacaga gttatcgagg cacatactcc accactgtca caggaagaac ctgccaagct   7380
tggtcatcta tgacaccaca ctcgcatagt cggaccccag aatactaccc aaatgctggc   7440
ttgatcatga actactgcag gaatccagat gctgtggcag ctccttattg ttatacgagg   7500
gatcccggtg tcaggtggga gtactgcaac ctgacgcaat gctcagacgc agaagggact   7560
gccgtcgcgc ctccgactgt taccccggtt ccaagcctag aggctccttc cgaacaagca   7620
ccgactgagc aaaggcctgg ggtgcaggag tgctaccatg gtaatggaca gagttatcga   7680
ggcacatact ccaccactgt cacaggaaga acctgccaag cttggtcatc tatgacacca   7740
cactcgcata gtcggacccc agaatactac ccaaatgctg gcttgatcat gaactactgc   7800
aggaatccag atgctgtggc agctccttat tgttatacga gggatcccgg tgtcaggtgg   7860
gagtactgca acctgacgca atgctcagac gcagaaggga ctgccgtcgc gcctccgact   7920
gttaccccgg ttccaagcct agaggctcct tccgaacaag caccgactga gcagaggcct   7980
ggggtgcagg agtgctacca cggtaatgga cagagttatc gaggcacata ctccaccact   8040
gtcactggaa gaacctgcca agcttggtca tctatgacac cacactcgca tagtcggacc   8100
ccagaatact acccaaatgc tggcttgatc atgaactact gcaggaatcc agatgctgtg   8160
gcagctcctt attgttatac gagggatccc ggtgtcaggt gggagtactg caacctgacg   8220
caatgctcag acgcagaagg gactgccgtc gcgcctccga ctgttacccc ggttccaagc   8280
ctagaggctc cttccgaaca agcaccgact gagcaaaggc ctggggtgca ggagtgctac   8340
catggtaatg gacagagtta tcgaggcaca tactccacca ctgtcacagg aagaacctgc   8400
caagcttggt catctatgac accacactcg catagtcgga ccccagaata ctacccaaat   8460
gctggcttga tcatgaacta ctgcaggaat ccagatgctg tggcagctcc ttattgttat   8520
acgagggatc ccggtgtcag gtgggagtac tgcaacctga cgcaatgctc agacgcagaa   8580
gggactgccg tcgcgcctcc gactgttacc ccggttccaa gcctagaggc tccttccgaa   8640
caagcaccga ctgagcaaag gcctggggtg caggagtgct accatggtaa tggacagagt   8700
tatcgaggca catactccac cactgtcaca ggaagaacct gccaagcttg gtcatctatg   8760
acaccacact cgcatagtcg gaccccagaa tactacccaa atgctggctt gatcatgaac   8820
tactgcagga atccagatgc tgtggcagct ccttattgtt atacgaggga tcccggtgtc   8880
aggtgggagt actgcaacct gacgcaatgc tcagacgcag aagggactgc cgtcgcgcct   8940
ccgactgtta ccccggttcc aagcctagag gctccttccg aacaagcacc gactgagcag   9000
aggcctgggg tgcaggagtg ctaccacggt aatggacaga gttatcgagg cacatactcc   9060
accactgtca ctggaagaac ctgccaagct tggtcatcta tgacaccaca ctcgcatagt   9120
cggaccccag aatactaccc aaatgctggc ttgatcatga actactgcag gaatccagat   9180
gctgtggcag ctccttattg ttatacgagg gatcccggtg tcaggtggga gtactgcaac   9240
ctgacgcaat gctcagacgc agaagggact gccgtcgcgc ctccgactgt taccccggtt   9300
ccaagcctag aggctccttc cgaacaagca ccgactgagc agaggcctgg ggtgcaggag   9360
tgctaccacg gtaatggaca gagttatcga ggcacatact ccaccactgt cactggaaga   9420
acctgccaag cttggtcatc tatgacacca cactcgcata gtcggacccc agaatactac   9480
ccaaatgctg gcttgatcat gaactactgc aggaatccag atgctgtggc agctccttat   9540
```

```
tgttatacga gggatcccgg tgtcaggtgg gagtactgca acctgacgca atgctcagac   9600
gcagaaggga ctgccgtcgc gcctccgact gttaccccgg ttccaagcct agaggctcct   9660
tccgaacaag caccgactga gcagaggcct ggggtgcagg agtgctacca cggtaatgga   9720
cagagttatc gaggcacata ctccaccact gtcactggaa gaacctgcca agcttggtca   9780
tctatgacac cacactcgca tagtcggacc ccagaatact acccaaatgc tggcttgatc   9840
atgaactact gcaggaatcc agatgctgtg gcagctcctt attgttatac gagggatccc   9900
ggtgtcaggt gggagtactg caacctgacg caatgctcag acgcagaagg gactgccgtc   9960
gcgcctccga ctgttacccc ggttccaagc ctagaggctc cttccgaaca agcaccgact  10020
gagcagaggc ctggggtgca ggagtgctac cacggtaatg gacagagtta tcgaggcaca  10080
tactccacca ctgtcactgg aagaacctgc caagcttggt catctatgac accacactcg  10140
catagtcgga ccccagaata ctacccaaat gctggcttga tcatgaacta ctgcaggaat  10200
ccagatcctg tggcagcccc ttattgttat acgagggatc ccagtgtcag gtgggagtac  10260
tgcaacctga cacaatgctc agacgcagaa gggactgccg tcgcgcctcc aactattacc  10320
ccgattccaa gcctagaggc tccttctgaa caagcaccaa ctgagcaaag gcctggggtg  10380
caggagtgct accacggaaa tggacagagt tatcaaggca catacttcat tactgtcaca  10440
ggaagaacct gccaagcttg gtcatctatg acaccacact cgcatagtcg gaccccagca  10500
tactacccaa atgctggctt gatcaagaac tactgccgaa atccagatcc tgtggcagcc  10560
ccttggtgtt atacaacaga tcccagtgtc aggtgggagt actgcaacct gacacgatgc  10620
tcagatgcag aatggactgc cttcgtccct ccgaatgtta ttctggctcc aagcctagag  10680
gctttttttg aacaagcact gactgaggaa acccccgggg tacaggactg ctactaccat  10740
tatggacaga gttaccgagg cacatactcc accactgtca caggaagaac ttgccaagct  10800
tggtcatcta tgacaccaca ccagcatagt cggaccccag aaaactaccc aaatgctggc  10860
ctgaccagga actactgcag gaatccagat gctgagattc gcccttggtg ttacaccatg  10920
gatcccagtg tcaggtggga gtactgcaac ctgacacaat gcctggtgac agaatcaagt  10980
gtccttgcaa ctctcacggt ggtcccagat ccaagcacag aggcttcttc tgaagaagca  11040
ccaacggagc aaagccccgg ggtccaggat tgctaccatg gtgatggaca gagttatcga  11100
ggctcattct ctaccactgt cacaggaagg acatgtcagt cttggtcctc tatgacacca  11160
cactggcatc agaggacaac agaatattat ccaaatggtg gcctgaccag gaactactgc  11220
aggaatccag atgctgagat tagtccttgg tgttatacca tggatcccaa tgtcagatgg  11280
gagtactgca acctgacaca atgtccagtg acagaatcaa gtgtccttgc gacgtccacg  11340
gctgtttctg aacaagcacc aacggagcaa agccccacag tccaggactg ctaccatggt  11400
gatggacaga gttatcgagg ctcattctcc accactgtta caggaaggac atgtcagtct  11460
tggtcctcta tgacaccaca ctggcatcag agaaccacag aatactaccc aaatggtggc  11520
ctgaccagga actactgcag gaatccagat gctgagattc gcccttggtg ttataccatg  11580
gatcccagtg tcagatggga gtactgcaac ctgacgcaat gtccagtgat ggaatcaact  11640
ctcctcacaa ctcccacggt ggtcccagtt ccaagcacag agcttccttc tgaagaagca  11700
ccaactgaaa acagcactgg ggtccaggac tgctaccgag gtgatggaca gagttatcga  11760
ggcacactct ccaccactat cacaggaaga acatgtcagt cttggtcgtc tatgacacca  11820
cattggcatc ggaggatccc attatactat ccaaatgctg gcctgaccag gaactactgc  11880
aggaatccag atgctgagat tcgcccttgg tgttacacca tggatcccag tgtcaggtgg  11940
```

gagtactgca acctgacacg atgtccagtg acagaatcga gtgtcctcac aactcccaca 12000 gtggccccgg ttccaagcac agaggctcct tctgaacaag caccacctga gaaaagccct 12060 gtggtccagg attgctacca tggtgatgga cggagttatc gaggcatatc ctccaccact 12120 gtcacaggaa ggacctgtca atcttggtca tctatgatac cacactggca tcagaggacc 12180 ccagaaaact acccaaatgc tggcctgacc gagaactact gcaggaatcc agattctggg 12240 aaacaaccct ggtgttacac aaccgatccg tgtgtgaggt gggagtactg caatctgaca 12300 caatgctcag aaacagaatc aggtgtccta gagactccca ctgttgttcc agttccaagc 12360 atggaggctc attctgaagc agcaccaact gagcaaaccc ctgtggtccg gcagtgctac 12420 catggtaatg gccagagtta tcgaggcaca ttctccacca ctgtcacagg aaggacatgt 12480 caatcttggt catccatgac accacaccgg catcagagga ccccagaaaa ctacccaaat 12540 gatggcctga caatgaacta ctgcaggaat ccagatgccg atacaggccc ttggtgtttt 12600 accatggacc ccagcatcag gtgggagtac tgcaacctga cgcgatgctc agacacagaa 12660 gggactgtgg tcgctcctcc gactgtcatc caggttccaa gcctagggcc tccttctgaa 12720 caagactgta tgtttgggaa tgggaaagga taccggggca agaaggcaac cactgttact 12780 gggacgccat gccaggaatg ggctgcccag gagccccata gacacagcac gttcattcca 12840 gggacaaata aatgggcagg tctggaaaaa aattactgcc gtaaccctga tggtgacatc 12900 aatggtccct ggtgctacac aatgaatcca agaaaacttt ttgactactg tgatatccct 12960 ctctgtgcat cctcttcatt tgattgtggg aagcctcaag tggagccgaa gaaatgtcct 13020 ggaagcattg taggggggtg tgtggcccac ccacattcct ggccctggca agtcagtctc 13080 agaacaaggt ttggaaagca cttctgtgga ggcaccttaa tatccccaga gtgggtgctg 13140 actgctgctc actgcttgaa gaagtcctca aggccttcat cctacaaggt catcctgggt 13200 gcacaccaag aagtgaacct cgaatctcat gttcaggaaa tagaagtgtc taggctgttc 13260 ttggagccca cacaagcaga tattgccttg ctaaagctaa gcaggcctgc cgtcatcact 13320 gacaaagtaa tgccagcttg tctgccatcc ccagactaca tggtcaccgc caggactgaa 13380 tgttacatca ctggctgggg agaaacccaa ggtacctttg ggactggcct tctcaaggaa 13440 gcccagctcc ttgttattga gaatgaagtg tgcaatcact ataagtatat ttgtgctgag 13500 catttggcca gaggcactga cagttgccag ggtgacagtg gagggcctct ggtttgcttc 13560 gagaaggaca aatacatttt acaaggagtc acttcttggg gtcttggctg tgcacgcccc 13620 aataagcctg gtgtctatgc tcgtgtttca aggtttgtta cttggattga gggaatgatg 13680 agaaataatt aattggacgg gagacagagt gaagcatcaa cctacttaga agctgaaacg 13740 tgggtaagga tttagcatgc tggaaataat agacagcaat caaacgaaga cactgttccc 13800 agctaccagc tatgccaaac cttggcattt ttggtatttt tgtgtataag cttttaaggt 13860 ctgactgaca aattctgtat taaggtgtca tagctatgac atttgttaaa aataaactct 13920 gcacttattt tgatttga 13938

<210> SEQ ID NO 861
<211> LENGTH: 25
<212> TYPE: DNA
<213> ORGANISM: Artificial Sequence
<220> FEATURE:
<223> OTHER INFORMATION: PCR Primer

<400> SEQUENCE: 861 cagctcctta ttgttatacg aggga 25

<210> SEQ ID NO 862
<211> LENGTH: 18
<212> TYPE: DNA
<213> ORGANISM: Artificial Sequence
<220> FEATURE:
<223> OTHER INFORMATION: PCR Primer

<400> SEQUENCE: 862 tgcgtctgag cattgcgt 18

<210> SEQ ID NO 863
<211> LENGTH: 24
<212> TYPE: DNA
<213> ORGANISM: Artificial Sequence
<220> FEATURE:
<223> OTHER INFORMATION: PCR Probe

<400> SEQUENCE: 863 cccggtgtca ggtgggagta ctgc 24

<210> SEQ ID NO 864
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 864 gcctcagtct tcttcgcacc 20

<210> SEQ ID NO 865
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 865 gcctcagtct tattcgcacc 20

<210> SEQ ID NO 866
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 866 gcctcagtat tattcgcacc 20

<210> SEQ ID NO 867
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 867 gcctcattat tattcgcacc 20

<210> SEQ ID NO 868
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 868 gcctcattat tattagcacc 20

<210> SEQ ID NO 869
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 869 gcctcattat tattatcacc 20

<210> SEQ ID NO 870
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 870 gcctaattat tattatcacc 20

<210> SEQ ID NO 871
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 871 gcctcagtct gcttcgcac 19

<210> SEQ ID NO 872
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 872 gcctcagtct gcttcgca 18

<210> SEQ ID NO 873
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 873 gcctcagtct gcttc 15

<210> SEQ ID NO 874
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 874 cctcagtctg cttcgcac 18

<210> SEQ ID NO 875
<211> LENGTH: 16

<212> TYPE: DNA
<213> ORGANISM: Artificial Sequence
<220> FEATURE:
<223> OTHER INFORMATION: Antisense Oligonucleotide

<400> SEQUENCE: 875 ctcagtctgc ttcgca 16

<210> SEQ ID NO 876
<211> LENGTH: 14
<212> TYPE: DNA
<213> ORGANISM: Artificial Sequence
<220> FEATURE:
<223> OTHER INFORMATION: Antisense Oligonucleotide

<400> SEQUENCE: 876 tcagtctgct tcgc 14

<210> SEQ ID NO 877
<211> LENGTH: 10
<212> TYPE: DNA
<213> ORGANISM: Artificial Sequence
<220> FEATURE:
<223> OTHER INFORMATION: Antisense Oligonucleotide

<400> SEQUENCE: 877 gcctcagtct 10

<210> SEQ ID NO 878
<211> LENGTH: 10
<212> TYPE: DNA
<213> ORGANISM: Artificial Sequence
<220> FEATURE:
<223> OTHER INFORMATION: Antisense Oligonucleotide

<400> SEQUENCE: 878 gcttcgcacc 10

<210> SEQ ID NO 879
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 879 uugaagccau acaccucuuu 20

<210> SEQ ID NO 880
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 880 ugaccaggac ugccuguucu 20

<210> SEQ ID NO 881
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 881 gaauagggcu guagcuguaa 20

<210> SEQ ID NO 882
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 882 uauacugauc aaauuguauc 20

<210> SEQ ID NO 883
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 883 uggaauucug guaugugaag 20

<210> SEQ ID NO 884
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 884 aaaucaaaug auugcuuugu 20

<210> SEQ ID NO 885
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 885 gugaugacac uugauuuaaa 20

<210> SEQ ID NO 886
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 886 gaagcugccu cuucuuccca 20

<210> SEQ ID NO 887
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 887 gagaguuggu cugaaaaauc 20

<210> SEQ ID NO 888
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 888 gtgcgcgcga gcccgaaatc 20

<210> SEQ ID NO 889
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 889 cuucuggcau ccgguuuagt t 21

<210> SEQ ID NO 890
<211> LENGTH: 466
<212> TYPE: DNA
<213> ORGANISM: M. fascicularis
<220> FEATURE:
<221> NAME/KEY: misc_feature
<222> LOCATION: 9
<223> OTHER INFORMATION: n = A,T,C or G

<400> SEQUENCE: 890 ggatcggcng accctgagct gcatatggct ggtaatctaa aaggagccta ccaaaataat 60 gaaataaaac acatctatac catctcttct gctgccttat cagcaagcta caaagcagac 120 actgttgcta aggttcaggg tgtggagttt agccatcggc tcaacacaga catcgctggg 180 ctggcttcag ccattgacat tagcacaaac tataattcag actcattgca tttcagcaat 240 gtcttccatt ctgtaatggc tccatttacc atgaccattg atacacatac aaatggcaac 300 gggaaacttg ttctctgggg agaacatact gggcagctgt atagcaaatt cctgttgaaa 360 gcagaacctc tggcattcac tttctctcat gattacaaag gctccacgag tcatcatctc 420 atgtctagga aaagcatcag tgcagctctt gaacacaaag tcagta 466

<210> SEQ ID NO 891
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 891 gcctcagtct gctttacacc 20

<210> SEQ ID NO 892
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 892 agattaccag ccatatgcag 20

<210> SEQ ID NO 893
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 893 cgagaggcgg acgggaccg 19

```
<210> SEQ ID NO 894
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 894

cgagaggcgg acgggaccgt t                                              21


<210> SEQ ID NO 895
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 895

ttgctctccg cctgccctgg c                                              21


<210> SEQ ID NO 896
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 896

gctctccgcc tgccctggc                                                 19


<210> SEQ ID NO 897
<211> LENGTH: 20
<212> TYPE: DNA
<213> ORGANISM: M. musculus

<400> SEQUENCE: 897

agattaccag ccatatgcag                                                20
```

What is claimed is:

1. An antisense compound 12 to 30 nucleobases in length, wherein said antisense compound is fully complementary within the range of nucleotides 5562-5625 of SEQ ID NO:3, and comprises at least one modified sugar moiety.

2. The antisense compound of claim 1, wherein said antisense compound is fully complementary within the range of nucleotides 5582-5625 of SEQ ID NO:3.

3. The antisense compound of claim 1, wherein said antisense compound is targeted to the range of nucleotides 5589-5608 of SEQ ID NO:3 and is fully complementary over its length to SEQ ID NO: 3.

4. The antisense compound of claim 1, wherein said antisense compound comprises at least 8 contiguous nucleobases of SEQ ID NO: 224.

5. The antisense compound of claim 1, wherein said antisense compound comprises SEQ ID NO: 224.

6. The antisense compound of claim 1, wherein the antisense compound comprises an antisense oligonucleotide.

7. The antisense compound of claim 1, wherein the antisense compound further comprises one or more modifications selected from the group consisting of a modified backbone and a modified nucleobase.

8. The antisense compound of claim 1, wherein the modified sugar moiety is selected from the group consisting of a 2'-methoxyethoxy modified sugar moiety, a 2'-methoxy modified sugar moiety, a 2'-O-alkyl modified sugar moiety, and a bicyclic nucleic acid sugar moiety.

9. The antisense compound of claim 1, wherein the antisense compound is single-stranded.

10. The antisense compound of claim 1, wherein the antisense compound is double-stranded.

11. A composition comprising the antisense compound of claim 1 and a pharmaceutically acceptable carrier or diluent.

12. The antisense compound of claim 1, wherein the antisense compound is covalently linked to a lipid moiety.

13. The antisense compound of claim 12 wherein the lipid moiety comprises a cholesterol.

14. The antisense compound of claim 1, wherein the antisense compound is 20 to 30 nucleobases in length.

15. The antisense compound of claim 1, wherein the antisense compound is 20 nucleobases in length.

16. The antisense compound of claim 1, wherein the antisense compound is a chimeric antisense compound.

17. An antisense compound 20 to 30 nucleobases in length comprising at least 13 contiguous nucleobases of SEQ ID NO: 224 and at least one modified sugar moiety. wherein said antisense compound specifically hybridizes to SEQ ID NO:3.

18. The antisense compound of claim 17. wherein the antisense compound is 20 nucleobases in length.

19. The antisense compound of claim 17, wherein the modified sugar moiety is a 2'-methoxyethoxy modified sugar moiety, a 2'-methoxy modified sugar moiety, a 2'-O-alkyl modified sugar moiety, or a bicyclic nucleic acid sugar moiety.

20. The antisense compound of claim 17, wherein the antisense compound is an antisense oligonucleotide.

21. The antisense compound of claim 20, wherein the antisense oligonucleotide is a chimeric antisense oligonucleotide.

22. The antisense compound of claim 21, wherein the chimeric antisense oligonucleotide comprises a gap segment of 2'-deoxynucleotides positioned between wing segments, wherein each nucleotide of each wing segment comprises a 2'-methoxyethoxy sugar moiety.

23. The antisense compound of claim 22, wherein the gap segment is ten 2'-deoxynucleotides in length and each wing segment comprises from one to nine 2'-methoxyethyoxy nucleotides.

24. The antisense compound of claim 22, wherein the gap segment is ten 2'-deoxynucleotides and each wing segment comprises five 2'-methoxyethoxy nucleotides.

25. The antisense compound of claim 17, wherein each internucleoside linkage is a phosphorothioate internucleoside linkage.

26. The antisense compound of claim 17, wherein each cytosine is a 5-methylcytosine.

27. The antisense compound of claim 17, wherein the antisense compound is covalently linked to a lipid moiety.

28. The antisense compound of claim 27, wherein the lipid moiety is cholesterol.

29. The antisense compound of claim 17, wherein the antisense compound is fully complementary to SEQ ID NO: 3.

30. The antisense compound of claim 17, wherein the antisense compound comprises SEQ ID NO: 224.

31. The antisense compound of claim 17, wherein the antisense compound consists of SEQ ID NO: 224.

32. An antisense oligonucleotide consisting of SEQ ID NO: 224, wherein nucleobases 1-5 and 16-20 comprise 2'-methoxyethoxy nucleotides, nucleobases 6-15 are 2'-deoxynucleotides, each internucleoside linkage is a phosphorothioate internucleoside linkage, and each cytosine is a 5-methylcytosine.

33. The antisense oligonucleotide of claim 32, wherein the antisense oligonucleotide is in a salt form.

34. The antisense oligonucleotide of claim 33, wherein the salt is sodium salt.

35. A composition comprising the antisense oligonucleotide of any of claim 17, 32, 33 or 34 and a pharmaceutically acceptable carrier or diluent.

36. The antisense compound of claim 17, wherein said antisense compound inhibits expression of apolipoprotein B mRNA in HepG2 cells by at least 40% when contacted with the HepG2 cells at a concentration of 50 nM.

*37. A method of inhibiting the expression of apolipoprotein B in human cells or tissues in vivo comprising contacting said cells or tissues with an antisense compound 12 to 30 nucleobases in length, wherein said antisense compound is fully complementary within the range of nucleotides 5562-5625 of SEQ ID NO:3, and comprises at least one modified sugar moiety.*

*38. A method of inhibiting the expression of apolipoprotein B in human cells or tissues in vivo comprising contacting said cells or tissues with an antisense compound 20 to 30 nucleobases in length comprising at least 13 contiguous nucleobases of SEQ ID NO: 224 and at least one modified sugar moiety, wherein said antisense compound specifically hybridizes to SEQ ID NO:3.*

*39. A method of inhibiting the expression of apolipoprotein B in human cells or tissues in vivo comprising contacting said cells or tissues with an antisense oligonucleotide consisting of SEQ ID NO: 224, wherein nucleobases 1-5 and 16-20 comprise 2'-methoxyethoxy nucleotides, nucleobases 6-15 are 2'-deoxynucleotides, each internucleoside linkage is a phosphorothioate internucleoside linkage, and each cytosine is a 5-methylcytosine.*

*40. A method of inhibiting the expression of apolipoprotein B mRNA in HepG2 cells by at least 40% comprising contacting said cells with an antisense compound 20 to 30 nucleobases in length comprising at least 13 contiguous nucleobases of SEQ ID NO: 224 and at least one modified sugar moiety, wherein said antisense compound specifically hybridizes to SEQ ID NO:3, wherein the antisense compound is at a concentration of 50 nM, and wherein said mRNA is inhibited by at least 40%.*

*41. An antisense compound 12 to 30 nucleobases in length, wherein said antisense compound is fully complementary within the range of nucleotides 5562-5625 of SEQ ID NO:3, wherein the antisense compound is chemically modified.*

*42. An antisense compound 20 to 30 nucleobases in length comprising at least 13 contiguous nucleobases of SEQ ID NO: 224, wherein the antisense compound is chemically modified, and wherein said antisense compound specifically hybridizes to SEQ ID NO:3.*

*43. An oligomeric compound 12 to 30 nucleobases in length, wherein said oligomeric compound is fully complementary within the range of nucleotides 5562-5625 of SEQ ID NO:3, and comprises at least one modified sugar moiety.*

*44. An oligomeric compound 20 to 30 nucleobases in length comprising at least 13 contiguous nucleobases of SEQ ID NO: 224 and at least one sugar moiety, and wherein said oligomeric compound specifically hybridizes to SEQ ID NO:3.*

*45. A method of inhibiting the expression of apolipoprotein B in human cells or tissues in vivo comprising contacting said cells or tissues with an antisense compound 12 to 30 nucleobases in length, wherein said antisense compound is fully complementary within the range of nucleotides 5562-5625 of SEQ ID NO:3, wherein the antisense compound is chemically modified.*

*46. A method of inhibiting the expression of apolipoprotein B in human cells or tissues in vivo comprising contacting said cells or tissues with an antisense compound 20 to 30 nucleobases in length comprising at least 13 contiguous nucleobases of SEQ ID NO: 224, wherein the antisense compound is chemically modified, and wherein said antisense compound specifically hybridizes to SEQ ID NO:3.*

*47. A method of inhibiting the expression of apolipoprotein B in human cells or tissues in vivo comprising contacting said cells or tissues with an oligomeric compound 12 to 30 nucleobases in length, wherein said oligomeric compound is fully complementary within the range of nucleotides 5562-5625 of SEQ ID NO:3, and comprises at least one modified sugar moiety.*

*48. A method of inhibiting the expression of apolipoprotein B in human cells or tissues in vivo comprising contacting said cells or tissues with an oligomeric compound 20 to 30 nucleobases in length comprising at least 13 contiguous nucleobases of SEQ ID NO: 224 and at least one sugar moiety, wherein said oligomeric compound specifically hybridizes to SEQ ID NO:3.*

*49. A method of inhibiting the expression of apolipoprotein B in human cells or tissues in vivo comprising contacting said cells or tissues with a conjugate compound, wherein said conjugate compound comprises an antisense compound 12 to*

*30 nucleobases in length, wherein said antisense compound is fully complementary within the range of nucleotides 5562-5625 of SEQ ID NO:3, and wherein said antisense compound is conjugated to an active drug substance.*

*50. A method of inhibiting the expression of apolipoprotein B in human cells or tissues in vivo comprising contacting said cells or tissues with a conjugate compound, wherein said conjugate compound comprises an antisense compound 20 to 30 nucleobases in length comprising at least 13 contiguous nucleobases of SEQ ID NO: 224, wherein said antisense compound specifically hybridizes to SEQ ID NO:3, and wherein said antisense compound is conjugated to an active drug substance.*

*51. A method of inhibiting the expression of apolipoprotein B in human cells or tissues in vivo comprising contacting said cells or tissues with a conjugate compound, wherein said conjugate compound comprises an oligomeric compound 12 to 30 nucleobases in length, wherein said oligomeric compound is fully complementary within the range of nucleotides 5562-5625 of SEQ ID NO:3, and wherein said oligomeric compound is conjugated to an active drug substance.*

*52. A method of inhibiting the expression of apolipoprotein B in human cells or tissues in vivo comprising contacting said cells or tissues with a conjugate compound, wherein said conjugate compound comprises an oligomeric compound 20 to 30 nucleobases in length comprising at least 13 contiguous nucleobases of SEQ ID NO: 224, wherein said oligomeric compound specifically hybridizes to SEQ ID NO:3, and wherein said oligomeric compound is conjugated to an active drug substance.*

*53. A method of inhibiting the expression of apolipoprotein B in human cells or tissues in vivo comprising contacting said cells or tissues with an antisense compound 12 to 30 nucleobases in length, wherein said antisense compound is fully complementary within the range of nucleotides 5562-5625 of SEQ ID NO:3, and comprises a modified backbone or modified nucleobase.*

*54. A method of inhibiting the expression of apolipoprotein B in human cells or tissues in vivo comprising contacting said cells or tissues with an antisense compound 20 to 30 nucleobases in length comprising at least 13 contiguous nucleobases of SEQ ID NO: 224 and a modified backbone or modified nucleobase, wherein said antisense compound specifically hybridizes to SEQ ID NO:3.*

*55. A method of inhibiting the expression of apolipoprotein B mRNA in HepG2 cells by at least 40% comprising contacting said cells with an antisense compound at a concentration of 50 nM, wherein said mRNA is inhibited by at least 40%, wherein said antisense compound is 20 to 30 nucleobases in length comprising at least 13 contiguous nucleobases of SEQ ID NO: 224 and a modified backbone or modified nucleobase, and wherein said antisense compound specifically hybridizes to SEQ ID NO:3.*

*56. A method of inhibiting the expression of apolipoprotein B in human cells or tissues in vivo comprising contacting said cells or tissues with an oligomeric compound 12 to 30 nucleobases in length, wherein said oligomeric compound is fully complementary within the range of nucleotides 5562-5625 of SEQ ID NO:3, and comprises a modified backbone or modified nucleobase.*

*57. A method of inhibiting the expression of apolipoprotein B in human cells or tissues in vivo comprising contacting said cells or tissues with an oligomeric compound 20 to 30 nucleobases in length comprising at least 13 contiguous nucleobases of SEQ ID NO: 224 and a modified backbone or modified nucleobase, wherein said oligomeric compound specifically hybridizes to SEQ ID NO:3.*

*58. A method of inhibiting the expression of apolipoprotein B mRNA in HepG2 cells by at least 40% comprising contacting said cells with an oligomeric compound at a concentration of 50 nM, wherein said mRNA is inhibited by at least 40%, wherein said oligomeric compound is 20 to 30 nucleobases in length comprising at least 13 contiguous nucleobases of SEQ ID NO: 224 and a modified backbone or modified nucleobase, and wherein said oligomeric compound specifically hybridizes to SEQ ID NO:3.*

* * * * *